(12) United States Patent
Uehara et al.

(10) Patent No.: US 12,251,446 B2
(45) Date of Patent: Mar. 18, 2025

(54) NUCLEIC ACID CONJUGATE

(71) Applicant: Kyowa Kirin Co., Ltd., Tokyo (JP)

(72) Inventors: Keiji Uehara, Tokyo (JP); Yasuhiro Suzuki, Tokyo (JP); Toshimasa Harumoto, Tokyo (JP); Hiroto Iwai, Tokyo (JP); Asana Makino, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 694 days.

(21) Appl. No.: 16/314,015

(22) PCT Filed: Jun. 30, 2017

(86) PCT No.: PCT/JP2017/024268
§ 371 (c)(1),
(2) Date: Dec. 28, 2018

(87) PCT Pub. No.: WO2018/004004
PCT Pub. Date: Jan. 4, 2018

(65) Prior Publication Data
US 2019/0192674 A1 Jun. 27, 2019

(30) Foreign Application Priority Data
Jun. 30, 2016 (JP) .................. 2016-131054

(51) Int. Cl.
| A61K 47/00 | (2006.01) |
| A61K 9/00 | (2006.01) |
| A61K 31/7088 | (2006.01) |
| A61K 47/54 | (2017.01) |
| A61K 47/60 | (2017.01) |
| A61K 48/00 | (2006.01) |
| C07H 21/02 | (2006.01) |
| C12N 15/09 | (2006.01) |
| C12N 15/113 | (2010.01) |

(52) U.S. Cl.
CPC ............ *A61K 47/60* (2017.08); *A61K 9/0019* (2013.01); *A61K 31/7088* (2013.01); *A61K 47/54* (2017.08); *A61K 48/00* (2013.01); *C07H 21/02* (2013.01); *C12N 15/09* (2013.01); *C12N 15/113* (2013.01)

(58) Field of Classification Search
None
See application file for complete search history.

(56) References Cited

U.S. PATENT DOCUMENTS

| 8,106,022 B2 | 1/2012 | Manoharan et al. |
| 8,273,357 B2 | 9/2012 | Hacohen et al. |
| 8,450,467 B2 | 5/2013 | Manoharan et al. |
| 8,828,956 B2 | 9/2014 | Manoharan et al. |
| 9,127,276 B2 | 9/2015 | Prakash et al. |
| 9,145,558 B2 | 9/2015 | Prakash et al. |
| 9,163,239 B2 | 10/2015 | Prakash et al. |
| 9,181,549 B2 | 11/2015 | Prakash et al. |
| 9,181,550 B2 | 11/2015 | Prakash et al. |
| 9,352,048 B2 | 5/2016 | Manoharan et al. |
| 9,370,581 B2 | 6/2016 | Manoharan et al. |
| 9,370,582 B2 | 6/2016 | Manoharan et al. |
| 9,399,775 B2 | 7/2016 | Rajeev et al. |
| 9,714,421 B2 | 7/2017 | Prakash et al. |
| 9,814,777 B2 | 11/2017 | Manoharan et al. |
| 9,867,882 B2 | 1/2018 | Manoharan et al. |
| 9,932,580 B2 | 4/2018 | Prakash et al. |
| 9,932,581 B2 | 4/2018 | Prakash et al. |
| 9,957,504 B2 | 5/2018 | Prakash et al. |
| 10,570,391 B2 | 2/2020 | Rajeev et al. |
| 10,683,499 B2 | 6/2020 | Prakash et al. |
| 10,745,700 B2 | 8/2020 | Uehara et al. |
| 2009/0004218 A1 | 1/2009 | Hacohen et al. |
| 2009/0239814 A1 | 9/2009 | Manoharan et al. |
| 2009/0247608 A1 | 10/2009 | Manoharan et al. |
| 2012/0136042 A1 | 5/2012 | Manoharan et al. |
| 2013/0178512 A1 | 7/2013 | Manoharan et al. |
| 2014/0179761 A1 | 6/2014 | Manoharan et al. |
| 2014/0315835 A1 | 10/2014 | Rajeev et al. |
| 2014/0343123 A1 | 11/2014 | Prakash et al. |
| 2015/0011615 A1 | 1/2015 | Manoharan et al. |
| 2015/0119444 A1 | 4/2015 | Manoharan et al. |
| 2015/0119445 A1 | 4/2015 | Manoharan et al. |
| 2015/0126718 A1 | 5/2015 | Prakash et al. |
| 2015/0126719 A1 | 5/2015 | Prakash et al. |
| 2015/0126720 A1 | 5/2015 | Prakash et al. |
| 2015/0176007 A1 | 6/2015 | Prakash et al. |
| 2016/0017323 A1 | 1/2016 | Prakash et al. |
| 2016/0051691 A1 | 2/2016 | Manoharan et al. |

(Continued)

FOREIGN PATENT DOCUMENTS

| WO | 2006/093524 | 9/2006 |
| WO | 2009/073809 | 6/2009 |

(Continued)

OTHER PUBLICATIONS

Barbuto et al., Nature Chemical Biology, 2013, 9: 250-256.*
Kreutz et al., Blood, 2013, 121: 2836-2844.*
Chabre et al., Advances in Carbohydrate Chemistry and Biochemistry, 2010, 63: 165-393.*
Chabre et al., Chemical Society Reviews, 2013, 42: 4507-4844.*
Berzi et al., Viruses, 2014, 6: 391-403.*
Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, vol. 10, No. 5, 1181-1187, 7 pages.

(Continued)

*Primary Examiner* — Ileana Popa
(74) *Attorney, Agent, or Firm* — Wenderoth, Lind & Ponack, L.L.P.

(57) ABSTRACT

The present invention provides a nucleic acid conjugate in which a sugar chain ligand is bonded to an oligonucleotide via a linker, the sugar chain ligand having O-bonded mannose at its non-reducing end.

12 Claims, 5 Drawing Sheets
Specification includes a Sequence Listing.

(56) References Cited

U.S. PATENT DOCUMENTS

| | | | |
|---|---|---|---|
| 2016/0076030 A1 | 3/2016 | Prakash et al. | |
| 2016/0076032 A1 | 3/2016 | Prakash et al. | |
| 2016/0090595 A1 | 3/2016 | Prakash et al. | |
| 2016/0090596 A1 | 3/2016 | Prakash et al. | |
| 2016/0257961 A1 | 9/2016 | Bradshaw et al. | |
| 2016/0355817 A1 | 12/2016 | Rajeev et al. | |
| 2016/0375137 A9 | 12/2016 | Manoharan et al. | |
| 2018/0002693 A1 | 1/2018 | Prakash et al. | |
| 2018/0044676 A1 | 2/2018 | Prakash et al. | |
| 2018/0273952 A1 | 9/2018 | Prakash et al. | |
| 2018/0273953 A1 | 9/2018 | Prakash et al. | |
| 2018/0326070 A1 | 11/2018 | Manoharan et al. | |
| 2019/0055554 A1 | 2/2019 | Prakash et al. | |
| 2019/0055558 A1 | 2/2019 | Uehara et al. | |
| 2019/0099493 A1 | 4/2019 | Manoharan et al. | |
| 2019/0184018 A1 | 6/2019 | Manoharan et al. | |
| 2019/0367914 A1 | 12/2019 | Prakash et al. | |
| 2020/0224198 A1 | 7/2020 | Prakash et al. | |
| 2020/0297853 A1 | 9/2020 | Manoharan et al. | |
| 2020/0318111 A1 | 10/2020 | Rajeev et al. | |

FOREIGN PATENT DOCUMENTS

| | | | |
|---|---|---|---|
| WO | 2011/000721 | | 1/2011 |
| WO | 2013/075035 | | 5/2013 |
| WO | 2014/179620 | | 11/2014 |
| WO | 2014/179629 | | 11/2014 |
| WO | WO 15/006740 | * | 1/2015 |
| WO | 2015/069932 | | 5/2015 |
| WO | 2015/105083 | | 7/2015 |
| WO | 2016/092372 | | 6/2016 |
| WO | 2017/131236 | | 8/2017 |

OTHER PUBLICATIONS

Obermajer et al., "Design, synthesis and activity evaluation of mannose-based DC-SIGN antagonists", Molecular Diversity, 2011, vol. 15, pp. 347-360.

Varga et al., "Selective Targeting of Dendritic Cell-Specific Intercellular Adhesion Molecule-3-Grabbing Nonintegrin (DC-Sign) with Mannose-Based Glycomimetics: Synthesis and Interaction Studies of Bis(benzylamide) Derivatives of a Pseudomannobioside", Chemistry—A European Journal, 2013, vol. 19, pp. 4786-4797.

Nair et al., "Multivalent N-Acetylgalactosamine-Conjugated siRNA Localizes in Hepatocytes and Elicits Robust RNAi-Mediated Gene Silencing", Journal of American Chemical Society, 2014, vol. 136, pp. 16958-16961.

Geijtenbeek et al., "Signalling through C-type lectin receptors: shaping immune responses", Nature Reviews Immunology, 2009, vol. 9, pp. 465-479.

Van Kooyk et al., "DC-Sign: Escape Mechanism for Pathogens", Nature Reviews Immunology, 2003, vol. 3, pp. 697-709.

Guzzi et al., "Detection and quantitative analysis of two independent binding modes of a small ligand responsible for DC-Sign clustering", Organic & Biomolecular Chemistry, 2016, vol. 14, No. 1, pp. 335-344.

Chabre et al., "Recent Trends in Glycodendrimer Syntheses and Applications", Current Topics in Medical Chemistry, 2008, vol. 8, pp. 1237-1285.

Viault et al., "The first "ready-to-use" benzene-based heterotrifunctional cross-linker for multiple bioconjugation", Organic & Biomolecular Chemistry, 2013, vol. 11, pp. 2693-2705, 13 pages.

Morvan et al., "DNA glycoclusters and DNA-based carbohydrate microarrays: From design to applications ǂ" RSC Advances, 2012, vol. 2, pp. 12043-12068, 27 pages.

* cited by examiner

[Figure 1]
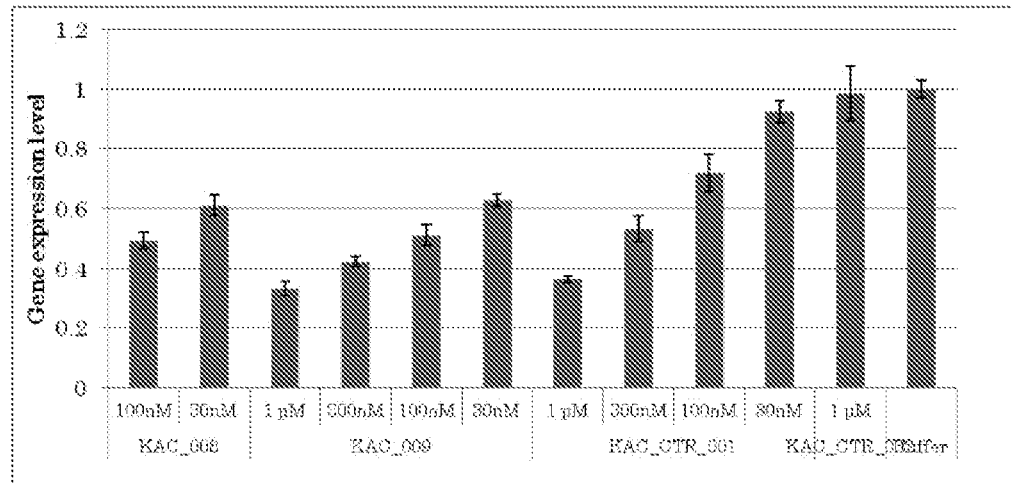
[Figure 2]
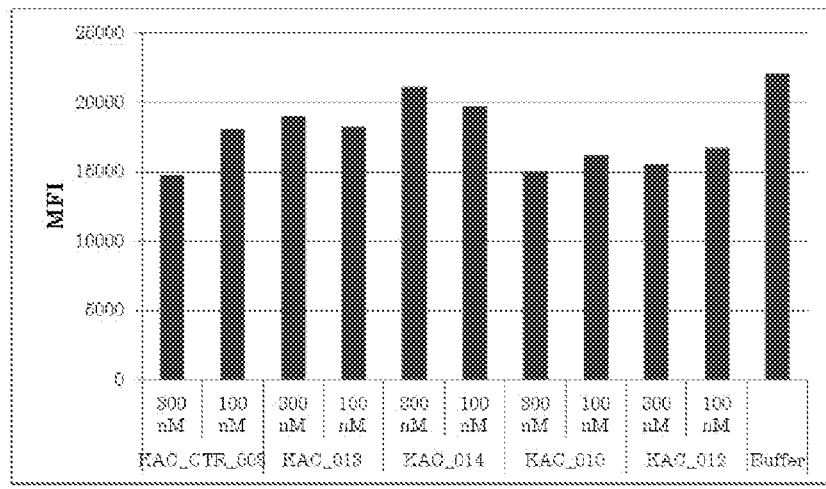
[Figure 3]
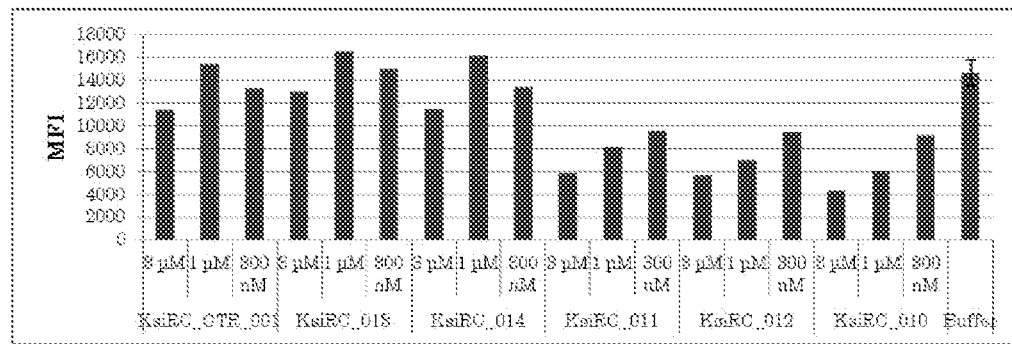

[Figure 4]
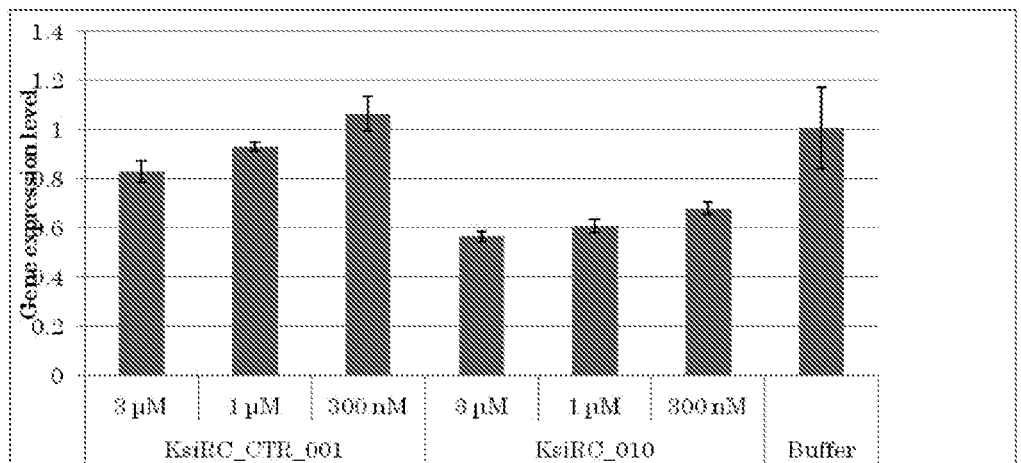
[Figure 5]
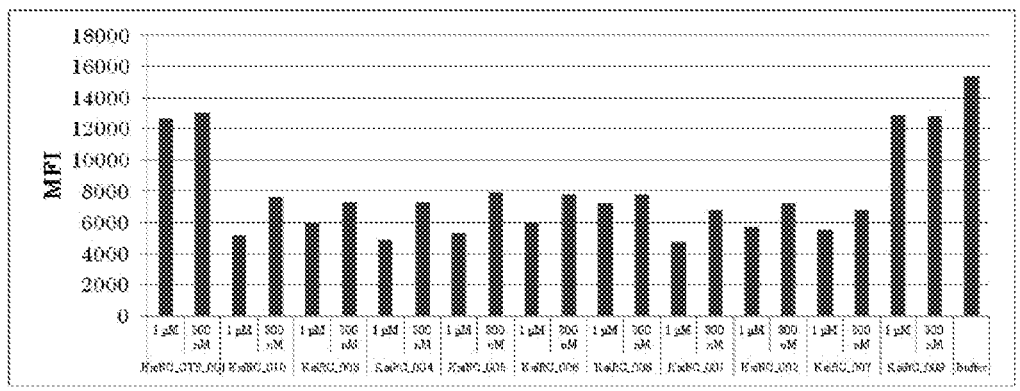
[Figure 6]
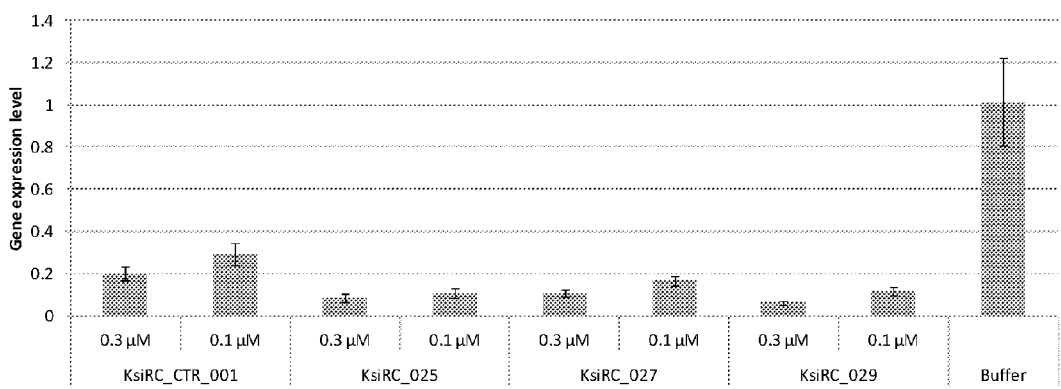

[Figure 7]
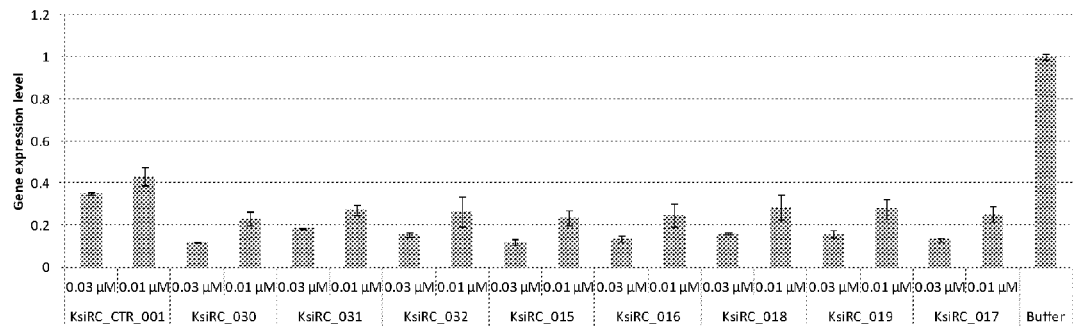
[Figure 8]
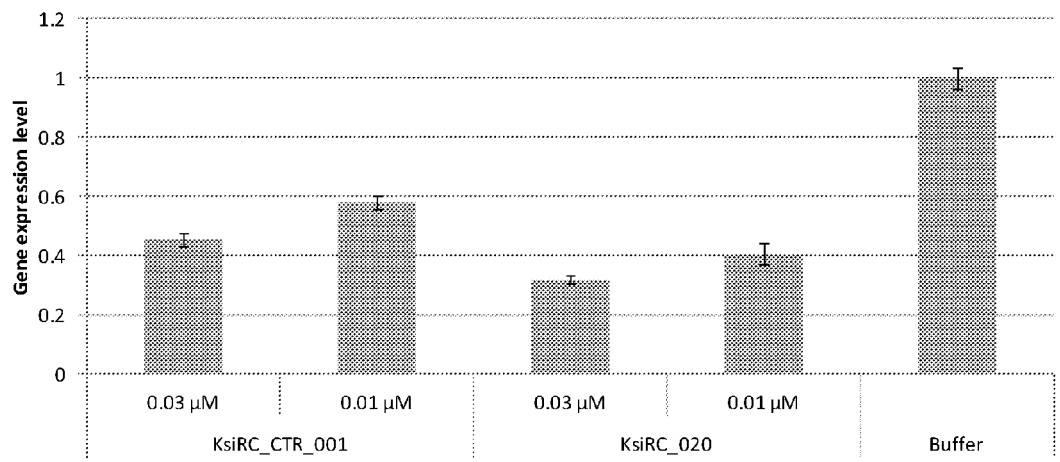
[Figure 9]
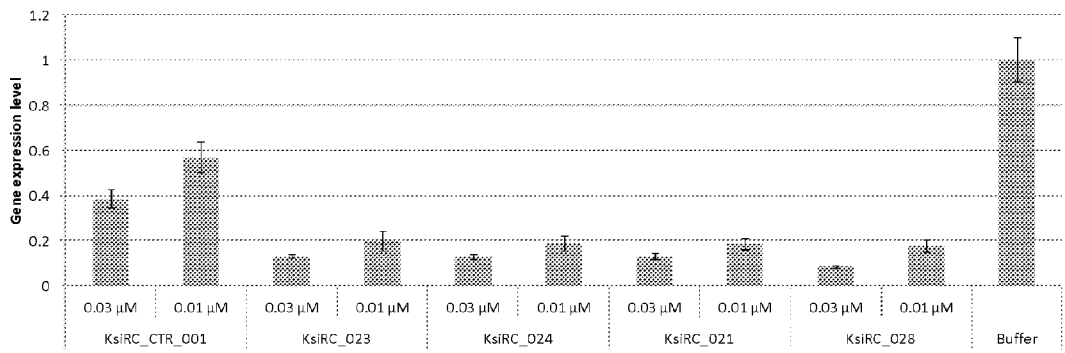

[Figure 10]
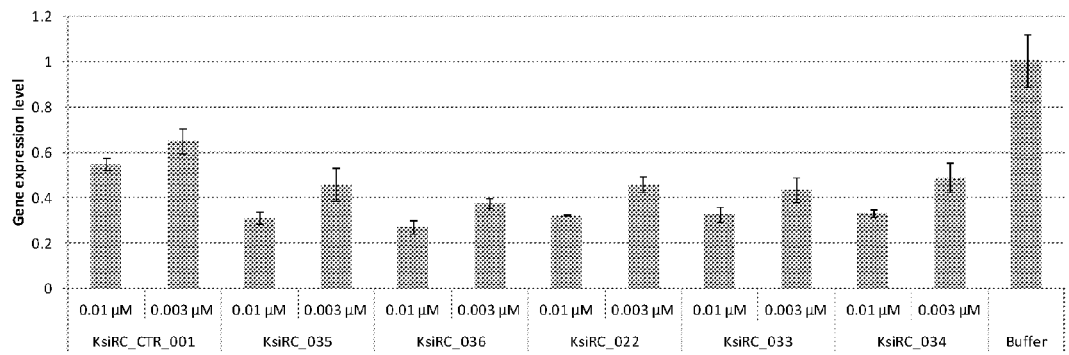
[Figure 11]
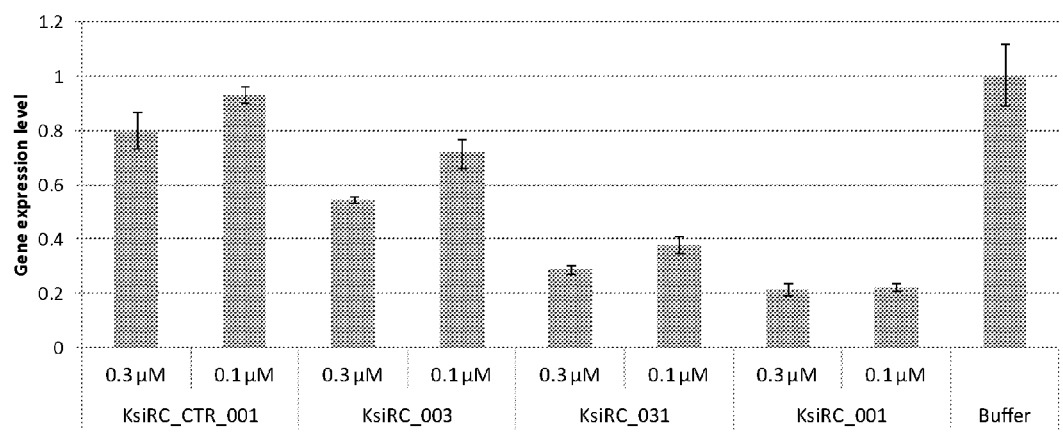
[Figure 12]
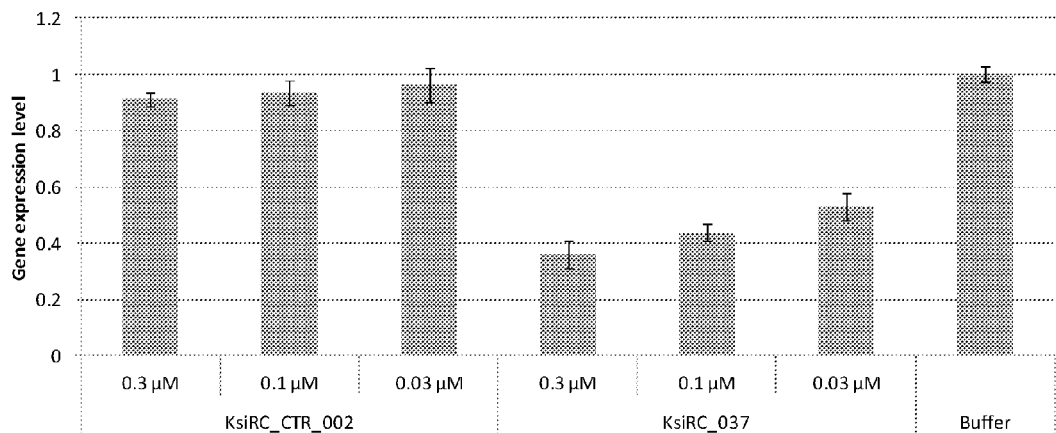

[Figure 13]
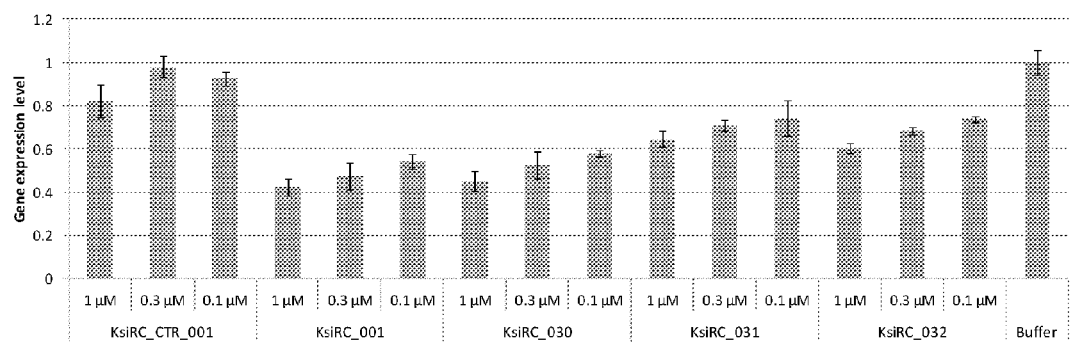

NUCLEIC ACID CONJUGATE

TECHNICAL FIELD

The present invention relates to a nucleic acid conjugate and a pharmaceutical composition comprising the nucleic acid conjugate, etc.

BACKGROUND ART

For example, antisenses, decoy nucleic acids, ribozymes, siRNA, miRNA and anti-miRNA are known as nucleic acid medicines. Such nucleic acid medicines are expected to be clinically applied to various previously difficult-to-treat diseases, because of their high versatility that permits control of every gene in cells.

Also, the nucleic acid medicines are expected as next-generation medicines following antibody or low-molecular medicines, because of their high target selectivity and activity in cells.

However, a problem of the nucleic acid medicines is difficult delivery to a target tissue.

Use of a conjugate of a targeting compound and a nucleic acid (nucleic acid conjugate) has been reported as one of the methods for effectively delivering the nucleic acid medicines in vivo. Examples of the targeting compound include ligands capable of binding to extracellularly expressed receptors. Among others, there are a plurality of reports on a nucleic acid conjugate that utilizes N-acetyl-D-galactosamine (GalNAc) or the like as a ligand capable of binding to an asialoglycoprotein receptor (ASGPR) very highly expressed on liver cells. In recent years, nucleic acid conjugates containing such ligands bound to siRNAs have been reported to be efficiently delivered to liver cells (Non Patent Literature 1).

Patent Literatures 1 and 2 disclose, for example, the following nucleic acid conjugate as a conjugate of a targeting compound and an oligonucleotide:

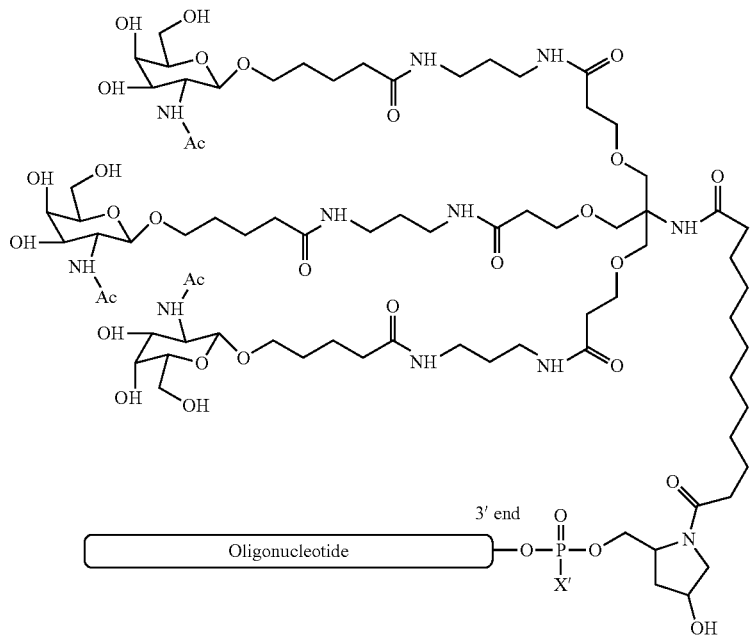

wherein Ac represents an acetyl group; hereinafter, the same holds true for the present specification.

Patent Literature 3 discloses a nucleic acid conjugate having the following structure having a sugar ligand-tether unit similar to that of Patent Literatures 1 and 2:

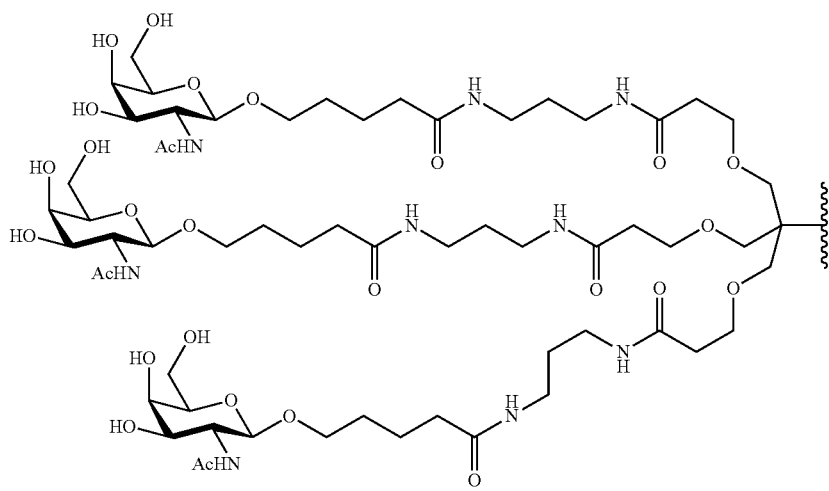

Patent Literature 4 discloses a nucleic acid conjugate having the following structure as a sugar ligand-tether unit:

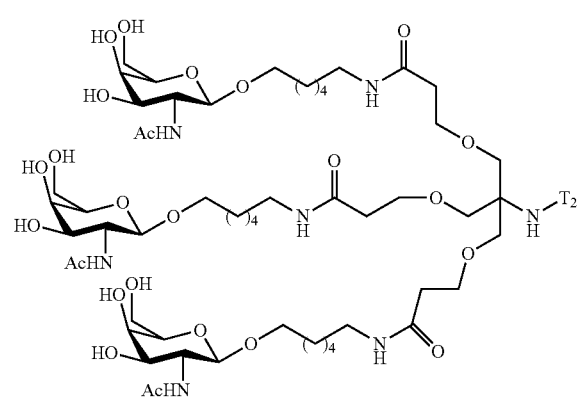

Most of the conventional nucleic acid conjugates as reported in Patent Literatures 1 to 4 target the liver as an organ and are thus limited by their scopes of application. Thus, there is a strong demand for the development of a nucleic acid conjugate effective for cells of a target organ other than the liver.

C-type lectins such as CD209 (also called DC-SIGN: dendritic cell-specific intercellular adhesion molecule-3-grabbing nonintegrin) and CD206 (also called MR1: macrophage mannose receptor 1) are expressed in cells of the immune system such as dendritic cells, macrophages, and neutrophils, and the capture of foreign matter such as viruses or bacteria has been reported as one of their functions. CD206 is expressed on the surface of macrophages or dendritic cells, while CD209 is expressed on the surface of dendritic cells of the skin or mucosal tissues or dendritic cells of lymphoid tissues of the tonsil, lymph nodes, the spleen, and the like. Both of them are known to participate in the capture of viruses such as HIV (Non Patent Literatures 2 and 3).

As a delivery technique using CD206 and CD209, Patent Literature 5 discloses use of a conjugate of a sugar molecule such as mannose or fucose and an antigen in immunity induction.

CITATION LIST

Patent Literature

Patent Literature 1: International Publication No. WO 2009/073809
Patent Literature 2: International Publication No. WO 2013/075035
Patent Literature 3: International Publication No. WO 2015/105083
Patent Literature 4: International Publication No. WO 2014/179620
Patent Literature 5: International Publication No. WO 2006/093524

Non Patent Literature

Non Patent Literature 1: Journal of American Chemical Society, 2014, Vol. 136, p. 16958?16961
Non Patent Literature 2: Nature Reviews Immunology, 2009, Vol. 9, p. 465?479
Non Patent Literature 3: Nature Reviews Immunology, 2003, Vol. 3, p. 697?709

SUMMARY OF INVENTION

Technical Problem

An object of the present invention is to provide a novel nucleic acid conjugate.

Solution to Problem

The present invention relates to the following (1) to (22):
(1)
A nucleic acid conjugate in which a sugar chain ligand is bonded to an oligonucleotide via a linker, the sugar chain ligand having O-bonded mannose at its non-reducing end.
(2)
The nucleic acid conjugate according to (1), wherein the sugar chain ligand has a structure that exhibits binding affinity for CD209 and/or CD206.
(3)
The nucleic acid conjugate according to (1) or (2), wherein the sugar chain ligand is bonded to a cyclohexane skeleton via an ether bond at position 1 of the O-bonded mannose.

(4)
The nucleic acid conjugate according to any of (1) to (3), wherein the sugar chain ligand has the following structure:

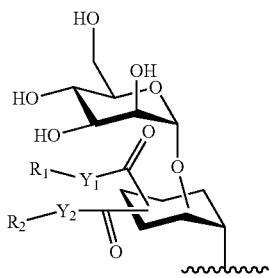

wherein
$R_1$ and $R_2$ are each independently a group selected from the group consisting of a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 3 to 20 carbon atoms, a substituted or unsubstituted aryl group, a substituted or unsubstituted heteroaryl group, a substituted or unsubstituted heteroalicyclic group, and a substituted or unsubstituted aralkyl group,
$Y_2$ and $Y_2$ are each independently a group selected from the group consisting of an oxygen atom, a sulfur atom, and $NR_3$, and
$R_3$ is a hydrogen atom or a substituted or unsubstituted alkyl group having 1 to 20 carbon atoms.

(5)
The nucleic acid conjugate according to any of (1) to (4), wherein the sugar chain ligand is represented by the following structure:

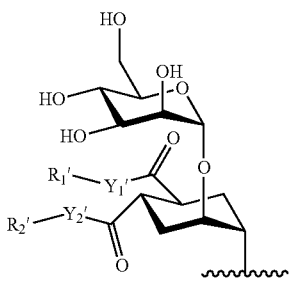

wherein
$R_1'$ and $R_2'$ are each independently a group selected from the group consisting of a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 3 to 20 carbon atoms, a substituted or unsubstituted aryl group, a substituted or unsubstituted heteroaryl group, a substituted or unsubstituted heteroalicyclic group, and a substituted or unsubstituted aralkyl group,
$Y_1'$ and $Y_2'$ are each independently a group selected from the group consisting of an oxygen atom, a sulfur atom, and $NR_3'$, and
$R_3'$ is a hydrogen atom or a substituted or unsubstituted alkyl group having 1 to 20 carbon atoms.

(6)
The nucleic acid conjugate according to (4) or (5), wherein each of $Y_1$, and $Y_2$ or $Y_1'$ and $Y_2'$ is NH.

(7)
The nucleic acid conjugate according to (6), wherein each of $R_1$ and $R_2$, or $R_1'$ and $R_2'$ is a substituted or unsubstituted aralkyl group.

(8)
The nucleic acid conjugate according to any of (1) to (7), wherein the sugar chain ligand is represented by the following structure:

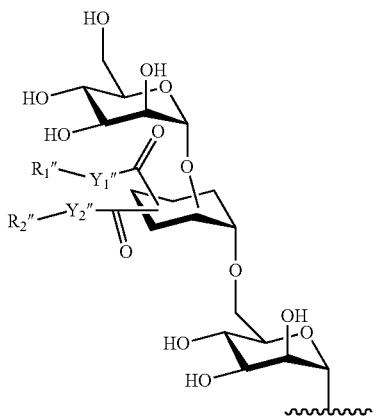

wherein
$R_1''$ and $R_2''$ are each independently a group selected from the group consisting of a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 3 to 20 carbon atoms, a substituted or unsubstituted aryl group, a substituted or unsubstituted heteroaryl group, a substituted or unsubstituted heteroalicyclic group, and a substituted or unsubstituted aralkyl group,
$Y_2''$ and $Y_2''$ are each independently a group selected from the group consisting of an oxygen atom, a sulfur atom, and $NR_3''$, and
$R_3''$ is a hydrogen atom or a substituted or unsubstituted alkyl group having 1 to 20 carbon atoms.

(9)
The nucleic acid conjugate according to (8), wherein the sugar chain ligand is represented by the following structure:

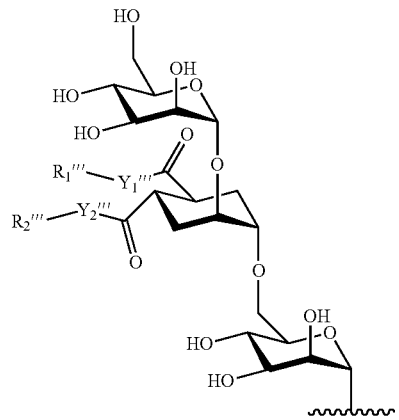

wherein
R$_1$''' and R$_2$''' are each independently a group selected from the group consisting of a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 3 to 20 carbon atoms, a substituted or unsubstituted aryl group, a substituted or unsubstituted heteroaryl group, a substituted or unsubstituted heteroalicyclic group, and a substituted or unsubstituted aralkyl group, Y$_1$''' and Y$_2$''' are each independently a group selected from the group consisting of an oxygen atom, a sulfur atom, and NR$_3$''', and R$_3$''' is a hydrogen atom or a substituted or unsubstituted alkyl group having 1 to 20 carbon atoms.

(10)
The nucleic acid conjugate according to any of (1) to (9), wherein the nucleic acid conjugate has 2 to 8 sugar chain ligands.

(11)
The nucleic acid conjugate according to any of (1) to (10), wherein the linker has any of the following structures:

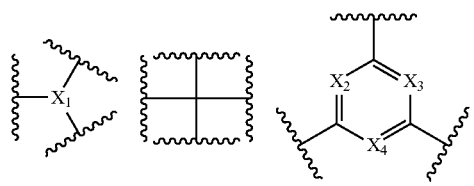

wherein
X$_1$ is CH or a nitrogen atom, and
X$_2$ to X$_4$ are each independently CH or a nitrogen atom.

(12)
The nucleic acid conjugate according to any of (1) to (11), wherein the linker has the following structure:

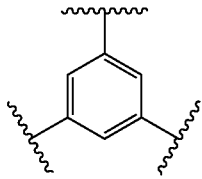 [SMILES: *c1cc(*)cc(*)c1]

(13)
The nucleic acid conjugate according to any of (1) to (12), wherein the linker has any of the following structures:

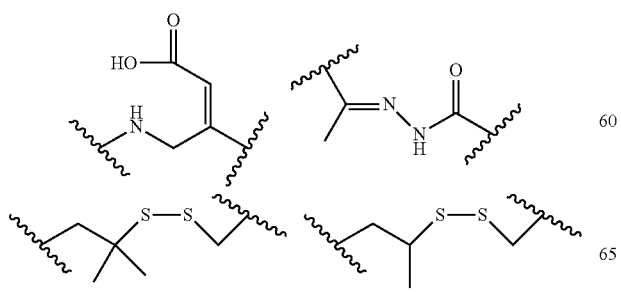

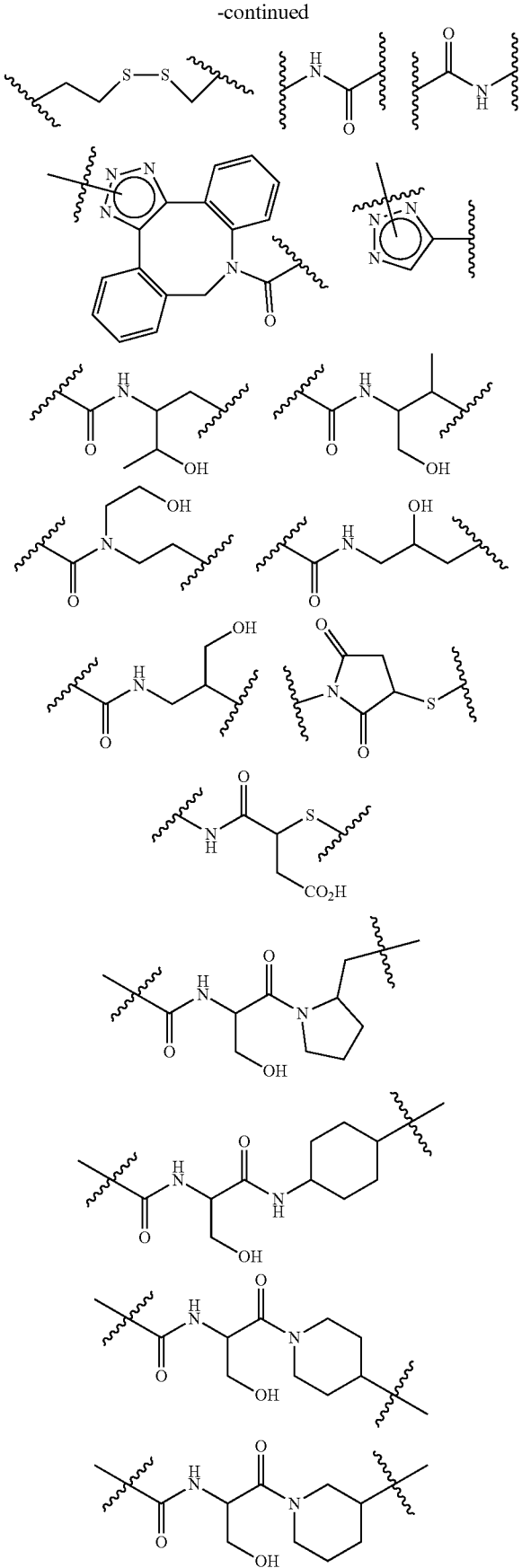

-continued
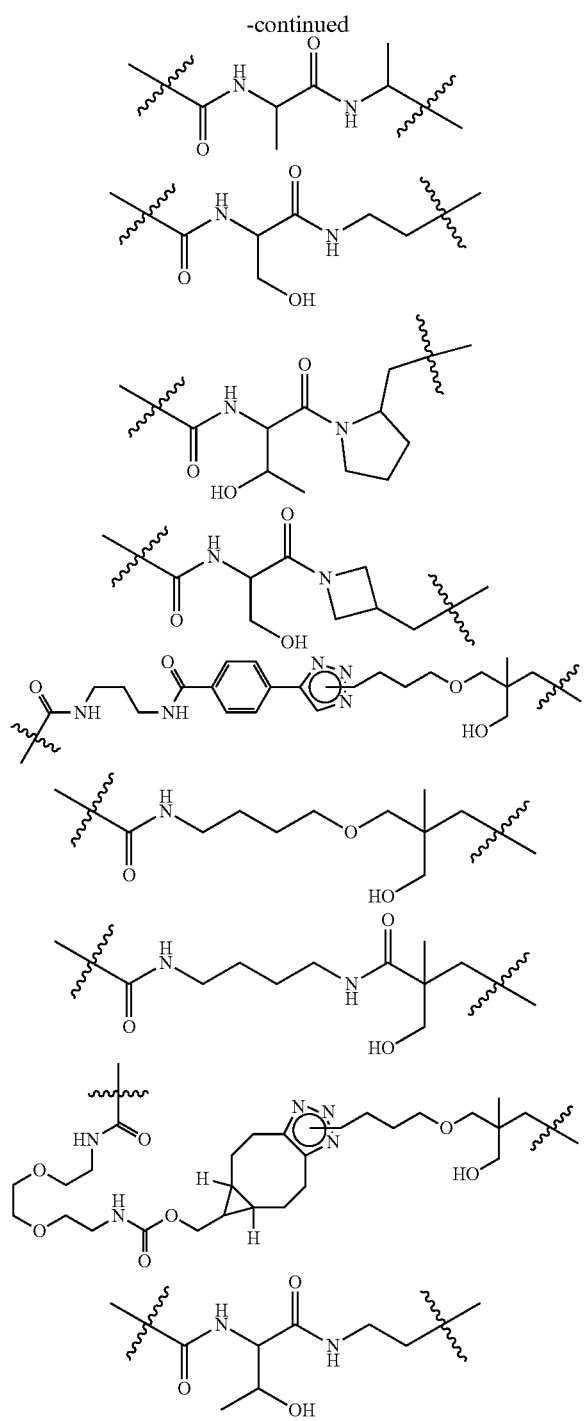
(14) The nucleic acid conjugate according to any of (1) to (13), wherein the linker has the following structure:
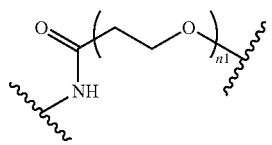
wherein
n1 is an integer of 1 to 100.
(15) The nucleic acid conjugate according to any of (1) to (13), wherein the linker has any of the following structures:
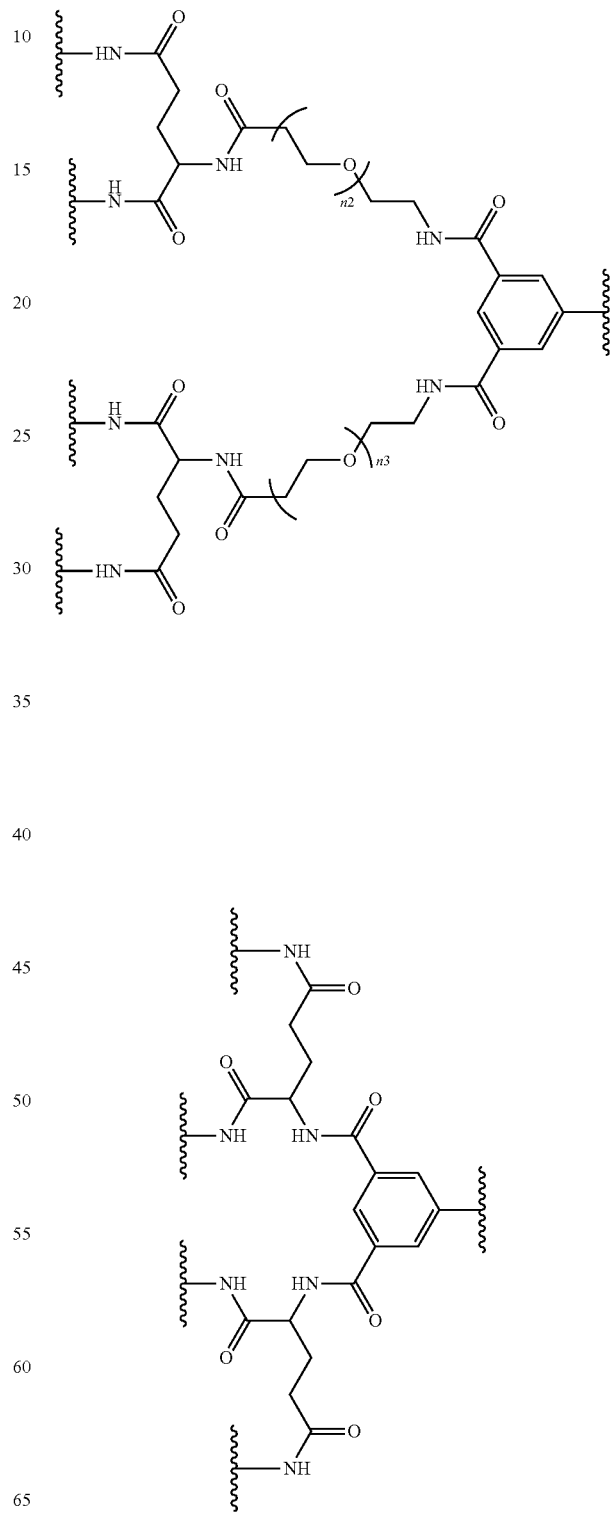

11
-continued
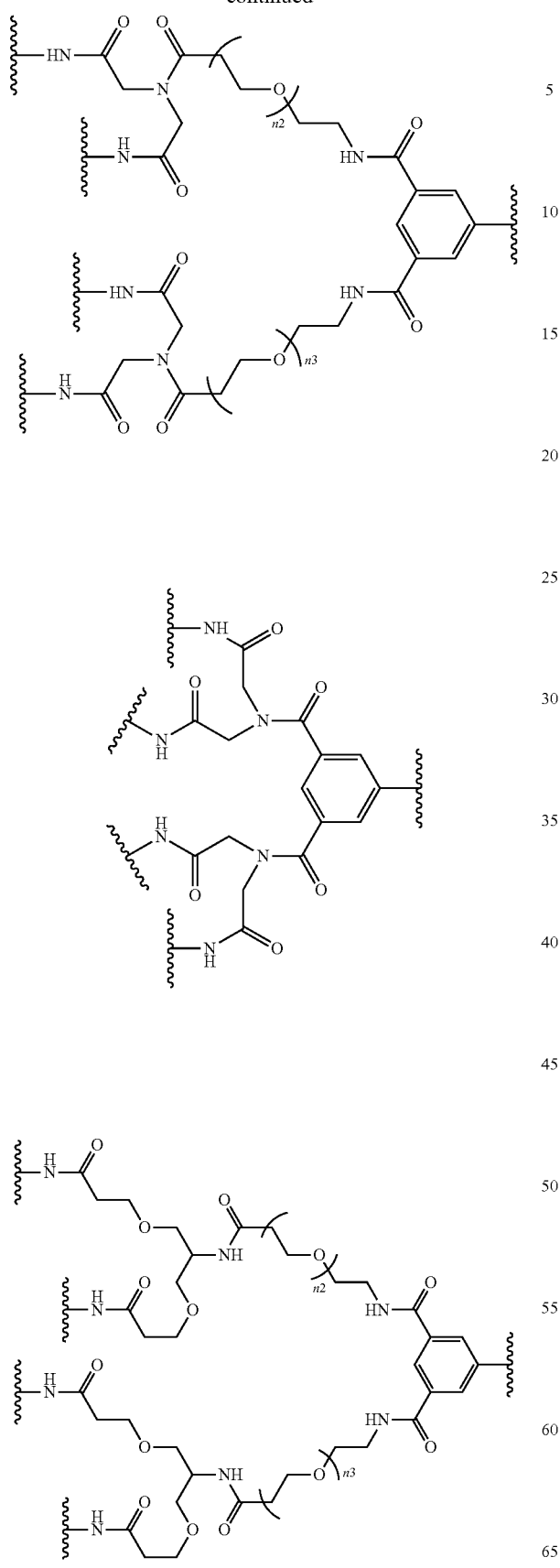
12
-continued
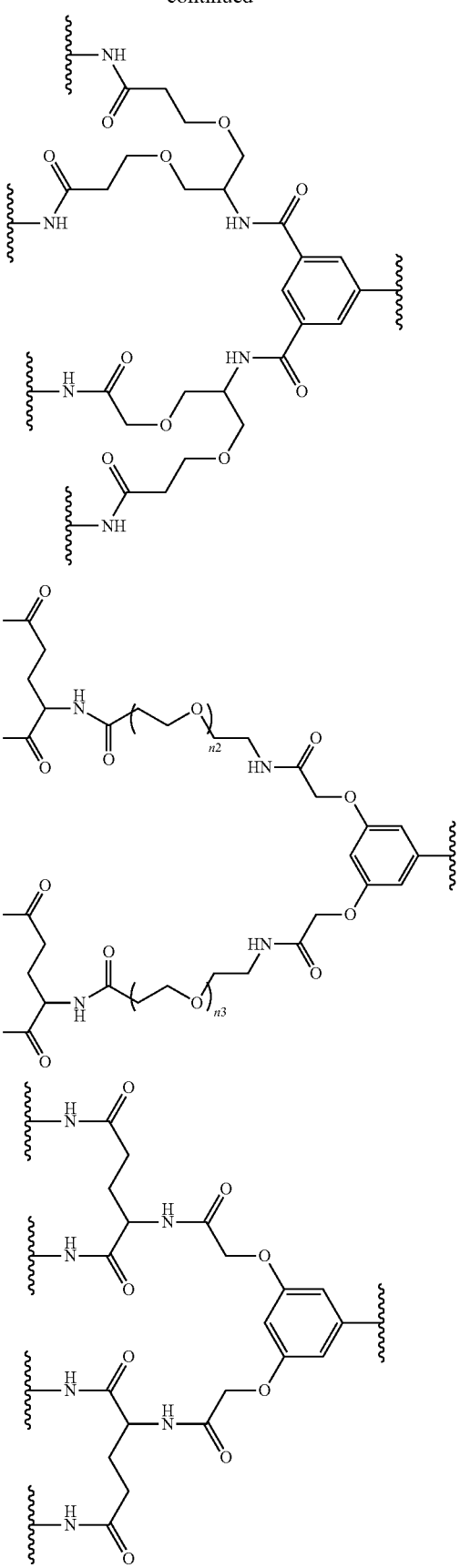

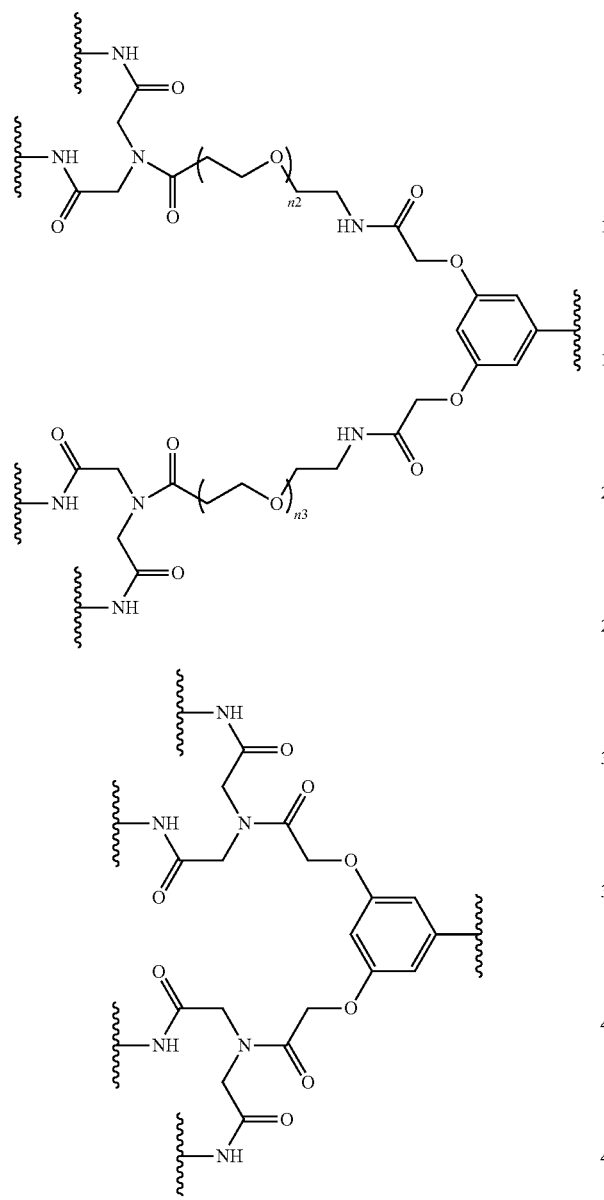

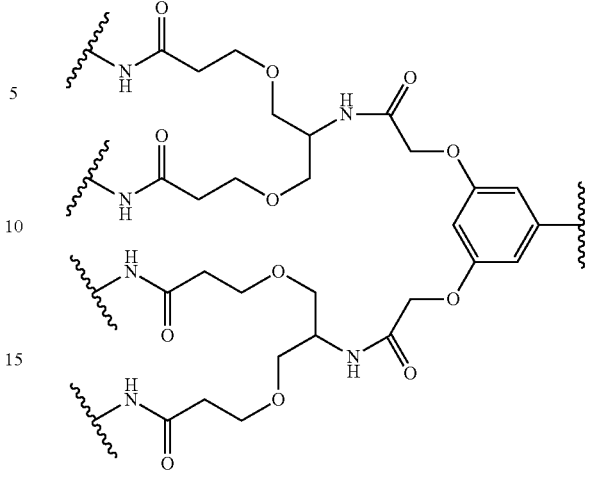

wherein n2 and n3 are each independently an integer of 1 to 100.

(16) The nucleic acid conjugate according to any of (1) to (15), wherein the oligonucleotide comprises a modified nucleotide.

(17) A pharmaceutical composition comprising the nucleic acid conjugate according to any of (1) to (16).

(18) The pharmaceutical composition according to (17), wherein the pharmaceutical composition is for transfer into a cell.

(19) The pharmaceutical composition according to (18), wherein the cell is a dendritic cell or a macrophage.

(20) The pharmaceutical composition according to any of (17) to (19), wherein the pharmaceutical composition is intravenously administered or subcutaneously administered.

(21) A method for treating or preventing a disease, comprising administering the nucleic acid conjugate according to any of (1) to (16) or the pharmaceutical composition according to any of (17) to (20) to a patient in need thereof.

(22) The treatment or prevention method according to (21), wherein the patient is a mammal.

Advantageous Effects of Invention

For example, a pharmaceutical composition comprising the nucleic acid conjugate of the present invention can be administered to mammals to treat various related diseases in vivo.

BRIEF DESCRIPTION OF DRAWINGS

FIG. 1 shows results of a mRNA knockdown test on human monocyte-derived dendritic cells using an antisense oligonucleotide (ASO) against CD45 in Test Example 1.

FIG. 2 shows results of a protein knockdown test on human monocyte-derived dendritic cells using ASO against beta-2 microglobulin (B2M) in Test Example 2.

FIG. 3 shows results of a protein knockdown test on human monocyte-derived dendritic cells using B2M-siRNA in Test Example 3.

FIG. 4 shows results of a mRNA knockdown test on human monocyte-derived dendritic cells using B2M-siRNA in Test Example 4.

FIG. 5 shows results of a protein knockdown test on human monocyte-derived dendritic cells using B2M-siRNA in Test Example 5.

FIG. 6 shows results of a protein knockdown test on human monocyte-derived dendritic cells using B2M-siRNA in Test Example 6.

FIG. 7 shows results of a protein knockdown test on human monocyte-derived dendritic cells using B2M-siRNA in Test Example 7.

FIG. 8 shows results of a protein knockdown test on human monocyte-derived dendritic cells using B2M-siRNA in Test Example 8.

FIG. 9 shows results of a protein knockdown test on human monocyte-derived dendritic cells using B2M-siRNA in Test Example 9.

FIG. 10 shows results of a protein knockdown test on human monocyte-derived dendritic cells using B2M-siRNA in Test Example 10.

FIG. 11 shows results of a protein knockdown test on mature human monocyte-derived dendritic cells using B2M-siRNA in Test Example 11.

FIG. 12 shows results of a protein knockdown test on mature human monocyte-derived dendritic cells using HPRT1-siRNA in Test Example 12.

FIG. 13 shows results of a protein knockdown test on human monocyte-derived macrophage cells using B2M-siRNA in Test Example 13.

DESCRIPTION OF EMBODIMENTS

The nucleic acid conjugate of the present invention is a nucleic acid conjugate in which a sugar chain ligand is bonded to an oligonucleotide via a linker, the sugar chain ligand having O-bonded mannose at its non-reducing end.

The nucleic acid conjugate has a sugar chain ligand, a linker, and an oligonucleotide as its intramolecular components. The sugar chain ligand and the oligonucleotide are linked to each other through a bond via the linker. The bond of the sugar chain ligand or the oligonucleotide to the linker is preferably a covalent bond.

The nucleic acid conjugate of the present invention has a sugar chain ligand-linker-oligonucleotide structure.

In the present invention, structures known in the art can be adopted for the linker and the oligonucleotide as long as the sugar chain ligand has O-bonded mannose at its non-reducing end.

Specifically, conventional nucleic acid conjugates known in the art having the respective structures of a sugar chain ligand, a linker and an oligonucleotide, the sugar chain ligand being the sugar chain ligand having 0-bonded mannose at its non-reducing end according to the present invention are included in the scope of the present invention.

In the present invention, the sugar chain ligand has O-bonded mannose at its non-reducing end.

Examples of the structure of the O-bonded mannose include the following structure:

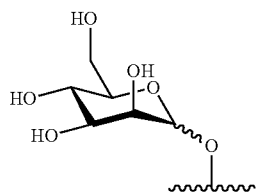

The O-linkage of the mannose may be an α-bond or may be a β-bond. Preferably, the O-linkage of the mannose is an α-bond.

Usually, sugar chains have non-reducing and reducing ends. In the present invention, the O-bonded mannose is located at the non-reducing end.

The phrase "O-bonded mannose is located at the non-reducing end" means that the outermost part of the sugar chain ligand has the O-bonded mannose and does not further have any other structure.

The sugar chain ligand means a group derived from a saccharide (monosaccharide, disaccharide, trisaccharide and polysaccharide, etc.) capable of binding to a receptor expressed on a target cell. Examples thereof include sugar chain ligands having a non-natural structure.

Examples of the monosaccharide serving as a saccharide unit include naturally occurring monosaccharides such as allose, aldose, arabinose, cladinose, erythrose, erythrulose, fructose, fucitol, fucosamine, fucose, fuculose, galactosamine, galactosaminitol, N-acetyl-galactosamine, galactose, glucosamine, N-acetyl-glucosamine, glucosaminitol, glucose, glucose-6-phosphate, gulose, glyceraldehyde, glyceromanno-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose, and xylulose. These monosaccharides are bonded to each other through glycoside bonds and present as naturally occurring saccharides.

In the present invention, the sugar chain ligand preferably has a non-natural structure. This means that a structure other than the monosaccharide described above is contained as the non-natural structure.

Each monosaccharide as the saccharide may be in a D form or an L form and may be a mixture of D and L forms at an arbitrary ratio.

The saccharide may contain deoxysugar (derived by the replacement of an alcoholic hydroxy group with a hydrogen atom), aminosugar (derived by the replacement of an alcoholic hydroxy group with an amino group), thiosugar (derived by the replacement of an alcoholic hydroxy group with thiol, the replacement of C=O with C=S, or the replacement of ring oxygen with sulfur), selenosugar, tellurosugar, azasugar (derived by the replacement of ring carbon with nitrogen), iminosugar (derived by the replacement of ring oxygen with nitrogen), phosphano-sugar (derived by the replacement of ring oxygen with phosphorus), phospha-sugar (derived by the replacement of ring carbon with phosphorus), C-substituted monosaccharide (derived by the replacement of a hydrogen atom on a nonterminal carbon atom with a carbon atom), unsaturated monosaccharide, alditol (derived by the replacement of a carbonyl group with a CHOH group), aldonic acid (derived by the replacement of an aldehyde group with a carboxy group), ketoaldonic acid, uronic acid, aldaric acid, or the like.

Examples of the aminosugar include amino monosaccharides as the saccharide, such as galactosamine, glucosamine, mannosamine, fucosamine, quinovosamine, neuraminic acid, muramic acid, lactosediamine, acosamine, bacillosamine, daunosamine, desosamine, forosamine, gallosamine, kanosamine, kansosamine, mycaminose, mycosamine, perosamine, pneumosamine, purpurosamine, and rhodosamine. The amino group of the aminosugar may be substituted with an acetyl group or the like.

In the present invention, the sugar chain ligand preferably has a structure that exhibits binding affinity for CD209 and/or CD206.

In the present invention, the O-bonded mannose is located at the non-reducing end so that the sugar chain ligand exhibits binding affinity for CD209 and/or CD206.

The sugar chain ligand that exhibits binding affinity for CD209 and/or CD206 allows the nucleic acid conjugate to bind to a receptor expressed on the surface of dendritic cells or macrophage cells so that the oligonucleotide can be delivered as a nucleic acid medicine to the cells.

The sugar chain ligand preferably has a structure bonded to a cyclohexane skeleton via an ether bond at position 1 of the mannose.

The cyclohexane skeleton is present as a non-natural structure in the sugar chain ligand. Examples of the structure bonded to a cyclohexane skeleton via an ether bond at position 1 of the mannose include the following structure:

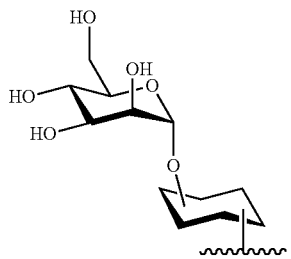

The cyclohexane ring may have a substituent. The glycoside bond of the mannose to the cyclohexane may be an α-bond or may be a β-bond.

The structure bonded to a cyclohexane skeleton via an ether bond at position 1 of the mannose is preferably, for example, the following structure:

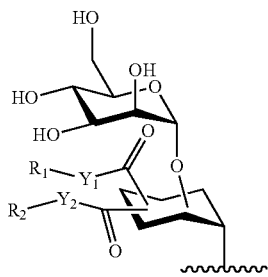

In the formula, $R_1$ and $R_2$ are each independently a group selected from the group consisting of a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 3 to 20 carbon atoms, a substituted or unsubstituted aryl group, a substituted or unsubstituted heteroaryl group, a substituted or unsubstituted heteroalicyclic group, and a substituted or unsubstituted aralkyl group, $Y_1$ and $Y_2$ are each independently a group selected from the group consisting of an oxygen atom, a sulfur atom, and $NR_3$, and $R_3$ is a hydrogen atom or a substituted or unsubstituted alkyl group having 1 to 20 carbon atoms.

In the present specification, the term "each independently" means that each group is a group selected from among choices independently of other groups recited at the same time therewith. These groups may be the same or different.

Examples of the substituted or unsubstituted alkyl group having 1 to 20 carbon atoms include, but are not particularly limited to, methyl, ethyl, propyl, cyclopropyl, isopropyl, butyl, cyclobutyl, isobutyl, pentyl, cyclopentyl, hexyl, cyclohexyl, heptyl, octyl, nonyl, decyl, pentadecyl, and icosyl.

Examples of the substituent for the substituted or unsubstituted alkyl group having 1 to 20 carbon atoms include a substituent selected from the group consisting of hydroxy, halogen, mercapto, nitro, cyano, carboxy, carbamoyl, C1-C3 alkoxy, C1-C3 alkylthio, amino, C1-C3 monoalkylamino, and C1-C3 dialkylamino.

The number of substituents is, for example, 1 to 3. In the case of having a plurality of substituents, the plurality of substituents may be the same or different.

In the present specification, the substituents for the substituted or unsubstituted alkenyl group having 2 to 20 carbon atoms, the substituted or unsubstituted alkynyl group having 3 to 20 carbon atoms, the substituted or unsubstituted aryl group, the substituted or unsubstituted heteroaryl group, and the substituted or unsubstituted aralkyl group are as defined in the substituent for the substituted or unsubstituted alkyl group having 1 to 20 carbon atoms.

The substituted or unsubstituted alkenyl group having 2 to 20 carbon atoms can be a group in which a substituted or unsubstituted alkyl group having 2 to 20 carbon atoms contains one or more double bonds. The substituted or unsubstituted alkynyl group having 3 to 20 carbon atoms can be a group in which a substituted or unsubstituted alkyl group having 3 to 20 carbon atoms contains one or more triple bonds.

Examples of the substituted or unsubstituted aryl group include, but are not particularly limited to, aromatic rings such as a phenyl group, a naphthyl group, and an anthracenyl group.

The substituted or unsubstituted heteroaryl group means a heteroaromatic ring having a nitrogen atom, an oxygen atom or a sulfur atom in the ring. Examples thereof include 5- or 6-membered aromatic rings having 1 to 3 atoms selected from a nitrogen atom, an oxygen atom and a sulfur atom.

The substituted or unsubstituted heteroalicyclic group means a heteroaliphatic ring having a nitrogen atom, an oxygen atom or a sulfur atom in the ring. Examples thereof include 5- or 6-membered aliphatic rings having 1 to 3 atoms selected from a nitrogen atom, an oxygen atom and a sulfur atom.

The substituted or unsubstituted aralkyl group can be a group in which a substituted or unsubstituted alkyl group is substituted with a substituted or unsubstituted aryl group. Examples thereof include groups in which a substituted or unsubstituted alkyl group having 1 to 20 carbon atoms contains one or more aryl groups as substituents and specifically include a substituted or unsubstituted benzyl group and a phenethyl group.

Each of $Y_1$ and $Y_2$ is preferably an oxygen atom, and NH is also preferred.

Preferably, $R_1$ and $R_2$ are each independently a substituted or unsubstituted alkyl group having 1 to 20 carbon atoms. Among others, each of $R_1$ and $R_2$ is preferably a methyl group. Also preferably, $R_1$ and $R_2$ are each independently a substituted or unsubstituted aralkyl group. More preferably, each of $Y_1$ and $Y_2$ is NH, and each of $R_1$ and $R_2$ is a substituted or unsubstituted aralkyl group. Still more preferably, each of $Y_1$ and $Y_2$ is NH, and each of $R_1$ and $R_2$ is a 4-hydroxybenzyl group, a 4-(hydroxymethyl)benzyl group or a 4-(methoxymethyl)benzyl group.

The specific structure bonded to a cyclohexane skeleton via an ether bond at position 1 of the mannose is not particularly limited and has, for example, the following structure:

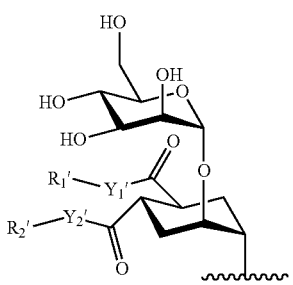

In the formula, $R_1'$, $R_2'$, $Y_1'$, $Y_2'$ and $R_3'$ are as defined in their corresponding $R_1$, $R_2$, $Y_1$, $Y_2$ and $R_3$.

Specific examples of the sugar chain ligand represented by any of the structures mentioned above can include sugar chain ligands having any of the following structures:

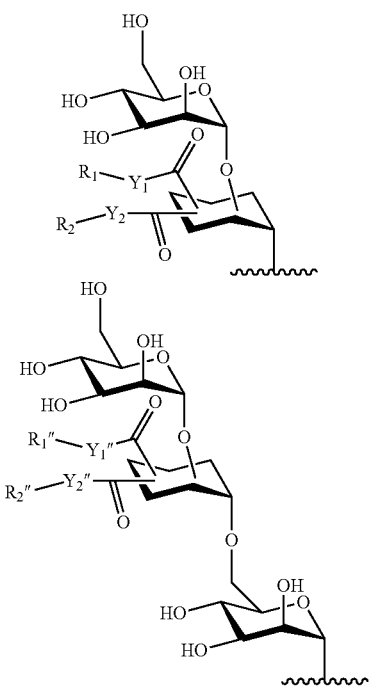

In the formulas, $R_1$, $R_2$, $Y_1$ and $Y_2$ are as defined above, $R_1''$, $R_2''$, $Y_1''$, $Y_2''$ and $R_3''$ are as defined in their corresponding $R_1$, $R_2$, $Y_1$, $Y_2$ and $R_3$, and the preferred combination of substituents is also as defined above.

More specific examples of the sugar chain ligand represented by any of the structures mentioned above can include sugar chain ligands having any of the following structures:

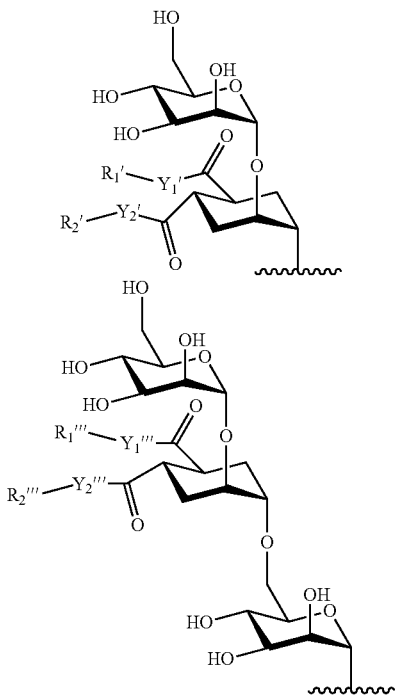

In the formulas, $R_1'$, $R_2'$, $Y_1'$ and $Y_2'$ are as defined above, $R_1'''$, $R_2'''$, $Y_1'''$, $Y_2'''$ and $R_3'''$ are as defined in their corresponding $R_1$, $R_2$, $Y_1$, $Y_2$ and $R_3$, and the preferred combination of substituents is also as defined above.

The sugar chain ligand structure according to the present invention can be produced with reference to International Publication No. WO 2011/000721, Molecular Diversity, 2011, Vol. 15, p. 347-360, Chemistry A European Journal, 2013, Vol. 19, p. 4786-4797 and ACS Chemical Biology, 2010, Vol. 5, p. 301-312.

In the present invention, an oligonucleotide known to be used as a nucleic acid medicine can be used as the "oligonucleotide". In the present invention, the nucleic acid medicine means a nucleotide that is used as an antisense, a decoy nucleic acid, a ribozyme, siRNA, miRNA, anti-miRNA or the like.

In the present invention, the linker and the oligonucleotide are not only bonded to the linker via position 3' or 5' of a sugar moiety constituting a nucleotide but may be bonded to the linker via a base moiety constituting the nucleotide. In the present invention, the oligonucleotide can be understood as a group having a structure that bonds the oligonucleotide to the linker. For example, when the oligonucleotide is bonded to the linker via —O—P(Z) (Z')O— (wherein Z and Z' are each independently an oxygen atom or a sulfur atom), the oligonucleotide represented by X may be understood as —O—P(Z) (Z')O-oligonucleotide.

The oligonucleotide may be a single-stranded or double-stranded oligonucleotide.

The linker and the oligonucleotide in the nucleic acid conjugate can be bonded to each other at a nucleotide of the oligonucleotide or the like and are bonded to each other, for example, at the 3' and/or 5' end of the oligonucleotide. When the oligonucleotide is double-stranded, linker is preferably bonded to the 3' and/or 5' end of a sense strand constituting the double-stranded nucleic acid, though the bond is not limited thereto.

In the present invention, a nucleic acid comprising a nucleotide sequence complementary to target mRNA is also referred to as an antisense nucleotide, and a nucleic acid comprising a nucleotide sequence complementary to the nucleotide sequence of the antisense nucleotide is also referred to as a sense nucleotide.

The oligonucleotide constituting the nucleic acid conjugate used in the present invention can have any shape as long as the oligonucleotide has the ability to control the expression of a target gene when transferred to mammalian cells. A single-stranded oligonucleotide or a double-stranded oligonucleotide is suitably used.

The oligonucleotide can be any molecule which is a polymer of nucleotides or molecules functionally equivalent to nucleotides. Examples thereof include DNA which is a polymer of deoxyribonucleotides, RNA which is a polymer of ribonucleotides, and a chimeric nucleic acid which is a polymer of DNA and RNA. Alternatively, the oligonucleotide may be a nucleotide polymer derived from DNA, RNA or a chimeric nucleic acid by the replacement of at least one nucleotide (deoxyribonucleotide, ribonucleotide, etc.) with a molecule functionally equivalent to the nucleotide. Uracil (U) in RNA and thymine (T) in DNA can be used interchangeably with each other.

Examples of the molecules functionally equivalent to nucleotides include nucleotide derivatives prepared by modifying nucleotides. For example, a modified deoxyribonucleotide or ribonucleotide molecule is suitably used for improving or stabilizing nuclease resistance, for enhancing affinity for a complementary strand nucleic acid, for enhancing cell permeability, or for visualizing the molecule, as compared with DNA or RNA.

Examples of the nucleotide derivatives include nucleotides modified at at least one of a sugar moiety, a phosphodiester bond and a base, such as nucleotides modified at the sugar moiety, nucleotides modified at the phosphodiester bond, and nucleotides modified at the base.

The nucleotide modified at the sugar moiety can be any nucleotide in which a portion or the whole of the chemical structure of its sugar is modified or substituted with an arbitrary substituent or substituted with an arbitrary atom. A 2'-modified nucleotide is preferably used.

Examples of the 2'-modified nucleotide include 2'-modified nucleotides in which the 2'-OH group of ribose is substituted with a substituent selected from the group consisting of OR, R, R'OR, SH, SR, $NH_2$, NHR, $NR_2$, $N_3$, CN, F, Cl, Br and I (R is alkyl or aryl, preferably alkyl having 1 to 6 carbon atoms, and R' is alkylene, preferably alkylene having 1 to 6 carbon atoms). Examples of the 2'-modification preferably include substitution with F, a methoxy group and/or an ethoxy group. Further examples thereof include 2'-modified nucleotides having substitution with a substituent selected from the group consisting of a 2-(methoxy)ethoxy group, a 3-aminopropoxy group, a 2-[(N,N-dimethylamino)oxy]ethoxy group, a 3-(N,N-dimethylamino)propoxy group, a 2-[2-(N,N-dimethylamino)ethoxy]ethoxy group, a 2-(methylamino)-2-oxoethoxy group, a 2-(N-methylcarbamoyl)ethoxy group and a 2-cyanoethoxy group.

Bridged nucleic acid (BNA) having two cyclic structures by the introduction of a bridged structure to the sugar moiety is also suitably used as the nucleotide modified at the sugar moiety. Specific examples thereof include locked nucleic acid (LNA) having the oxygen atom at position 2' and the carbon atom at position 4' bridged via methylene [Tetrahedron Letters, 38, 8735 (1997); and Tetrahedron, 54, 3607 (1998)], ethylene bridged nucleic acid (ENA) [Nucleic Acid Research, 32, e175 (2004)], constrained ethyl (cEt) [The Journal of Organic Chemistry 75, 1569 (2010)], amido-bridged nucleic acid (AmNA) [Chem Bio Chem 13, 2513 (2012)] and 2'-0,4'-C-spirocyclopropylene bridged nucleic acid (scpBNA) [Chem. Commun., 51, 9737 (2015)].

Further examples of the nucleotide modified at the sugar moiety include peptide nucleic acid (PNA) [Acc. Chem. Res., 32, 624 (1999)], oxy-peptide nucleic acid (OPNA) [J. Am. Chem. Soc., 123, 4653 (2001)] and peptide ribonucleic acid (PRNA) [J. Am. Chem. Soc., 122, 6900 (2000)].

The nucleotide modified at the phosphodiester bond can be any nucleotide in which a portion or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, and a nucleotide resulting from the substitution of the phosphodiester bond with a phosphoramidate bond and preferably include a nucleotide resulting from the substitution of the phosphodiester bond with a phosphorothioate bond.

The nucleotide modified at the base can be any nucleotide in which a portion or the whole of the chemical structure of its base is modified or substituted with an arbitrary substituent or substituted with an arbitrary atom. Examples thereof include a nucleotide resulting from the substitution of an oxygen atom in the base with a sulfur atom, a nucleotide resulting from the substitution of a hydrogen atom with an alkyl group having 1 to 6 carbon atoms or a halogen group, a nucleotide resulting from the substitution of a methyl group with a hydrogen atom, a hydroxymethyl group or an alkyl group having 2 to 6 carbon atoms, and a nucleotide resulting from the substitution of an amino group with an alkyl group having 1 to 6 carbon atoms, an alkanoyl group having 1 to 6 carbon atoms, an oxo group, a hydroxy group, or the like. In a preferred aspect of the present invention, 5-methylcytosine (5-mC) is also used instead of cytosine (C) as the nucleotide modified at the base.

Examples of the nucleotide derivatives also include nucleotides or nucleotides modified at at least one of a sugar moiety, a phosphodiester bond and a base which contain an additional chemical substance, such as peptide, protein, sugar, lipid, phospholipid, phenazine, folate, phenanthridine, anthraquinone, acridine, fluorescein, rhodamine, coumarin, or a dye, added thereto directly or via a linker, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, Cy5-added nucleotide derivatives, Cy3-added nucleotide derivatives, 6-FAM-added nucleotide derivatives, and biotin-added nucleotide derivatives.

The nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

The oligonucleotide also encompasses molecules in which a portion or the whole of the atoms is substituted with an atom having an atomic mass number different therefrom (isotope).

In the present specification, the term "complementation" means a relationship capable of forming a base pair between two bases and refers to a relationship taking a double helix structure as the whole duplex region via a mild hydrogen bond, for example, the relationship between adenine and thymine or uracil, and the relationship between guanine and cytosine.

In the present specification, the term "complementary" not only means the case where two nucleotide sequences are completely complementary to each other, but means that 0 to 30%, 0 to 20% or 0 to 10% of a mismatch base can be present between the nucleotide sequences, and, for example, an antisense oligonucleotide complementary to target mRNA may contain the substitution of one or more bases in its nucleotide sequence completely complementary to a partial nucleotide sequence of the target mRNA. Specifically, the antisense oligonucleotide may have 1 to 8, preferably 1 to 6, 1 to 4 or 1 to 3, particularly, 2 or 1 mismatch bases for a target sequence of a target gene.

Also, the term "complementary" encompasses the case where two nucleotide sequences, one of which is completely complementary to the other nucleotide sequence, have the addition and/or deletion of one or more bases. For example, target mRNA and the antisense oligonucleotide may have 1 or 2 bulge bases in the antisense strand and/or target mRNA region by the addition and/or deletion of base(s) in the antisense oligonucleotide.

Hereinafter, the term "complementary" is described to also encompass "complementation".

The antisense oligonucleotide used in the present invention is an oligonucleotide complementary to DNA encoding the target gene or a mRNA precursor, mRNA, a microRNA precursor or microRNA transcribed from the DNA encoding the target gene, and inhibits the function of the DNA, the mRNA precursor, the mRNA, the microRNA precursor or the microRNA by forming a duplex with the DNA, the mRNA precursor or the mRNA targeted by the antisense oligonucleotide.

The antisense oligonucleotide includes not only an oligonucleotide completely complementary to its target DNA, mRNA precursor, mRNA, microRNA precursor or microRNA, but an oligonucleotide having one or several mismatches as long as the oligonucleotide can hybridize under stringent conditions to the DNA, the mRNA precursor, the mRNA, the microRNA precursor or the microRNA.

The antisense oligonucleotide may be introduced into the form of a hairpin oligomer or a cyclic oligomer and may contain a structural factor such as an internal or terminal bulge or loop as long as the nucleic acid hybridizes to the target gene.

The length of the antisense oligonucleotide is 8 to 80 bases, preferably 8 to 30 bases. The length can be, for example, 8 to 20 bases, 10 to 20 bases, 13 to 20 bases, 13 to 16 bases, 13 bases, 14 bases, 15 bases, 16 bases, 17 bases, 18 bases, 19 bases, or 20 bases.

The antisense oligonucleotide, when transferred into cells, can bind to its complementary mRNA precursor or mRNA and sterically inhibit the translation thereof into a protein, inhibiting the expression of the target gene.

The antisense oligonucleotide can also bind to its complementary microRNA precursor or microRNA in cells and sterically inhibit the function of the microRNA.

The antisense oligonucleotide may bind to its complementary mRNA or mRNA precursor in cells and cleave the mRNA or the mRNA precursor. Action mediated by RNase H which is an endonuclease that cleaves the RNA strand of a duplex of RNA and DNA is known as such an example. When the antisense oligonucleotide of the present invention in cells forms a duplex with the mRNA or the mRNA precursor, the duplex can be recognized by RNase H, which then enzymatically can degrade the complementary mRNA strand.

An antisense oligonucleotide having 4 to 80 consecutive DNA regions is preferred for inducing the cleavage of the mRNA or the mRNA precursor by RNase H. In this case, the antisense oligonucleotide preferably has 0 to 80%, more preferably 10 to 60%, further preferably 20 to 50%, of a nucleotide modified at the sugar moiety. When the antisense oligonucleotide has a nucleotide modified at the sugar moiety, the number of the consecutive DNA regions is more preferably 4 to 20, further preferably 4 to 15, most preferably 5 to 10. The position of the nucleotide modified at the sugar moiety in the antisense oligonucleotide is preferably near the 5' end and/or near the 3' end and is more preferably a position within 25% of the whole length from the 5' end and/or a position within 25% of the whole length from the 3' end.

The antisense oligonucleotide can also induce the inhibition of the expression of a target gene by forming a duplex with its complementary oligonucleic acid and transferring the double-stranded nucleic acid into cells (see International Publication No. WO 2005/113571). In this case, the position of modification of the double-stranded nucleic acid with a ligand is preferably the 5' or 3' end of the complementary oligonucleic acid.

The antisense oligonucleotide used in the present invention can also increase the expression of a target gene by using a nucleotide sequence complementary to a promoter sequence or the like of the target gene (see International Publication Nos. WO 2013/173601 and WO 2013/173637).

Examples of a method for producing the antisense oligonucleotide include, but are not particularly limited to, methods using chemical synthesis known in the art, and enzymatic transcription methods. Examples of the methods using chemical synthesis known in the art can include a phosphoramidite method, a phosphorothioate method, a phosphotriester method, and a CEM method [Nucleic Acid Research, 35, 3287 (2007)]. The antisense oligonucleotide can be synthesized using, for example, ABI3900 high-throughput nucleic acid synthesizer (manufactured by Applied Biosystems, Inc.). After the completion of synthesis, dissociation from a solid phase, deprotection of a protective group and purification of the compound of interest, etc. are performed. Desirably, an antisense oligonucleotide having a purity of 90% or higher, preferably 95% or higher is obtained by the purification. Examples of the enzymatic transcription methods for producing the antisense oligonucleotide of the present invention include methods based on transcription using a plasmid or DNA having the nucleotide sequence of interest as a template and phage RNA polymerase, for example, T7, T3, or SP6 RNA polymerase.

The double-stranded oligonucleotide used in the present invention may be constituted by any oligonucleotide or derivative thereof as long as the oligonucleotide or the derivative is a nucleic acid comprising a nucleotide sequence complementary to a partial nucleotide sequence of target mRNA and/or a nucleic acid comprising a nucleotide sequence complementary to the nucleotide sequence of the nucleic acid.

The double-stranded oligonucleotide used in the present invention can have any length as long as the nucleic acid comprising a nucleotide sequence complementary to the target mRNA sequence and the nucleic acid comprising a nucleotide sequence complementary to the nucleotide sequence of the nucleic acid can form a duplex. The sequence length that allows formation of the duplex is usually 11 to 35 bases, preferably 15 to 30 bases, more preferably 17 to 25 bases, further preferably 17 to 23 bases, particularly preferably 19 to 23 bases.

In the present invention, a single-stranded nucleic acid that consists of a nucleic acid comprising a nucleotide sequence complementary to the target mRNA sequence and inhibits the expression of the target protein, or a double-stranded nucleic acid that consists of a nucleic acid comprising a nucleotide sequence complementary to the target mRNA sequence and a nucleic acid comprising a nucleotide sequence complementary to the nucleotide sequence of the nucleic acid and inhibits the expression of the target protein is suitably used as the double-stranded oligonucleotide inhibiting the expression of the target protein.

The double-stranded oligonucleotide can also increase the expression of a target gene by using a molecule consisting of a nucleic acid comprising a nucleotide sequence complementary to a promoter sequence or the like of the target gene and a nucleic acid comprising a nucleotide sequence complementary to the nucleotide sequence of the nucleic acid [Nucleic Acid Research, 41, 10086 (2013); and Hepatology, 59, 216 (2014)].

The double-stranded oligonucleotide refers to nucleotides having a duplex region formed by the pairing of two oligonucleotides. The duplex region refers to a moiety in which nucleotides or derivatives thereof, constituting the two strands have formed a duplex by constituting base pairs. The duplex region is usually 11 to 27 base pairs, preferably 15 to 25 base pairs, more preferably 15 to 23 base pairs, further preferably 17 to 21 base pairs.

Each single-stranded oligonucleotide constituting the double-stranded oligonucleotide usually consists of 11 to 30 bases, preferably 15 to 29 bases, more preferably 15 to 27 bases, further preferably 15 to 25 bases, particularly preferably 17 to 23 bases.

The double-stranded oligonucleotide may have a non-duplex-forming additional nucleotide or nucleotide derivative on the 3' or 5' side subsequent to the duplex region. This non-duplex-forming moiety is referred to as an overhang. When the double-stranded oligonucleotide has an overhang, the nucleotide constituting the overhang may be a ribonucleotide, a deoxyribonucleotide or a derivative thereof.

A double-stranded oligonucleotide having an overhang consisting of 1 to 6 bases, usually 1 to 3 bases, at the 3' or 5' end of at least one of the strands is used as the double-stranded oligonucleotide having the overhang. A double-stranded oligonucleotide having an overhang consisting of 2 bases is preferably used. Examples thereof include double-stranded oligonucleotides having an overhang consisting of dTdT or UU. The overhang can be present in only the antisense oligonucleotide, only the sense oligonucleotide, and both the antisense oligonucleotide and the sense oligonucleotide. A double-stranded oligonucleotide having an overhang in the antisense oligonucleotide is preferably used. The antisense oligonucleotide comprises the duplex region and the overhang subsequent thereto.

A nucleic acid consisting of a sequence identical to the nucleotide sequence of a target gene or the nucleotide sequence of its complementary strand may be used in the double-stranded oligonucleotide. A double-stranded nucleic acid consisting of a nucleic acid derived from the nucleic acid by the truncation of 1 to 4 bases from the 5' or 3' end of at least one strand, and a nucleic acid comprising a nucleotide sequence complementary to the nucleotide sequence of the nucleic acid may be used.

The double-stranded oligonucleotide may be double-stranded RNA (dsRNA) comprising a RNA duplex, double-stranded DNA (dsDNA) comprising a DNA duplex, or a hybrid nucleic acid comprising a RNA-DNA duplex. Alternatively, the double-stranded oligonucleotide may be a chimeric nucleic acid having two strands, one or both of which consists of DNA and RNA. Double-stranded RNA (dsRNA) is preferred.

Preferably, the 2nd nucleotide counted from the 5' end of the antisense oligonucleotide is complementary to the 2nd deoxyribonucleotide counted from the 3' end of the target mRNA sequence. More preferably, the 2nd to 7th nucleotides counted from the 5' end of the antisense oligonucleotide are completely complementary to the 2nd to 7th deoxyribonucleotides counted from the 3' end of the target mRNA sequence. Further preferably, the 2nd to 11th nucleotides counted from the 5' end of the antisense oligonucleotide are completely complementary to the 2nd to 11th deoxyribonucleotides counted from the 3' end of the target mRNA sequence. Also preferably, the 11th nucleotide counted from the 5' end of the antisense oligonucleotide is complementary to the 11th deoxyribonucleotide counted from the 3' end of the target mRNA sequence. More preferably, the 9th to 13th nucleotides counted from the 5' end of the antisense oligonucleotide are completely complementary to the 9th to 13th deoxyribonucleotides counted from the 3' end of the target mRNA sequence. Further preferably, the 7th to 15th nucleotides counted from the 5' end of the antisense oligonucleotide are completely complementary to the 7th to 15th deoxyribonucleotides counted from the 3' end of the target mRNA sequence.

The double-stranded oligonucleotide preferably contains 50 to 100%, more preferably 70 to 100%, further preferably 90 to 100%, of a modified nucleotide with respect to the nucleotides within the double-stranded nucleic acid region.

The double-stranded oligonucleotide can be chemically synthesized and can generally be synthesized by use of a solid-phase oligonucleotide synthesis method (see, for example, Usman et al., U.S. Pat. Nos. 5,804,683; 5,831,071; 5,998,203; 6,117,657; 6,353,098; 6,362,323; 6,437,117; and 6,469,158; Scaringe et al., U.S. Pat. Nos. 6,111,086; 6,008, 400; and 6,111,086).

RNA may be produced enzymatically or by partial or total organic synthesis. A modified ribonucleotide can be introduced enzymatically or by organic synthesis in vitro. In one aspect, each strand is chemically prepared. A method for chemically synthesizing a RNA molecule is known in the art [see Nucleic Acids Research, 32, 936 (1998)].

Examples of the RNA used in the present invention include RNA comprising a sequence of 15 to 30 consecutive bases, preferably 17 to 25 consecutive bases, more preferably 19 to 23 consecutive bases (hereinafter, referred to as sequence X) of mRNA of a target gene, and a sequence of bases complementary (hereinafter referred to as complementary sequence X') to the sequence X, for example, double-stranded RNA consisting of a sense oligonucleotide comprising sequence X and an antisense oligonucleotide comprising complementary sequence X', and RNA having a hairpin structure of the sense oligonucleotide and the antisense oligonucleotide connected via a spacer oligonucleotide.

Examples of the sense oligonucleotide comprising sequence X include RNA comprising only the sequence X as bases (hereinafter, referred to as a sequence X strand), and RNA having 1 to 6, preferably 2 to 4 same or different nucleotides added to the 3' or 5' end, or both, of the sequence X strand.

Examples of the antisense oligonucleotide comprising complementary sequence X' include RNA comprising only the complementary sequence X' as bases (hereinafter, referred to as a complementary sequence X' strand), and double-stranded RNA having 1 to 6, preferably 2 to 4 same or different nucleotides added to the 3' or 5' end, or both, of the complementary sequence X' strand.

The spacer oligonucleotide in the RNA having a hairpin structure of the sense oligonucleotide comprising sequence X and the antisense oligonucleotide comprising complementary sequence X', connected via the spacer oligonucleotide is preferably nucleotides of 6 to 12 bases, and the 5' terminal sequence thereof is preferably UU. Examples of the spacer oligonucleotide include an oligonucleotide consisting of a nucleotide sequence UUCAAGAGA. As for the order of the two RNA strands connected via the spacer oligonucleotide, either of them may be located on the 5' side, and the sense strand comprising sequence X is preferably located on the 5' side.

The nucleotides to be added to the sequence X strand and the complementary sequence X' strand, and the bases of the spacer oligonucleotide may be any one type or plural types selected from guanine, adenine, cytosine, thymine and uracil. A sugar bonded to each base may be ribose, deoxyribose or ribose substituted at the 2'-hydroxy group with a modifying group. The nucleotides to be added are more preferably any one type or two types selected from uridylic acid (U) and deoxythymidylic acid (dT). The sequence of the bases of the nucleotides to be added to the 3' end of the sequence X strand may be the same as the sequence of bases of nucleotides adjacent to sequence X within the mRNA of the target gene. The sequence of the bases of the nucleotides to be added to the 3' end of the complementary sequence X' strand may be complementary to the sequence of bases of nucleotides adjacent to sequence X within the mRNA of the target gene.

More preferred examples of the RNA used in the present invention include (a) double-stranded RNA consisting of a sense oligonucleotide comprising sequence X and an antisense oligonucleotide comprising complementary sequence X', wherein: the sequence X is a sequence of 19 to 21 consecutive bases of the mRNA of the target gene; the sense oligonucleotide consists of a sequence X strand and 2 to 4 same or different nucleotides added to the 3' end of the sequence X strand; and the antisense oligonucleotide consists of a complementary sequence X' strand and 2 to 4 same or different nucleotides added to the 3' end of the complementary sequence X' strand, (b) double-stranded RNA consisting of a sense oligonucleotide comprising sequence X and an antisense oligonucleotide comprising complementary sequence X', wherein: the sequence X is a sequence of 23 to 25 consecutive bases of the mRNA of the target gene; the sense oligonucleotide is a sequence X strand; and the antisense oligonucleotide is a complementary sequence X' strand, and (c) double-stranded RNA consisting of a sense oligonucleotide comprising sequence X and an antisense oligonucleotide comprising complementary sequence X', wherein: the sequence X is a sequence of 23 to 27 consecutive bases of the mRNA of the target gene; the sense oligonucleotide consists of a sequence X strand and 2 to 4 same or different nucleotides added to the 3' end of the sequence X strand; the antisense oligonucleotide consists of a complementary sequence X' strand and 2 to 4 same or different nucleotides added to the 3' end of the complementary sequence X' strand; and the sequence of the bases of the nucleotides to be added to the 3' end of the complementary sequence X' strand is complementary the sequence of the bases of nucleotides adjacent to sequence X within the mRNA of the target gene.

Further examples of the RNA used in the present invention preferably include RNA having an inhibitory effect on the expression of the target gene through the use of RNA interference (RNAi).

The single-stranded oligonucleotide is synthesized by use of a solid-phase phosphoramidite method [see Nucleic Acids Research, 30, 2435 (1993)], deprotected, and desalted on NAP-5 column (Amersham Pharmacia Biotech Ltd., Piscataway, NJ). The oligomer is purified by ion-exchange high-performance liquid chromatography (IE-HPLC) on Amersham Source 15Q column (1.0 cm, height: 25 cm; Amersham Pharmacia Biotech Ltd., Piscataway, NJ) using a linear gradient in a 15-minute step. The gradient shifts from buffer solution A:B of 90:10 to buffer solution A:B of 52:48. The buffer solution A is 100 mmol/L Tris, pH 8.5, and the buffer solution B is 100 mmol/L Tris, pH 8.5 (1 mol/L NaCl). A sample is monitored at 260 nm, and a peak corresponding to full-length oligonucleotide species is collected, pooled, desalted on NAP-5 column, and freeze-dried.

The purity of each single-stranded oligonucleotide is determined by capillary electrophoresis (CE) using Beckman PACE 5000 (Beckman Coulter, Inc., Fullerton, Calif.). The CE capillary has an inside diameter of 100 and contains ssDNA 100R Gel (Beckman-Coulter, Inc.). Typically, approximately 0.6 nmole of the oligonucleotide is injected to the capillary, and CE is carried out in an electric field of 444 V/cm, followed by the detection of UV absorbance at 260 nm. An electrophoresis buffer solution containing modified Tris-borate and 7 mol/L urea is purchased from Beckman Coulter, Inc. A single-stranded oligonucleotide having at least 90% purity evaluated by CE is obtained for use in an experiment mentioned below. Compound identity is verified by matrix-assisted laser desorption/ionization time of flight (MALDI-TOF) mass spectrometry using Voyager DE™ Biospectometry workstation (Applied Biosystems, Inc., Foster City, Calif.) according to manufacturer's recommended protocol. The relative molecular mass of the single-stranded oligonucleotide can be obtained within 0.2% of a predicted molecular mass.

The single-stranded oligonucleotide is resuspended at a concentration of 100 μmol/L in a buffer solution consisting of 100 mmol/L potassium acetate and 30 mmol/L HEPES, pH 7.5. The complementary sense strand and the antisense strand are mixed in equimolar amounts to obtain a final solution of 50 μmol/L double-stranded oligonucleotide. The sample is heated to 95° C. for 5 minutes and cooled to room temperature before use. The double-stranded nucleic acid is preserved at −20° C. The single-stranded oligonucleotide is freeze-dried or stored at −80° C. in nuclease-free water.

In the present invention, an arbitrary linker known to be used as a nucleic acid conjugate can be used as the "linker".

Examples of the linker structure that can be adopted include structures disclosed in International Publication Nos. WO 2009/073809, WO 2013/075035, WO 2015/105083, WO 2014/179620, WO 2015/006740, and WO 2017/010575.

The linker may have a linear structure and preferably has any of structures serving as branched structures given below.

For example, the linker having the branch as described below allows the nucleic acid conjugate to have a plurality of sugar chain ligands in the molecule. Such a nucleic acid conjugate preferably has 2 to 8 sugar chain ligands.

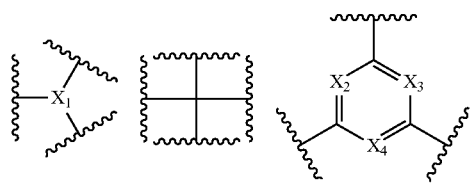
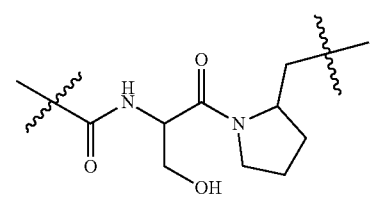
In the formulas,
X₁ is CH or a nitrogen atom, and
X₂ to X₄ are each independently CH or a nitrogen atom.
Preferably, the linker further has any of the following structures:
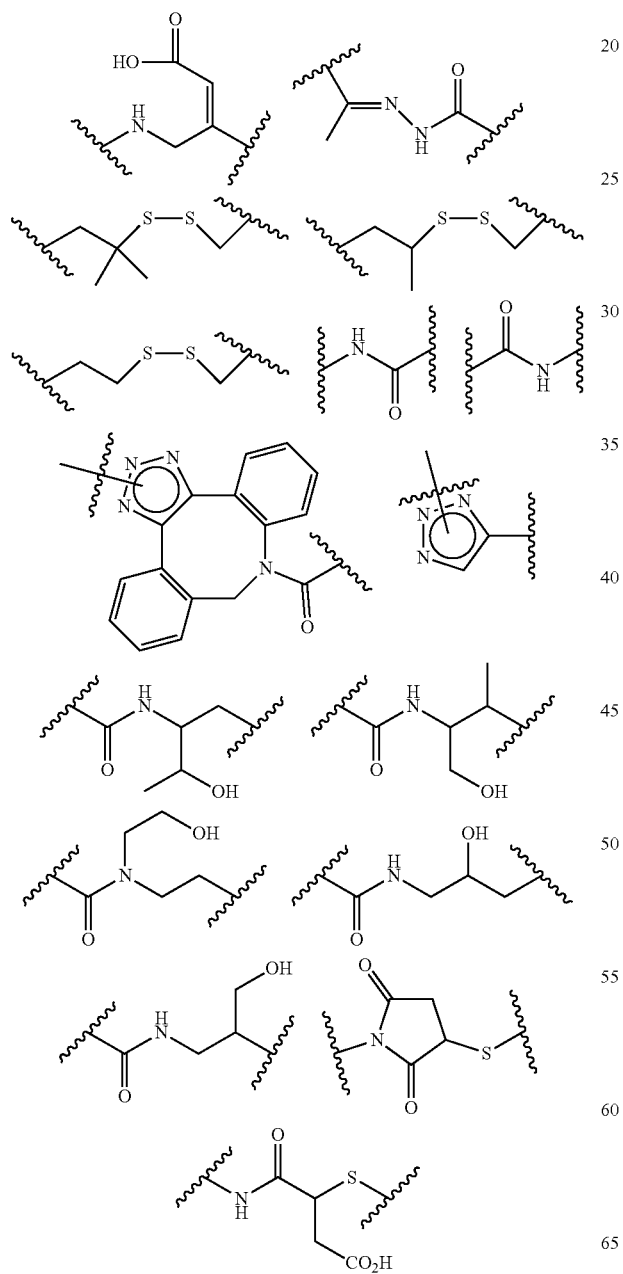
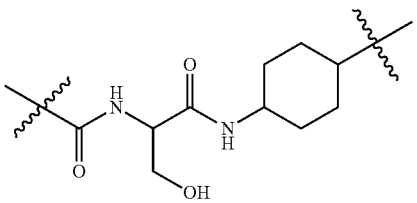
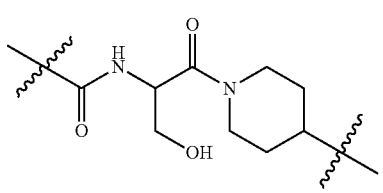
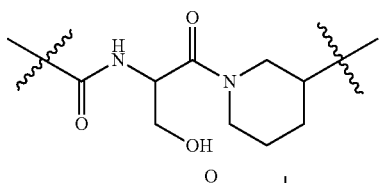
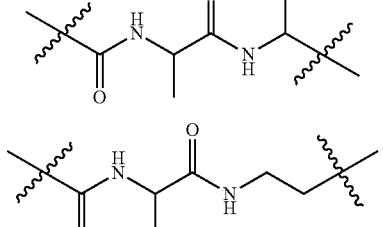
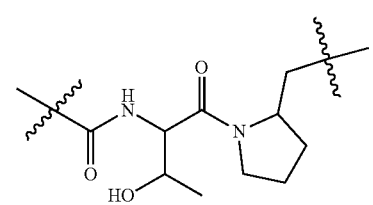
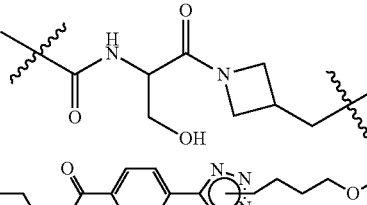
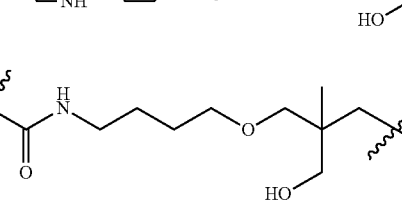

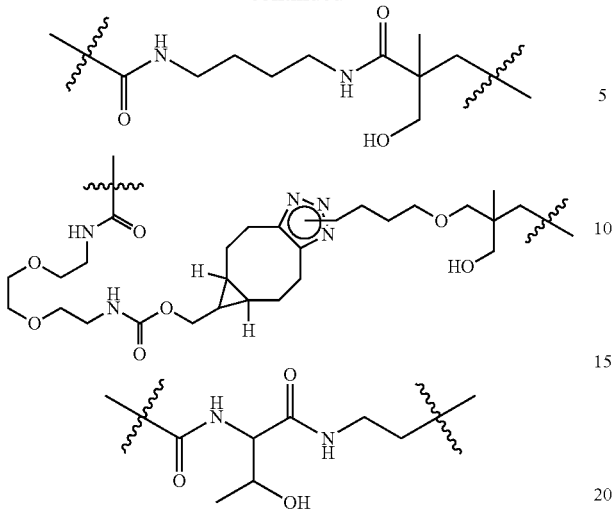

In the present invention, the linker having any of the following structures can be produced with reference to, for example, International Publication Nos. WO 2009/073809, WO 2013/075035, WO 2015/105083, WO 2014/179620, WO 2015/006740, and WO 2017/010575.

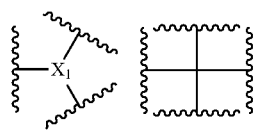

$X_1$ is as defined above.

In the present invention, when the linker has the following structure, the nucleic acid conjugate of the present invention can be produced by a method as listed below.

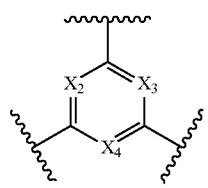

$X_2$ to $X_4$ are each independently as defined above. All of $X_2$ to $X_4$ are, for example, CH. In this case, the linker has the following structure:

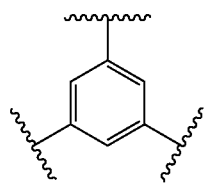 [SMILES: *c1cc(*)cc(*)c1]

In such a case, the nucleic acid conjugate of the present invention is preferably a nucleic acid conjugate represented by the following formula 1:

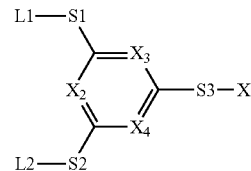
Formula 1

In formula 1,

X is an oligonucleotide, $X_2$ to $X_4$ are each independently as defined above, L1 and L2 are each independently a sugar chain ligand, and S1, S2 and S3 are each independently a substructure constituting a linker.

In formula 1, the following structure represents a linker:

Each of S1, S2 and S3 is a substructure constituting the linker, and $X_2$ to $X_4$ are each independently as defined above.

Hereinafter, the nucleic acid conjugate of formula 1 will be described. The description about formula 1 can be applied to nucleic acid conjugates instead having the following structures:

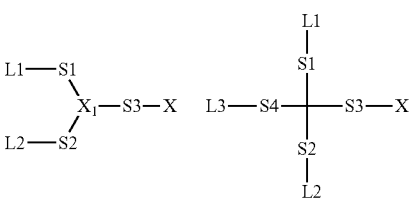

S4 can be understood as having the same meaning as in S1 and S2, $X_1$ is as defined above, and L3 is a sugar chain ligand.

In formula 1, S1 and S2 can each be bonded to the benzene ring at an ortho-, meta- or para-position with respect to the substitution position of S3 on the benzene ring. A nucleic acid conjugate represented by formula 1-1 given below is preferred. The bonds of S1 and S2 to the benzene ring in formula 1 mean that the bonds can be at arbitrary positions other than the substitution position of S3 on the benzene ring.

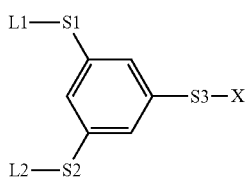

Formula 1-1

In formula 1-1,

X, L1, L2, S1, S2 and S3 are each as defined above.

In the present specification, the phrase "as defined above" means that, when formula 1-1 is taken as an example, each of X, L1, L2, S1 and S2 in formula 1-1 can be the same group as in the definition about each of X, L1, L2, S1 and S2 described above in formula 1.

In the present invention, the oligonucleotide is not only bonded to S3 via position 3' or 5' of a sugar moiety constituting a nucleotide but may be bonded to S3 via a base moiety constituting the nucleotide. In the present invention, the oligonucleotide can be understood as a group having a structure that bonds the oligonucleotide to S3. For example, when the oligonucleotide is bonded to S3 via —O—P(Z)(Z')O— (wherein Z and Z' are each independently an oxygen atom or a sulfur atom), the oligonucleotide represented by X may be understood as —O—P(Z) (Z')O-oligonucleotide.

In formula 1, S1 and S2 are not particularly limited as long as their structures link sugar chain ligands L1 and L2 to the benzene ring. A structure known in the art for use in nucleic acid conjugates may be adopted. S1 and S2 may be the same or may be different.

Sugar chain ligands L1 and L2 are preferably linked to S1 and S2 through glycoside bonds. S1 and S2 may each be linked to the benzene ring, for example, through a —CO—, —NH—, —O—, —S—, —O—CO—, —S—CO—, —NH—CO—, —CO—O—, —CO—S— or —CO—NH— bond.

S3 is a linker having a binding site to the oligonucleotide and is not particularly limited as long as its structure links oligonucleotide X to the benzene ring. A structure known in the art for use in nucleic acid conjugates may be adopted.

Oligonucleotide X is preferably linked to S3 through a phosphodiester bond. S3 may be linked to the benzene ring, for example, through a —CO—, —NH—, —O—, —S—, —O—CO—, —S—CO—, —NH—CO—, —CO—O—, —CO—S— or —CO—NH— bond.

For example, structures disclosed in International Publication Nos. WO 2009/073809, WO 2013/075035, WO 2015/105083, WO 2014/179620, and WO 2015/006740 may be adopted as a substructure constituting linkers S1, S2 and S3.

In the present invention, the nucleic acid conjugate is preferably a nucleic acid conjugate having a structure represented by the following formula 2:

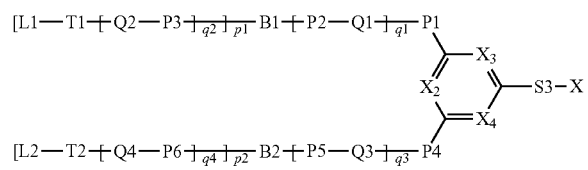

Formula 2

In formula 2,

X, $X_2$ to $X_4$, L1, L2 and S3 are each as defined above,

P1, P2, P3, P4, P5 and P6, and T1 and T2 are each independently absent, or —CO—, —NH—, —O—, —S—, —O—CO—, —S—CO—, —NH—CO—, —CO—O—, —CO—S— or —CO—NH—, Q1, Q2, Q3 and Q4 are each independently absent, or substituted or unsubstituted alkylene having 2 to 12 carbon atoms or —(CH$_2$CH$_2$O)$_n$—CH$_2$CH$_2$— wherein n is an integer of 0 to 99, B1 and B2 are each independently a bond, or any structure represented by the following formula 2-1, wherein each of the terminal dots in each structure is a binding site to P2 or P3, or P5 or P6, and m1, m2, m3 and m4 are each independently an integer of 0 to 10:

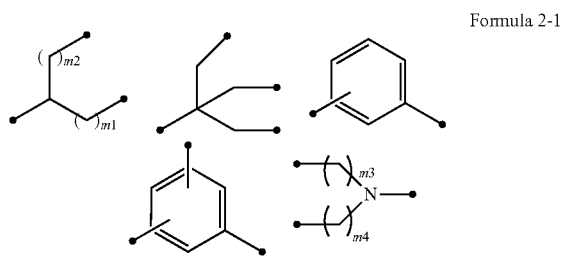

Formula 2-1 p1 and p2 are each independently an integer of 1, 2 or 3, and q1, q2, q3 and q4 are each independently an integer of 0 to 10, provided that when each of p1 and p2 is an integer of 2 or 3, each P3 and P6, Q2 and Q4, $T_1$ and T2 or L1 and L2 are the same or different.

P1 and P4 are each independently absent, or —CO—, —NH—, —O—, —S—, —O—CO—, —S—CO—, —NH—CO—, —CO—O—, —CO—S— or —CO—NH— and are each preferably —O—, —O—CO$_3$—NH—CO— or —CO—NH—, preferably —O—, —NH—CO— or —CO—NH—, further preferably —NH—CO—.

When P1 or P4 is, for example, —NH—CO—, a substructure —NH—CO-benzene ring is present.

Q1, Q2, Q3 and Q4 are each independently absent, or substituted or unsubstituted alkylene having 1 to 12 carbon atoms or —(CH$_2$CH$_2$O)$_n$—CH$_2$CH$_2$— wherein n is an integer of 1 to 99, and are each preferably substituted or unsubstituted alkylene having 1 to 12 carbon atoms, more preferably unsubstituted alkylene having 1 to 12 carbon atoms, further preferably unsubstituted alkylene having 1 to 6 carbon atoms, still further preferably unsubstituted alkylene having 1 to 4 carbon atoms.

P2 and P5 are each independently absent, or —CO—, —NH—, —O—, —S—, —O—CO—, —S—CO—, —NH—CO—, —CO—O—, —CO—S— or —CO—NH— and are each preferably absent, —CO—O— or —CO—NH—, more preferably absent or —CO—NH—. When each of P2 and P5 is, for example, —CO—NH—, substructures B1-CO—NH-Q1 and B2-CO—NH-Q3 are present.

-(P2-Q1)$_{q1}$- and -(P5-Q3)$_{q3}$- are each independently preferably absent, or any structure represented by the following formulas 3-1 to 3-3:

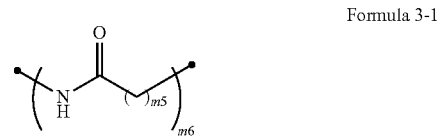

Formula 3-1

Formula 3-2

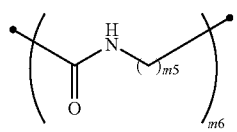

Formula 3-3

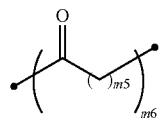

In formulas 3-1 to 3-3, m5 and m6 are each independently an integer of 0 to 10, and each of the terminal dots in the structures of formulas 3-1 to 3-3 is a binding site to B1 or B2, or P1 or P4.

B1 and B2 are each independently a bond, or any structure represented by the following formulas, wherein each of the terminal dots in each structure is a binding site to P2 or P3, or P5 or P6, and m1, m2, m3 and m4 are each independently an integer of 0 to 10:

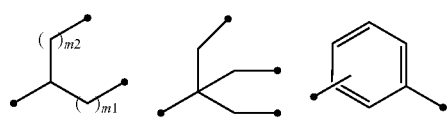

Each of B1 and B2 is preferably a group derived from an amino acid such as glutamic acid, aspartic acid, lysine, including non-natural amino acids such as iminodiacetic acid, or an amino alcohol such as 1,3-propanediol. When B1 and B2 are groups derived from glutamic acid or aspartic acid, it is preferred that the amino group of each glutamic acid or aspartic acid should be bonded while P2 and P5 should be —NH—CO— bonds. When B1 and B2 are groups derived from lysine, it is preferred that the carboxyl group of each lysine should be bonded while P2 and P5 should be —CO—NH— bonds. When B1 and B2 are groups derived from iminodiacetic acid, it is preferred that the amino group of each iminodiacetic acid should be bonded while P2 and P5 should be —CO— bonds.

Preferably, $X_2$ to $X_4$ are each independently CH. More preferably, $X_2$ to $X_4$ are CH at the same time.

In the present invention, the nucleic acid conjugate is preferably a nucleic acid conjugate having any structure represented by the following formulas 4-1 to 4-9:

Formula 4-1

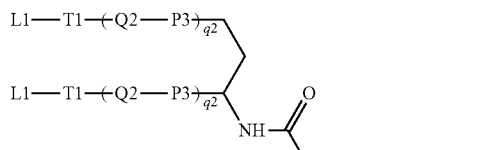

Formula 4-2

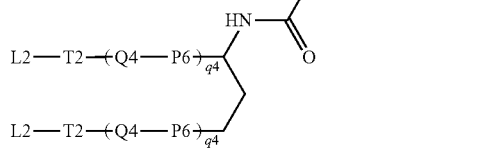

Formula 4-3

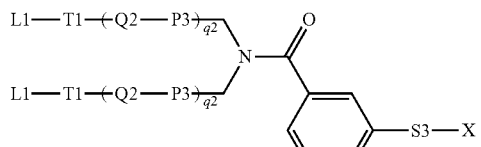

Formula 4-4

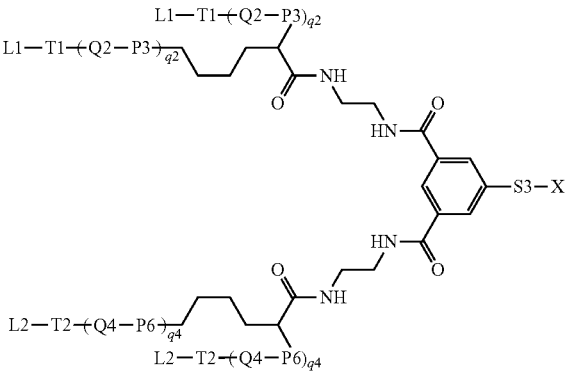

Formula 4-5

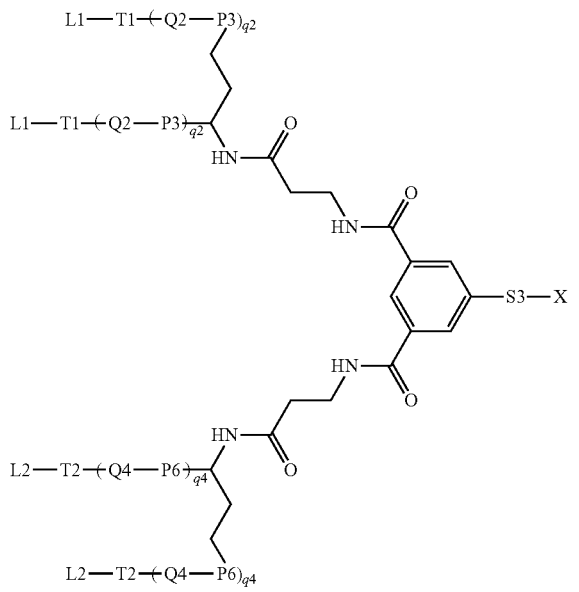

Formula 4-6

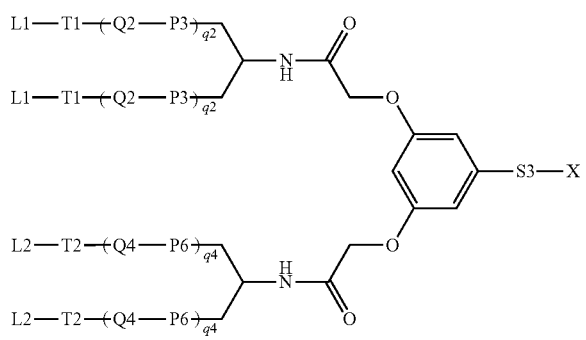

Formula 4-7

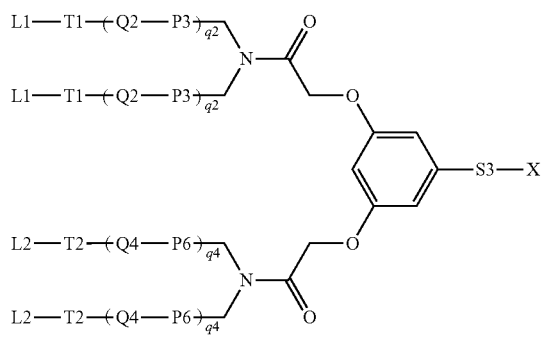

Formula 4-8

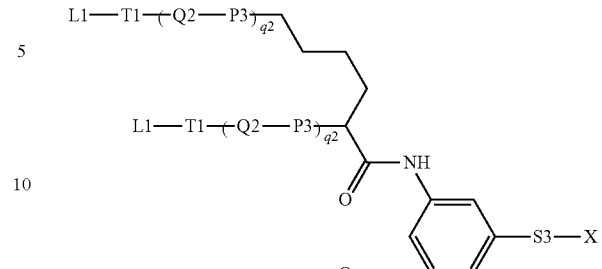

Formula 4-9

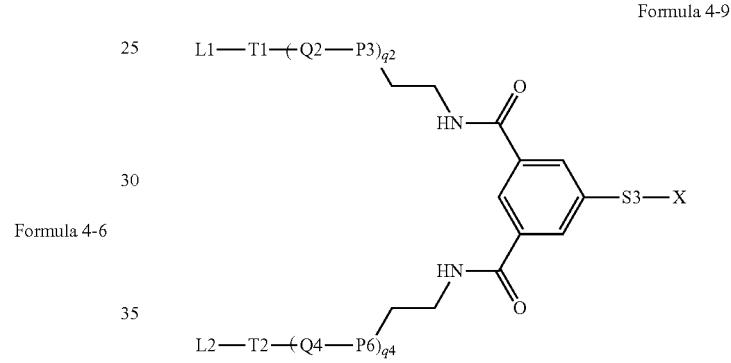

In formulas 4-1 to 4-9,

X, L1, L2, S3, P3, P6, T1, T2, Q2, Q4, q2 and q4 are each as defined above.

P3 and P6 are each independently absent, or —CO—, —NH—, —O—, —S—, —O—CO—, —S—CO—, —NH—CO—, —CO—O—, —CO—S— or —CO—NH— and are each preferably —OCO— or —NH—CO—, more preferably —NH—CO—. When each of P3 and P6 is, for example, —NH—CO—, substructures B1-NH—CO-Q2 and B2-NH—CO-Q4 are present.

T1 and T2 are each independently absent, or —CO—, —NH—, —O—, —S—, —O—CO—, —S—CO—, —NH—CO—, —CO—O—, —CO—S— or —CO—NH— and are each preferably —O— or —S—, more preferably —O—.

In the present invention, the nucleic acid conjugate is preferably a nucleic acid conjugate having a structure represented by formula 5 given below.

In formula 5, P1 and P4 in formula 2 are the same; P2 and P5 in formula 2 are the same; P3 and P6 in formula 2 are the same; Q1 and Q3 in formula 2 are the same; Q2 and Q4 in formula 2 are the same; B1 and B2 in formula 2 are the same; T1 and T2 in formula 2 are the same; L1 and L2 in formula 2 are the same; p1 and p2 in formula 2 are the same; q1 and q3 in formula 2 are the same; and q2 and q4 in formula 2 are the same.

Formula 5

$$\left[L1-T1-(Q2-P3)_{q2}\right]_{p1}-B1-(P2-Q1)_{q1}-P1$$
$$\left[L1-T1-(Q2-P3)_{q2}\right]_{p1}-B1-(P2-Q1)_{q1}-P1$$

with a phenyl-S3—X terminus

In formula 5,

X, S3, P1, P2, P3, Q1, Q2, B1, T1, L1, p1, q1 and q2 are each as defined above.

X, S3, P1, P2, P3, Q1, Q2, B1, T1, L1, p1, q1 and q2 in formula 5 can each be any of the preferred groups mentioned above. P1 is preferably —CO—NH—, —NH—CO— or —O—.

-(P2-Q1)q1- in formula 5 is preferably absent, or any structure represented by formulas 3-1 to 3-3 described above.

In the present invention, the nucleic acid conjugate is preferably a nucleic acid conjugate having any structure represented by the following formulas 6-1 to 6-9:

Formula 6-1

Formula 6-2

Formula 6-3

Formula 6-4

Formula 6-5

Formula 6-6
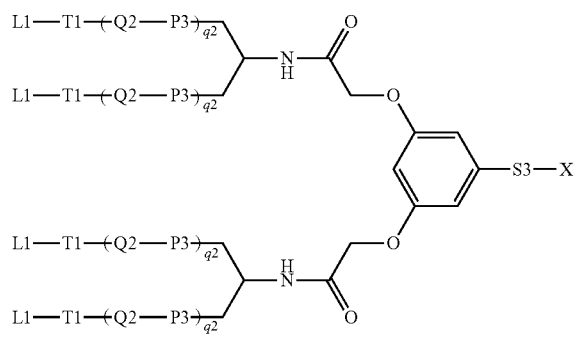
Formula 6-8
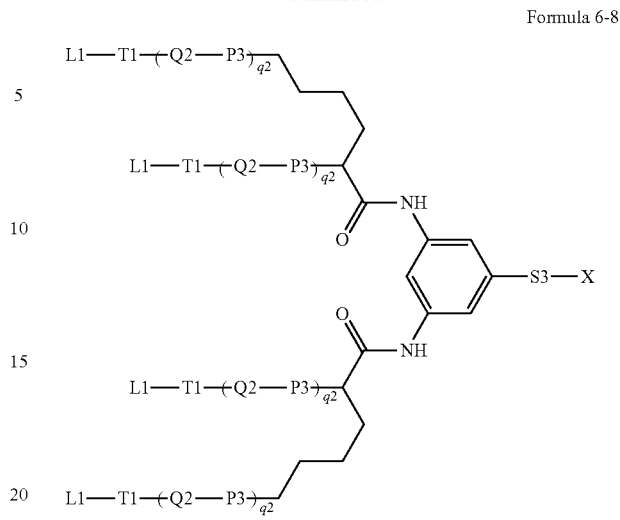
Formula 6-9
Formula 6-7
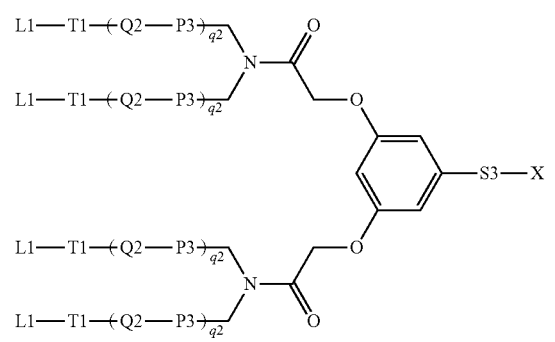
In formulas 6-1 to 6-9,
X, S3, P3, Q2, T1, and L1 are each as defined above.
In the present invention, the nucleic acid conjugate is preferably a nucleic acid conjugate having any structure represented by the following formulas 7-1 to 7-9:
Formula 7-1
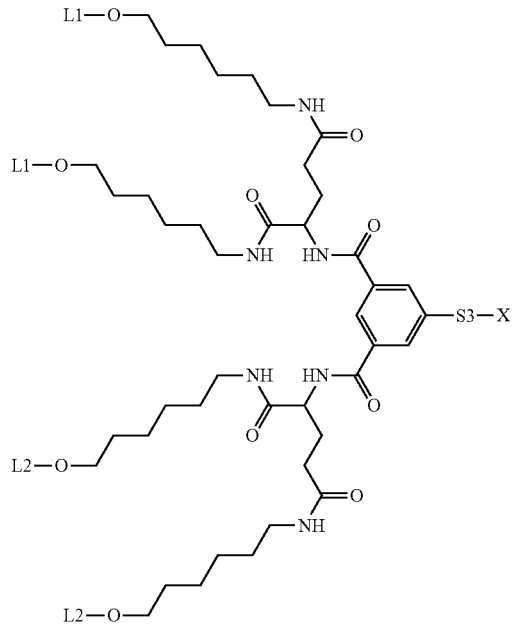
Formula 7-2
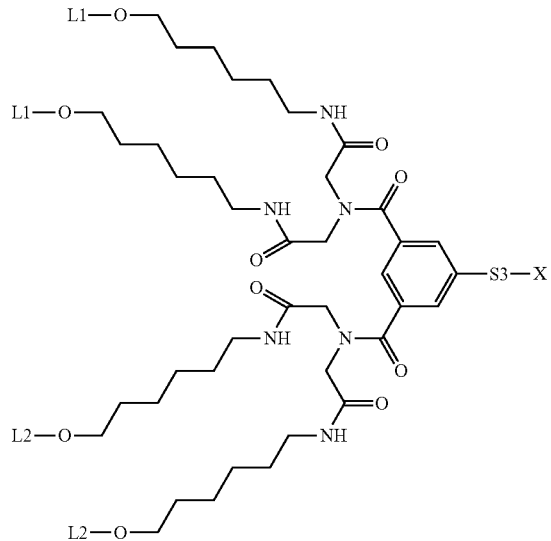

Formula 7-3
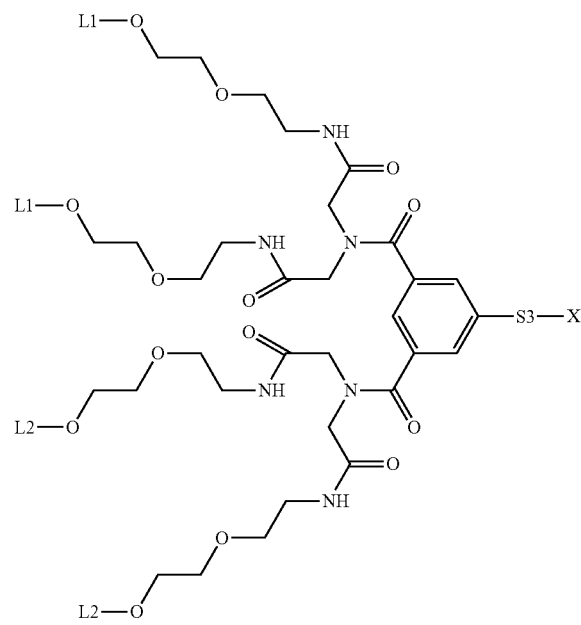
Formula 7-4
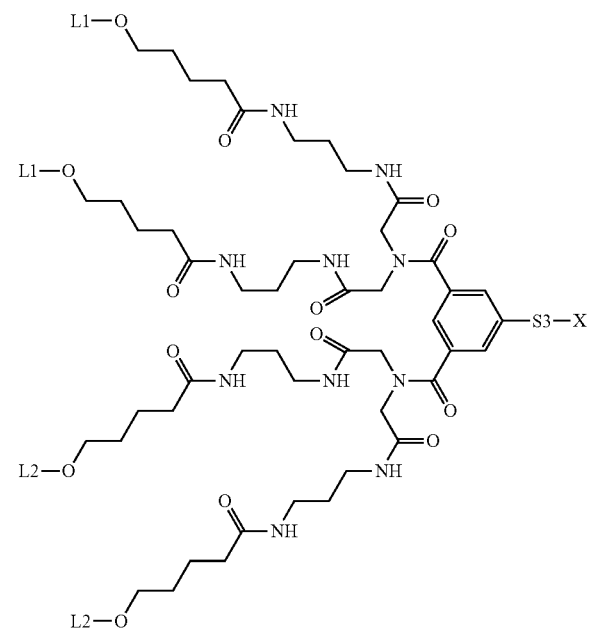
Formula 7-5
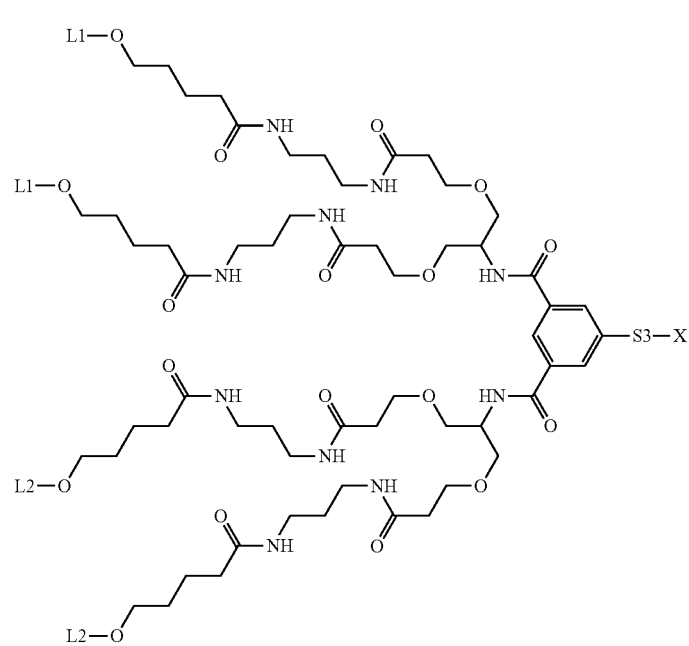

Formula 7-6
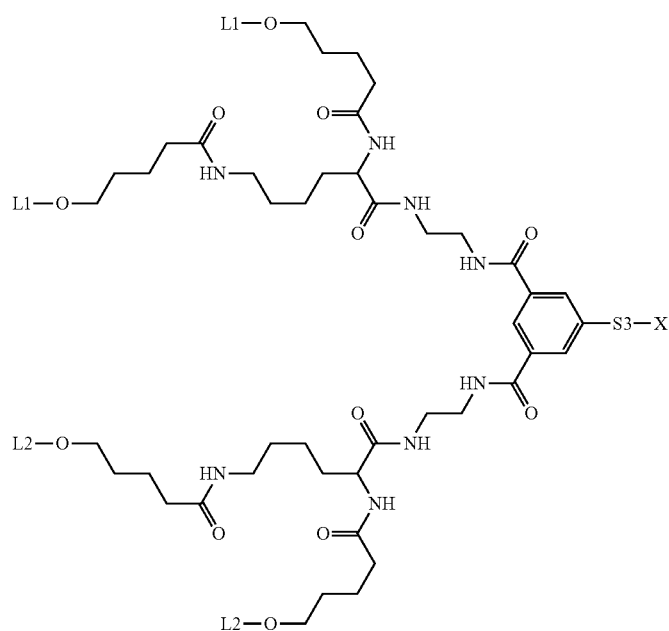
Formula 7-7
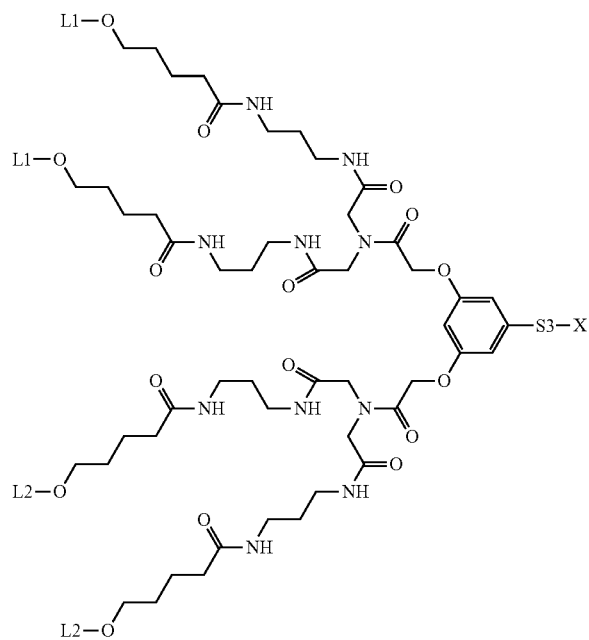
Formula 7-8
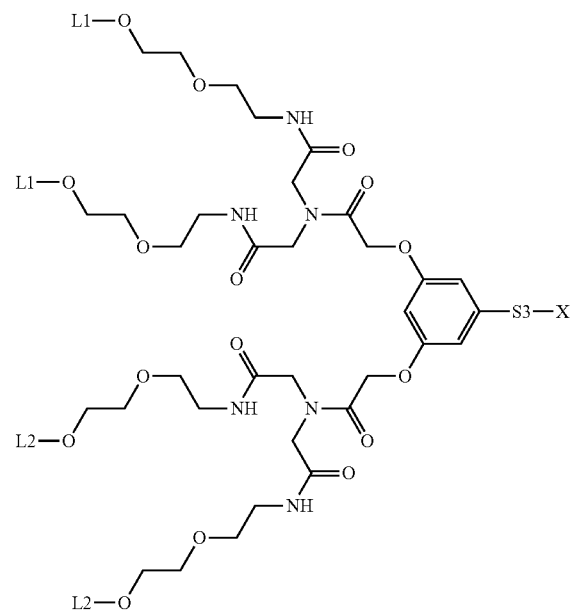

Formula 7-9
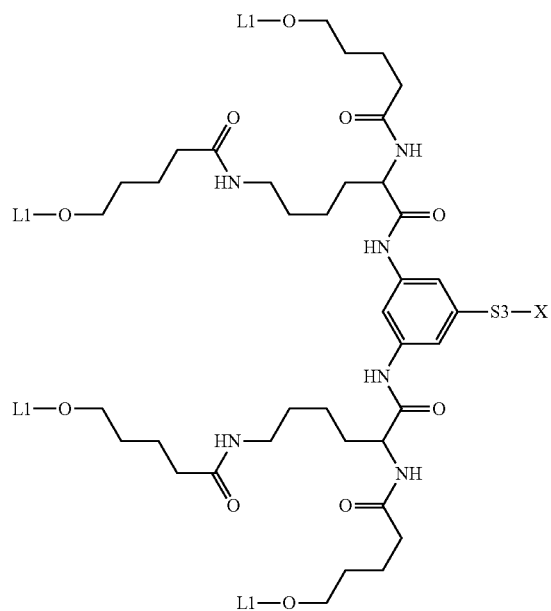
Formula 7-10
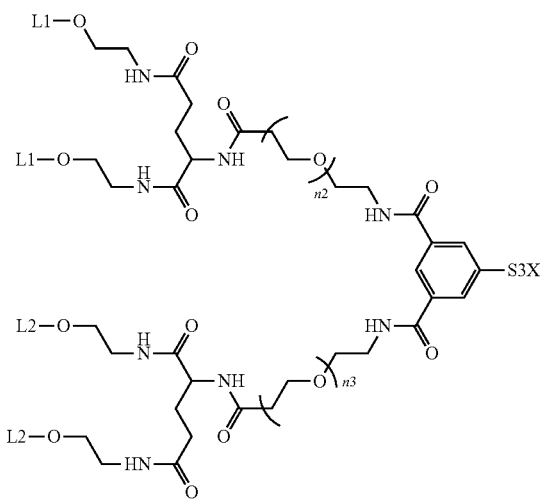
Formula 7-11
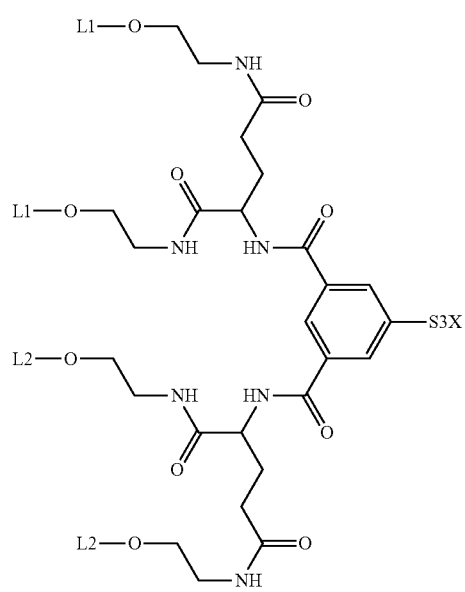
Formula 7-12
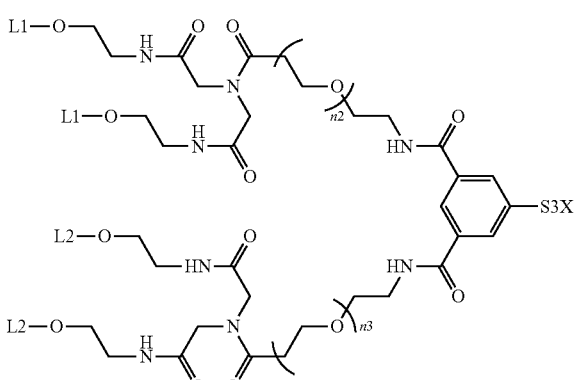
Formula 7-13
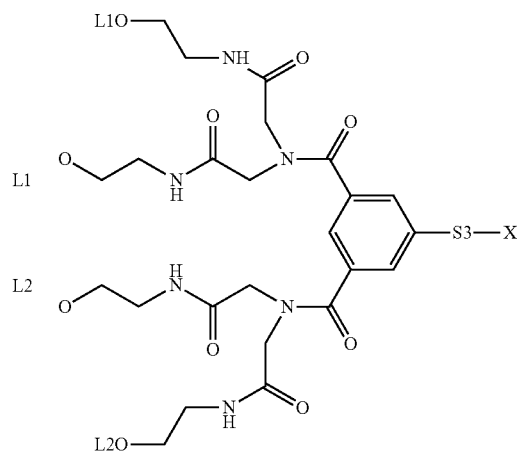

Formula 7-14
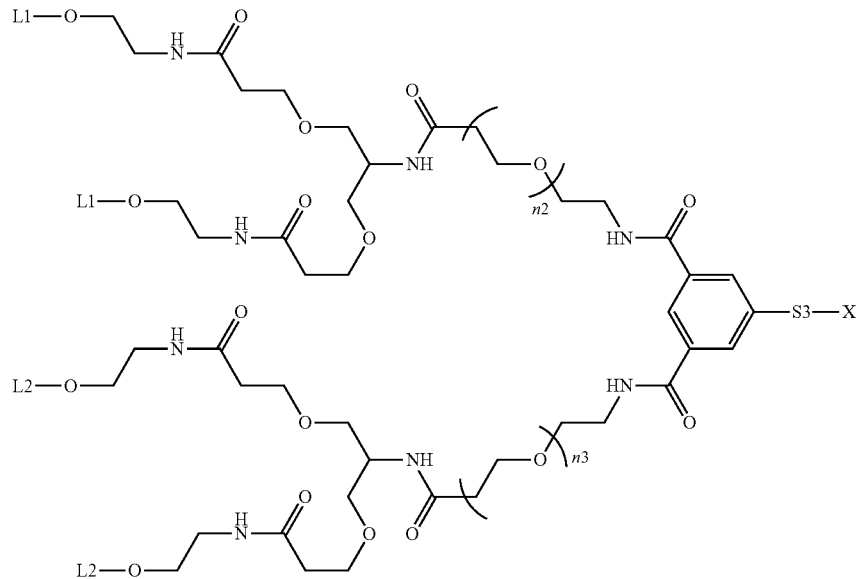
Formula 7-15
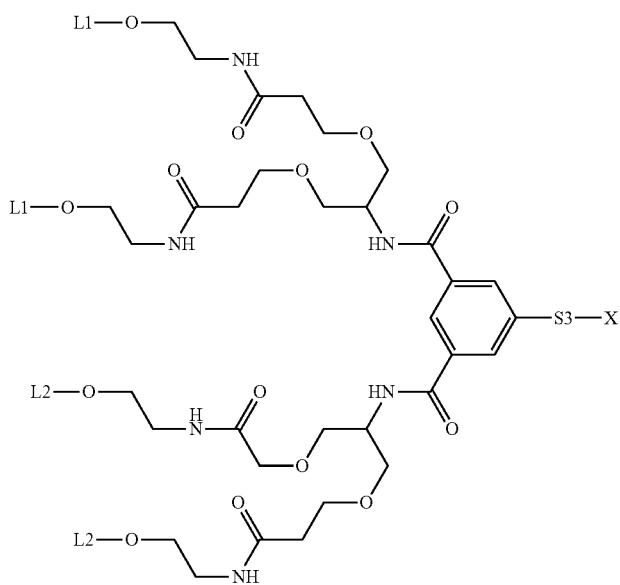

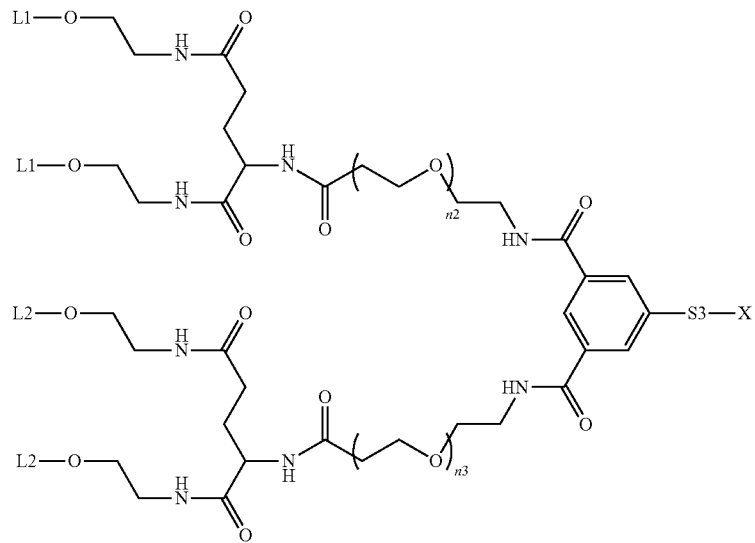
Formula 7-16
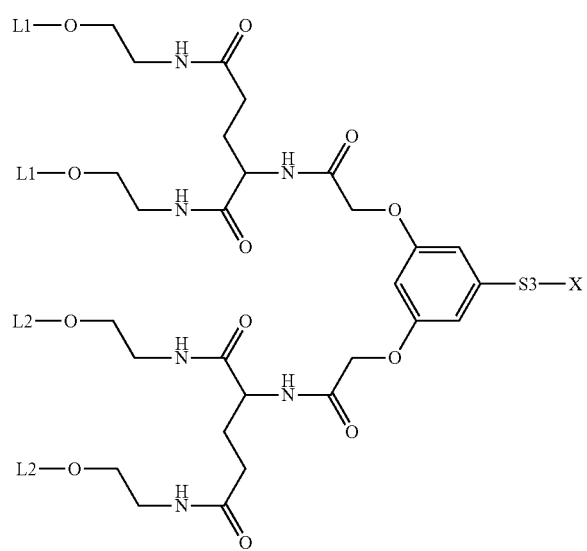
Formula 7-17

-continued
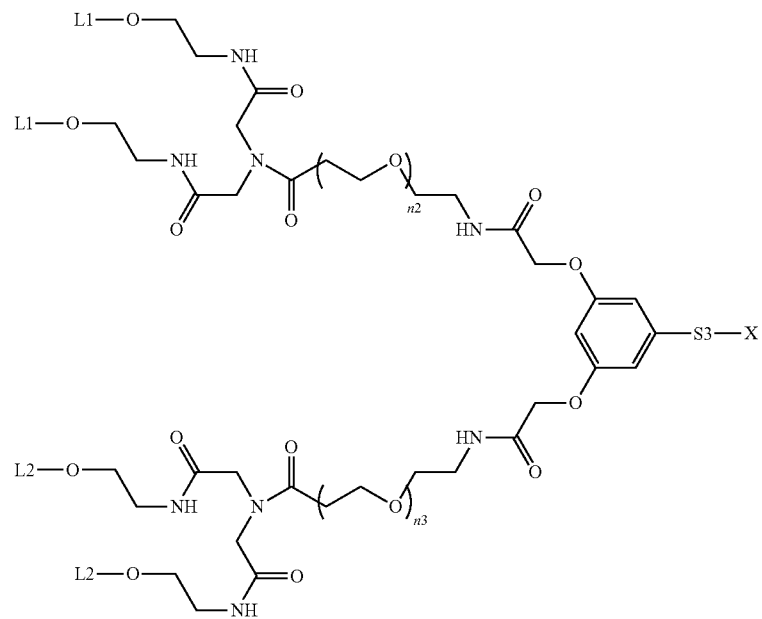
Formula 7-18
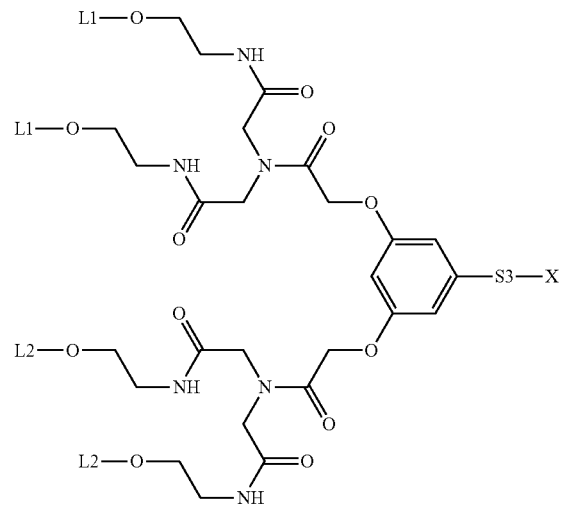
Formula 7-19

Formula 7-20

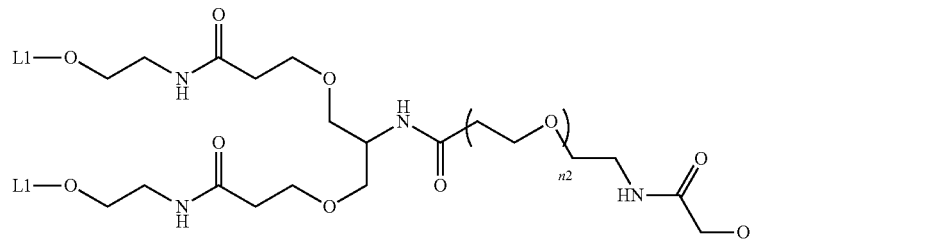

Formula 7-21

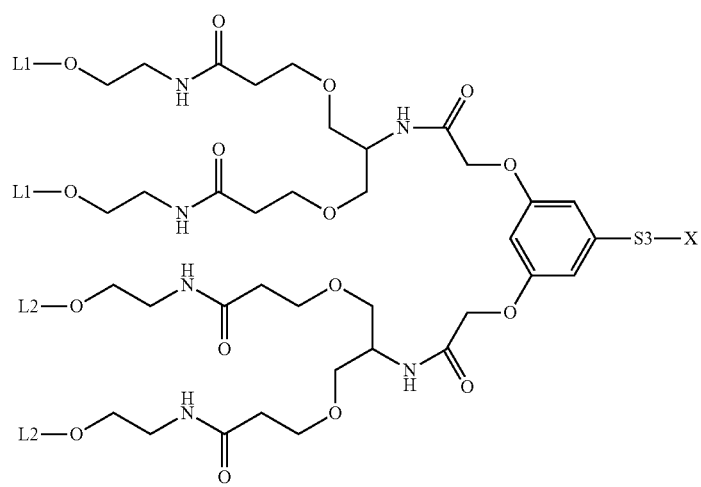

In formulas 7-1 to 7-21,

X, L1, L2, S3, n2 or n3 are each as defined above. L1 and L2 may be the same or may be different and is preferably the same.

A nucleic acid derivative other than the nucleic acid conjugate having any structure represented by formulas 7-1 to 7-9 can also be produced by introducing alkylene chains differing in chain length as each alkylene group moiety in formulas 7-1 to 7-9, or by replacing an amide bond or the like with another bond.

As mentioned above, the linker used in the nucleic acid conjugate of the present invention preferably has the following structure:

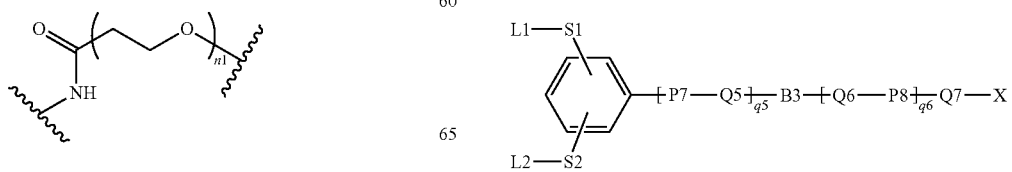

wherein n1 is an integer of 1 to 100.

n1 is preferably an integer of 5 to 95, more preferably an integer of 10 to 80, further preferably an integer of 15 to 60, still further preferably an integer of 20 to 40.

n2 and n3 are the same as or different from each other and each are preferably an integer of 5 to 95, more preferably an integer of 10 to 80, further preferably an integer of 15 to 60, still further preferably an integer of 20 to 40.

In the present invention, the nucleic acid conjugate is preferably a nucleic acid conjugate having a structure represented by the following formula 11:

Formula 11

In formula 11,

L1, L2, S1 and S2 are each as defined above,

P7 and P8 are each independently absent, or —CO—, —NH—, —O—, —S—, —O—CO—, —S—CO—, —NH—CO—, —CO—O—, —CO—S— or —CO—NH—, Q5, Q6 and Q7 are each independently absent, or substituted or unsubstituted alkylene having 1 to 12 carbon atoms or —(CH$_2$CH$_2$O)$_{n8}$—CH$_2$CH$_2$— wherein n8 is an integer of 0 to 99, B3 is any structure represented by the following formula 11-1, wherein the broken lines respectively mean bonds to Q5 and Q6:

Formula 11-1

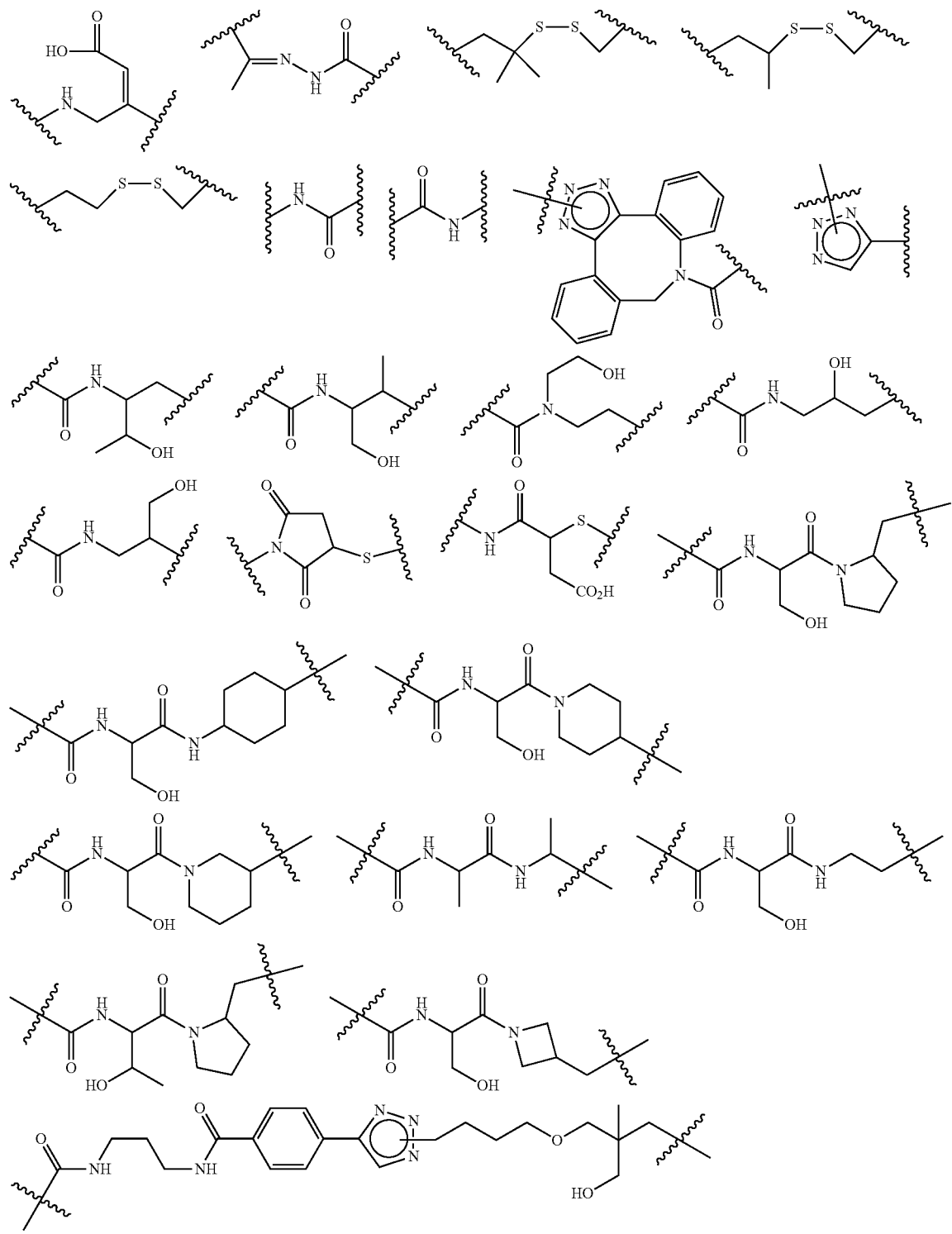

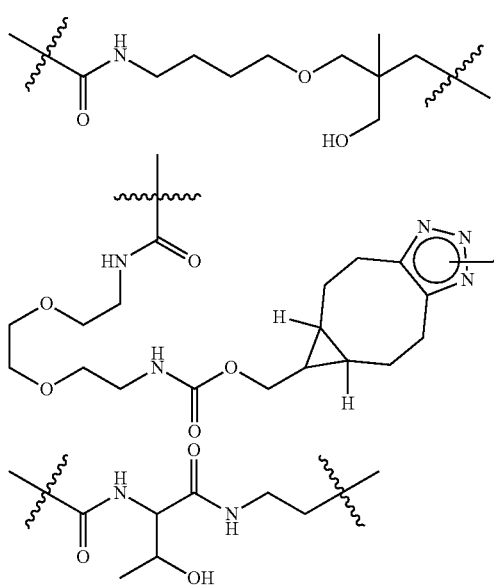
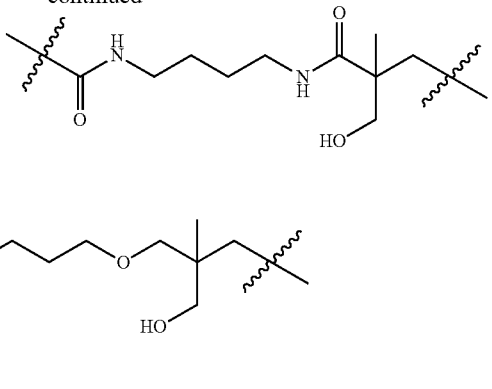

and q5 and q6 are each independently an integer of 0 to 10.

P7 is absent, or —CO—, —NH—, —O—, —S—, —O—CO—, —S—CO—, —NH—CO—, —CO—O—, —CO—S— or —CO—NH— and is preferably —O—, —NH—CO— or —CONH—, more preferably —O— or —NH—CO—. When P7 is, for example, —O—, a substructure benzene ring-O— is present.

P8 is absent, or —CO—, —NH—, —O—, —S—, —O—CO—, —S—CO—, —NH—CO—, —CO—O—, —CO—S— or —CO—NH—. When P8 is present, P8 is preferably —CO—O— or —CO—NH—, more preferably —CO—NH—. When P8 is, for example, —CO—NH—, a substructure Q6-CO—NH— is present.

Q5, Q6 and Q7 are each independently absent, or substituted or unsubstituted alkylene having 1 to 12 carbon atoms or —(CH$_2$CH$_2$O)$_{n8}$—CH$_2$CH$_2$— wherein n8 is an integer of 0 to 99, and are each preferably substituted or unsubstituted alkylene having 1 to 12 carbon atoms, more preferably unsubstituted alkylene having 1 to 12 carbon atoms, further preferably unsubstituted alkylene having 1 to 6 carbon atoms, still further preferably unsubstituted alkylene having 1 to 4 carbon atoms.

Preferably, -(P7-Q5)$_{q5}$- is —O—(CH$_2$)$_{m15}$—NH— or —NH—CO—(CH$_2$)$_{m16}$—NH—, and m15 and m16 are each independently an integer of 1 to 10.

In the present invention, the nucleic acid conjugate is preferably a nucleic acid conjugate having any structure represented by the following formulas 12-1 to 12-12:

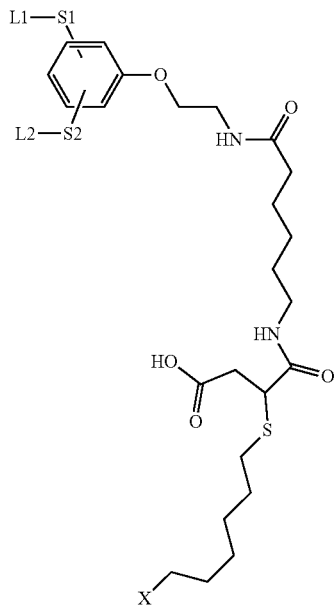

Formula 12-1

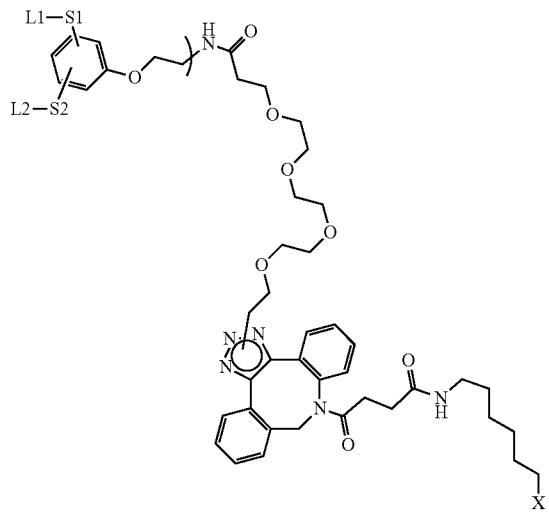

Formula 12-2

Formula 12-3
Formula 12-4
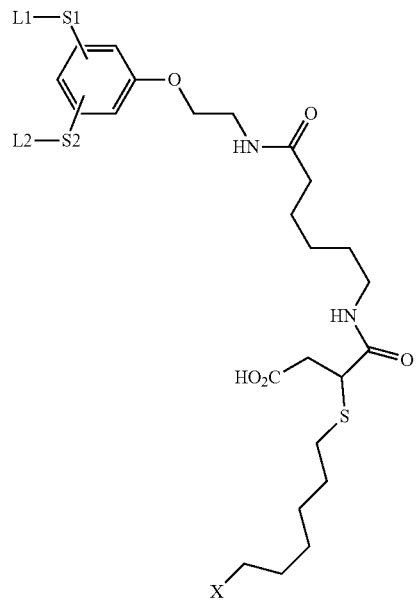
Formula 12-5
Formula 12-6
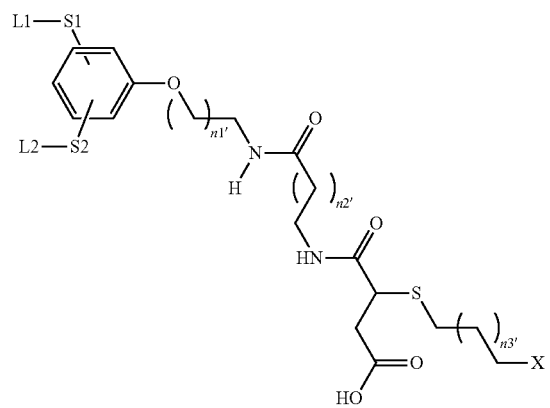

-continued
Formula 12-7
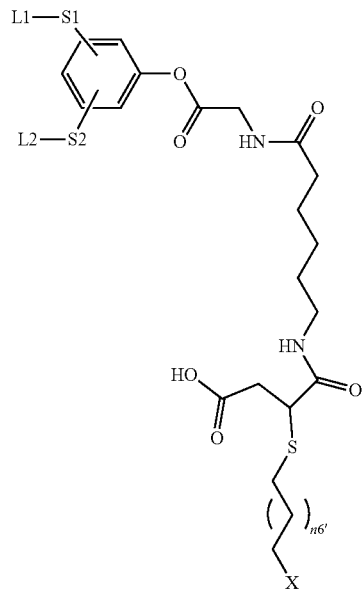
Formula 12-8
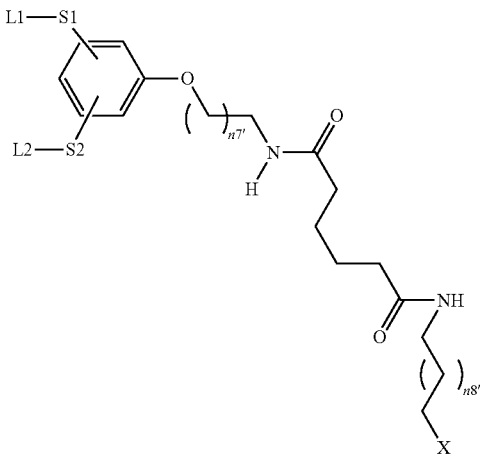
Formula 12-9
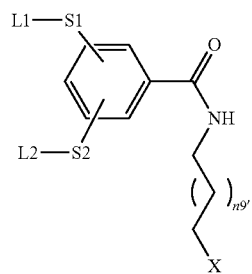
Formula 12-10
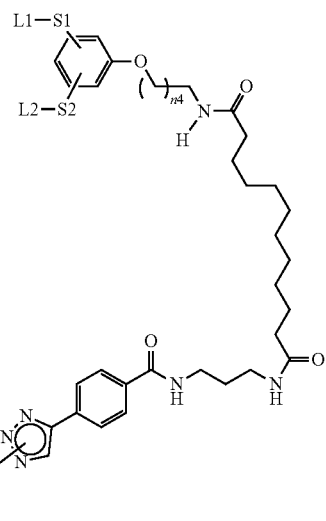
Formula 12-11
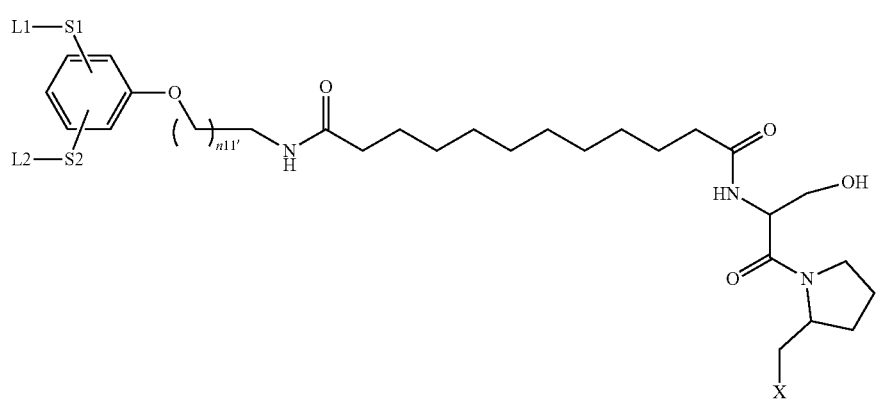

Formula 12-12

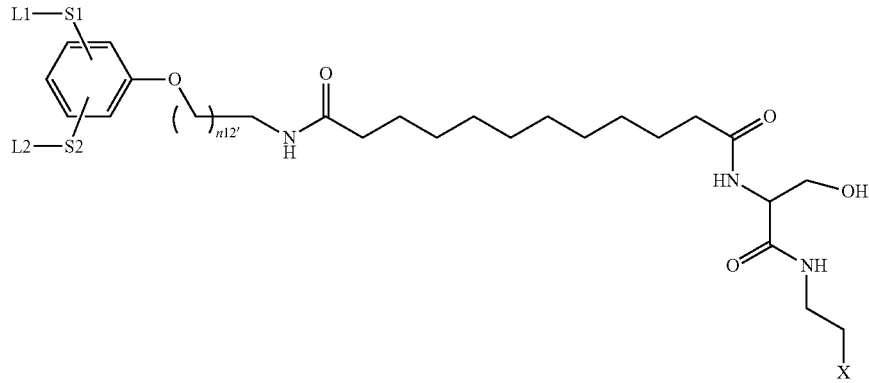

In formulas 12-1 to 12-12,

X, L1, L2, S1 and S2 are each as defined above, and n1' to n12' are each independently an integer of 1 to 10.

In another preferred aspect of the present invention, the nucleic acid conjugate has any of the following structures:

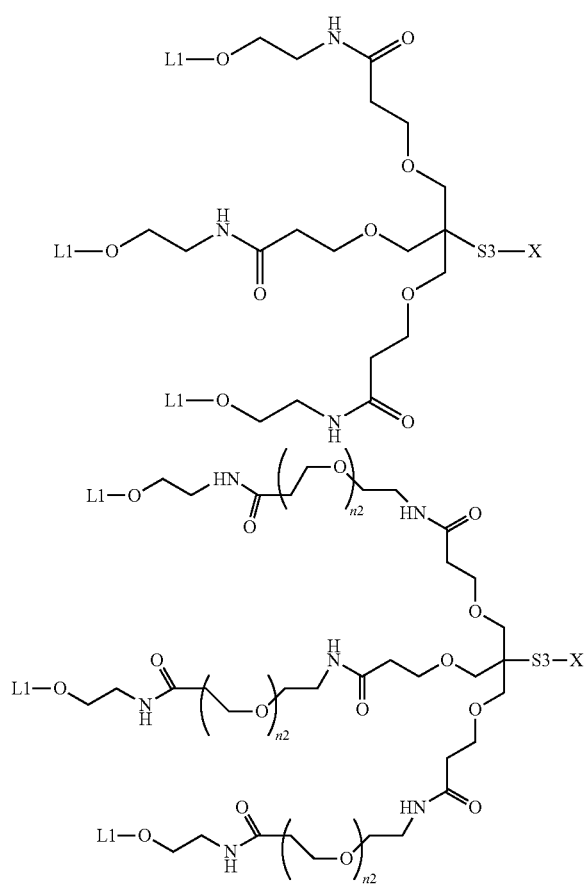

In the formulas,

X, L1, S3 and n2 are each as defined above.

The nucleic acid conjugate of the present invention is preferably a nucleic acid conjugate having both the structures of formula 2 and formula 11 as the nucleic acid conjugate represented by formula 1. The nucleic acid conjugate has the structure of formula 11, and formula 2 may be any of formulas 4-1 to 4-9, may be any of formulas 6-1 to 6-9, or may be any of formulas 7-1 to 7-9. When formula 2 is any of formulas 4-1 to 4-9, formulas 6-1 to 6-9, or formulas 7-1 to 7-9, formula 11 may be any of formulas 12-1 to 12-12. The nucleic acid conjugate of the present invention is more preferably a nucleic acid conjugate having both of any one structure of formulas 4-1 to 4-9 and any one structure of formulas 12-1 to 12-12, a nucleic acid conjugate having both of any one structure of formulas 6-1 to 6-9 and any one structure of formulas 12-1 to 12-12, or a nucleic acid conjugate having both of any one structure of formulas 7-1 to 7-9 and any one structure of formulas 12-1 to 12-12, as the nucleic acid conjugate represented by formula 1.

In the present specification, the sugar chain ligand represented by "Ligand", "L1", etc. may include a portion (e.g., —O—(CH$_2$)$_2$—) of the linker bonded directly to the sugar chain ligand.

The nucleic acid conjugate of the present invention may form a salt with a pharmaceutically acceptable anion when hydrogen ions are coordinated to a lone pair of electrons on any nitrogen atom.

In the present invention, examples of the pharmaceutically acceptable anion include: inorganic ions such as chloride ions, bromide ions, nitrate ions, sulfate ions, and phosphate ions; and organic acid ions such as acetate ions, oxalate ions, maleate ions, fumarate ions, citrate ions, benzoate ions, and methanesulfonate ions.

A method for producing the nucleic acid conjugate of the present invention will be described. In the production methods given below, if defined groups react under conditions of the production methods or are unsuitable for carrying out the production methods, the compounds of interest can be produced by use of methods for introducing and removing protective groups commonly used in organic synthetic chemistry [e.g., methods described in Protective Groups in Organic Synthesis, third edition, T.W. Greene, John Wiley & Sons Inc. (1999)] or the like. If necessary, the order of reaction steps including substituent introduction and the like may be changed.

The nucleic acid polymer represented by formula 1 can also be synthesized by solid-phase synthesis.

The nucleic acid polymer represented by formula 1 can be synthesized with reference to a method for synthesizing a linker structure known in the art for nucleic acid conjugates.

The synthesis of a L1-benzene ring unit having linker S1 or a L2-benzene ring unit having linker S2 in the nucleic acid conjugate represented by formula 1 will be described by taking the nucleic acid conjugate represented by formula 2 as an example.

The L1-benzene ring unit and the L2-benzene ring unit in the nucleic acid conjugate represented by formula 2 has linkages by P1, P2, P3, P4, P5, and P6, and T1 and T2.

The —CO—, —NH—, —O—, —S—, —O—CO—, —S—CO—, —NH—CO—, —CO—O—, —CO—S— or —CO—NH— bond represented by P1, P2, P3, P4, P5, and P6, and T1 and T2 can be appropriately synthesized by selecting a starting material suitable for forming the structure represented by formula 2 with reference to methods for binding reaction described in, for example, The Fourth Series of Experimental Chemistry 19, "Synthesis of Organic Compound I", Maruzen Co., Ltd. (1992) and The Fourth Series of Experimental Chemistry 20, "Synthesis of Organic Compound II", Maruzen Co., Ltd. (1992).

A substructure of the L1-benzene ring unit can be produced by sequentially bonding a compound having Q1 as a substructure and a compound having B1 as a substructure to the benzene ring.

The L1-benzene ring unit structure can be produced by separately synthesizing a compound having L1 and Q2 as a substructure, and bonding the compound having L1 and Q2 as a substructure to a compound having a substructure of a L1-benzene ring unit having the benzene ring, Q1 and B1 as a substructure.

Likewise, a substructure of the L2-benzene ring unit can be produced by sequentially bonding a compound having Q3 as a substructure and a compound having B2 as a substructure to the benzene ring.

The L2-benzene ring unit structure can be produced by separately synthesizing a compound having L2 and Q4 as a substructure, and bonding the compound having L2 and Q4 as a substructure to a compound having a substructure of a L2-benzene ring unit having the benzene ring, Q3 and B2 as a substructure.

Examples of the compound having Q1 as a substructure and the compound having Q3 as a substructure include compounds having a hydroxy group, a carboxyl group, an amino group, and/or a thiol group at both ends of alkylene having 1 to 10 carbon atoms or —(CH$_2$CH$_2$O)$_n$—CH$_2$CH$_2$—.

Examples of the compound having B1 as a substructure and the compound having B2 as a substructure include compounds having any structure represented by the following formula 2-1 and having a hydroxy group, a carboxyl group, an amino group, or a thiol group at each of the terminal dots in each structure:

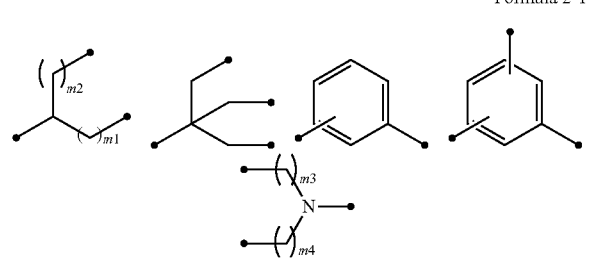

Formula 2-1

Specific examples of the compound having B1 as a substructure and the compound having B2 as a substructure include glycol, glutamic acid, aspartic acid, lysine, Tris, iminodiacetic acid, and 2-amino-1,3-propanediol. Glutamic acid, aspartic acid, lysine, or iminodiacetic acid are preferred.

The L1-benzene ring unit structure may be produced by synthesizing a compound having L1, Q2 and B1 as a substructure and then bonding this compound to a compound having Q1 and the benzene ring.

The L2-benzene ring unit structure may be produced by synthesizing a compound having L2, Q4 and B2 as a substructure and then bonding this compound to a compound having Q3 and the benzene ring.

In the present invention, the substructure [L1-T1-(Q2-P3)$_{q2}$-]$_{p1}$-B1-(P2-Q1)$_{q1}$-P1- and the substructure [L2-12-(Q3-P6)$_{q4}$-]$_{p2}$-B2-(P5-Q3)$_{q3}$-P2- may be the same or different and are preferably the same.

Examples of the unit corresponding to L1-T1-Q2 in the sugar chain ligand include L3-T1-Q2-COOH and L3-T1-(Q2-P3)$_{q2-1}$-Q2-NH$_2$. Specific examples thereof include L3-O-alkylene having 1 to 12 carbon atoms-COOH and L3-alkylene having 1 to 12 carbon atoms-CO—NH-alkylene having 2 to 12 carbon atoms-NH$_2$.

L3 is not particularly limited as long as L3 is a sugar chain ligand derivative that is converted to L1 by deprotection. The substituent on the sugar chain ligand is not particularly limited as long as the substituent is routinely used in the field of carbohydrate chemistry. An Ac group is preferred.

Specifically, the L1-benzene ring unit having linker S1 or the L2-benzene ring unit having linker S2 can be synthesized by appropriately increasing or decreasing the number of carbon atoms of an alkylene chain, and using a compound with a terminal amino group or a terminal carboxyl group converted to a group capable of forming a —CO—, —NH—, —O—, —S—, —O—CO—, —S—CO—, —NH—CO—, —CO—O—, —CO—S— or —CO—NH— bond, with reference to a method described in Examples. Mannose derivatives, mannose or N-acetylgalactosamine is taken as an example of sugar chain ligand L1 in Examples. However, sugar ligand L1 may be changed to other sugar chain ligands for the practice.

The synthesis of an X-benzene ring unit having linker S3 in the nucleic acid conjugate represented by formula 1 will be described by taking the nucleic acid conjugate represented by formula 11 as an example.

The X-benzene ring unit in the nucleic acid conjugate represented by formula 11 has bonds represented by P7 and P8 in addition to the bond of the oligonucleotide.

The —CO—, —NH—, —O—, —S—, —O—CO—, —S—CO—, —NH—CO—, —CO—O—, —CO—S— or —CO—NH— bond represented by P7 and P8 can be appropriately synthesized by selecting a starting material suitable for forming the structure represented by formula 11 with reference to methods for binding reaction described in, for example, The Fourth Series of Experimental Chemistry 19, "Synthesis of Organic Compound I", Maruzen Co., Ltd. (1992) and The Fourth Series of Experimental Chemistry 20, "Synthesis of Organic Compound II", Maruzen Co., Ltd. (1992).

A substructure of the X-benzene ring unit can be produced by sequentially bonding a compound having Q5 as a substructure and a compound having B3 as a substructure to the benzene ring.

The X-benzene ring unit structure can be produced by separately synthesizing a compound having X and Q7 as a substructure or a compound having X and Q6 as a substructure, and bonding the compound having X and Q7 as a substructure or the compound having X and Q6 as a substructure to a compound having a substructure of a X-benzene ring unit having the benzene ring and Q5 as a substructure to construct the B3 moiety.

Specifically, the case of having an azide group at the end of the compound having a substructure of an X-benzene ring unit having the benzene ring and Q5 as a substructure will be taken as an example. The X-benzene ring unit structure can be produced by reacting an oligonucleotide allowed to have a terminal binding functional group as disclosed in Examples so that a triazole ring is formed by cycloaddition to construct the B3 moiety.

Examples of the compound having Q5 as a substructure, the compound having Q6 as a substructure, and the compound having Q7 as a substructure include compounds having a hydroxy group, a carboxyl group, an amino group, and/or a thiol group at both ends of alkylene having 1 to 10 carbon atoms or —(CH$_2$CH$_2$O)$_{n8}$—CH$_2$CH$_2$—.

The L1-benzene ring unit structure, the L2-benzene ring unit structure, and the X-benzene ring unit structure can be sequentially produced. It is preferred to synthesize the L1-benzene ring unit structure and the L2-benzene ring unit structure and then bond the X-benzene ring unit structure thereto. Particularly, it is preferred to introduce X having the oligonucleotide moiety into the compound near the final step of sugar chain ligand conjugate synthesis.

Production Method 1

A L1-benzene ring unit structure and a L2-benzene ring unit structure in which each of P1 and P4 in formula 1-1 is —NH—CO—, —O—CO— or —S—CO— can be produced by the following method.

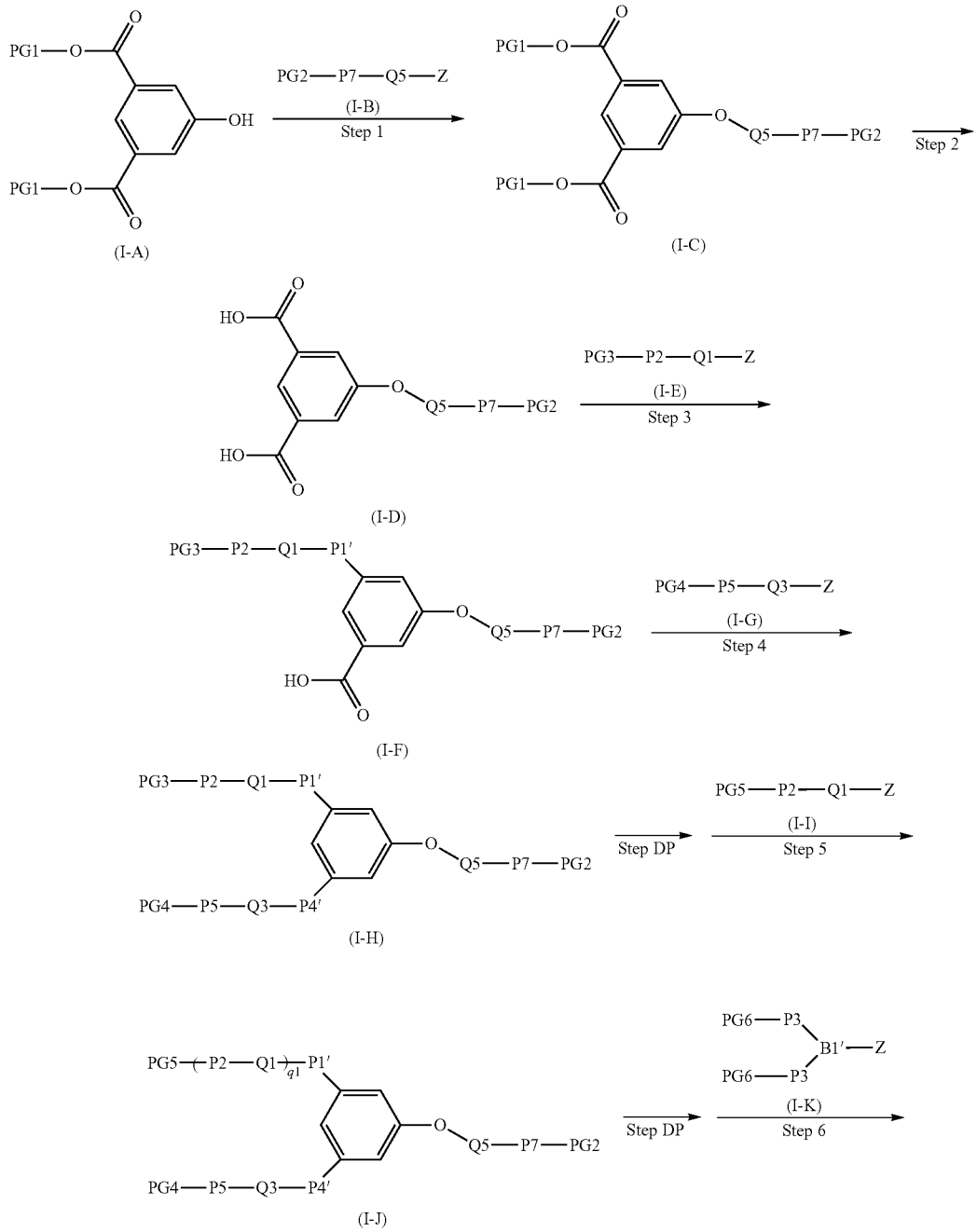

-continued

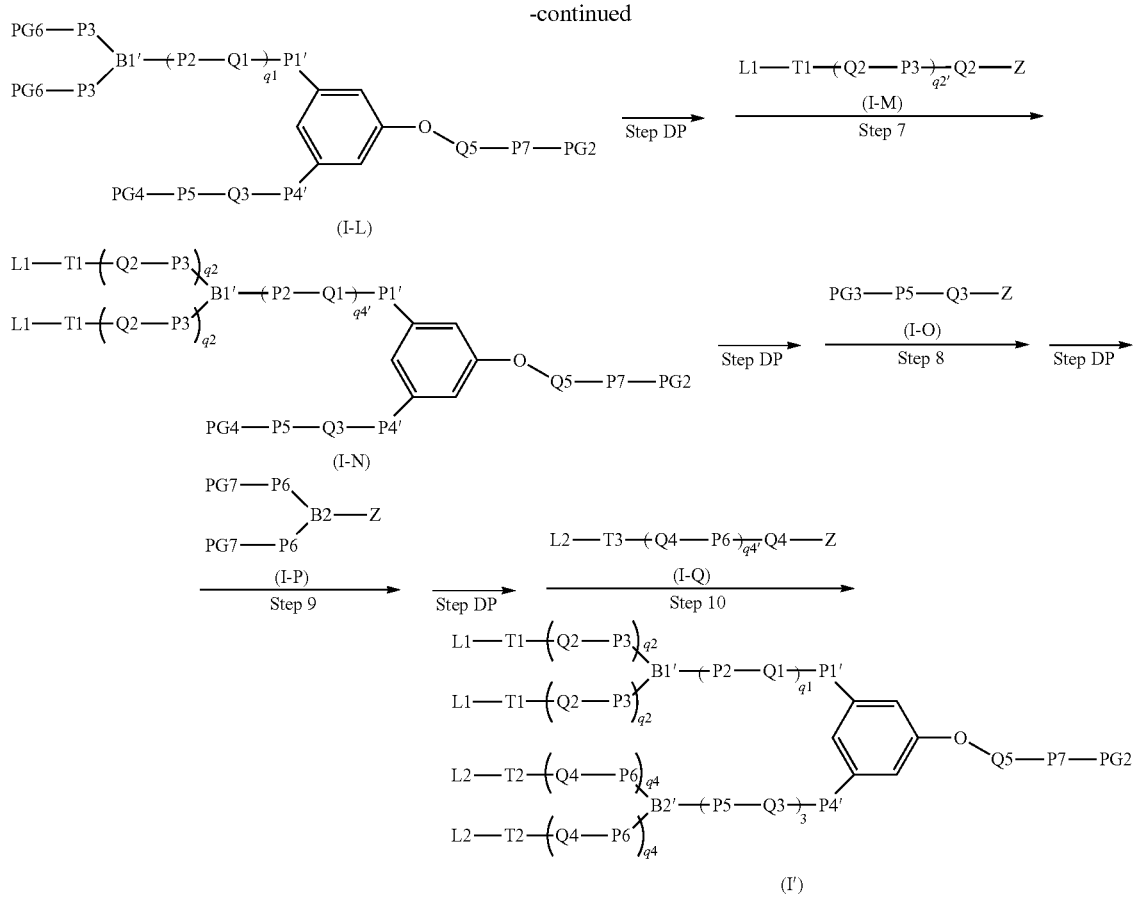

wherein Q1, Q2, Q3, Q4, Q5, P2, P3, P5, P6, P7, T1, T2, L1, L2, q1, q2, q3 and q4 are each as defined above, q2' represents an integer smaller by 1 than q2, q4' represents an integer smaller by 1 than q4, P1' and P4' each independently represent —NH—CO—, —O—CO— or —S—CO—, Z represents H, OH, NH$_2$, SH, a chlorine atom, a bromine atom, an iodine atom, methanesulfonyloxy, p-toluenesulfonyloxy or carboxylic acid, B1' and B2' each represent any one structure of the following formulas, and PG1, PG2, PG3, PG4, PG5, PG6 and PG7 each represent an appropriate protective group.

Formulas:

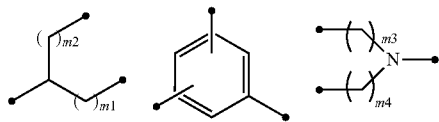

m1, m2, m3 and m4 each independently represent an integer of 0 to 10.

Step 1

Compound (I-C) can be produced by adding polymer-supported triphenylphosphine to compound (I-A) with compound (I-B) in a solvent such as tetrahydrofuran, and reacting the mixture with a solution of diisopropyl azodicarboxylate in toluene under ice cooling.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide (DMF), N,N-dimethylacetamide, N-methylpyrrolidone, pyridine, and water. These solvents may be used alone or as a mixture.

Compound (I-A) can be obtained as a commercially available product.

Step 2

Compound (I-D) can be produced by reacting compound (I-C) under ice cooling in the presence of a base in a solvent such as methanol.

Examples of the solvent include those listed in step 1 of production method 1.

Examples of the base include cesium carbonate, potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), and N,N-dimethyl-4-aminopyridine (DMAP).

Step 3

Compound (1-F) can be produced by reacting compound (I-D) with compound (I-E) at a temperature between room temperature and 200° C. for 5 minutes to 100 hours in the presence of 1 to 30 equivalents of a base, a condensing agent and, if necessary, 0.01 to 30 equivalents of an additive without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide (DMF), N,N-dimethylacetamide, N-methylpyrrolidone, and pyridine. These solvents may be used alone or as a mixture.

Examples of the base include those listed in step 2 of production method 1.

Examples of the condensing agent include 1,3-dicyclohexanecarbodiimide (DCC), 1-ethyl-3-(3-dimethylaminopropyl)carbodiimide hydrochloride (EDC), carbonyldiimidazole, benzotriazol-1-yloxytris(dimethylamino)phosphonium hexafluorophosphate, (benzotriazol-1-yloxy)tripyrrolidinophosphonium hexafluorophosphate, 0-(7-azabenzotriazol-1-yl)-N,N,N',N'-tetramethyluronium hexafluorophosphate (HATU), 0-(benzotriazol-1-yl)-N,N,N',N'-tetramethyluronium hexafluorophosphate (HBTU), and 2-chloro-1-methylpyridinium iodide.

Examples of the additive include 1-hydroxybenzotriazole (HOBt) and 4-dimethylaminopyridine (DMAP).

Step 4

Compound (I-H) can be produced under the same conditions as in step 3 of production method 1 using compound (I-F) and compound (I-G).

Step 5

Compound (I-J) can be produced under the same conditions as in step 3 of production method 1 using compound (I-H) and compound (I-I).

Compound (I-J) having q1 adjusted to the desired value can be produced by repetitively performing step DP and step 5.

Step 6

Compound (I-L) can be produced under the same conditions as in step 3 of production method 1 step 2 of production method 1 using compound (I-J) and compound (I-K).

Step 7

Compound (I-N) can be produced under the same conditions as in step 3 of production method 1 using compound (I-L) and compound (I-M).

Steps 8 to 10

Compound (I') can be produced under the same conditions as in step 3 of production method 1 using compound (I-O), compound (I-P) and compound (I-Q).

Compound (I') having q3 adjusted to the desired value can be produced by repetitively performing step DP and step 8.

Step DP

A method commonly used in organic synthetic chemistry [e.g., a method described in Protective Groups in Organic Synthesis, third edition, T.W. Greene, John Wiley & Sons Inc. (1999)] can be appropriately used in production.

Compound (I-B), compound (I-E), compound (I-G), compound (I-I), compound (I-K), compound (I-M), compound (I-O), compound (I-P) and compound (I-Q) can be obtained as commercially available products, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7th Edition" in combination or methods equivalent thereto.

Production Method 2

A L1-benzene ring unit structure and a L2-benzene ring unit structure in which each of P1 and P4 in formula 2 is —O—, and each of $X_2$ to $X_4$ is CH can be produced by the following method.

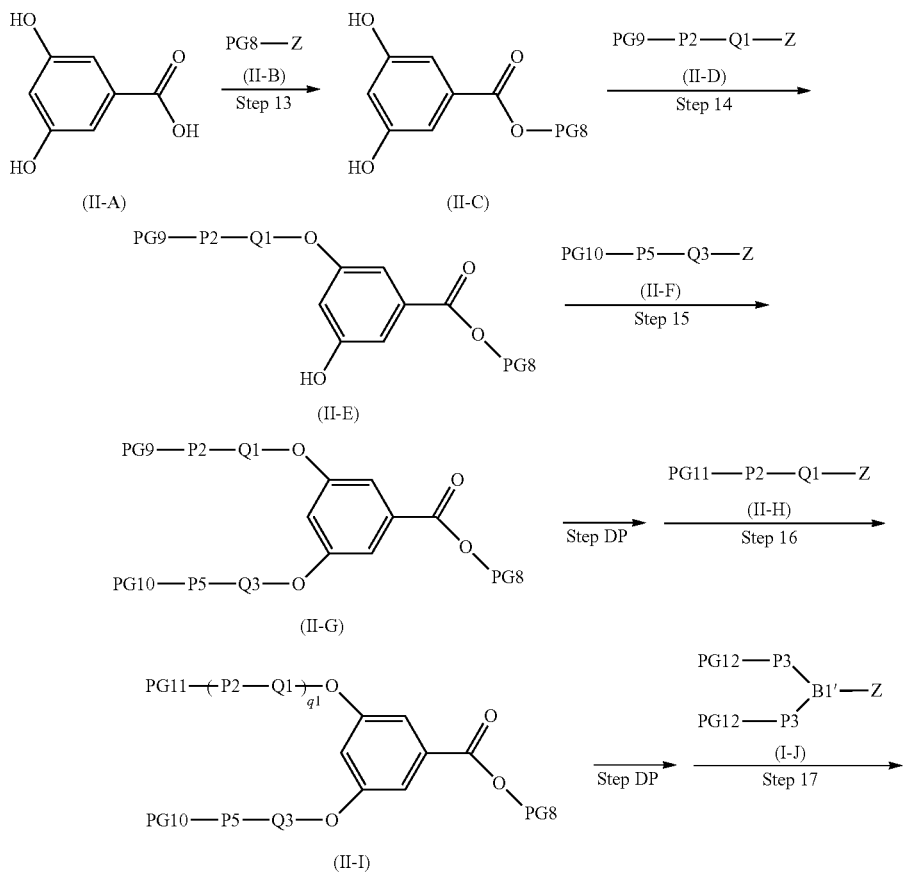

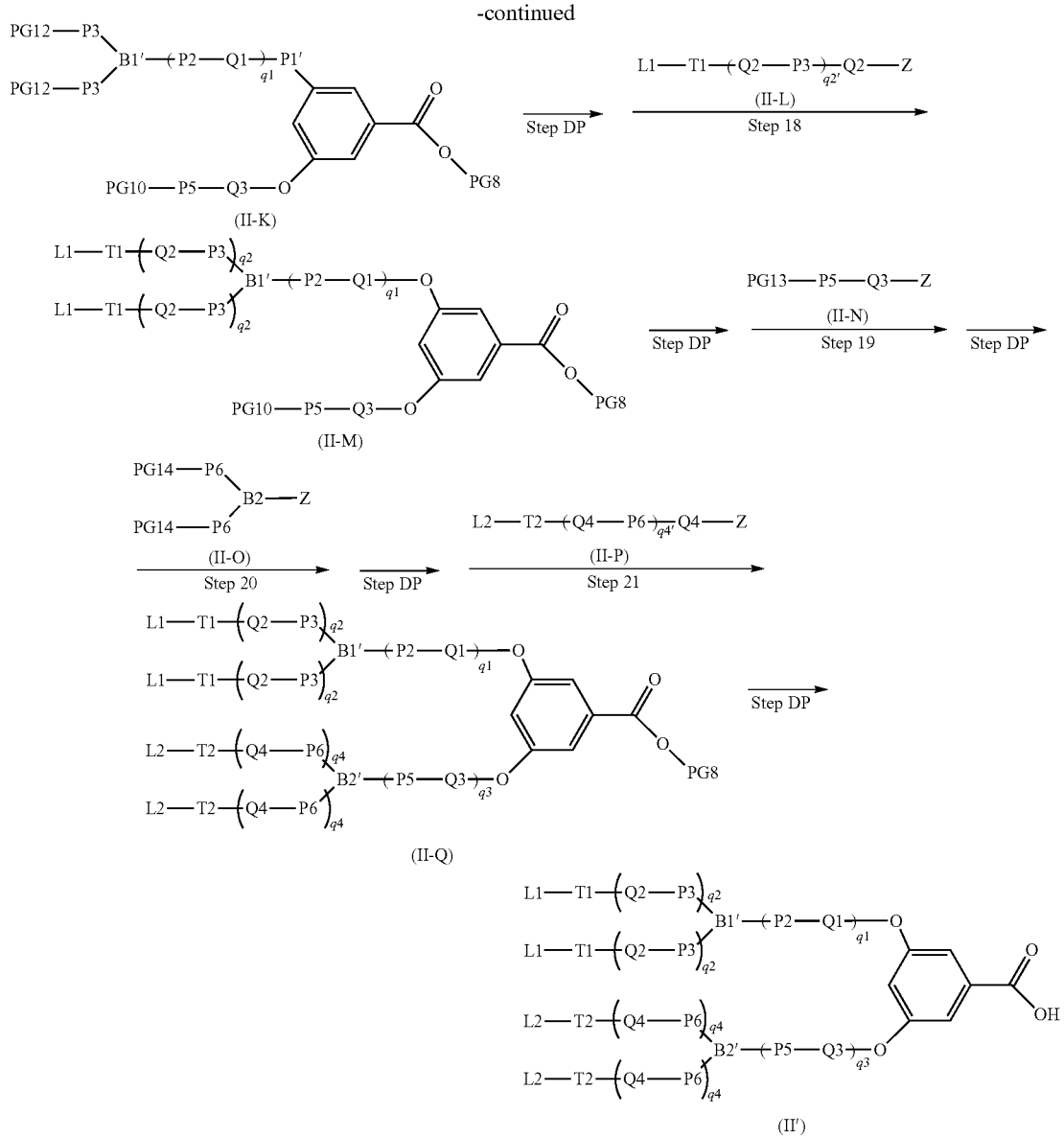

wherein Q1, Q2, Q3, Q4, P2, P3, P5, P6, T1, T2, L1, L2, q1, q2, q3, q4, q2', q4', Z, B1' or B2' are each as defined above, and PG8, PG9, PG10, PG11, PG12, PG13 and PG14 each represent an appropriate protective group.

Step 13

Compound (II-C) can be produced by dissolving compound (II-A) and compound (II-B) in a solvent such as N,N'-dimethylformamide, adding a base such as potassium bicarbonate to the solution, and reacting the mixture at room temperature to 200° C. for 5 minutes to 100 hours.

Examples of the solvent include those listed in step 2 of production method 1.

Examples of the base include those listed in step 3 of production method 1.

Step 14

Compound (II-E) can be produced by dissolving compound (II-C) and compound (II-D) in a solvent such as N,N'-dimethylformamide, adding a base such as potassium bicarbonate to the solution, and reacting the mixture at room temperature to 200° C. for 5 minutes to 100 hours.

Examples of the solvent include those listed in step 2 of production method 1.

Examples of the base include those listed in step 3 of production method 1.

Compound (II-A) can be obtained as a commercially available product.

Step 15

Compound (II-G) can be produced under the same conditions as in step 3 of production method 1 using compound (II-E) and compound (II-F).

Step 16

Compound (II-I) can be produced under the same conditions as in step 3 of production method 1 using compound (II-G) and compound (II-H).

Compound (II-I) having q1 adjusted to the desired value can be produced by repetitively performing step DP and step 16.

Step 17

Compound (II-K) can be produced under the same conditions as in step 2 of production method 1 using compound (II-I) and compound (II-J).

Step 18

Compound (II-M) can be produced under the same conditions as in step 3 of production method 1 using compound (II-K) and compound (II-L).

Steps 19 to 21

Compound (II') can be produced under the same conditions as in step 3 of production method 1 using compound (II-M), compound (II-N), compound (II-O) and compound (II-P).

Compound (II') having q3 adjusted to the desired value can be produced by repetitively performing step DP and step 19.

Step DP

A method commonly used in organic synthetic chemistry [e.g., a method described in Protective Groups in Organic Synthesis, third edition, T.W. Greene, John Wiley & Sons Inc. (1999)] can be appropriately used in production.

Compound (II-B), compound (II-D), compound (II-F), compound (II-H), compound (II-J), compound (II-L), compound (II-N), compound (II-O) and compound (II-P) can be obtained as commercially available products, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7th Edition" in combination or methods equivalent thereto.

In the present invention, a compound represented by the following formula 6 is obtained as an intermediate.

Formula 6

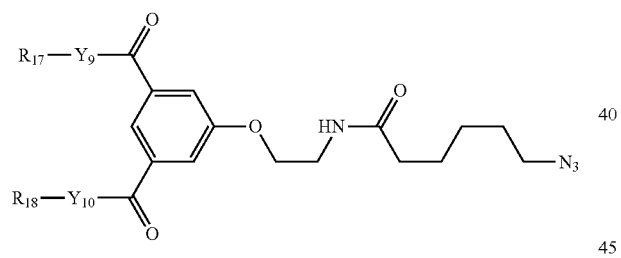

wherein
- $Y_9$ and $Y_{10}$ may be groups represented by P1 and P4 and each are preferably an oxygen atom or —NH—,
- $R_{17}$ and $R_{18}$ are each independently a hydrogen atom, a maleimide group, a substituted or unsubstituted alkyl group having 1 to 20 carbon atoms, a t-butoxycarbonyl group (Boc group), a benzyloxycarbonyl group (Z group), a 9-fluorenylmethyloxycarbonyl group (Fmoc group), -[Q8-P9]$_{q7}$-R$_{19}$, or -[Q9-P10]$_{q8}$-B4-[(P11-Q10)$_{q7}$]$_{p3}$-T3-L3,
- P9 to P11 and T3 are each independently absent, or —CO—, —NH—, —O—, —S—, —O—CO—, —S—CO—, —NH—CO—, —CO—O—, —CO—S— or —CO—NH—,
- each of Q8 to Q10 is absent, or substituted or unsubstituted alkylene having 2 to 12 carbon atoms, —CH$_2$CH$_2$—(OCH$_2$CH$_2$O)n- or —CH$_2$CH$_2$—(CH$_2$CH$_2$O)n-CH$_2$CH$_2$—, n is an integer of 0 to 99,
- R19 is a hydrogen atom, a maleimide group, a substituted or unsubstituted alkyl group having 1 to 20 carbon atoms, a t-butoxycarbonyl group (Boc group), a benzyloxycarbonyl group (Z group), or a 9-fluorenylmethyloxycarbonyl group (Fmoc group),
- B4 is a bond or a carbon skeleton structure selected from the group consisting of the following formulas, wherein each of the terminal dots in each carbon skeleton structure is a binding site to a carbonyl group or P9, and m1 and m2 are each independently an integer of 0 to 10:

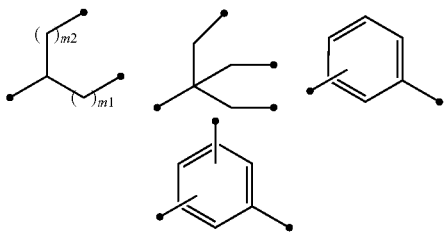

- p3 is an integer of 1, 2 or 3,
- q7 is an integer of 0 to 10, and
- L3 is an optionally protected sugar chain ligand.

In the present invention, the nucleic acid conjugate of the present invention can be produced by reacting a compound of formula 6 having a sugar chain ligand with a compound of formula 7.

Formula 7

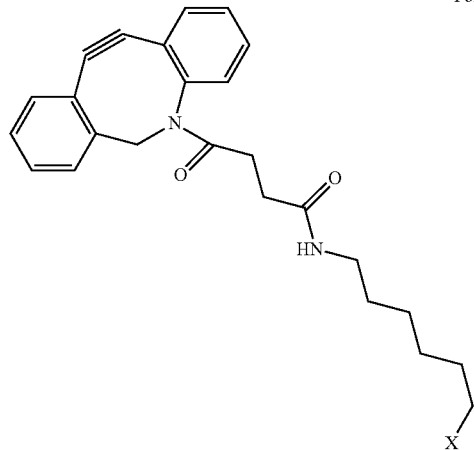

The nucleic acid conjugate described in the present specification may be obtained as a salt, for example, an acid-addition salt, a metal salt, an ammonium salt, an organic amine-addition salt, or an amino acid-addition salt.

Examples of the acid-addition salt include: inorganic acid salts such as hydrochloride, sulfate, and phosphate; and organic acid salts such as acetate, maleate, fumarate, citrate, and methanesulfonate. Examples of the metal salt include: alkali metal salts such as sodium salt and potassium salt; alkaline earth metal salts such as magnesium salt and calcium salt; and aluminum salt and zinc salt. Examples of the ammonium salt include salts of ammonium, tetramethylammonium, and the like. Examples of the organic amine-addition salt include addition salts of morpholine, piperidine, and the like. Examples of the amino acid-addition salt include addition salts of lysine, glycine, phenylalanine, and the like.

In the case of preparing the salt of the nucleic acid conjugate described in the present specification, the conjugate obtained in the form of the desired salt can be purified directly, or the conjugate obtained in a free form can be dissolved or suspended in an appropriate solvent, and a corresponding acid or base is added to the solution or the suspension, followed by isolation or purification. In order to convert counter ions forming the conjugate salt to different counter ions, the conjugate salt can be dissolved or suspended in an appropriate solvent, and then, several equivalents to a large excess of an acid, a base and/or a salt (e.g., an inorganic salt such as sodium chloride or ammonium chloride) is added to the solution or the suspension, followed by isolation or purification.

Some nucleic acid conjugates described in the present specification may have stereoisomers such as geometric isomers and optical isomers, tautomers, or the like. All possible isomers and mixtures thereof are also encompassed in the present invention.

The nucleic acid conjugate described in the present specification may be present in the form of an adduct with water or various solvents. These adducts are also encompassed in the present invention.

The nucleic acid conjugate of the present invention further encompasses molecules in which a portion or the whole of the atoms is substituted with an atom having an atomic mass number different therefrom (isotope) (e.g., a deuterium atom).

Specific examples of the nucleic acid conjugate of the present invention will be shown. However, the nucleic acid conjugate of the present invention is not limited thereto. In the drawings, each band-like structure represents an oligonucleotide.

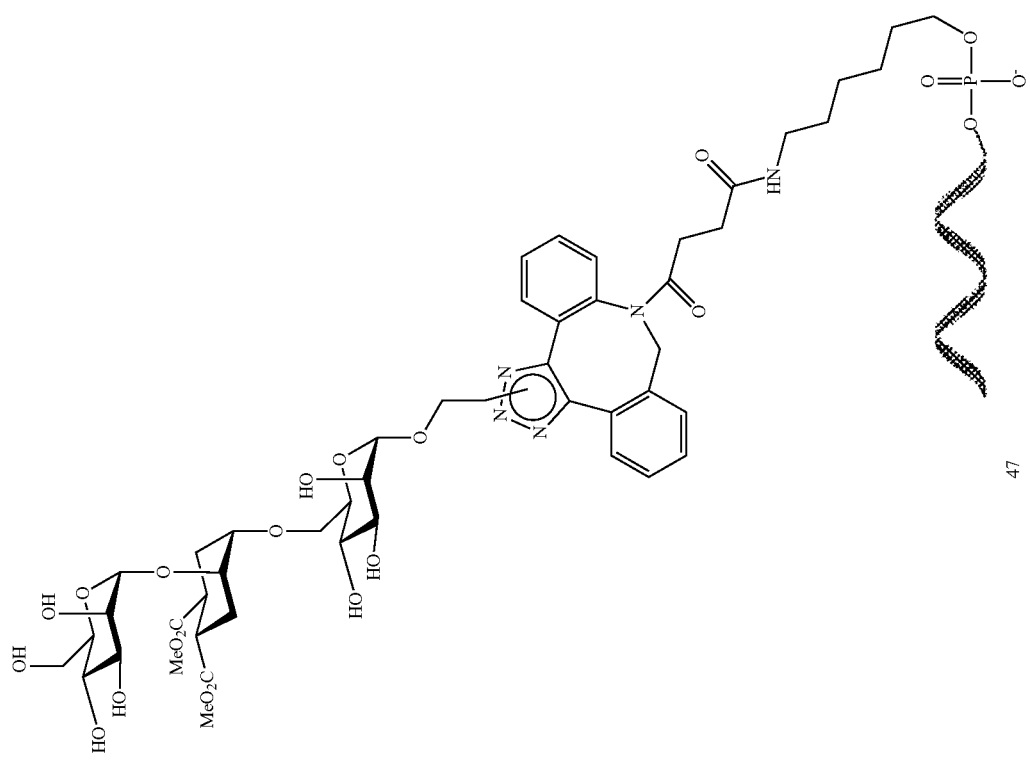

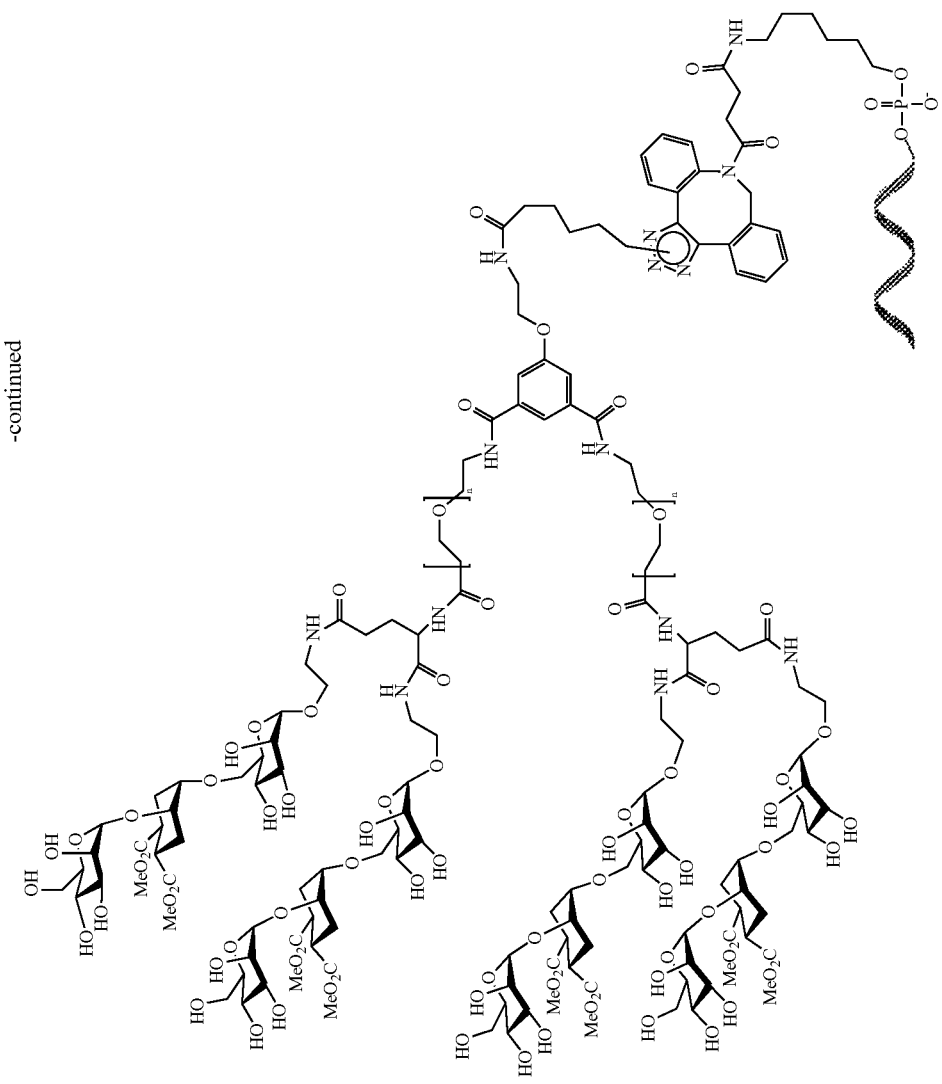
49a: n = 12
49b: n = 24

-continued
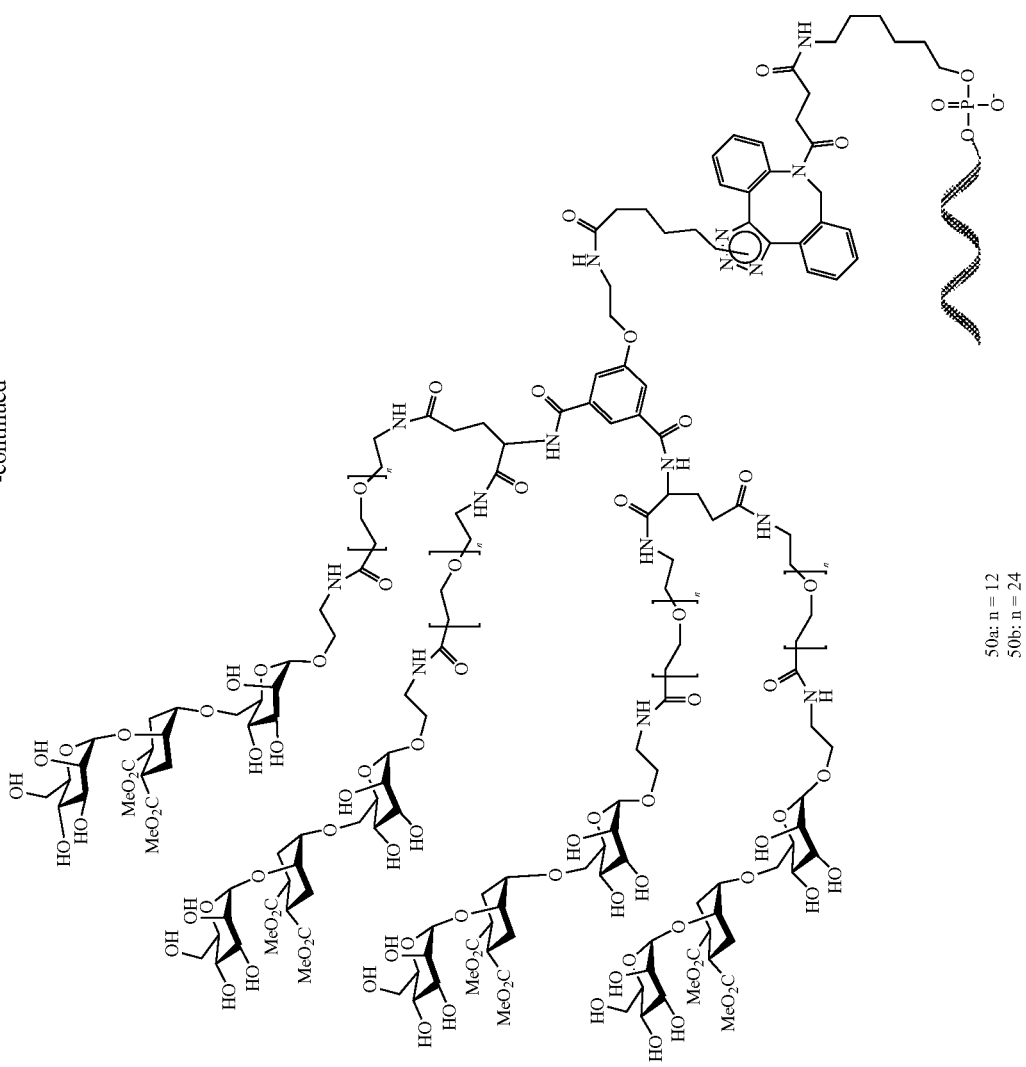
50a: n = 12
50b: n = 24

-continued
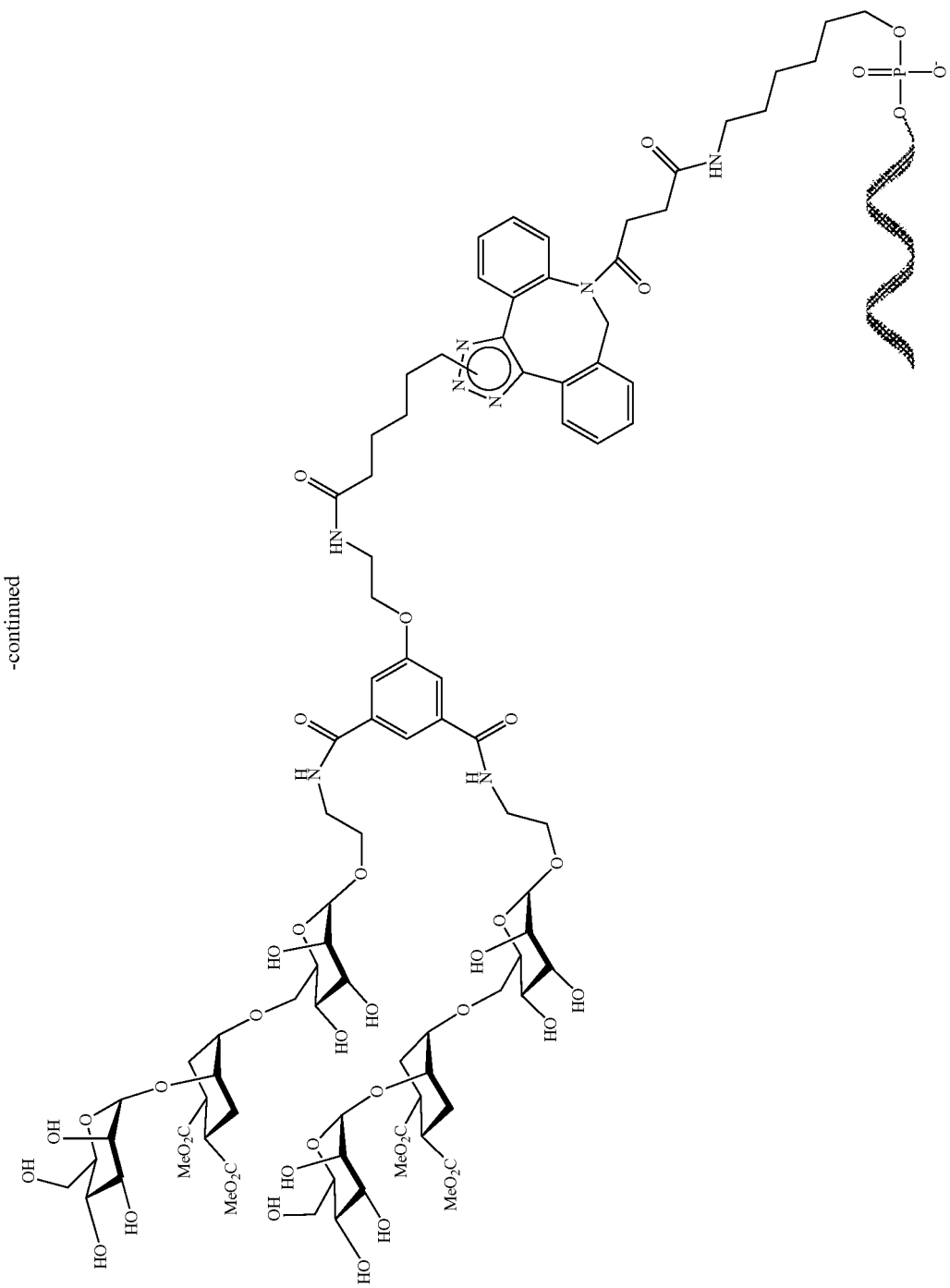
51

-continued
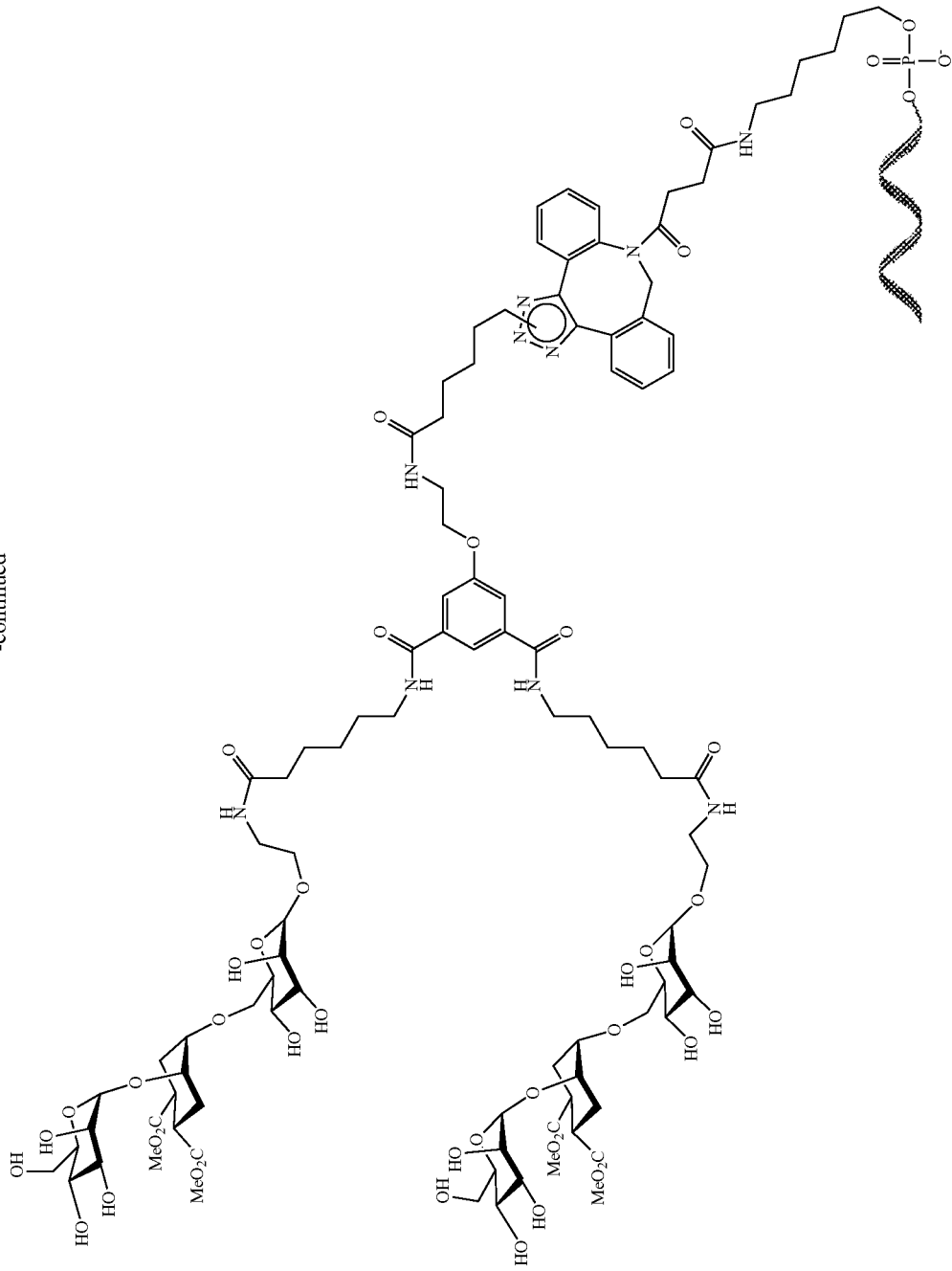
52

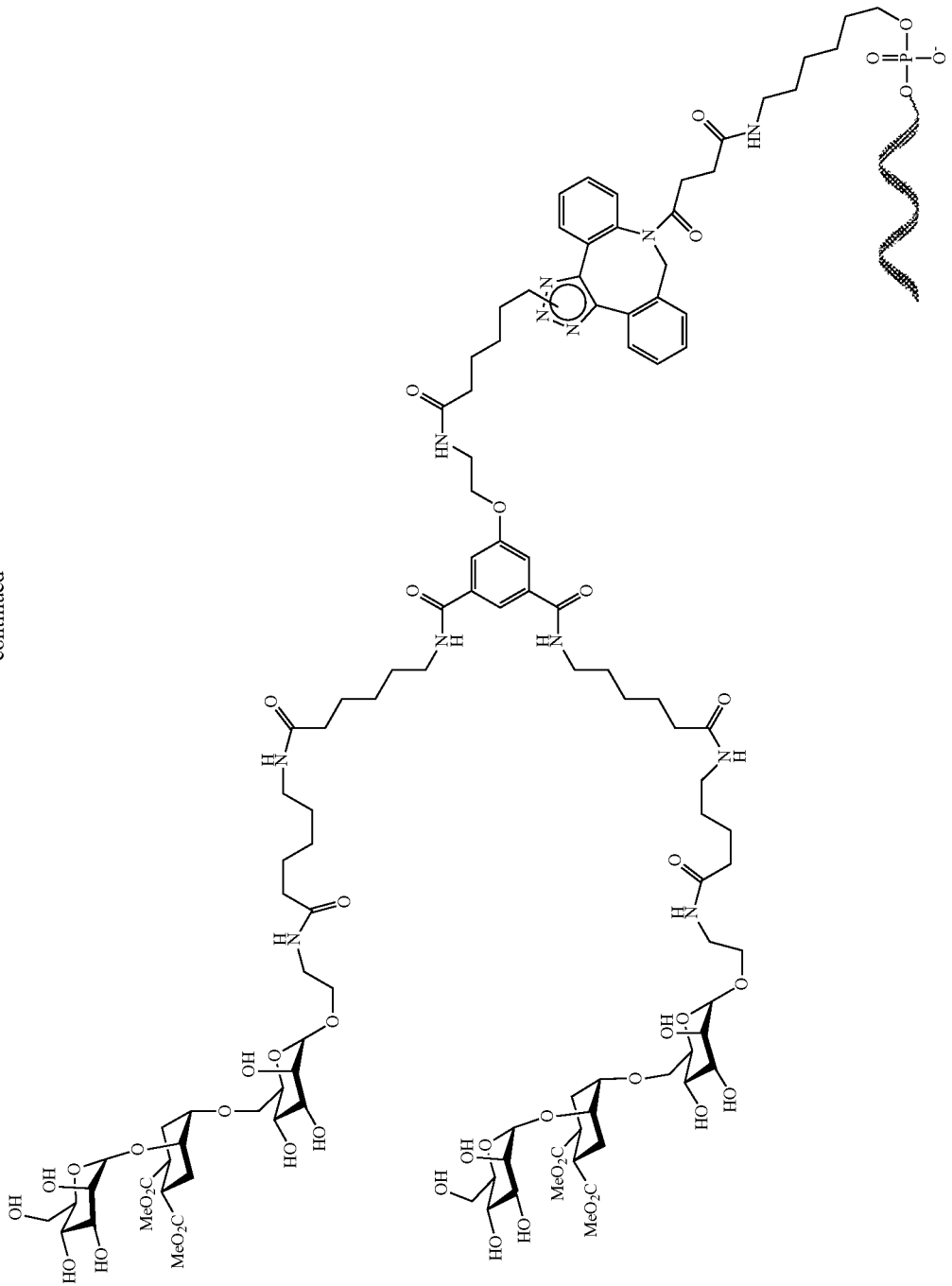

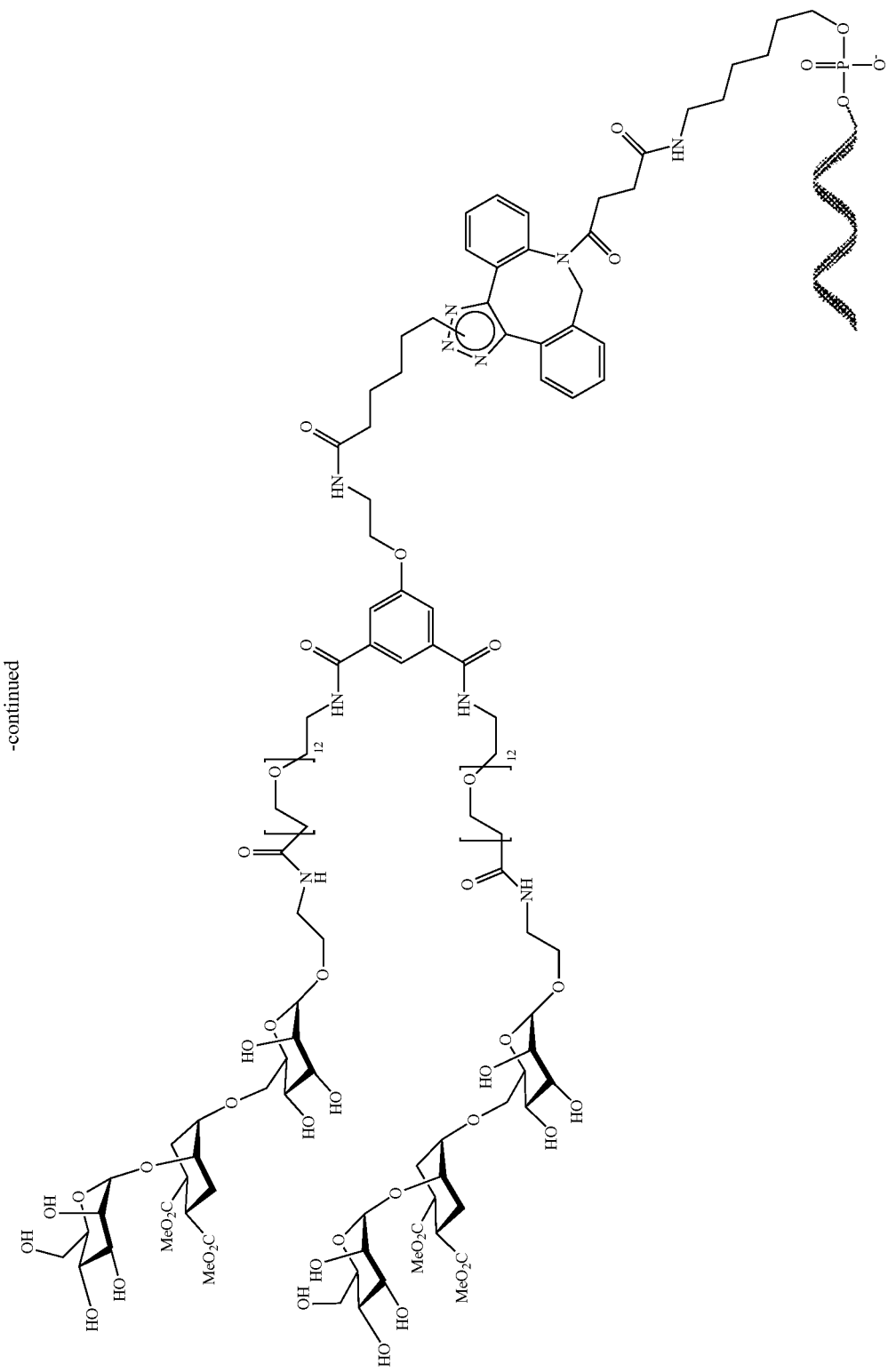

-continued
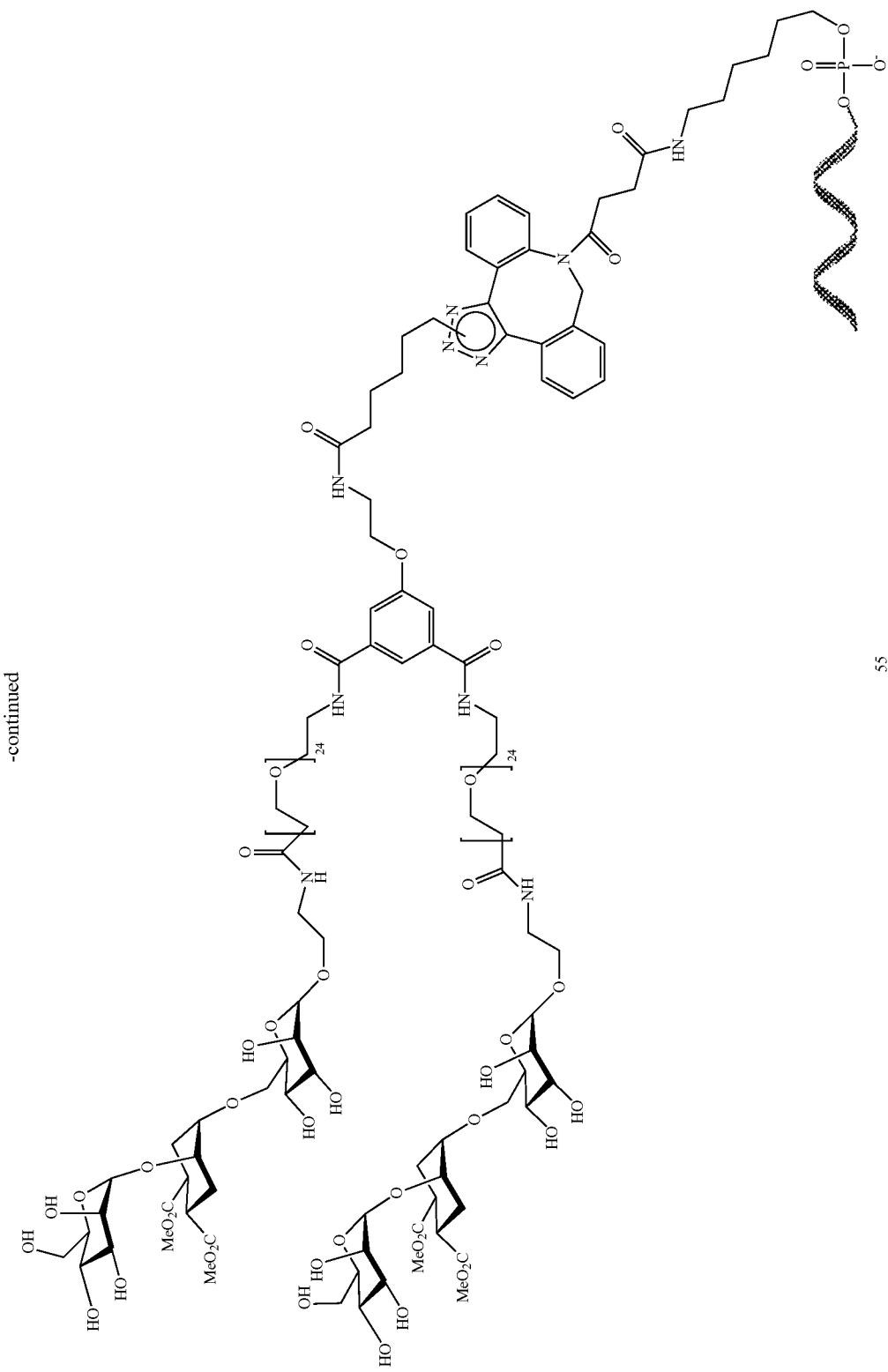

-continued
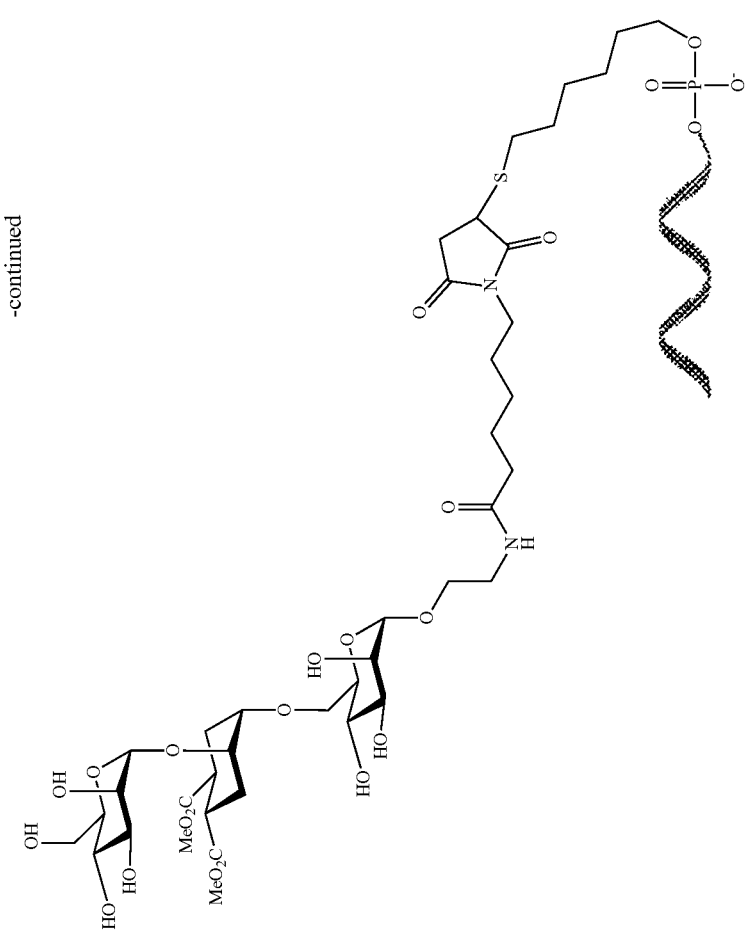
56

-continued
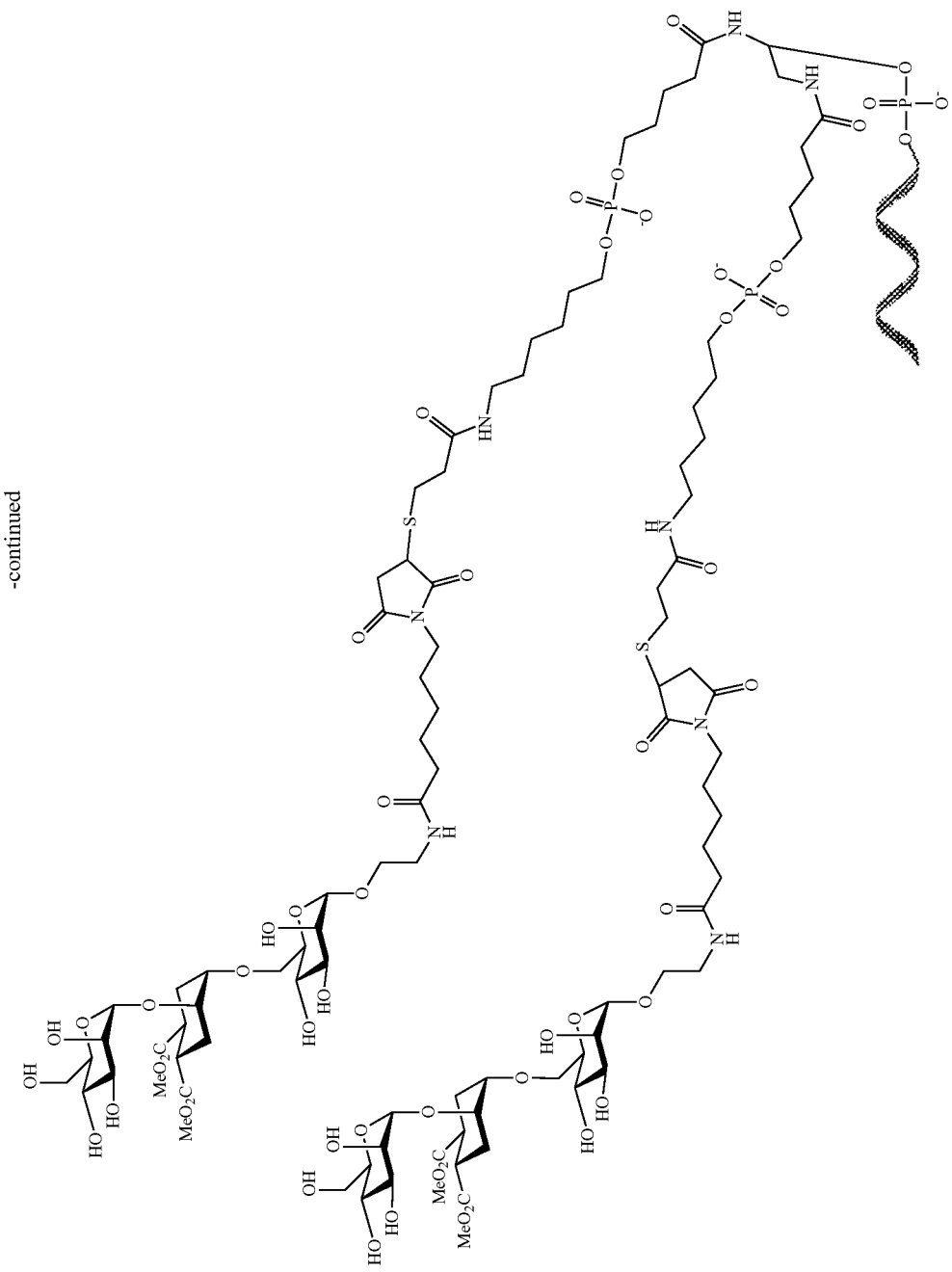
56

-continued
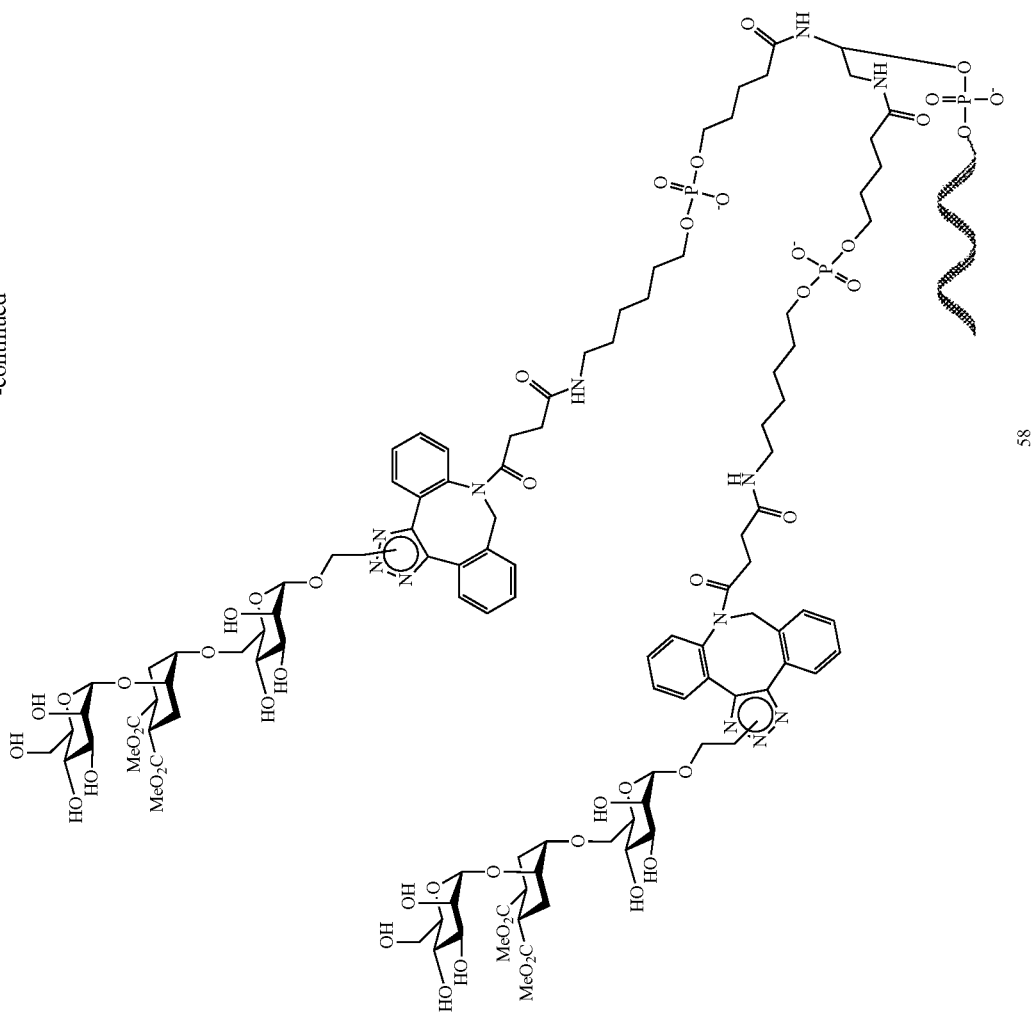
58

-continued
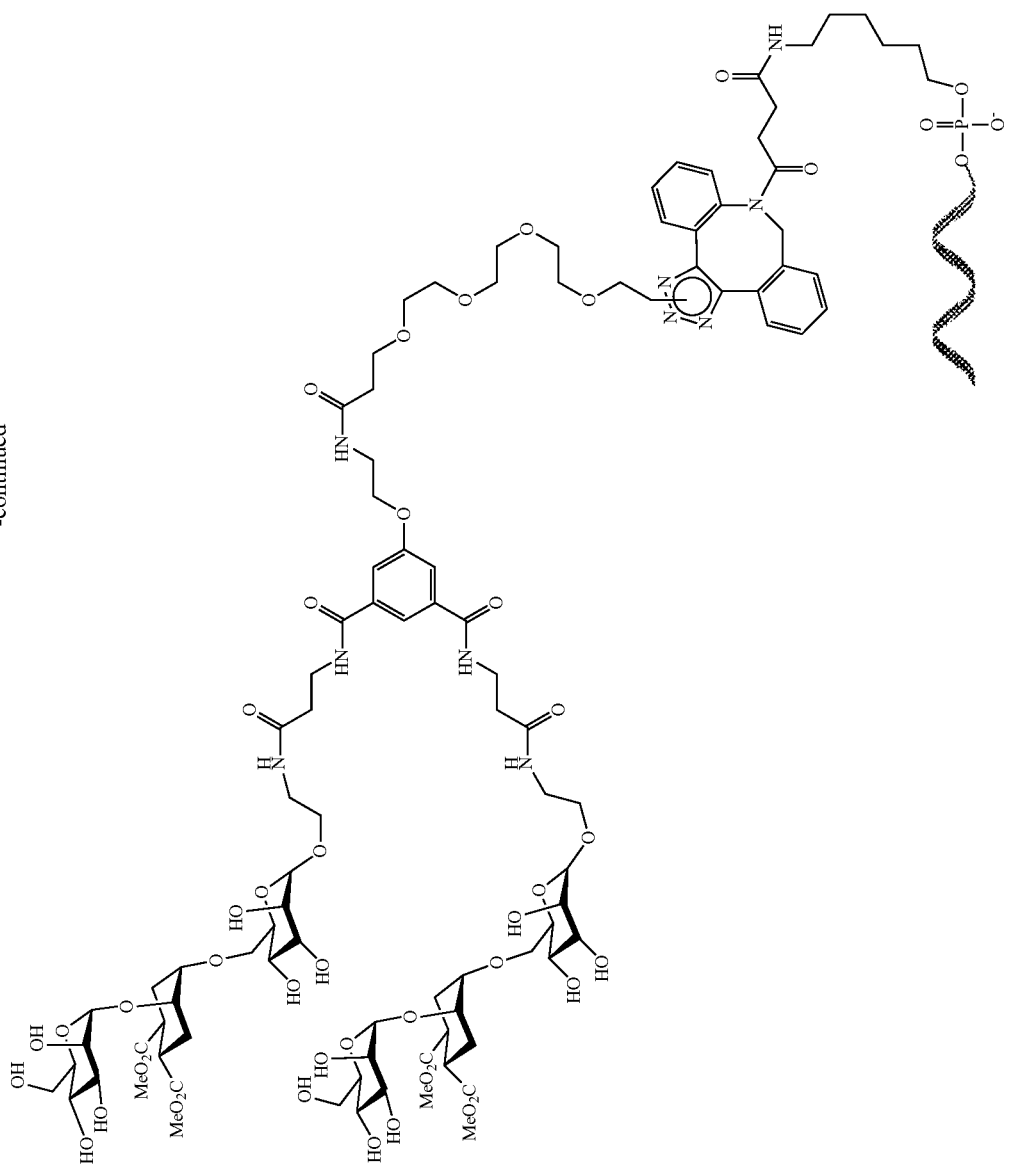

-continued
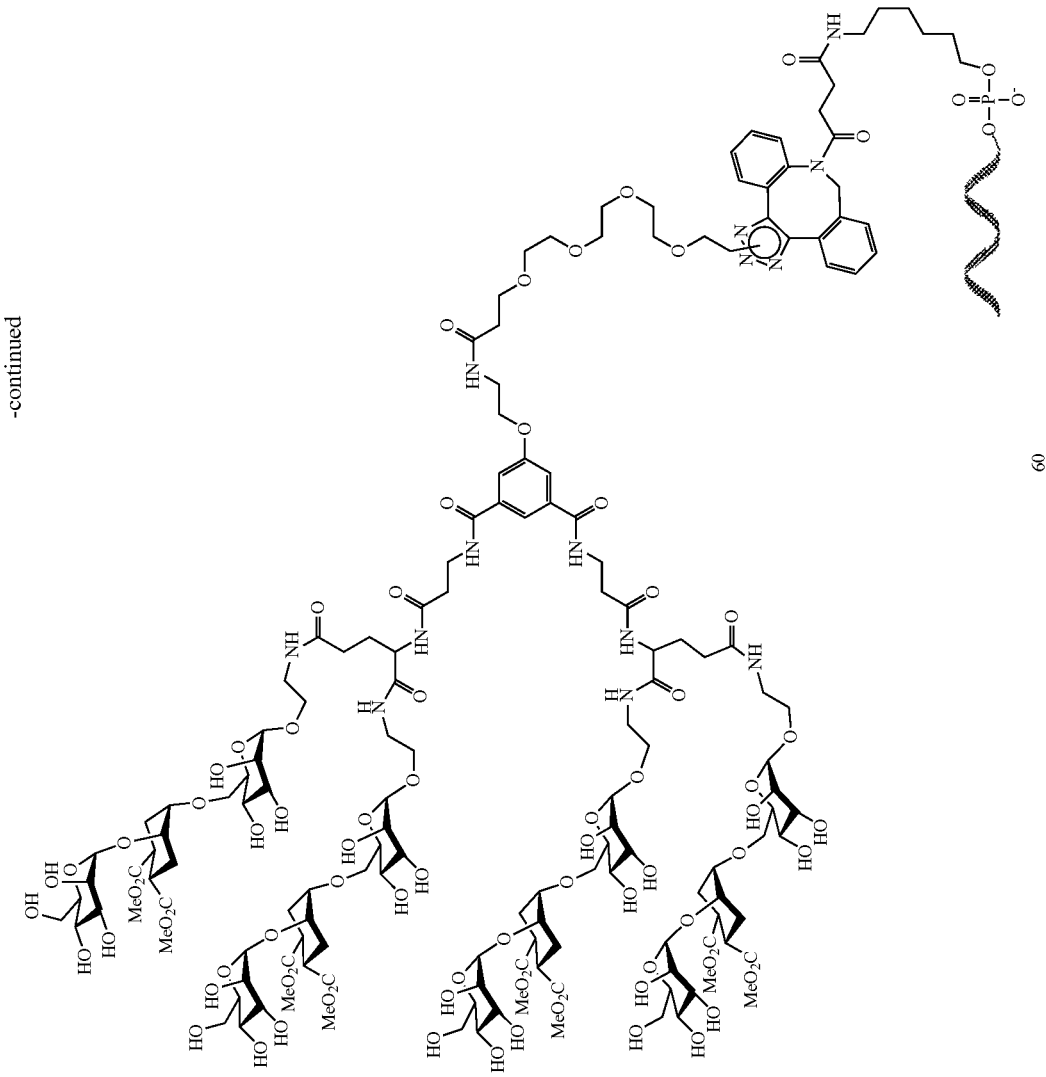

-continued
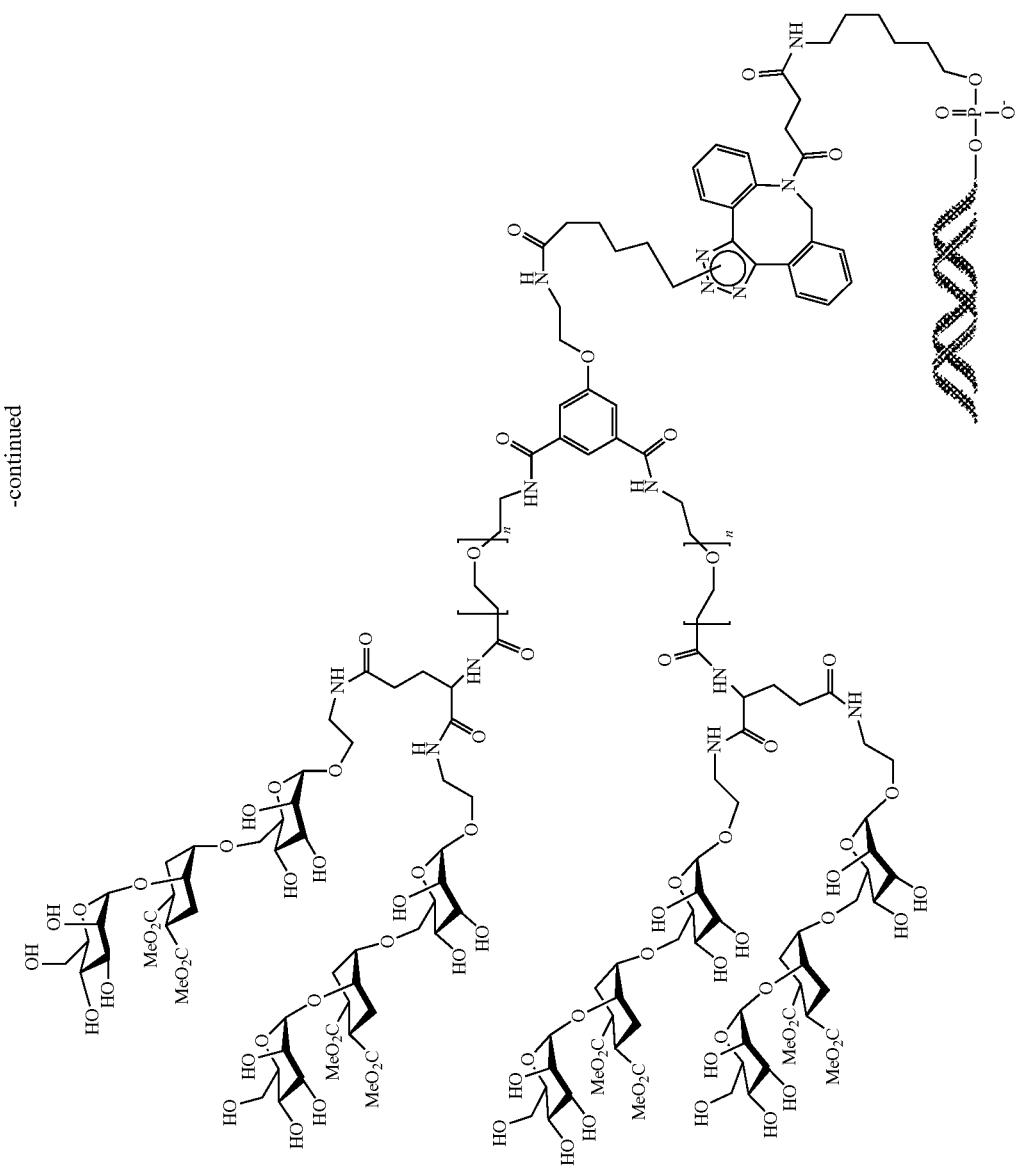
61: n = 24

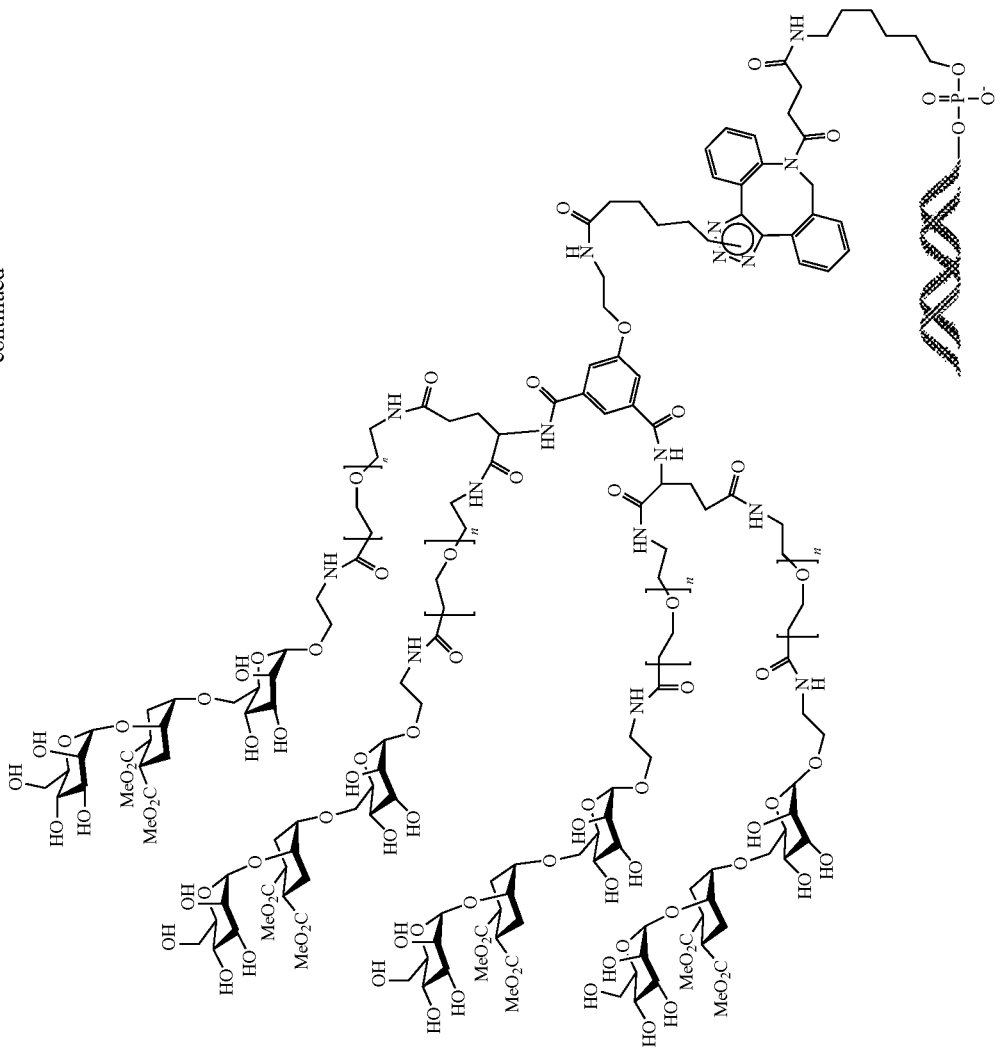

-continued
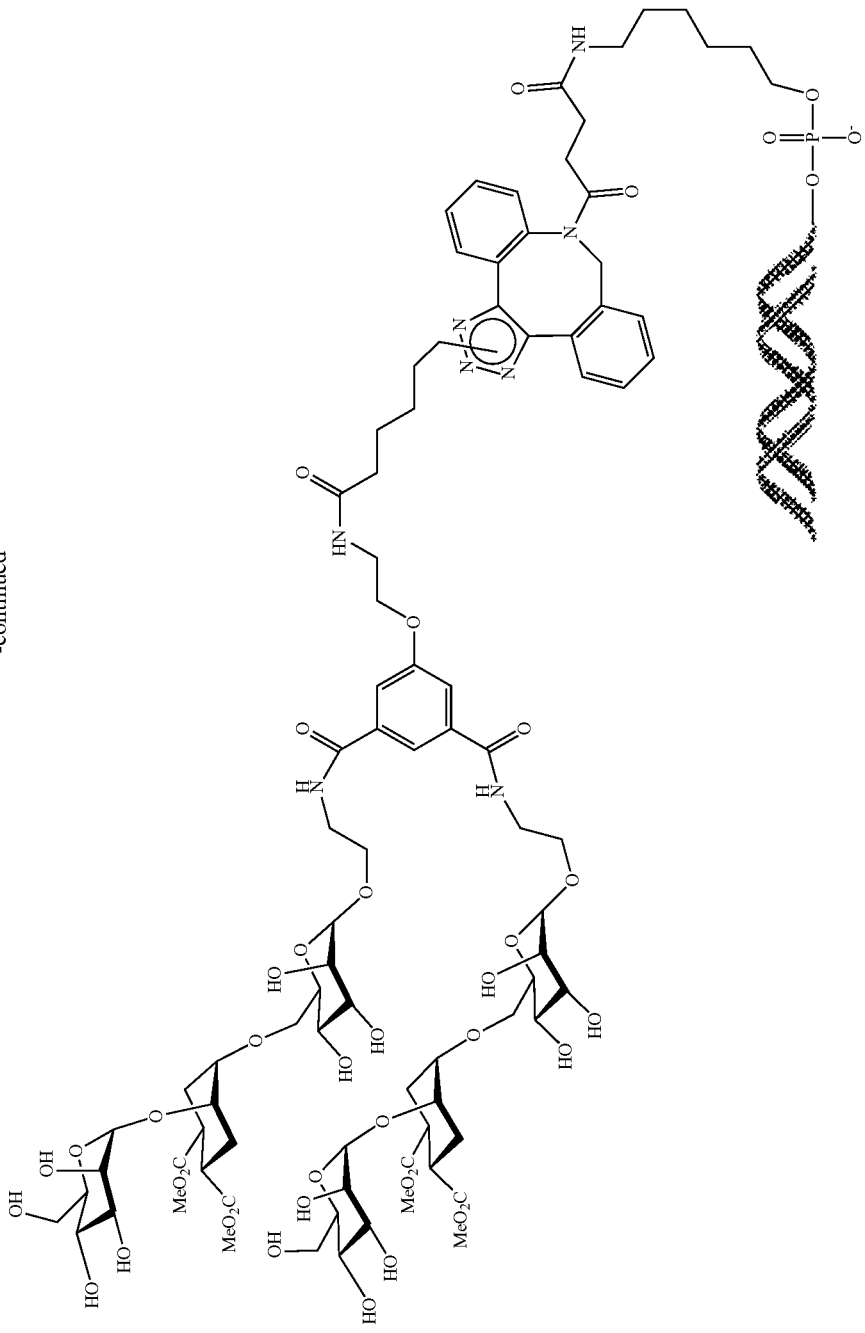
63

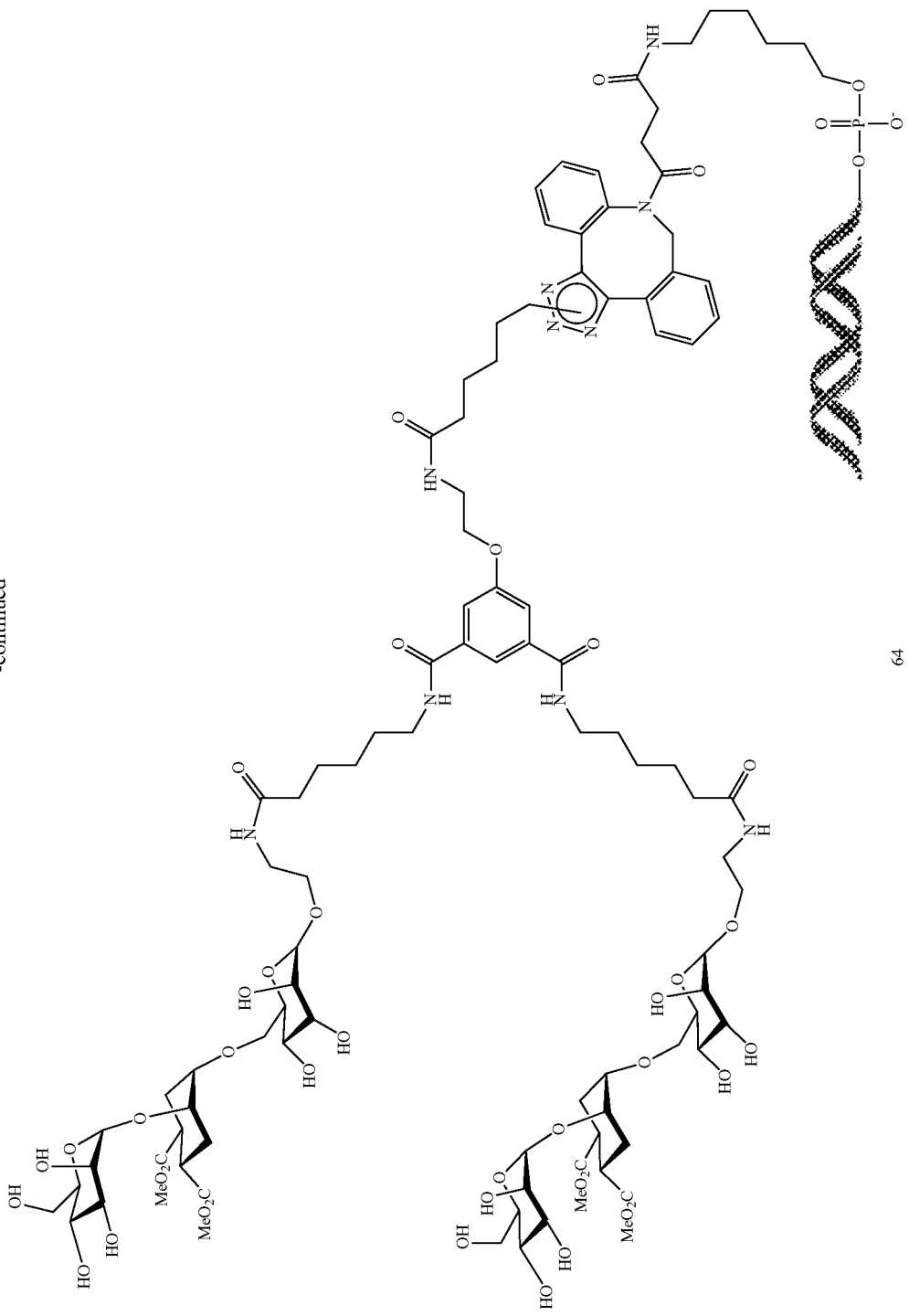

-continued
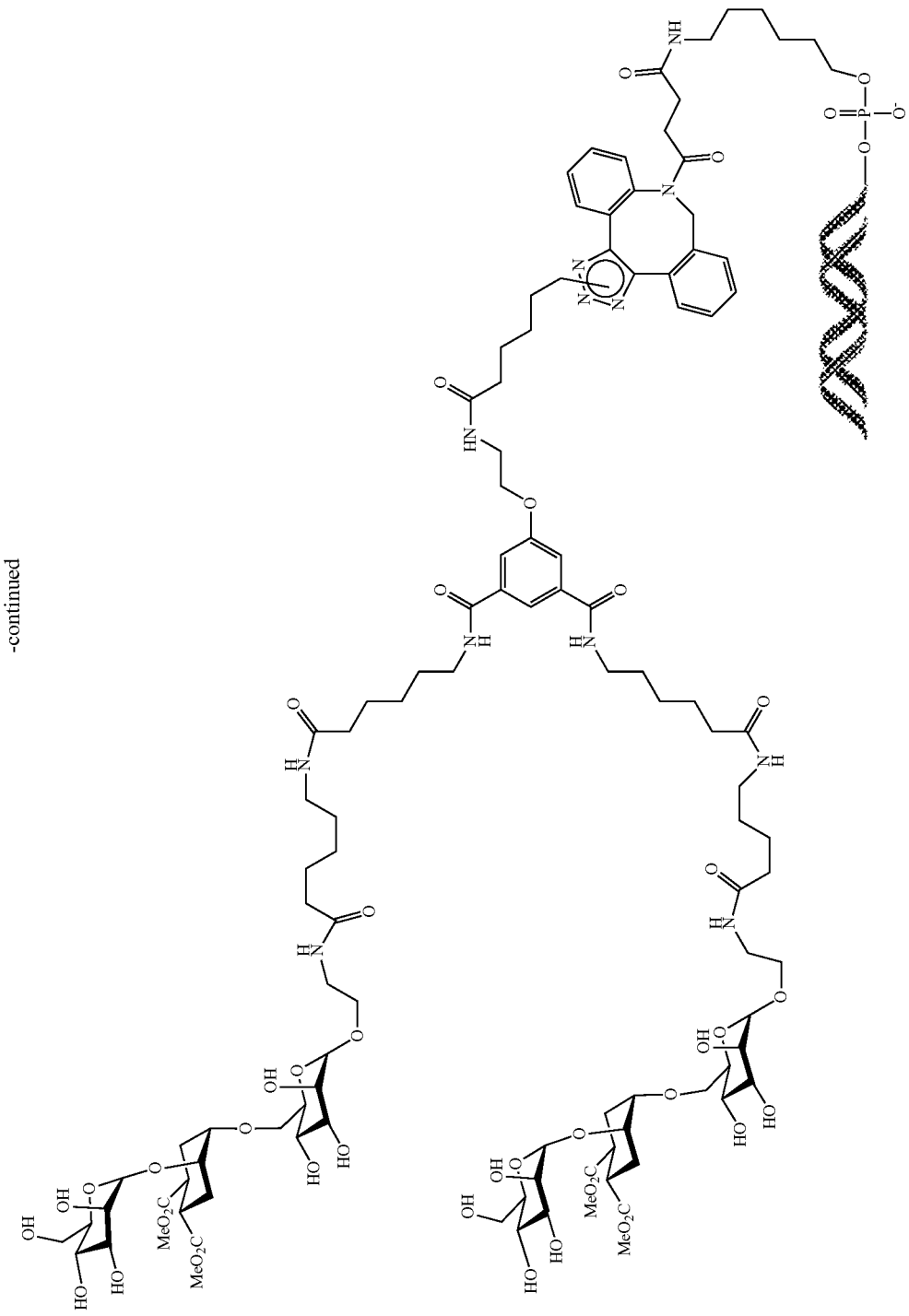
65

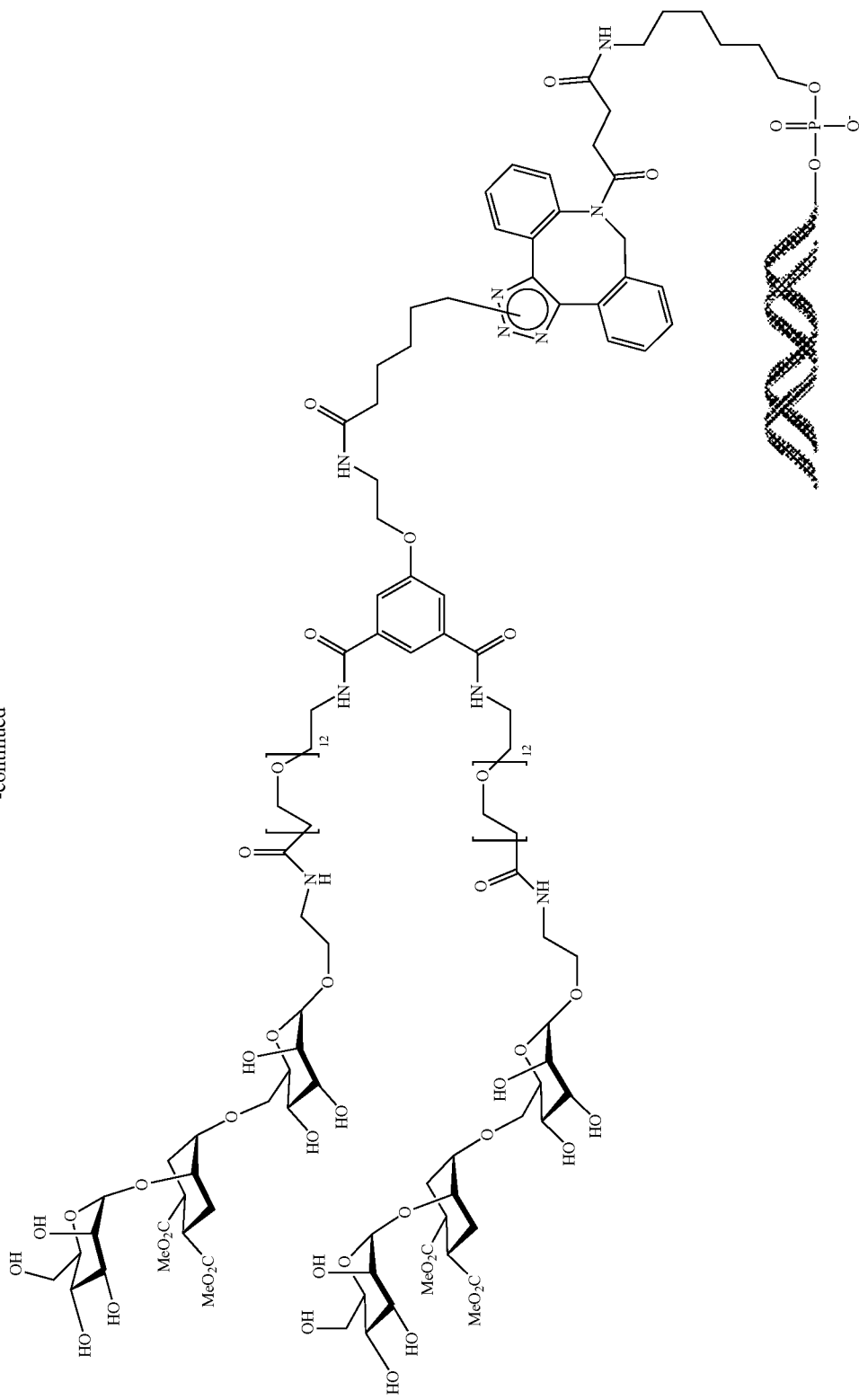

67
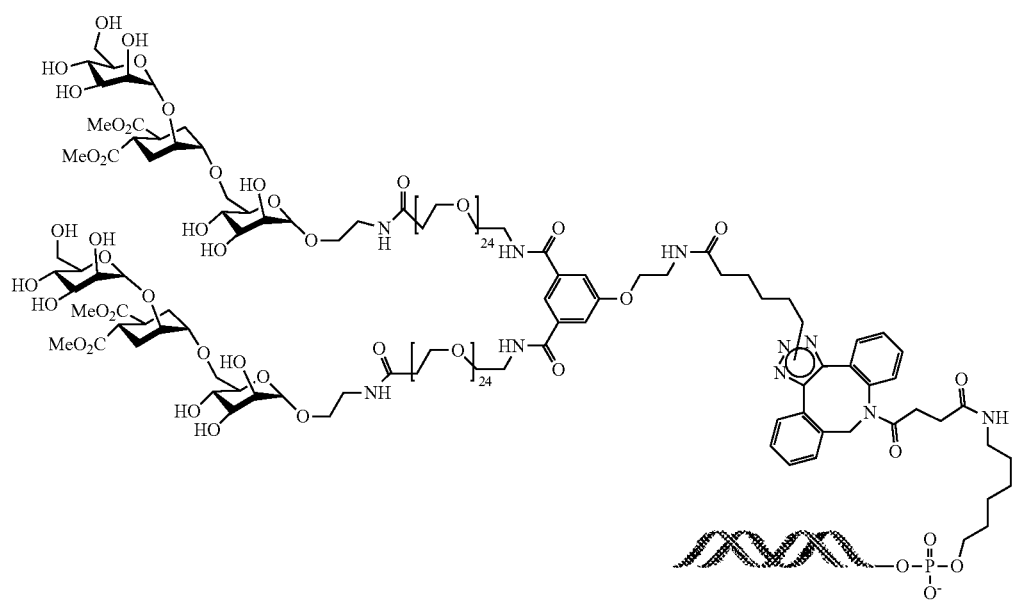
68
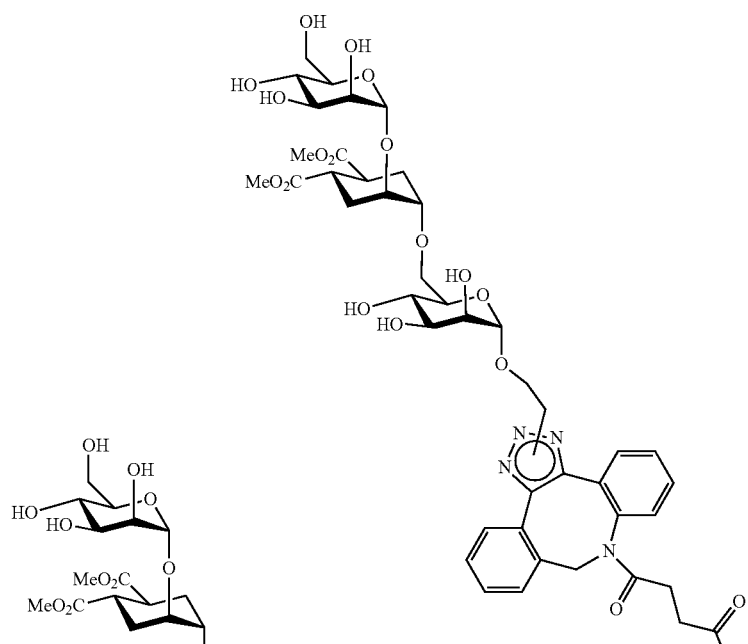

121
122
-continued
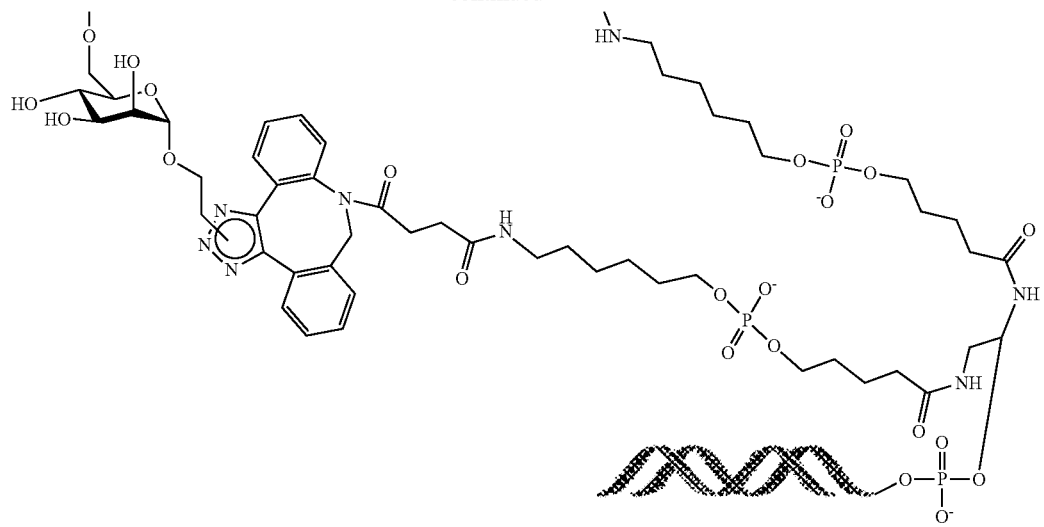
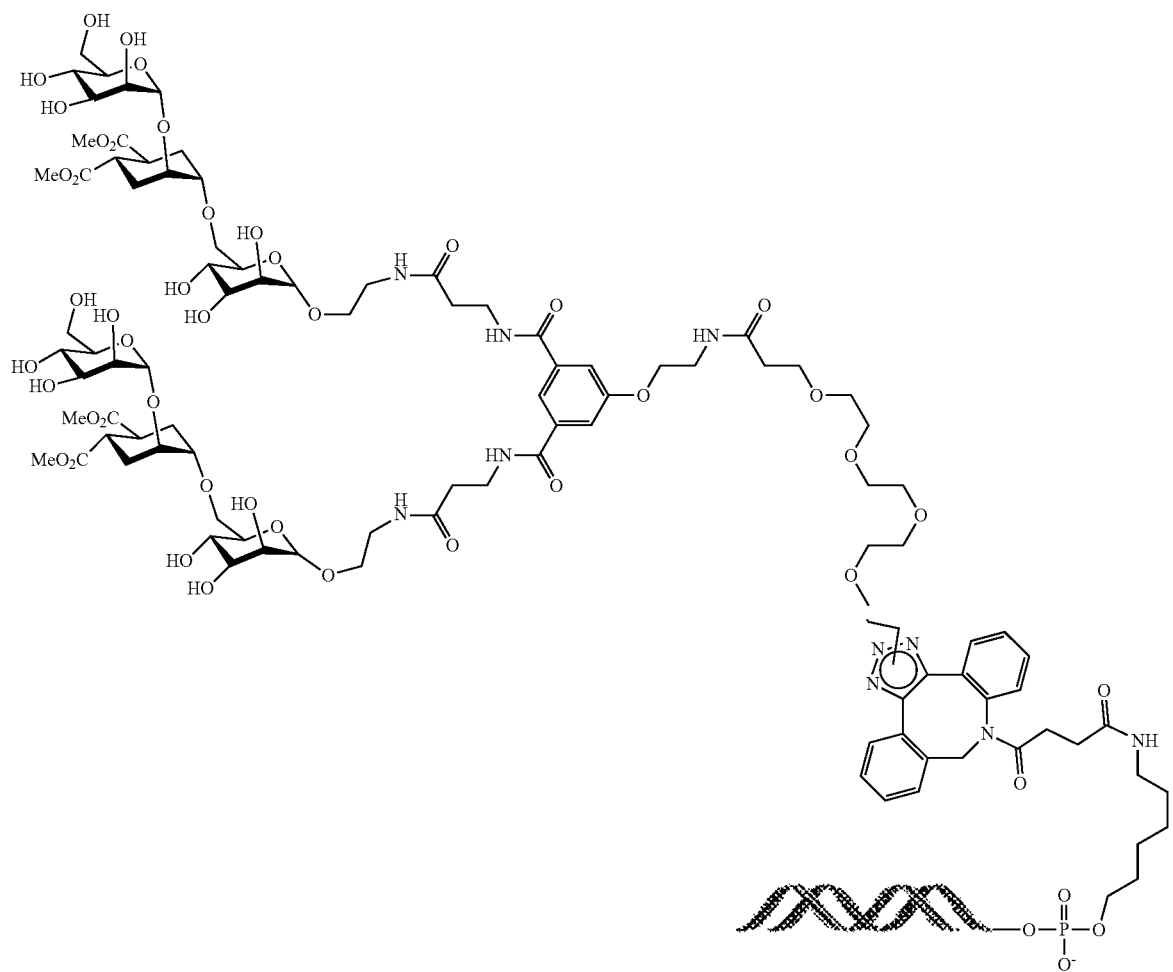

-continued
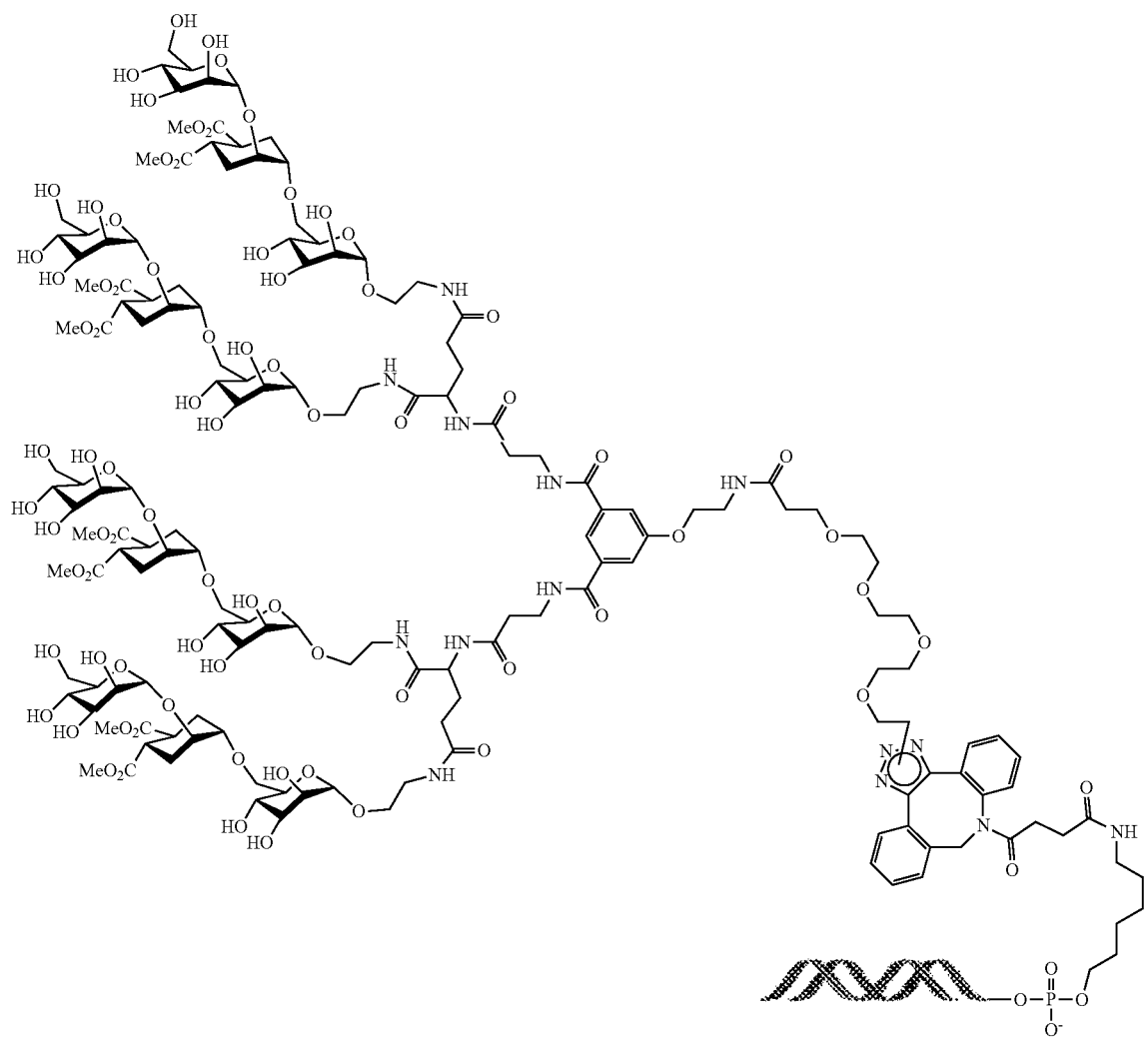
70

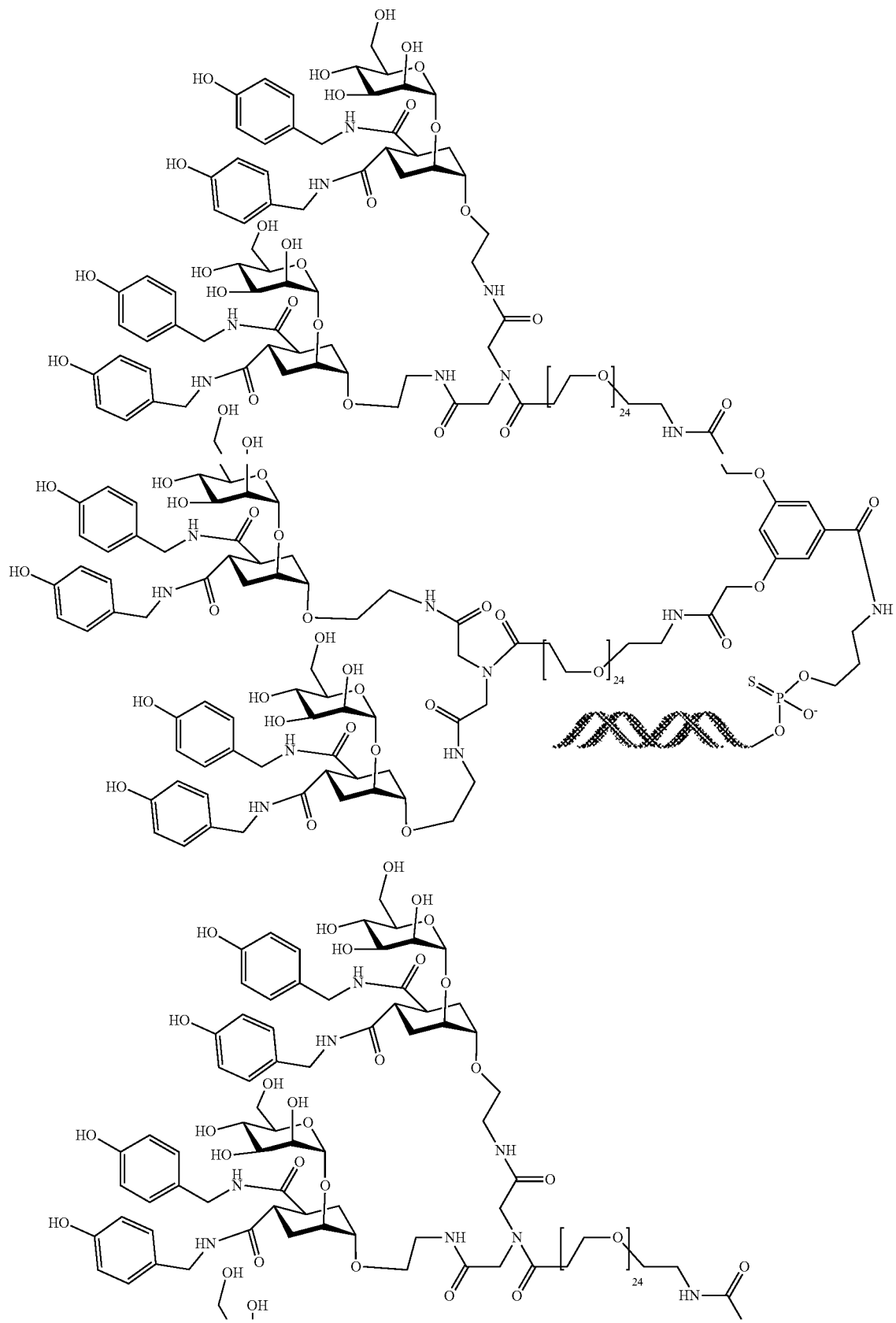
125 126

127 128
-continued
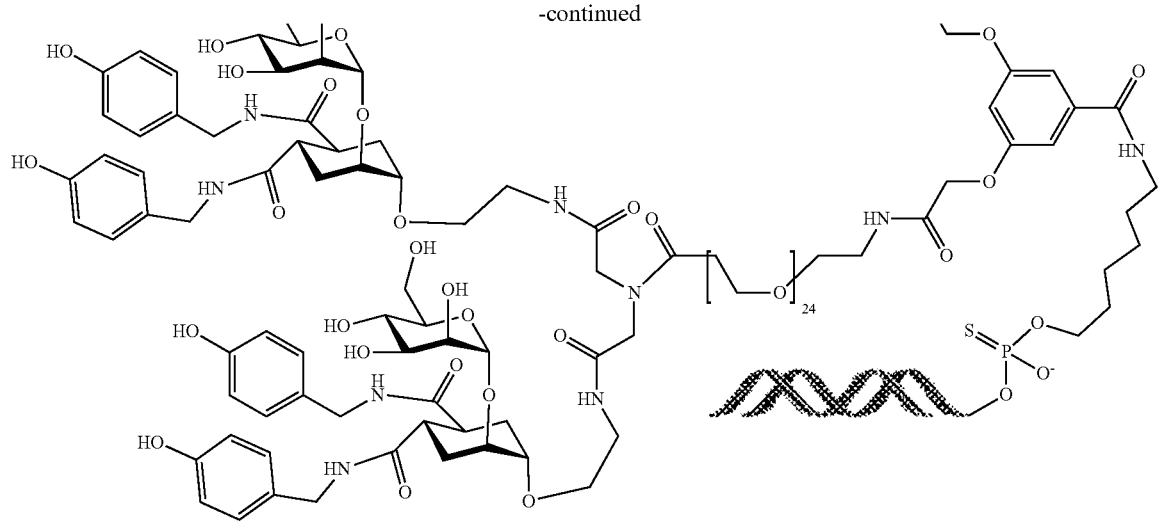
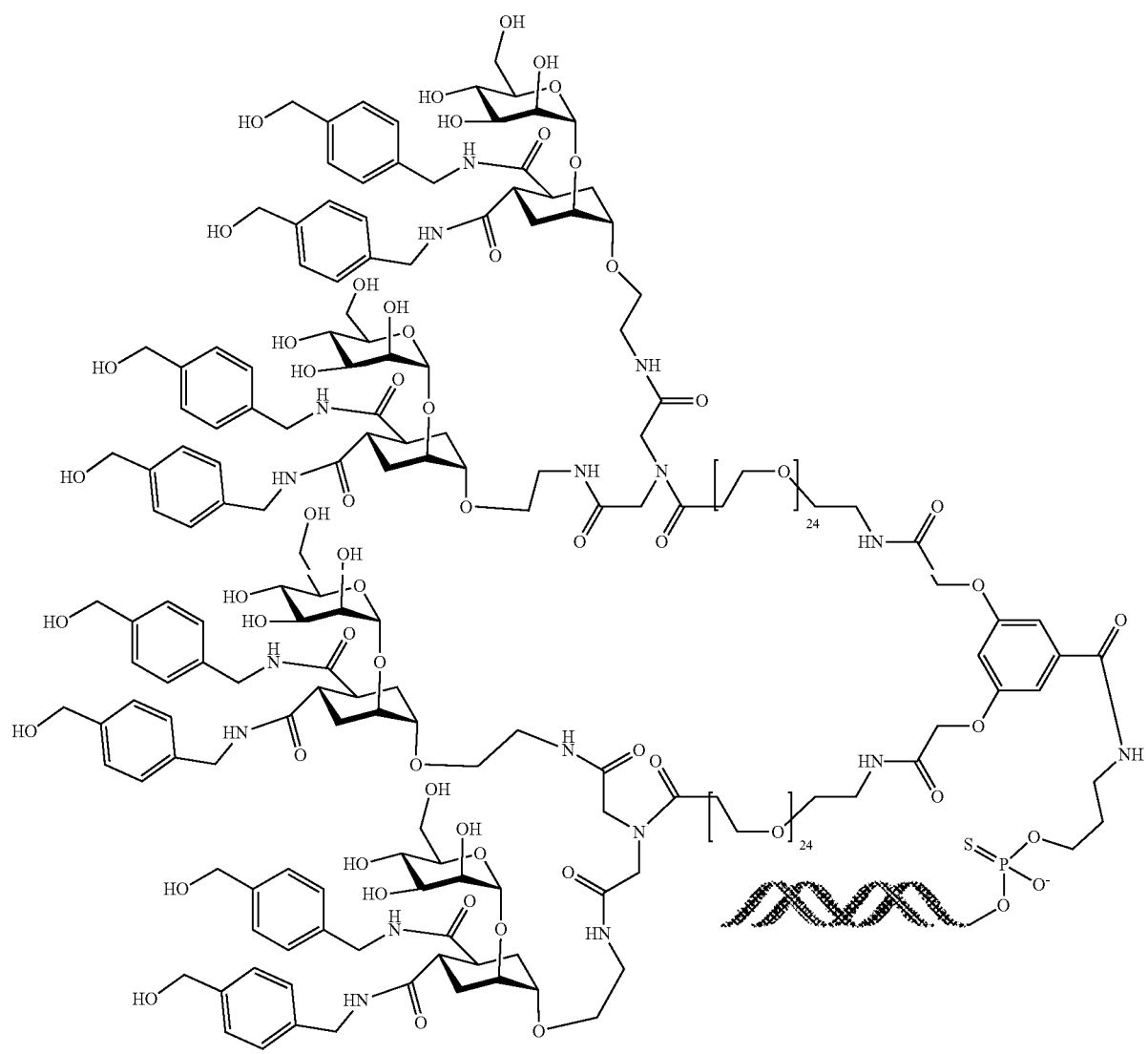

-continued
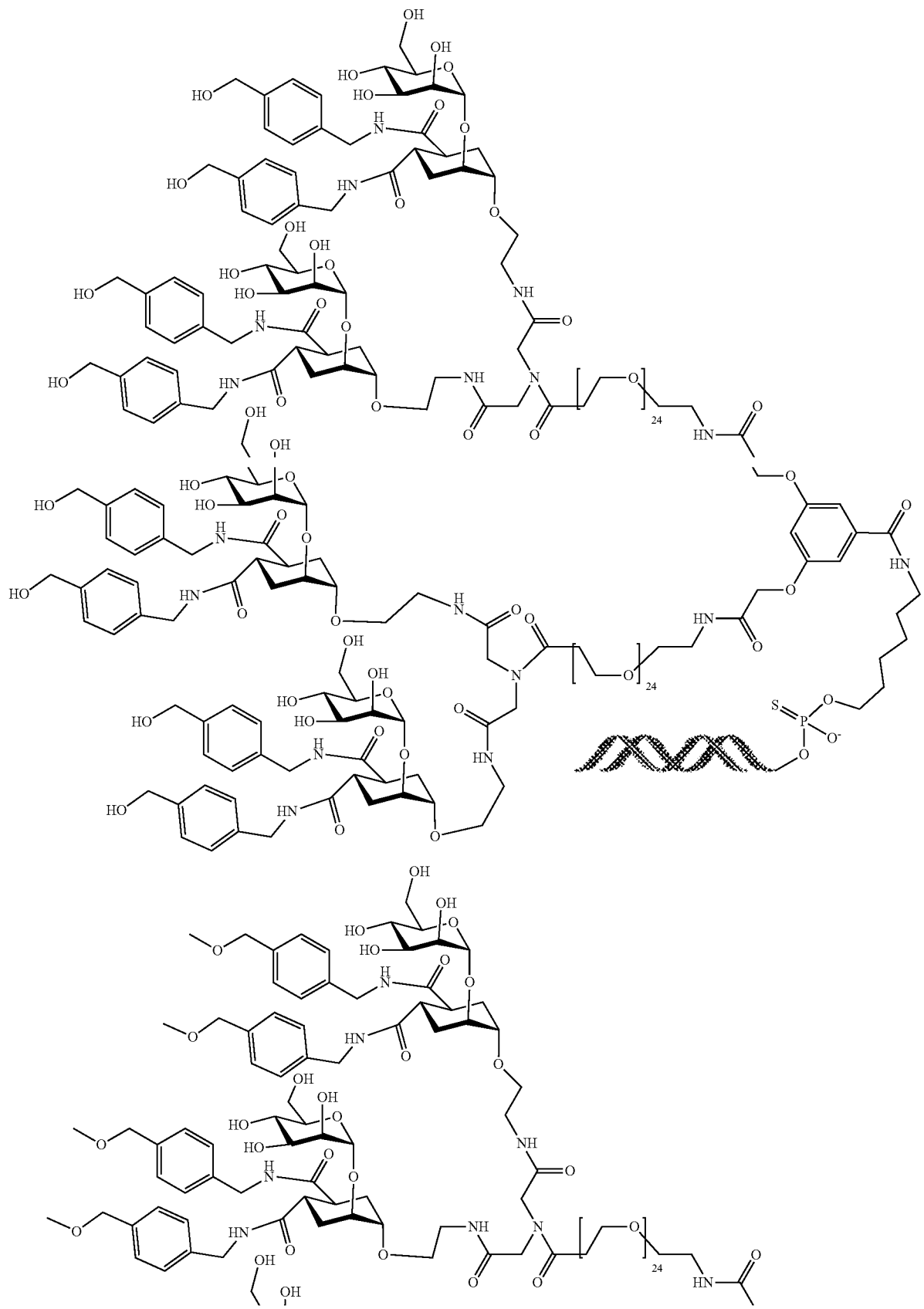

131 132
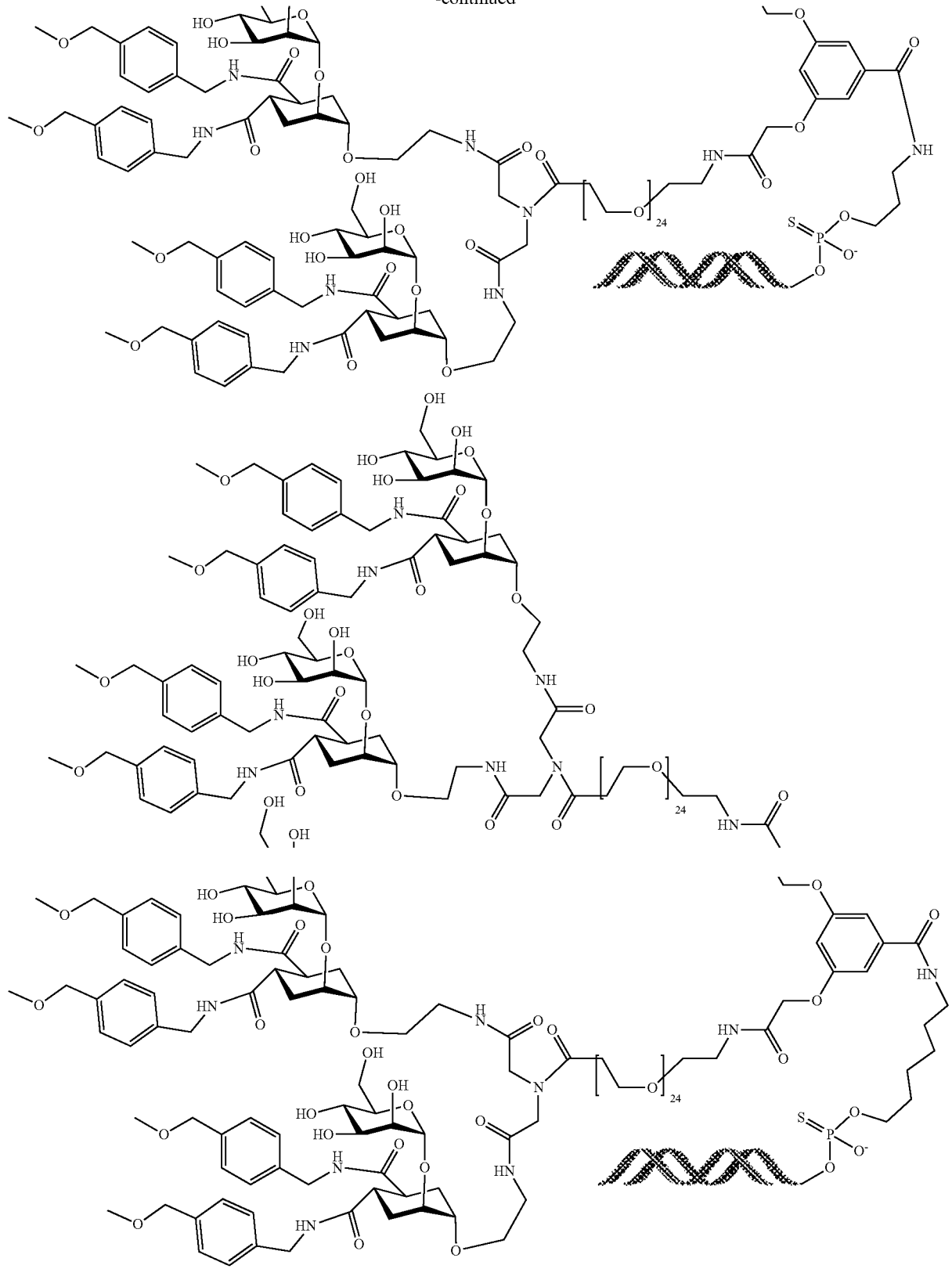
The pharmaceutical composition of the present invention comprises the nucleic acid conjugate. The nucleic acid conjugate of the present invention, owing to having O-bonded mannose at the non-reducing end of the sugar chain ligand, is recognized by a target cell and transferred into the cell.

The nucleic acid conjugate of the present invention can be used in the treatment of diseases related to a target gene by inhibiting (reducing or silencing) the expression of the target gene in vivo when administered to a mammal.

In the case of using the nucleic acid conjugate of the present invention as a therapeutic agent or a prophylactic agent, the administration route is not particularly limited, and an administration route most effective for treatment is desirably used. Examples thereof include intravenous administration, subcutaneous administration and intramuscular administration. Intravenous administration is preferred.

The dose differs depending on the pathological condition or age of the recipient, the administration route, etc. The dose can be, for example, a daily dose of 0.1 μg to 1000 mg, more preferably 1 to 100 mg, in terms of the amount of the double-stranded oligonucleotide.

Examples of the preparation appropriate for intravenous administration or intramuscular administration include injections. A prepared liquid formulation may be used directly in the form of, for example, an injection. Alternatively, the liquid formulation may be used after removal of the solvent by, for example, filtration or centrifugation, or the liquid formulation may be used after being freeze-dried and/or may be used after being supplemented with, for example, an excipient such as mannitol, lactose, trehalose, maltose, or glycine and then freeze-dried.

In the case of an injection, the liquid formulation or the solvent-free or freeze-dried composition is preferably mixed with, for example, water, an acid, an alkali, various buffer solutions, physiological saline, or an amino acid transfusion, to prepare the injection. Alternatively, the injection may be prepared by the addition of, for example, an antioxidant such as citric acid, ascorbic acid, cysteine, or EDTA or a tonicity agent such as glycerin, glucose or sodium chloride. Also, the injection can also be cryopreserved by the addition of a cryopreserving agent such as glycerin.

EXAMPLES

Next, the present invention will be specifically described with reference to Examples and Test Examples. However, the present invention is not limited by these Examples and Test Examples. Proton nuclear magnetic resonance spectra ($^1$H NMR) shown in Examples were measured at 270 MHz, 300 MHz or 400 MHz, and no exchangeable proton may be clearly observed depending on compounds and measurement conditions. Signal multiplicity is indicated as usually used, and br represents an apparently broad signal.

Example 1 Synthesis of Linker Unit—1

Synthesis of Compound 9

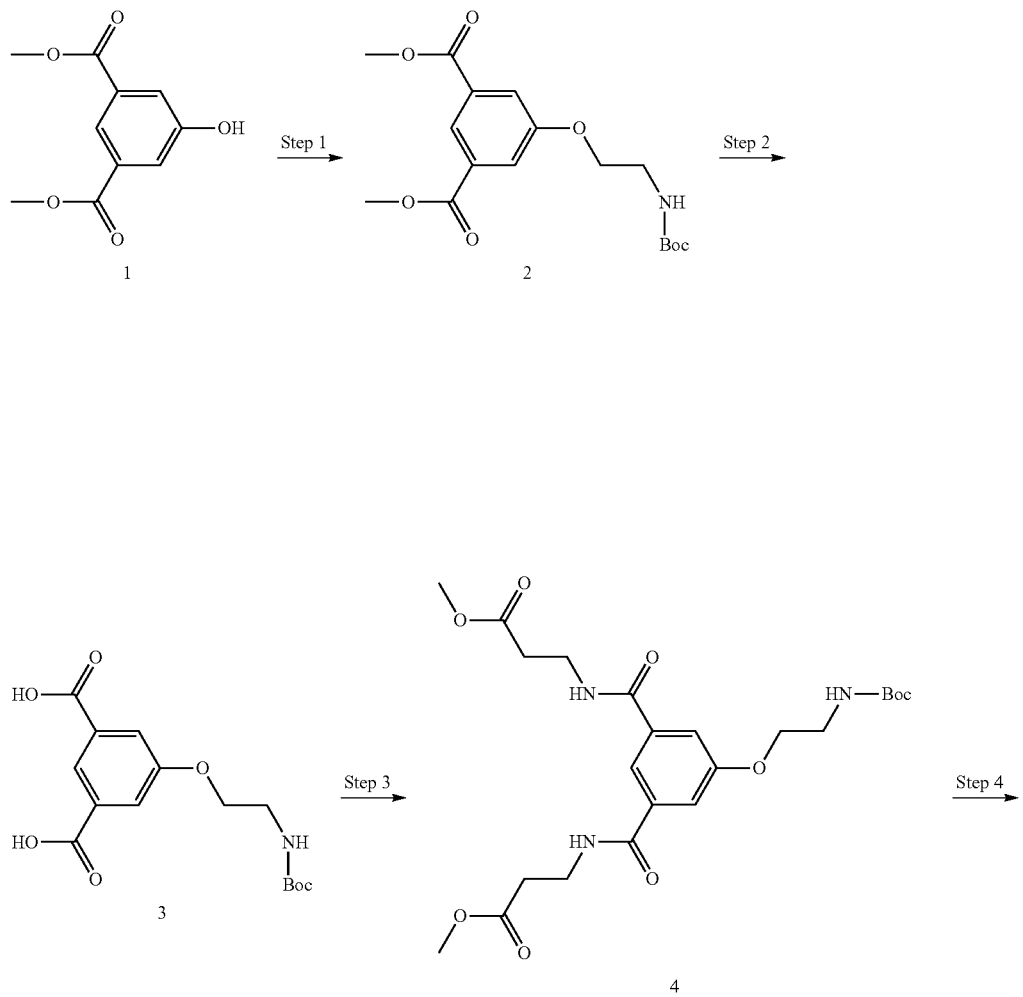

-continued
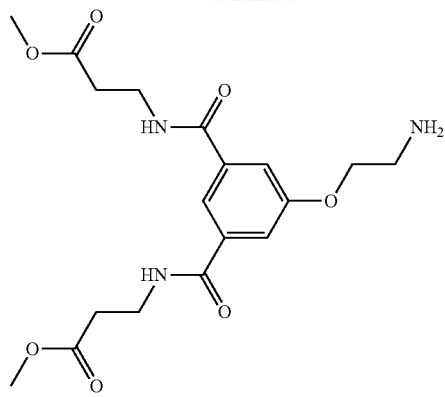
5
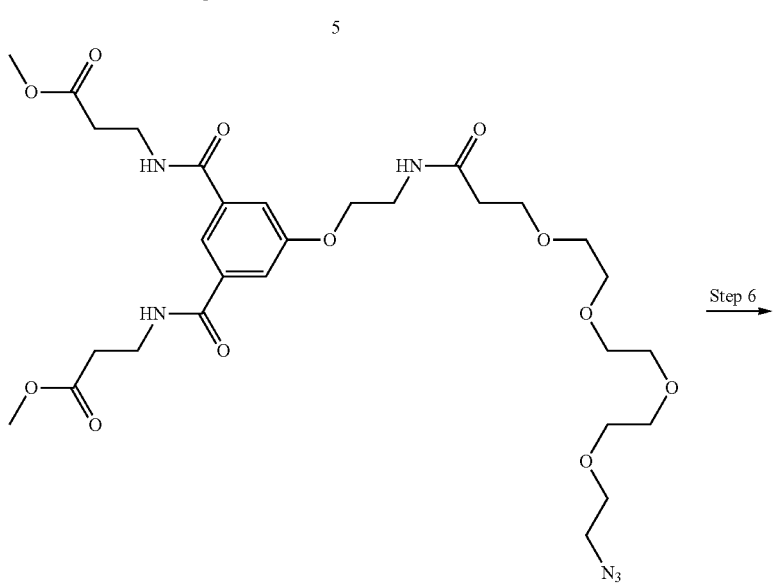
6
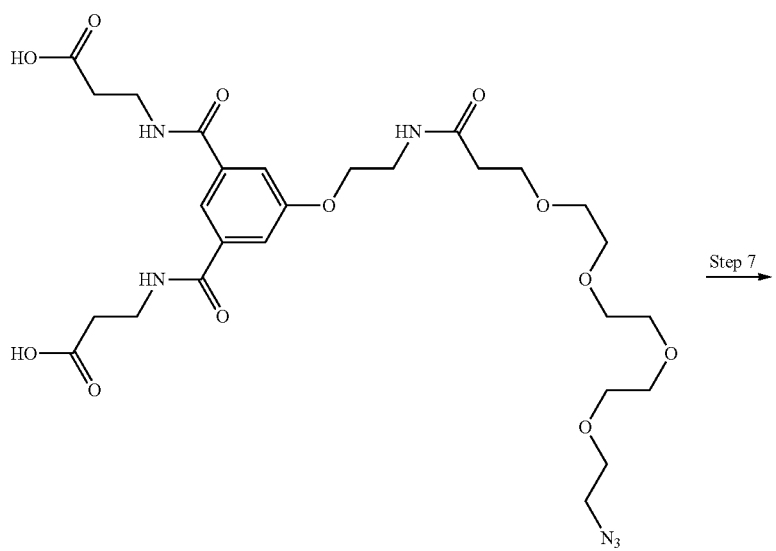
7

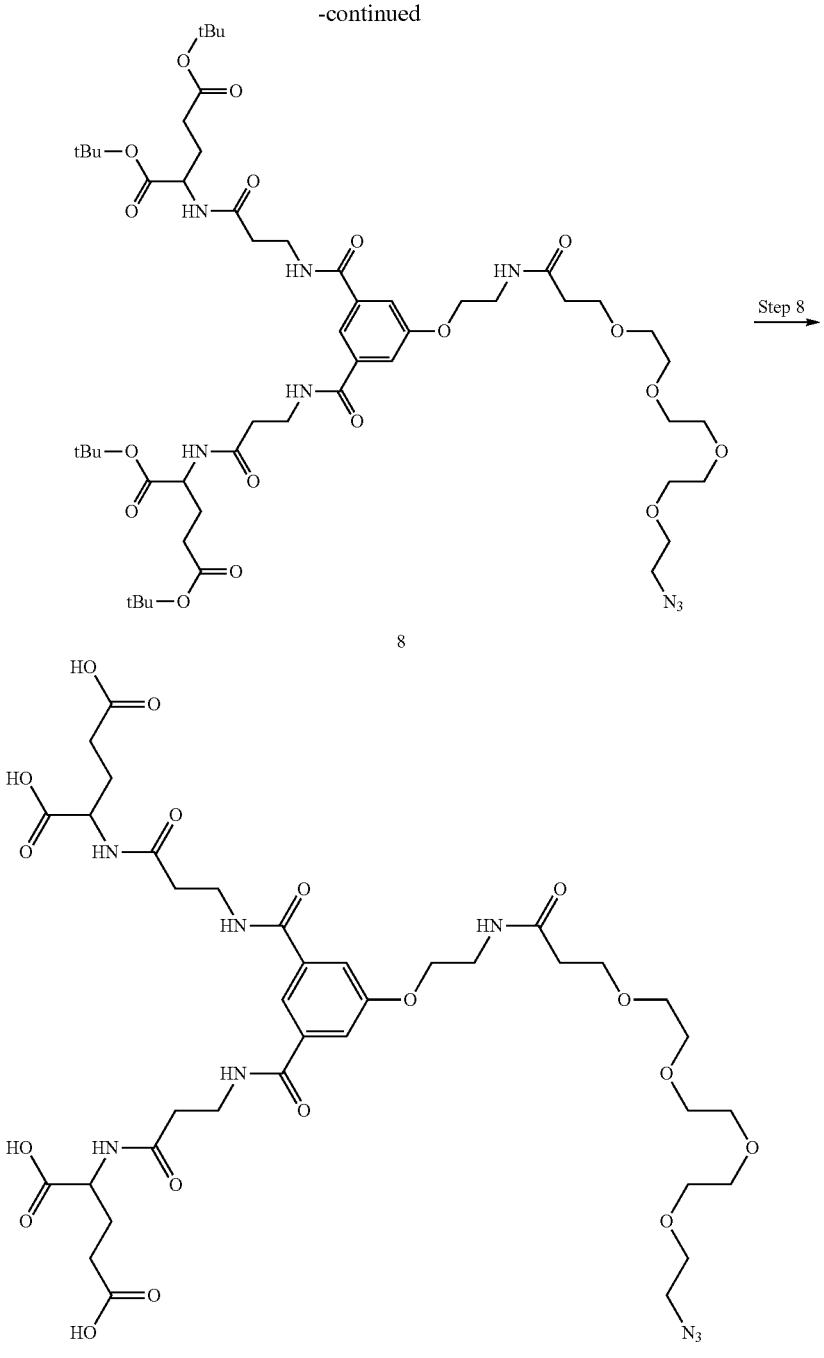

Step 1

Dimethyl 5-hydroxyisophthalate (compound 1, manufactured by Wako Pure Chemical Industries, Ltd., 5.0443 g, 24 mmol) was dissolved in tetrahydrofuran (manufactured by Wako Pure Chemical Industries, Ltd., 25 mL). To the solution, 2-(tert-butoxycarbonylamino)-1-ethanol (manufactured by Tokyo Chemical Industry Co., Ltd., 4.0343 g, 25.03 mmol), and polymer-supported triphenylphosphine (manufactured by Aldrich Co. LLC, 6.61 g, 25.2 mmol) were added, then a 40% solution of diisopropyl azodicarboxylate (DIAD) in toluene (manufactured by Tokyo Chemical Industry Co., Ltd., 13.26 mL, 25.2 mmol) was added under ice cooling, and the mixture was stirred overnight at room temperature. The reaction solution was filtered, and the solvent in the filtrate was distilled off under reduced pressure. Then, the residue was purified by amino silica gel column chromatography (hexane/ethyl acetate=95/5 to 80/20) to obtain compound 2 (5.3071 g, yield: 63%).

ESI-MS m/z: 254 (M+H)$^+$, detected as a Boc-deprotected form

Step 2

Compound 2 (5.3071 g, 15.02 mmol) synthesized in step 1 was dissolved in methanol (25 mL). To the solution, a 2 mol/L aqueous sodium hydroxide solution (manufactured by Wako Pure Chemical Industries, Ltd., 13 mL) was added under ice cooling, and the mixture was stirred at room temperature for 4 hours. The reaction solution was ice-cooled, and a 10% aqueous citric acid solution was added thereto, followed by extraction with ethyl acetate. Then, the organic layer was washed with saturated saline and dried over anhydrous magnesium sulfate. The solvent was distilled off under reduced pressure to quantitatively obtain compound 3.

ESI-MS m/z: 324 (M−H)⁻

Step 3

Compound 3 (0.9372 g, 2.8809 mmol) synthesized in step 2 and β-alanine methyl ester hydrochloride (manufactured by Tokyo Chemical Industry Co., Ltd., 0.8082 g, 5.7902 mmol) were dissolved in N,N'-dimethylformamide (10 mL). To the solution, diisopropylethylamine (2.52 mL, 14.40 mmol) and 2-(1H-benzotriazol-1-yl)-1,1,3,3-tetramethyluronium hexafluorophosphate (2.1908 g, 5.76 mmol) were added, and the mixture was stirred overnight at room temperature. The reaction solution was ice-cooled, and a 10% aqueous citric acid solution was added thereto, followed by extraction with chloroform. Then, the organic layer was washed with a saturated aqueous solution of sodium bicarbonate and saturated saline and dried over anhydrous magnesium sulfate. The solvent was distilled off under reduced pressure to quantitatively obtain compound 4.

ESI-MS m/z: 496 (M+H)⁺

Step 4

Compound 4 (0.9622 g, 1.9518 mmol) synthesized in step 3 was dissolved in dichloromethane (10 mL). To the solution, trifluoroacetic acid (2.5 mL, 32.4 mmol) was added under ice cooling, and the mixture was stirred at room temperature for 2 hours. The solvent in the reaction solution was distilled off under reduced pressure to quantitatively obtain compound 5.

ESI-MS m/z: 396 (M+H)⁺

Step 5

Compound 5 (0.1146 g, 0.290 mmol) synthesized in step 4 and N-succinimidyl 15-azido-4,7,10,13-tetraoxapentadecanoic acid (N3-PEG4-NHS, manufactured by Tokyo Chemical Industry Co., Ltd., 0.0750 g, 0.1931 mmol) were dissolved in tetrahydrofuran (6 mL). To the solution, diisopropylethylamine (0.337 mL, 1.931 mmol) was added, and the mixture was stirred at room temperature for 2 hours. The solvent was distilled off under reduced pressure, and the residue was purified by silica gel column chromatography (chloroform/methanol) to quantitatively obtain compound 6.

ESI-MS m/z: 669 (M+H)⁺

Step 6

Compound 7 was quantitatively obtained in the same way as in step 2 using compound 6 (0.1291 g, 0.193 mmol) synthesized in step 5.

ESI-MS m/z: 641 (M+H)⁺

¹H-NMR (DMSO-D6) δ: 2.35 (2H, t, J=7.2 Hz), 2.51-2.54 (4H, m), 3.38-3.65 (24H, m), 4.07 (2H, t, J=5.4 Hz), 7.51 (2H, br s), 7.89 (1H, br s), 8.13 (1H, dd, J=5.3, 2.7 Hz), 8.63 (2H, t, J=5.4 Hz)

Step 7

Compound 8 (0.0521 g, yield: 24%) was obtained in the same way as in step 3 using compound 7 (0.1252 g, 0.193 mmol) synthesized in step 6 and L-glutamic acid di-tert-butyl ester (manufactured by Watanabe Chemical Industries, Ltd., 0.1180 g, 0.399 mmol).

ESI-MS m/z: 1124 (M+H)⁺

Step 8

Compound 8 (0.0521 g, 0.0464 mmol) synthesized in step 7 was dissolved in dichloromethane (2 mL). To the solution, trifluoroacetic acid (0.2 mL, 32.4 mmol) was added under ice cooling, and the mixture was stirred overnight at room temperature. The solvent in the reaction solution was distilled off under reduced pressure to quantitatively obtain compound 9.

ESI-MS m/z: 899 (M+H)⁺

¹H-NMR (DMSO-D6) δ: 1.70-1.82 (2H, m), 1.90-2.02 (2H, m), 2.23-2.30 (4H, m), 2.35 (2H, t, J=5.3 Hz), 2.44 (4H, t, J=7.4 Hz), 3.38-3.65 (24H, m), 4.07 (2H, t, J=5.3 Hz), 4.17-4.26 (2H, m), 7.51 (2H, d, J=1.3 Hz), 7.89 (1H, br s), 8.13 (1H, dd, J=10.0, 5.0 Hz), 8.21 (2H, d, J=7.6 Hz), 8.57 (2H, t, J=5.8 Hz)

Example 2 Synthesis of Linker Unit—2

Synthesis of Compound 19

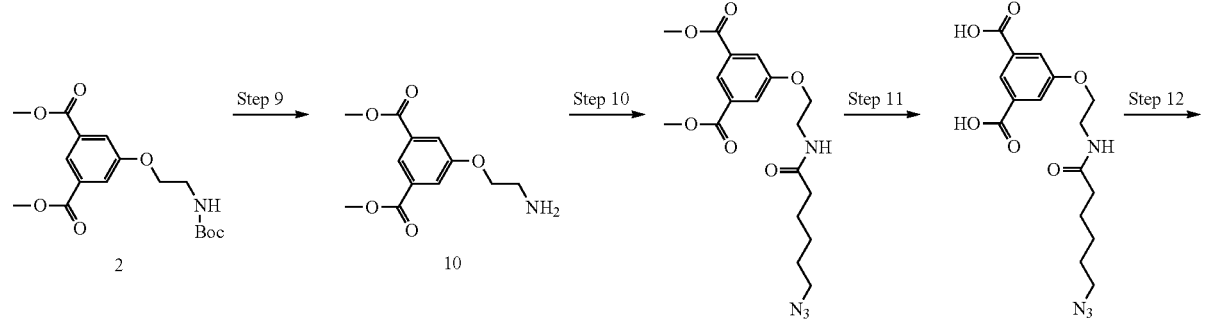

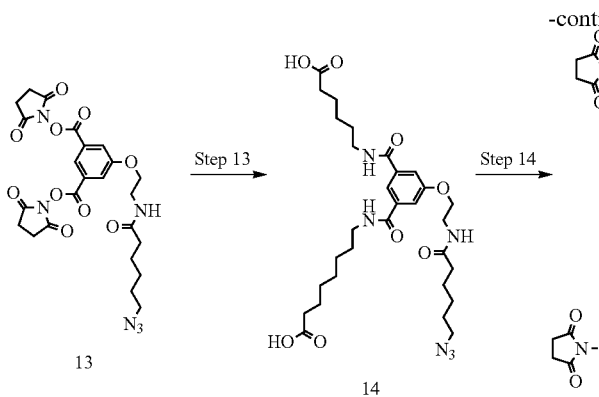

13

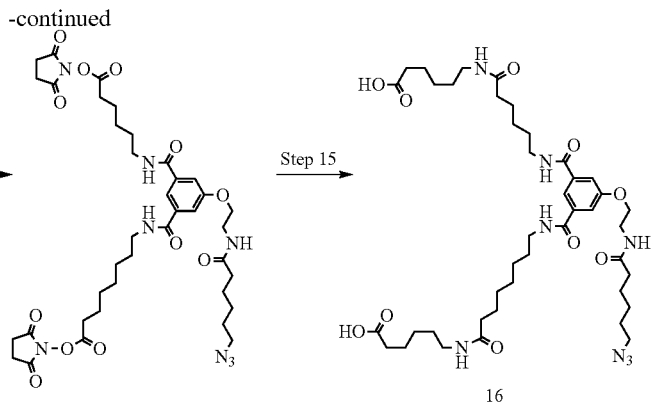

-continued

14

15

16

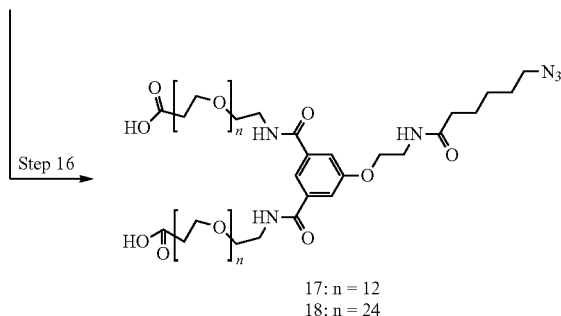

17: n = 12
18: n = 24

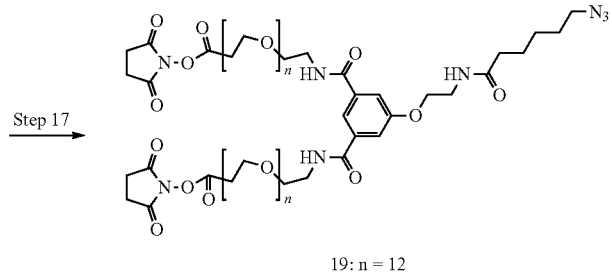

19: n = 12
20: n = 24

Step 9

Compound 10 was quantitatively obtained in the same way as in step 4 of Example 1 using compound 2 (2.1 g, 5.940 mmol) synthesized in step 1 of Example 1.

ESI-MS m/z: 254 (M+H)$^+$ $^1$H-NMR (DMSO-D6) δ: 3.26 (2H, t, J=5.1 Hz), 3.90 (6H, s), 4.30 (2H, t, J=5.1 Hz), 7.77 (2H, dd, J=1.5, 0.8 Hz), 8.13 (1H, dd, J=1.4, 0.7 Hz).

Step 10

Compound 11 (0.248 g, yield: 38%) was obtained in the same way as in step 5 of Example 1 using compound 10 (0.427 g, 1.686 mmol) synthesized in step 9 and 6-azidohexanoic acid pyrrolidinyl ester (0.6 g, 2.360 mmol) synthesized by the method described in Organic & Biomolecular chemistry, Vol. 13, p. 1778?1791, 2015.

ESI-MS m/z: 393 (M+H)$^+$ $^1$H-NMR (CDCl$_3$) δ: 1.37-1.44 (2H, m), 1.64-1.69 (4H, m), 2.23 (2H, t, J=7.5 Hz), 3.25 (2H, t, J=6.8 Hz), 3.71 (2H, dd, J=5.3, 2.7 Hz), 3.95 (6H, s), 4.13 (2H, t, J=6.7 Hz), 7.75 (2H, dd, J=1.5, 0.8 Hz), 8.30 (1H, dd, J=1.4, 0.7 Hz).

Step 11

Compound 12 was quantitatively obtained in the same way as in step 2 of Example 1 using compound 11 (0.248 g, 0.632 mmol) synthesized in step 10.

ESI-MS m/z: 365 (M+H)$^+$ $^1$H-NMR (MeOD) δ: 1.37-1.41 (2H, m), 1.60-1.65 (4H, m), 2.25 (2H, t, J=7.4 Hz), 3.25 (2H, t, J=6.7 Hz), 3.63 (2H, t, J=4.9 Hz), 4.18 (2H, t, J=5.2 Hz), 7.79 (2H, dd, J=1.6, 0.8 Hz), 8.27 (1H, dd, J=1.4, 0.7 Hz).

Step 12

Compound 12 (0.230 mg, 0.631 mmol) obtained in step 11 was dissolved in tetrahydrofuran (274.7 μL). To the solution, N-hydroxysuccinimide (0.174 g, 1.515 mmol) and 1-ethyl-3-(3-dimethylaminopropyl)carbodiimide hydrochloride (0.313 g, 1.515 mmol) were added, and the mixture was stirred overnight at room temperature in an argon atmosphere. The solvent was distilled off under reduced pressure, followed by extraction with chloroform. Then, the organic layer was washed with saturated saline and dried over anhydrous magnesium sulfate. The solvent was distilled off under reduced pressure to obtain a crude product of compound 13.

ESI-MS m/z: 559 (M+H)$^+$

Step 13

Compound 13 (0.200 g, 0.358 mmol) synthesized in step 12, 6-aminohexanoic acid (manufactured by Nacalai Tesque, Inc., 0.141 g, 1.074 mmol) and diisopropylethylamine (0.139 mL, 1.074 mmol) were stirred overnight at room temperature in a phosphate buffer solution/dimethyl sulfoxide mixed solvent (v/v=1/1, 50 mL). A 10% citric acid solution (50 mL) was added to the reaction solution, followed by extraction with chloroform. Then, the organic layer was washed with a saturated aqueous solution of sodium bicarbonate and saturated saline and dried over anhydrous magnesium sulfate. The solvent was distilled off under reduced pressure to obtain compound 14 (0.157 g, yield: 74%).

ESI-MS m/z: 591 (M+H)$^+$ $^1$H-NMR (DMSO-D6) δ: 1.26-1.33 (8H, m), 1.51-1.53 (10H, m), 2.10 (2H, t, J=7.2 Hz), 2.21 (4H, t, J=7.4 Hz), 3.25 (8H, t, J=6.5 Hz), 4.08 (2H, t, J=5.4 Hz), 7.48-7.51 (2H, br m), 7.87-7.89 (1H, br m), 8.07-8.08 (1H, br m), 8.53-8.54 (2H, br m).

Step 14

Compound 15 was quantitatively obtained in the same way as in step 12 using compound 14 (0.1442 g, 0.2441 mmol) synthesized in step 13.

ESI-MS m/z: 785 (M+H)$^+$

Step 15

Compound 16 was quantitatively obtained in the same way as in step 13 using compound 15 (0.0958 g, 0.1221 mmol) synthesized in step 14.

ESI-MS m/z: 818 (M+H)$^+$

Step 16

1) Synthesis of Compound 17

Compound 17 (0.0580 g, yield: 99%) was obtained in the same way as in step 13 using compound 13 (0.0209 g, 0.0375 mmol) synthesized in step 12 and carboxyl-(12 ethylene glycol) ethylamine (manufactured by Thermo Fisher Scientific Inc., 0.0674 g, 0.1091 mmol).

ESI-MS m/z: 1564 (M+H)$^+$

2) Synthesis of Compound 18

Compound 18 (0.0144 g, yield: 79%) was obtained in the same way as in step 13 using compound 13 (0.0047 g, 0.00654 mmol) synthesized in step 12 and carboxyl-(24 ethylene glycol) ethylamine (manufactured by Thermo Fisher Scientific Inc., 0.0225 g, 0.01963 mmol).

ESI-MS m/z: 2622 (M+H)$^+$

Step 17

1) Synthesis of Compound 19

Compound 19 was quantitatively obtained in the same way as in step 12 using compound 17 (0.0580 g, 0.0375 mmol) synthesized in step 16.

ESI-MS m/z: 1759 (M+H)$^+$ $^1$H-NMR (DMSO-D6) δ: 1.22-1.25 (6H, m), 2.10 (2H, t, J=7.5 Hz), 2.81 (8H, br s), 2.93 (4H, t, J=6.1 Hz), 3.26-3.27 (6H, m), 3.43-3.45 (2H, m), 3.49-3.50 (92H, m), 3.71 (4H, t, J=6.0 Hz), 4.07 (2H, t, J=6.0 Hz), 7.53 (2H, dd, J=1.5, 0.8 Hz), 7.93 (1H, dd, J=1.5, 0.8 Hz), 8.05-8.07 (1H, br m), 8.59-8.61 (2H, br m).

2) Synthesis of Compound 20

Compound 20 was quantitatively obtained in the same way as in step 12 using compound 18 (0.0580 g, 0.0375 mmol) synthesized in step 16.

ESI-MS m/z: 2817 (M+H)$^+$

Example 3 Synthesis of Linker Unit—3

Synthesis of Compound 22

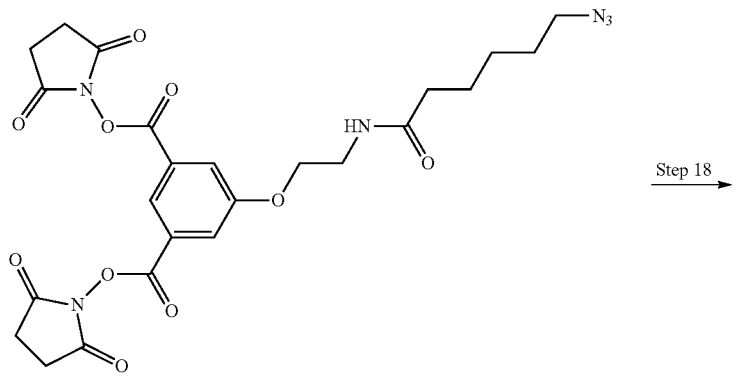

13

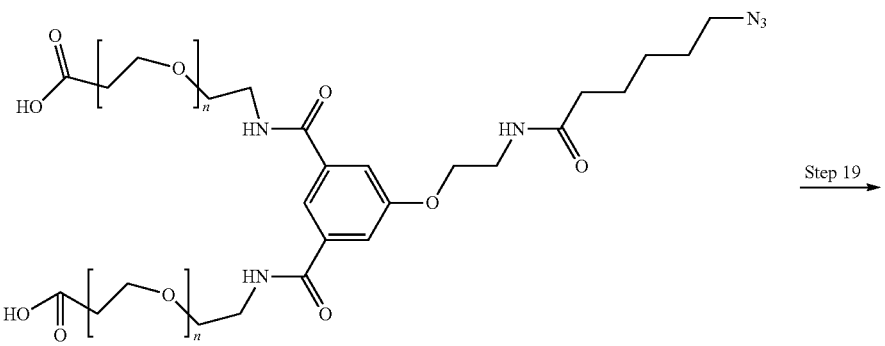

17: n = 12
18: n = 24

-continued

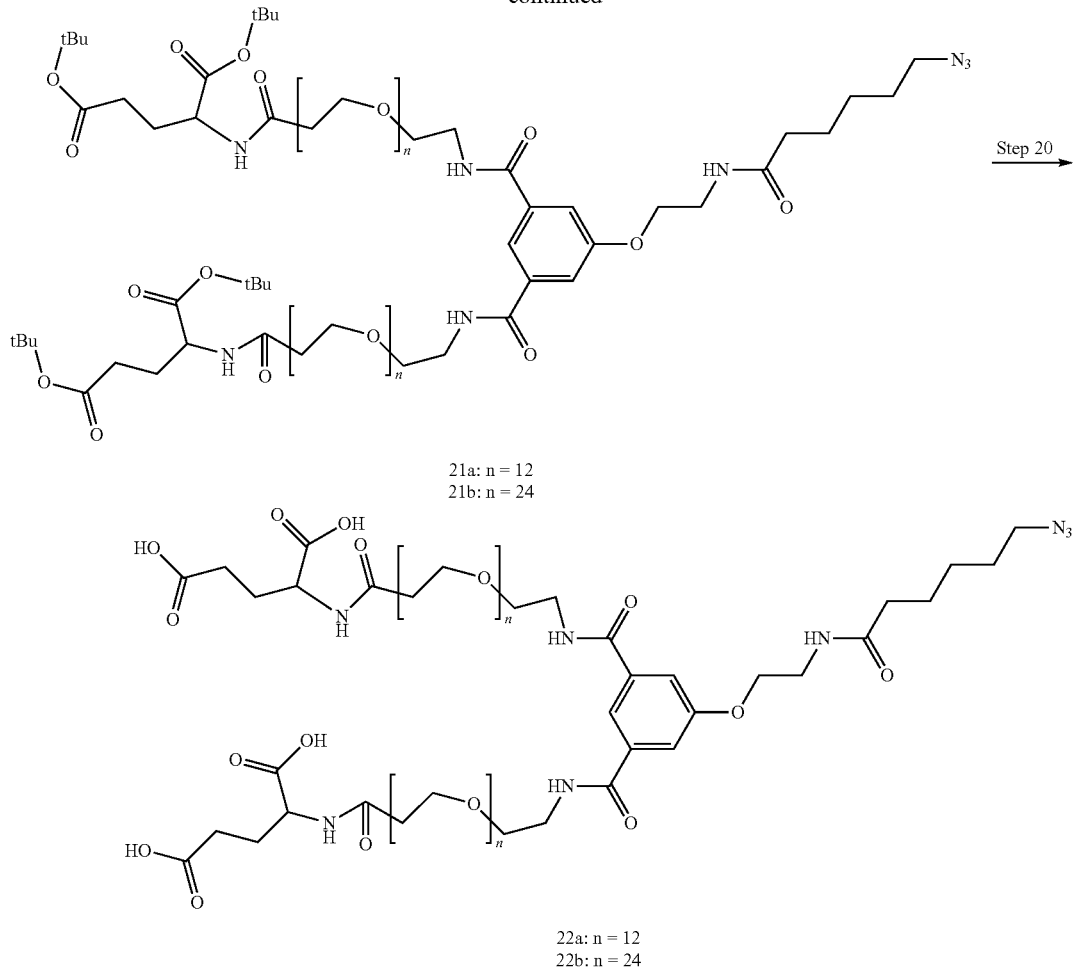

21a: n = 12
21b: n = 24

22a: n = 12
22b: n = 24

Step 18

(a); Compound 13 (10 mg, 17.9 μmol) synthesized in step 12 of Example 2 was dissolved in a mixed solution of tetrahydrofuran (90 μL) and a phosphate buffer solution (90 μL). To the solution, carboxyl-(12 oligoethylene glycol) ethylamine (manufactured by Thermo Fisher Scientific Inc., 22.1 mg, 35.8 μmol) was added, and the mixture was stirred at room temperature for 1 hour in an argon atmosphere. The solvent was distilled off under reduced pressure, followed by extraction with chloroform and a 10% aqueous citric acid solution. Then, the organic layer was dried over anhydrous magnesium sulfate. The solvent was distilled off under reduced pressure to obtain a crude product of compound 17.

ESI-MS m/z: 1564 (M+H)$^+$ (b); Compound 13 (10 mg, 17.9 μmol) synthesized in step 12 of Example 2 was dissolved in a mixed solution of tetrahydrofuran (90 μL) and a phosphate buffer solution (90 μL). To the solution, carboxyl-(24 oligoethylene glycol) ethylamine (manufactured by Thermo Fisher Scientific Inc., 41 mg, 35.8 μmol) was added, and the mixture was stirred at room temperature for 1 hour in an argon atmosphere. The solvent was distilled off under reduced pressure, followed by extraction with chloroform and a 10% aqueous citric acid solution. Then, the organic layer was dried over anhydrous magnesium sulfate. The solvent was distilled off under reduced pressure to obtain a crude product of compound 18.

ESI-MS m/z: 2622 (M+H)$^+$

Step 19

(a); Compound 17 (14 mg, 8.9 μmol) synthesized in step 18 was dissolved in tetrahydrofuran (90 μL). To the solution, L-glutamic acid di-tert-butyl ester (manufactured by Watanabe Chemical Industries, Ltd., 5.2 mg, 17.9 μmol), 2-(1H-benzotriazol-1-yl)-1,1,3,3-tetramethyluronium hexafluorophosphate (6.8 mg, 17.9 μmol), and diisopropylethylamine (3.1 μL, 17.9 μmol) were added, and the mixture was stirred overnight at room temperature in an argon atmosphere. The solvent was distilled off under reduced pressure, followed by extraction with chloroform. Then, the organic layer was washed with saturated saline and dried over anhydrous magnesium sulfate. Then, the residue was purified by reverse-phase high-performance liquid chromatography to obtain compound 21a (4.5 mg, yield: 25%).

ESI-MS m/z: 2046 (M+H)$^+$ $^1$H-NMR (CDCl3) δ: 1.44-1.46 (36H, m), 1.61-1.66 (4H, m), 1.89-1.91 (4H, m), 2.06-2.16 (2H, m), 2.20-2.37 (6H, m), 2.50 (4H, t, J=6.0 Hz), 3.26 (2H, t, J=6.8 Hz), 3.59-3.68 (98H, m), 3.71-3.76 (4H, m), 4.14 (2H, t, J=5.2 Hz), 4.48-4.50 (2H, m), 7.59 (2H, dd, J=1.3, 0.6 Hz), 7.92 (1H, br s).

(b); Compound 18 (23.4 mg, 8.9 μmol) synthesized in step 18 was dissolved in tetrahydrofuran (90 μL). To the solution, L-glutamic acid α,γ-di(t-butyl ester) hydrochloride (5.2 mg, 17.9 μmol), 2-(1H-benzotriazol-1-yl)-1,1,3,3-tetramethyluronium hexafluorophosphate (6.8 mg, 17.9 μmol), and diisopropylethylamine (3.1 μL, 17.9 μmol) were added, and the mixture was stirred overnight at room temperature in an argon atmosphere. The solvent was distilled off under reduced pressure, followed by extraction with chloroform. Then, the organic layer was washed with saturated saline and dried over anhydrous magnesium sulfate. Then, the residue was purified by reverse-phase high-performance liquid chromatography to obtain compound 21b (7.4 mg, yield: 27%).

ESI-MS m/z: 1553 (M−2H)$^{2-}$ $^{1}$H-NMR (CDCl3) δ: 1.44 (18H, s), 1.46 (18H, s), 1.62-1.67 (4H, m), 1.86-1.89 (2H, m), 2.20-2.36 (10H, m), 2.51 (4H, t, J=5.8 Hz), 3.26 (2H, t, J=7.0 Hz), 3.63-3.65 (194H, m), 3.73-3.76 (4H, m), 4.14 (2H, t, J=5.1 Hz), 4.46-4.50 (2H, m), 7.60 (2H, dd, J=1.0, 0.5 Hz), 7.92 (1H, br s)

Step 20

(a); Compound 22a was quantitatively obtained in the same way as in step 8 of Example 1 using compound 21a (4.5 mg, 2.1 μmol) synthesized in step 19.

ESI-MS m/z: 1822 (M+H)$^{+}$ (b); Compound 22b was quantitatively obtained in the same way as in step 8 of Example 1 using compound 21b (4.5 mg, 2.1 μmol) synthesized in step 19.

ESI-MS m/z: 2878 (M+H)$^{+}$

Example 4 Synthesis of Linker Unit—4

Synthesis of Compound 26

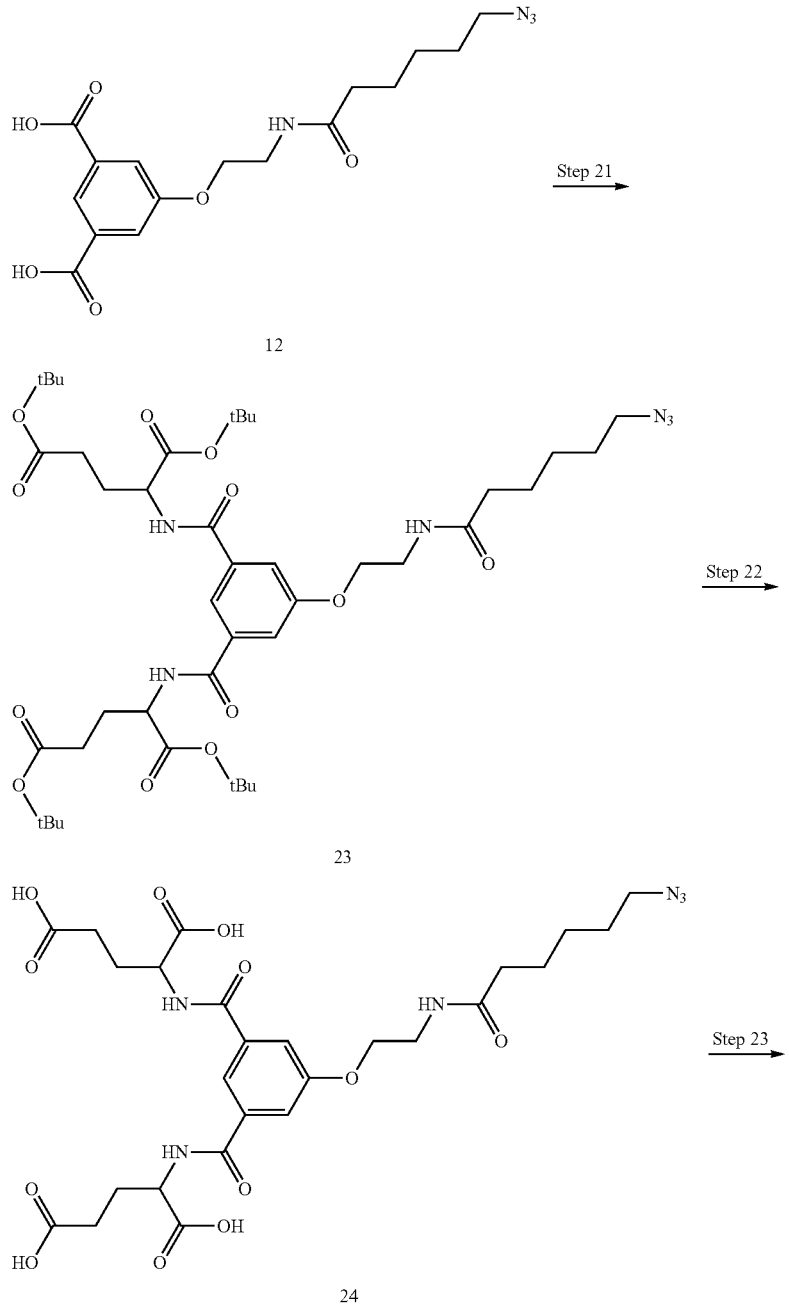

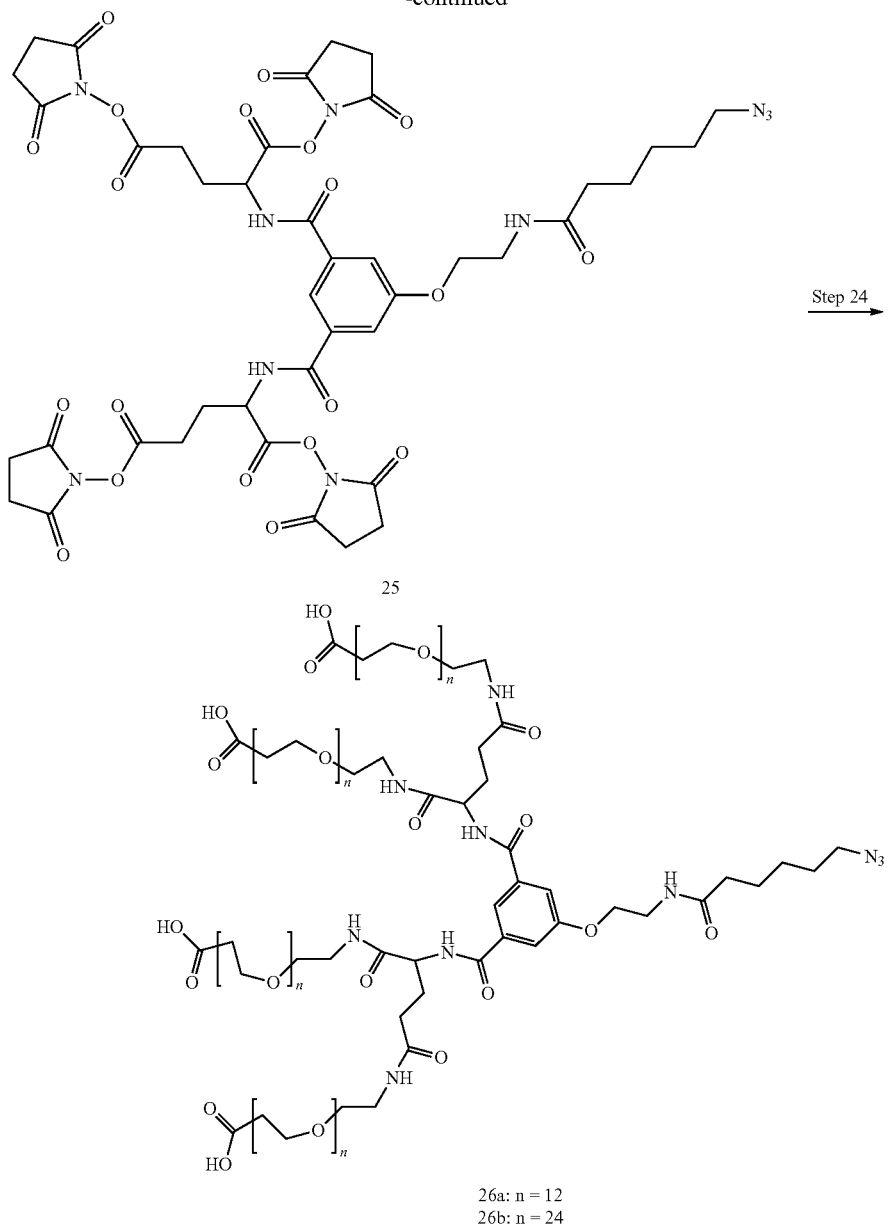

26a: n = 12
26b: n = 24

Step 21

Compound 12 (10 mg, 27.4 µmol) synthesized in step 11 of Example 2 was dissolved in tetrahydrofuran (274.7 µmol). To the solution, L-glutamic acid di-tert-butyl ester (manufactured by Watanabe Chemical Industries, Ltd., 32.5 mg, 109.8 µmol), 2-(1H-benzotriazol-1-yl)-1,1,3,3-tetramethyluronium hexafluorophosphate (41.7 mg, 109.8 µmol), and diisopropylethylamine (24.2 µL, 137.3 µmol) were added, and the mixture was stirred overnight at room temperature in an argon atmosphere. The solvent was distilled off under reduced pressure, followed by extraction with chloroform and a 10% aqueous citric acid solution. Then, the organic layer was dried over anhydrous magnesium sulfate. The solvent was distilled off under reduced pressure to obtain a crude product of compound 23.

ESI-MS m/z: 847 (M+H)$^+$

Step 22

Compound 23 (139.4 mg, 164.6 µmol) synthesized in step 21 was dissolved in methylene chloride (1.3 mL) and trifluoroacetic acid (0.3 mL), and the solution was stirred overnight at room temperature. The solvent was distilled off under reduced pressure to quantitatively obtain compound 24.

ESI-MS m/z: 623 (M+H)$^+$

Step 23

Compound 24 (100 mg, 160.7 µmol) synthesized in step 22 was dissolved in dimethylamine (1 mL). To the solution, N-hydroxysuccinimide (81.3 mg, 707 µmol) and 1-ethyl-3-(3-dimethylaminopropyl)carbodiimide hydrochloride (135.4 mg, 707 µmol) were added, and the mixture was stirred overnight at room temperature in an argon atmosphere to obtain a crude product of compound 25.

ESI-MS m/z: 1011 (M+H)$^+$

Step 24

(a); Compound 25 (16.2 mg, 16 µmol) synthesized in step 23 was dissolved in a phosphate buffer solution (95 µL). To the solution, carboxyl-(ethylene glycol) ethylamine (80.4 mg, 129.8 µmol) was added, and the mixture was stirred at room temperature for 1 hour in an argon atmosphere. The solvent was distilled off under reduced pressure, and the residue was purified by reverse-phase high-performance liquid chromatography to obtain compound 26a (6.2 mg, yield: 21%).

ESI-MS m/z: 1511 $(M+2H)^{2+}$ (b); Compound 25 (16.2 mg, 16 µmol) synthesized in step 23 was dissolved in a phosphate buffer solution (95 µL). To the solution, carboxyl-(ethylene glycol) ethylamine (149.3 mg, 129.8 µmol) was added, and the mixture was stirred at room temperature for 1 hour in an argon atmosphere. The solvent was distilled off under reduced pressure, and the residue was purified by reverse-phase high-performance liquid chromatography to obtain compound 26b (5.5 mg, yield: 11%).

ESI-MS m/z: 2566 $(M+2H)^{2+}$

Example 5 Synthesis of Sugar Chain Ligand-Linker Unit—1

Synthesis of Compounds 27 and 28

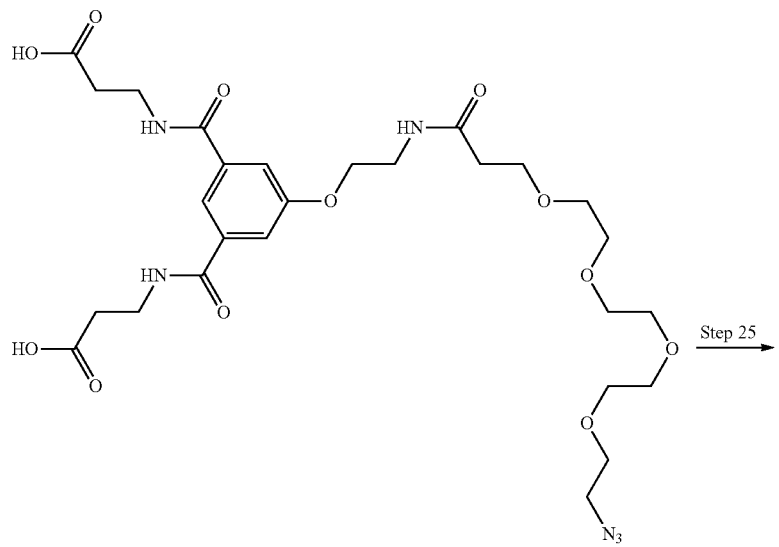

7

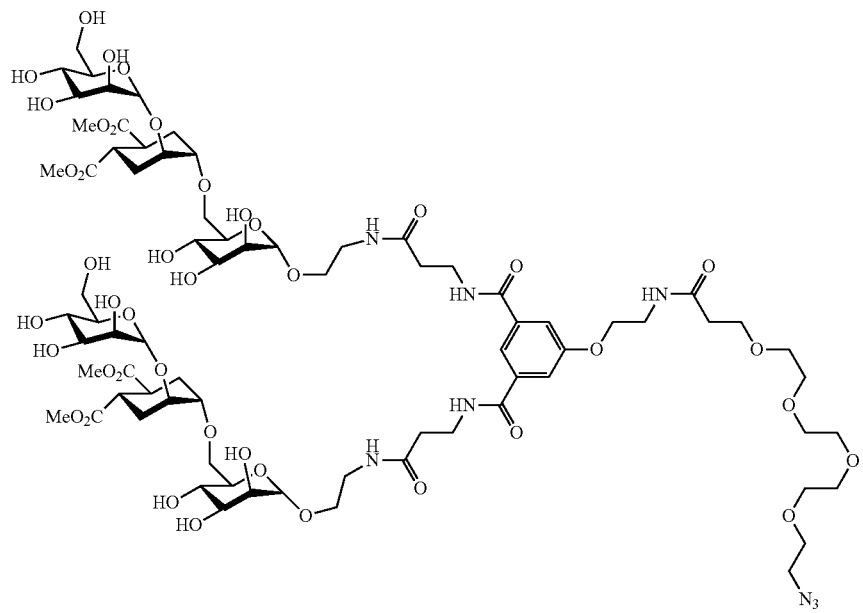

27

-continued

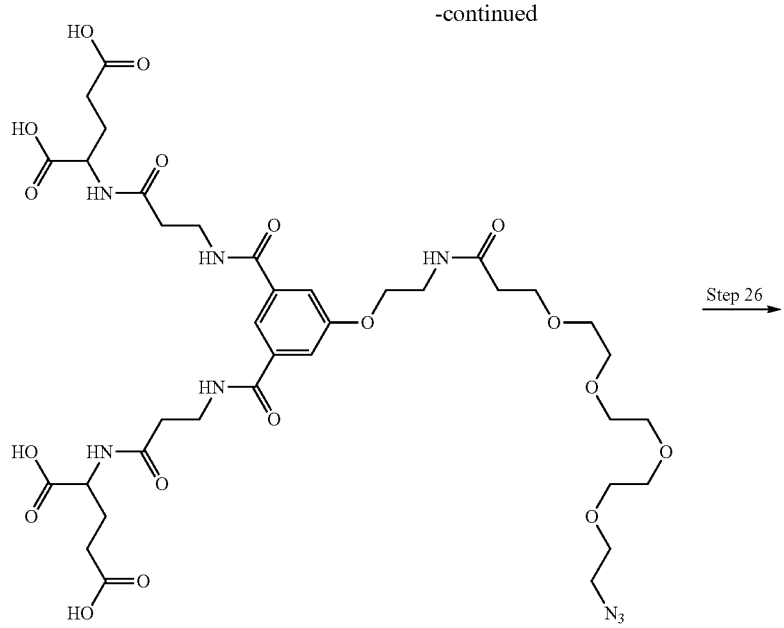

9

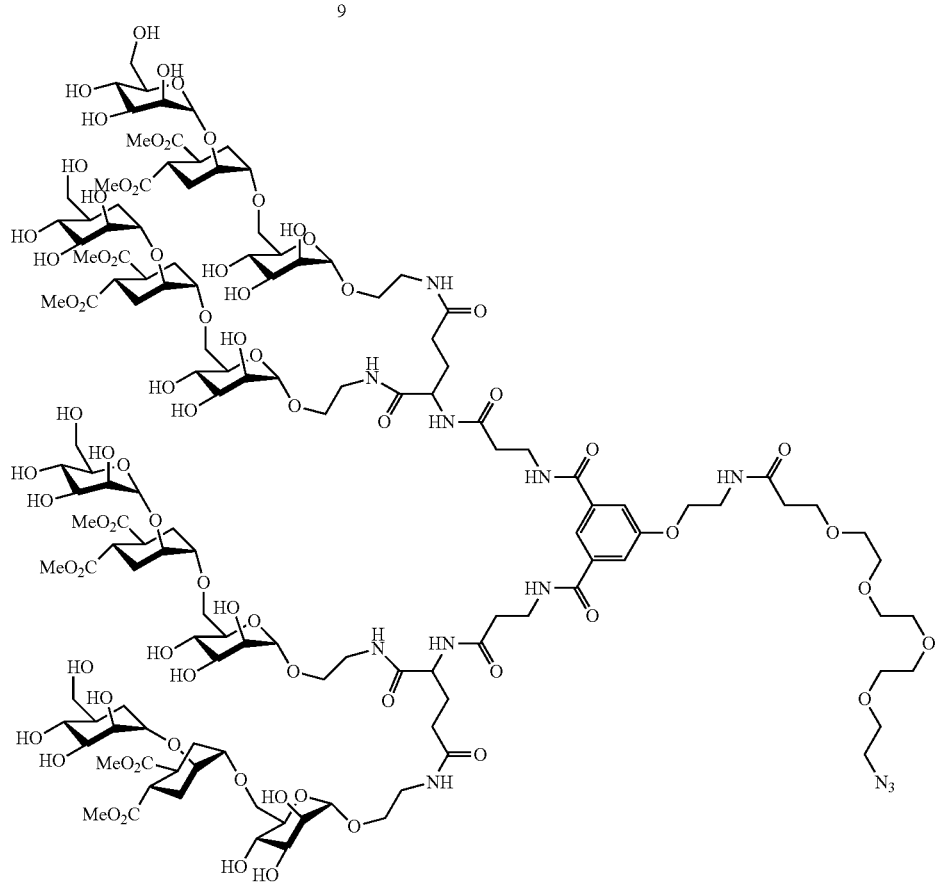

28

Step 25

Compound 7 (0.8 mg, 1.249 μmol) synthesized in step 6 of Example 1, aminoethyl group-modified α(1,2)α(1,6) pseudomannotriose (3.0 mg, 5.0 μmol) synthesized by the method described in ACS Chemical Biology, Vol. 5, p. 301?312, 2010, 2-(1H-benzotriazol-1-yl)-1,1,3,3-tetramethyluronium hexafluorophosphate (3.8 mg, 10 μmol), and diisopropylethylamine (1.7 μL, 10 μmol) were dissolved in N,N-dimethylacetamide (1 mL), and the solution was left standing at room temperature for 2 days. The mixture was purified by reverse-phase high-performance liquid chromatography to obtain compound 25 (1.6 mg, yield: 71%).

ESI-MS m/z: 1802 (M−H)⁻

Step 26

Compound 26 (2.3 mg, yield: 68%) was obtained in the same way as in step 25 using compound 9 (0.9 mg, 1.04 μmol) synthesized in step 8 of Example 1 and α(1,2)α(1,6) pseudomannotriose (8.34 g, 8.34 μmol) described in step 25.

ESI-MS m/z: 1611 (M−2H)²⁻

Example 6 Synthesis of Sugar Chain Ligand-Linker Unit—2

Synthesis of compounds 29, 30, 31, 32, and 33

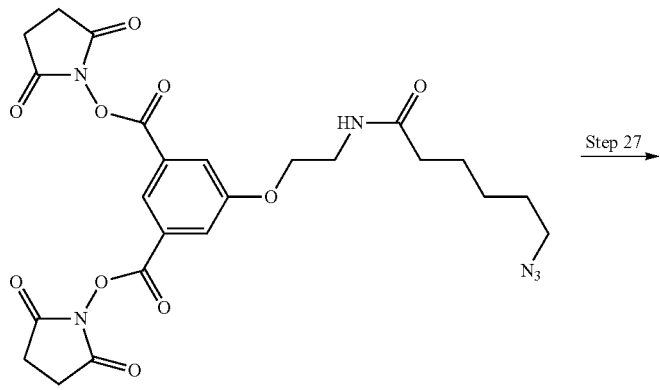

13

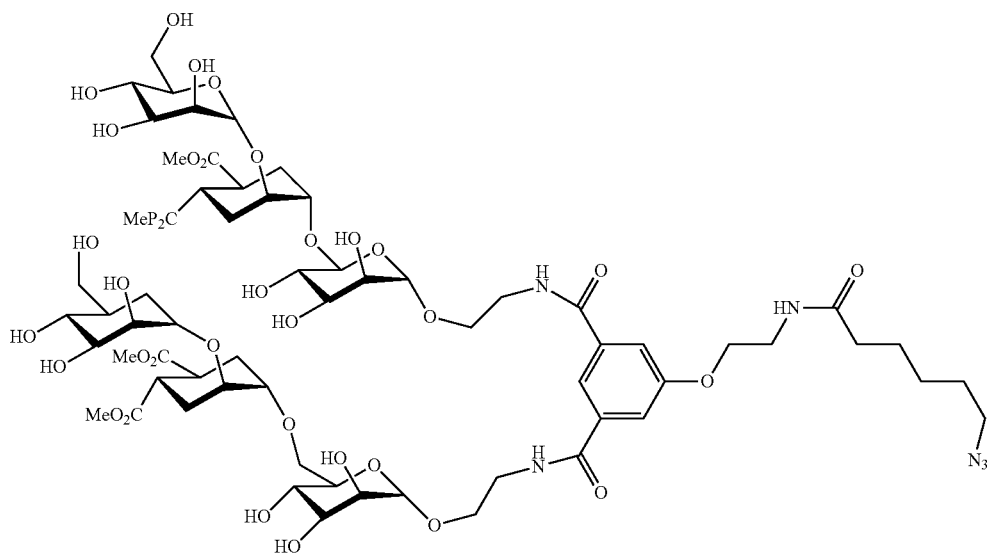

29

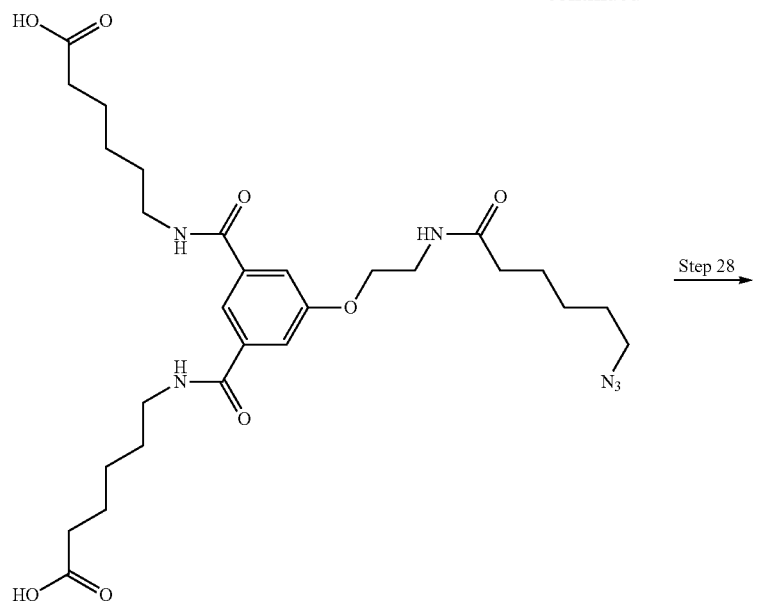
Step 28
14
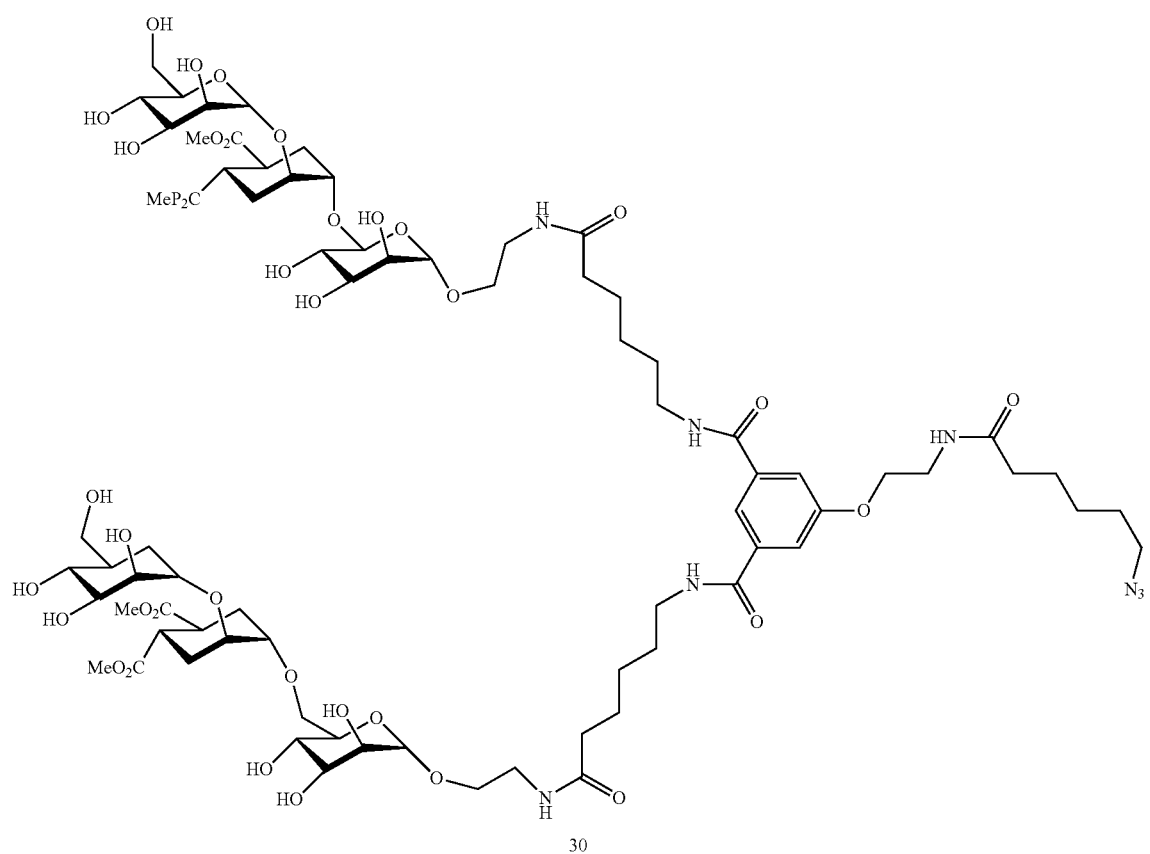
30

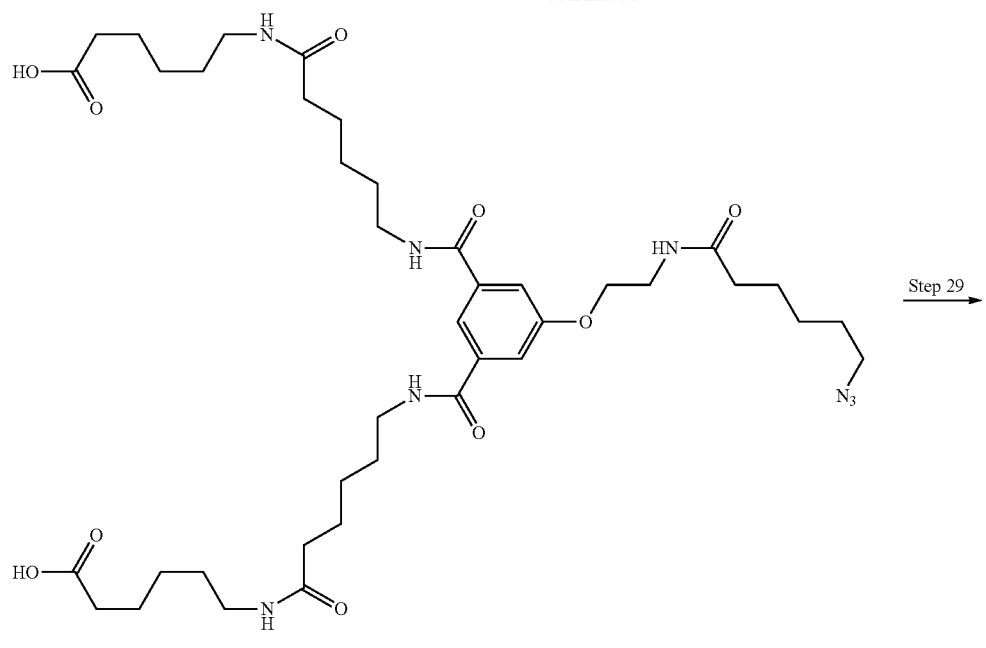
16
Step 29 →
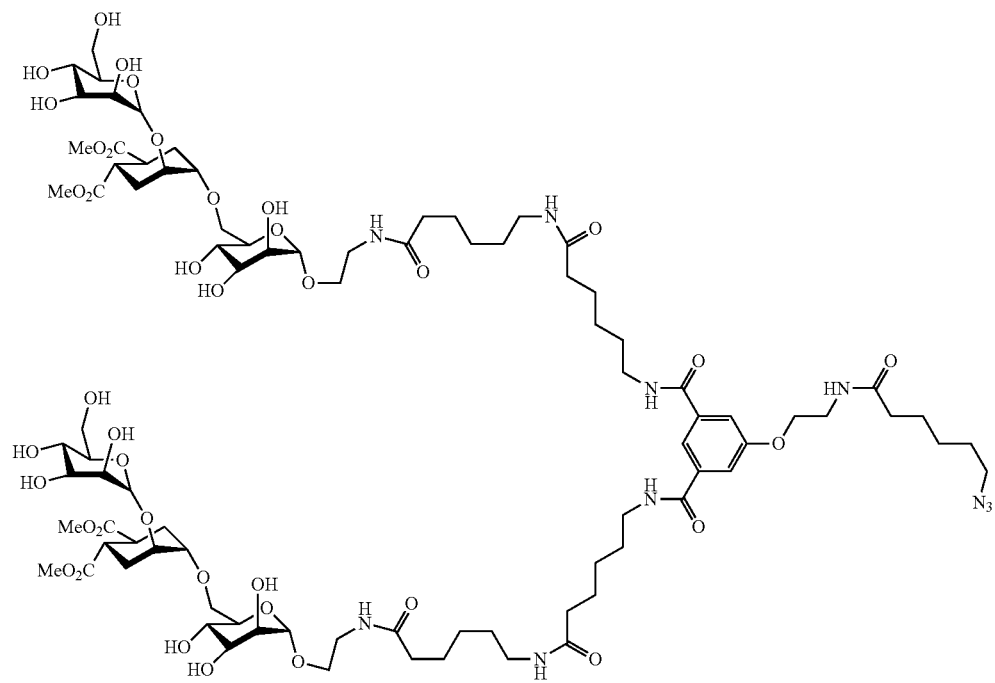
31

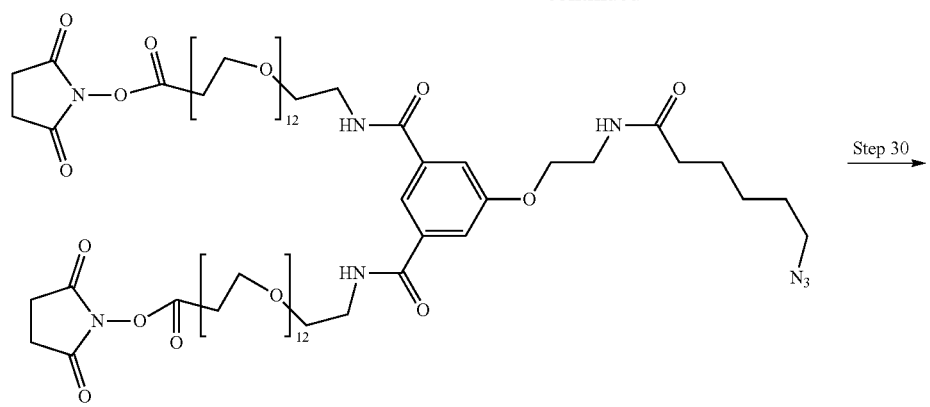
19
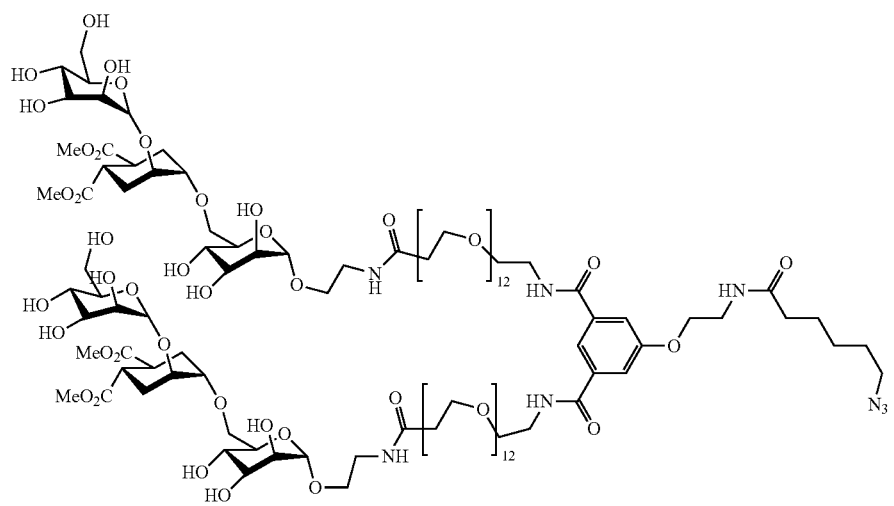
32
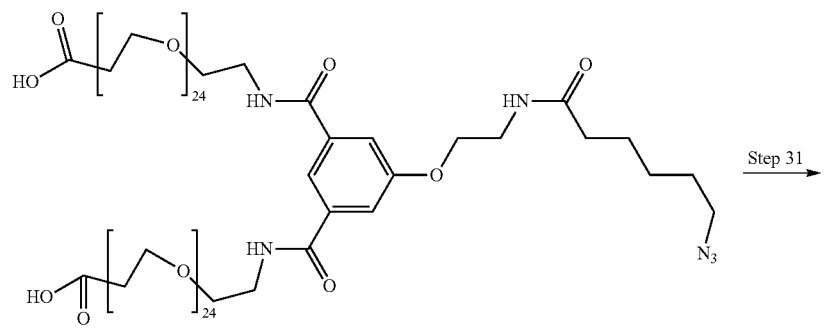
18

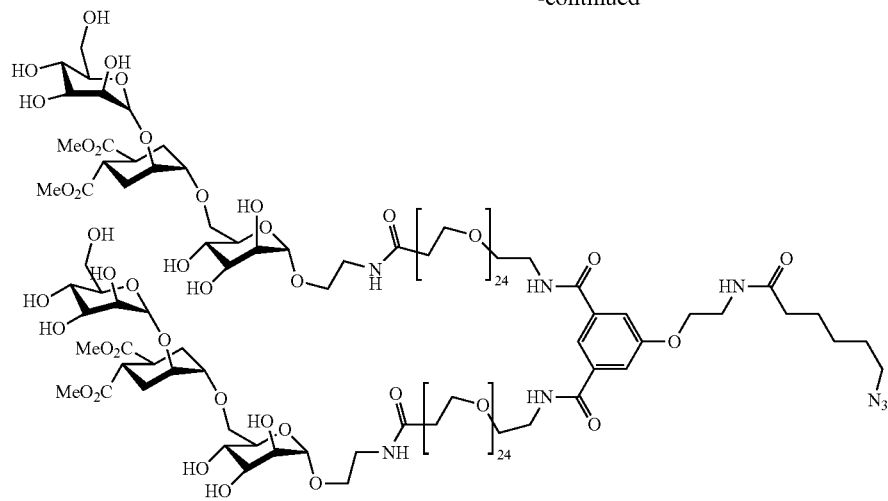

33

Step 27
Compound 29 (1.1 mg, yield: 65%) was obtained in the same way as in step 13 of Example 2 using compound 13 (0.6 mg, 0.00111 mmol) synthesized in step 12 of Example 2 and α(1,2)α(1,6) pseudomannotriose (2.0 mg, 0.00334 mmol) described in step 25 of Example 5.
ESI-MS m/z: 1528 (M+H)$^+$ Step 28
Compound 30 (0.3 mg, yield: 15%) was obtained in the same way as in step 25 of Example 5 using compound 14 (0.66 mg, 0.00111 mmol) synthesized in step 13 of Example 2.
ESI-MS m/z: 1754 (M+H)$^+$ Step 29
Compound 31 (0.4 mg, yield: 18%) was obtained in the same way as in step 25 of Example 5 using compound 16 (0.91 mg, 0.00111 mmol) synthesized in step 15 of Example 2.
ESI-MS m/z: 1981 (M+H)$^+$ Step 30
Compound 32 (0.5 mg, yield: 17%) was obtained in the same way as in step 13 of Example 2 using compound 19 (1.95 mg, 0.00111 mmol) synthesized in step 17 of Example 2.
ESI-MS m/z: 2728 (M+H)$^+$ Step 31
Compound 33 (2.2 mg, yield: 52%) was obtained in the same way as in step 25 of Example 5 using compound 18 (2.91 mg, 0.00111 mmol) synthesized in step 16 of Example 2.
ESI-MS m/z: 1892 (M+2H)$^{2+}$ Example 7 Synthesis of Sugar Chain Ligand-Linker Unit—3

Synthesis of compounds 34 and 35

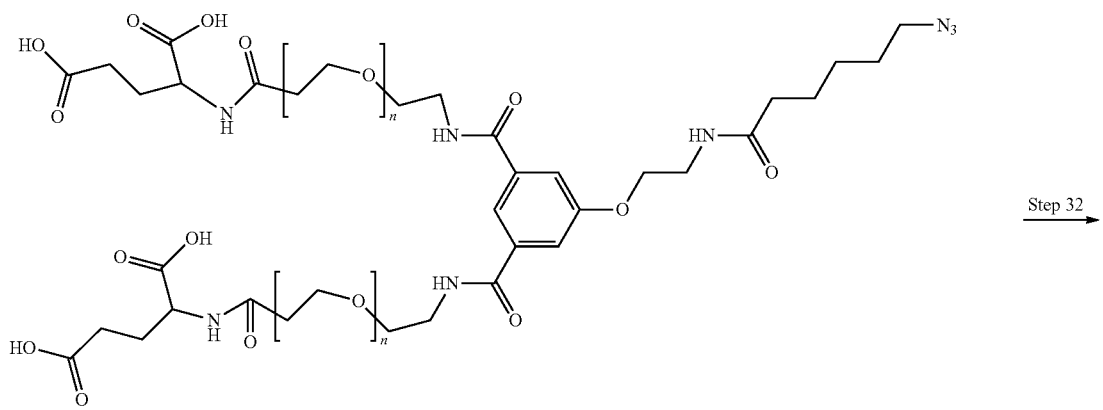

22a: n = 12
22b: n = 24

-continued
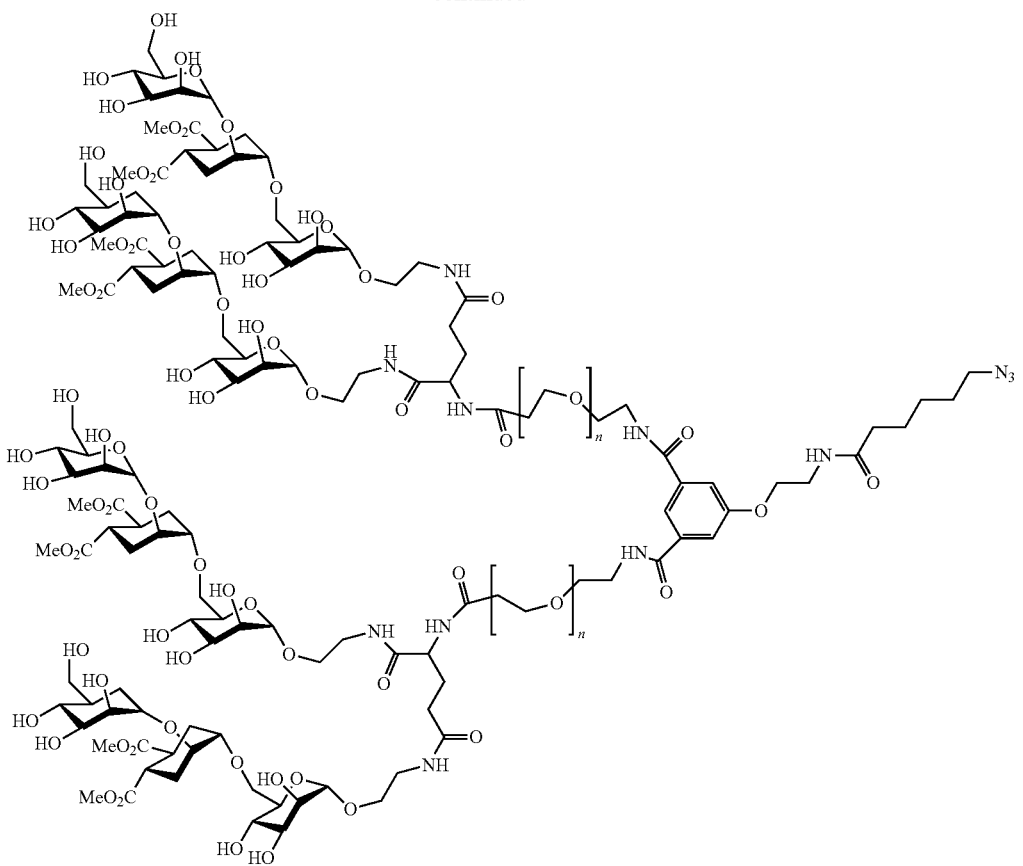
34a: n = 12
34b: n = 24
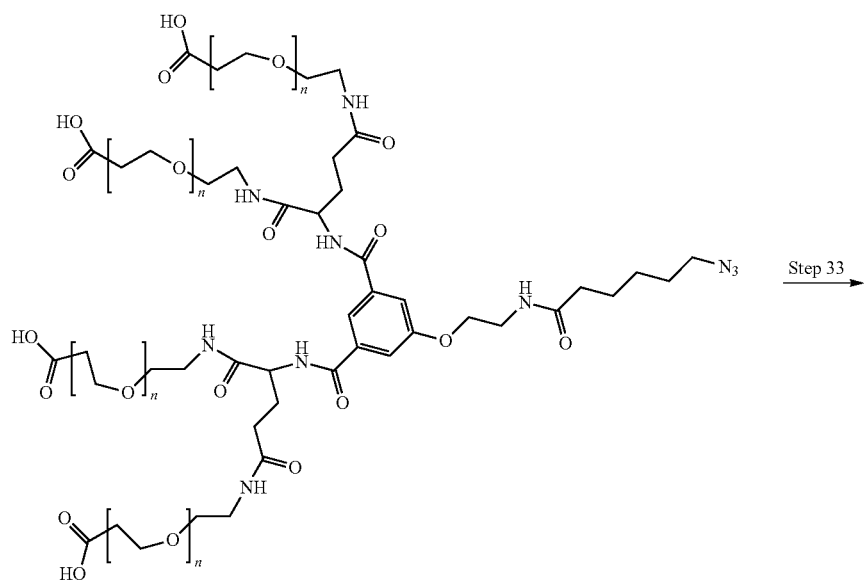
26a: n = 12
26b: n = 24
Step 33

-continued

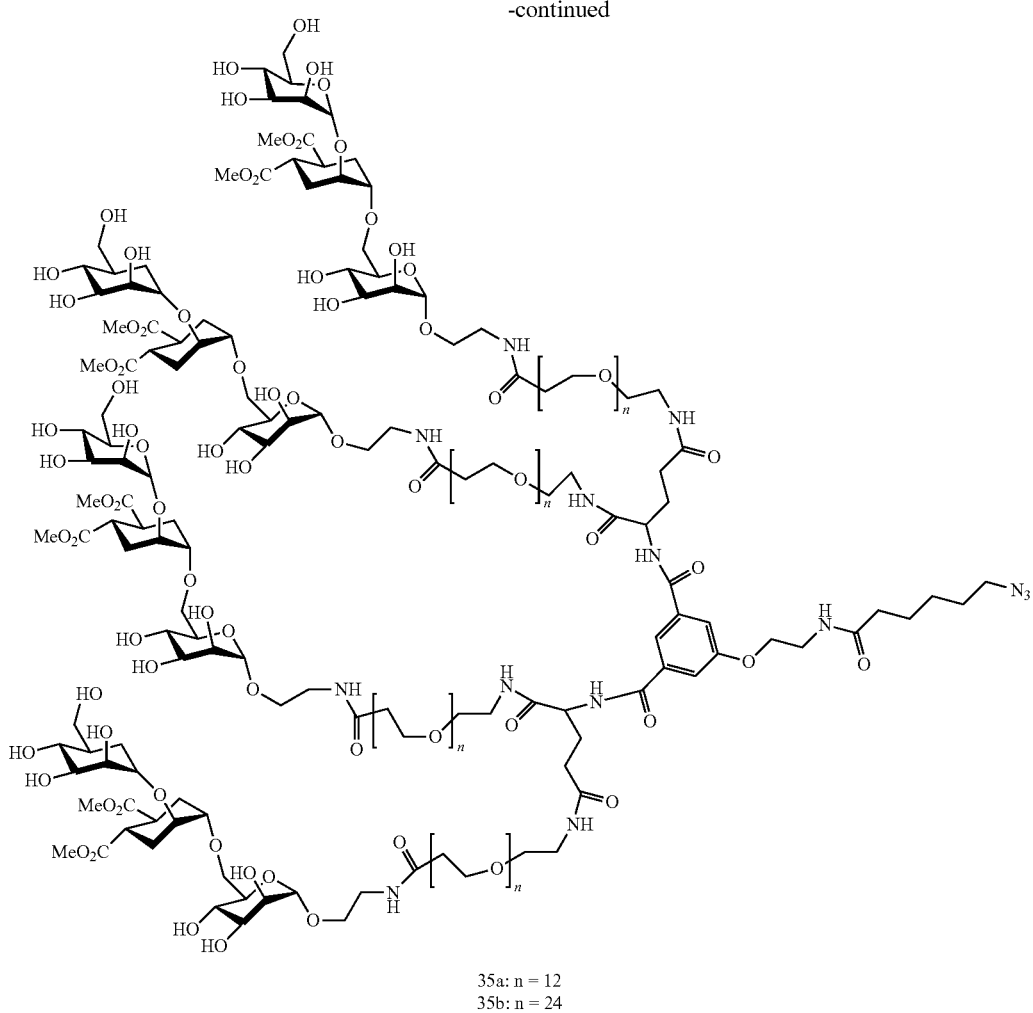

35a: n = 12
35b: n = 24

Step 32

(a); Compound 34a (2 mg, yield: 44%) was obtained in the same way as in step 25 of Example 5 using compound 22a (2 mg, 1.1 μmol) obtained in step 20 of Example 3.

ESI-MS m/z: 2073 (M−2H)$^{2-}$ (b); Compound 34b (1.8 mg, yield: 37%) was obtained in the same way as in step 25 of Example 5 using compound 22a (3.1 mg, 1.1 μmol) obtained in step 20 of Example 3.

ESI-MS m/z: 2601 (M−2H)$^{2-}$

Step 33

(a); Compound 35a (3 mg, yield: 55%) was obtained in the same way as in step 25 of Example 5 using compound 26a (3.1 mg, 1.1 μmol) obtained in step 24 of Example 4.

ESI-MS m/z: 2671 (M−2H)$^{2-}$ (b); Compound 35b (2.2 mg, yield: 56%) was obtained in the same way as in step 25 of Example 5 using compound 26b (2.7 mg, 0.5 μmol) obtained in step 24 of Example 4.

ESI-MS m/z; 2486 (M−2H)$^{2-}$

Comparative Example 1 Synthesis of Sugar Chain Ligand-Linker Unit—4

Synthesis of Compound 38

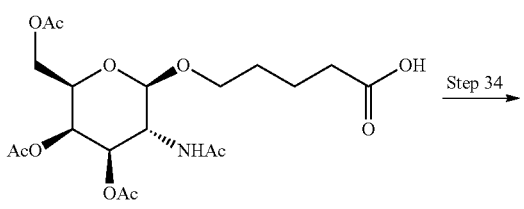

36

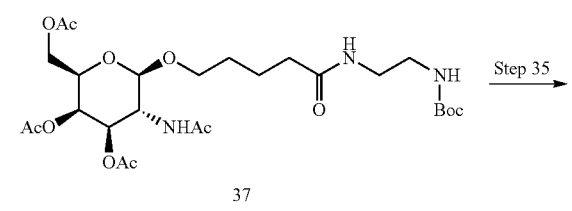

37

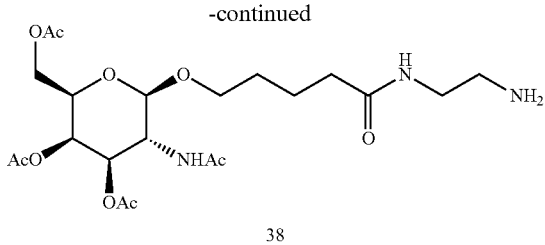

38

Step 34

Compound 36 (0.9602 g, 2.1460 mmol) synthesized by the method described in Journal of American Chemical Society, Vol. 136, p. 16958-16961, 2014 was dissolved in N,N'-dimethylformamide (10 mL). To the solution, N-Boc-ethylenediamine (manufactured by Sigma-Aldrich Co. LLC, 0.6877 g, 4.292 mmol), diisopropylethylamine (1.90 mL, 10.87 mmol), and 2-(1H-benzotriazol-1-yl)-1,1,3,3-tetramethyluronium hexafluorophosphate (manufactured by Wako Pure Chemical Industries, Ltd., 1.6437 g, 4.3229 mmol) were added, and the mixture was stirred overnight at room temperature. Water was added to the reaction solution, followed by extraction with chloroform twice. Then, the organic layer was washed with saturated saline and dried over anhydrous magnesium sulfate. The solvent was distilled off under reduced pressure to obtain a crude product of compound 37.

ESI-MS m/z: 590 (M+H)$^+$

Step 35

Compound 37 (1.2654 g, 2.1460 mmol) synthesized in step 34 was dissolved in dichloromethane (15 mL). To the solution, trifluoroacetic acid (4 mL) was added, and the mixture was stirred overnight at room temperature. Water was added to the reaction solution, followed by extraction with ethyl acetate. Then, the organic layer was washed with saturated saline and dried over anhydrous magnesium sulfate. The solvent was distilled off under reduced pressure, followed by elution by reverse-phase column chromatography (water/methanol=80/20) to obtain compound 38 (0.3879 g, yield: 37%).

ESI-MS m/z: 490 (M+H)$^+$ $^1$H-NMR (DMSO-D6) δ: 1.46-1.52 (4H, m), 1.78 (3H, s), 1.90 (3H, s), 2.00 (3H, s), 2.08 (2H, t, J=7.4 Hz), 2.11 (3H, s), 2.85 (2H, t, J=6.3 Hz), 3.27 (2H, dd, J=12.3, 6.2 Hz), 3.67-3.69 (1H, m), 3.68-3.73 (1H, m), 3.86-3.90 (1H, m), 4.01-4.04 (3H, m), 4.49 (1H, d, J=8.4 Hz), 4.97 (1H, dd, J=11.3, 3.4 Hz), 5.22 (1H, d, J=3.5 Hz), 7.86 (1H, d, J=9.1 Hz), 7.95-8.02 (1H, m).

Comparative Example 2 Synthesis of Sugar Chain Ligand-Linker Unit—5

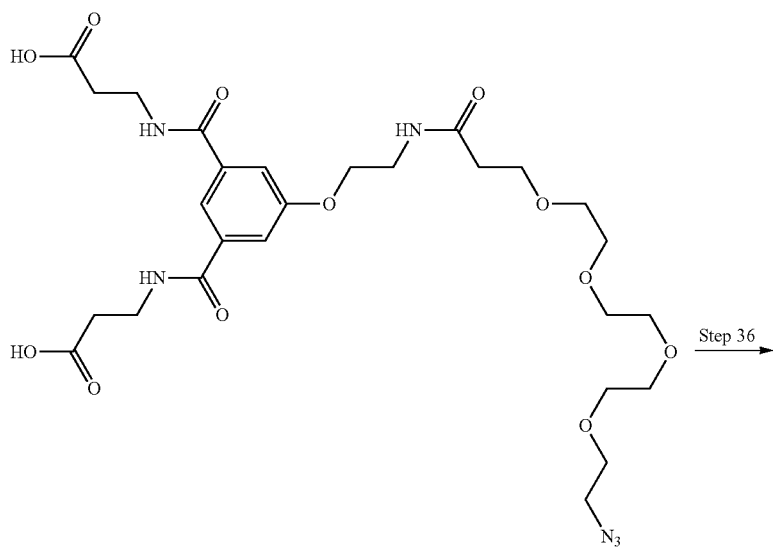

7

171                               172
-continued
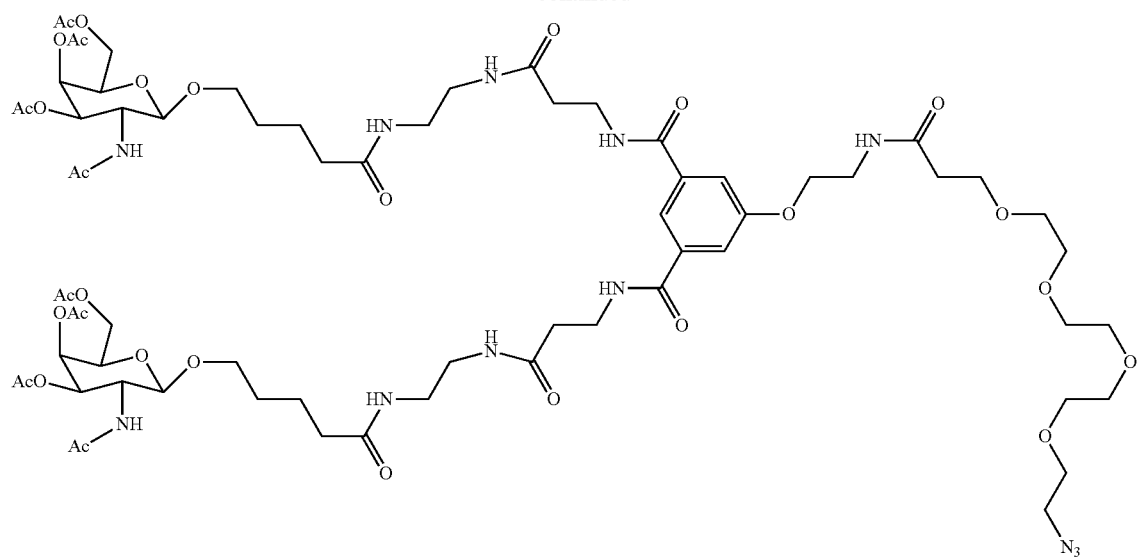
39
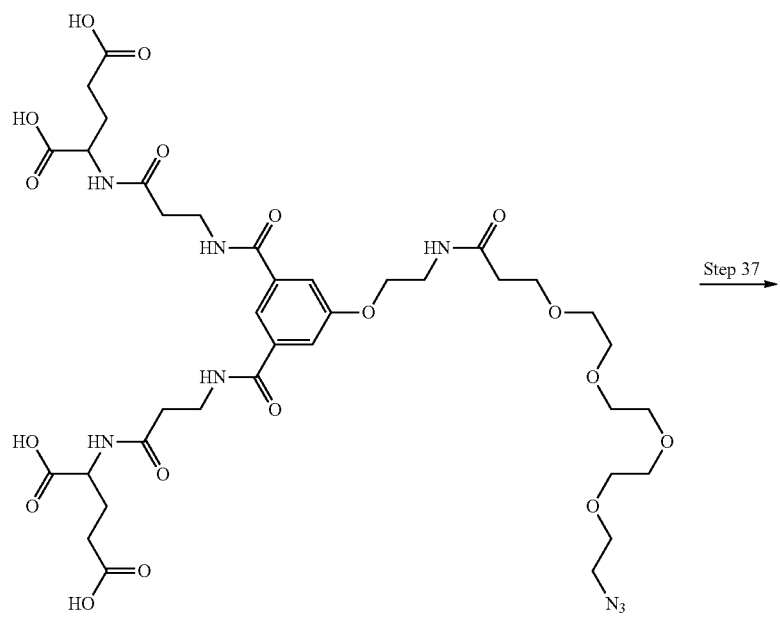
9
Step 37

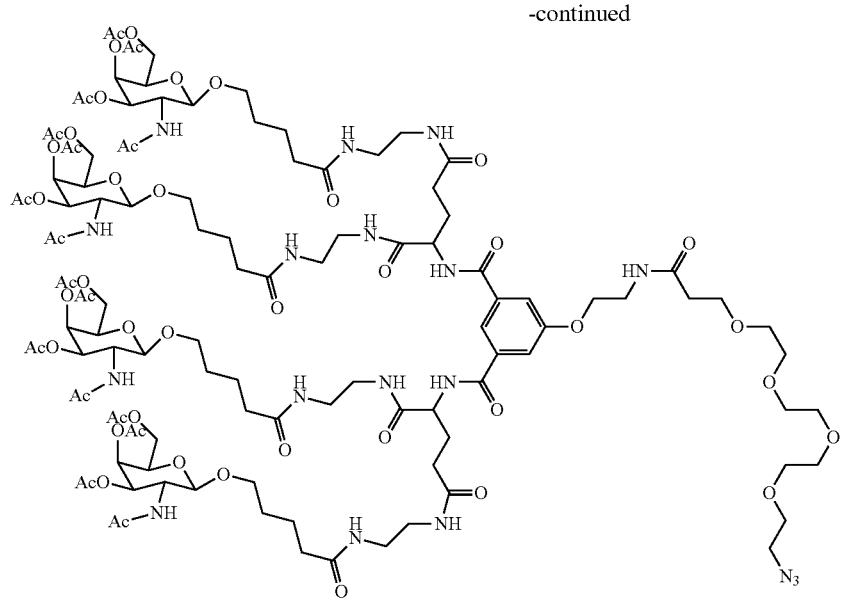

40

Synthesis of Compound 39
Step 36
Compound 39 (7 mg, yield: 65%) was obtained in the same way as in step 25 of Example 5 using compound 7 (4.36 mg, 0.006 mmol) synthesized in step 6 of Example 1 and compound 38 (10 mg, 0.02 mmol) synthesized in step 35 of Comparative Example 1.
ESI-MS m/z: 1581 (M−H)$^{-}$ Synthesis of Compound 40
Step 37
Compound 39 (22 mg, yield: 72%) was obtained in the same way as in step 25 of Example 5 using compound 9 (10 mg, 0.011 mmol)) synthesized in step 8 of Example 1 and compound 38 (43.9 mg, 0.090 mmol) synthesized in step 35 of Comparative Example 1.
ESI-MS m/z: 2785 (M−2H)$^{2-}$ Example 8 Synthesis of Nucleic Acid Conjugate—1

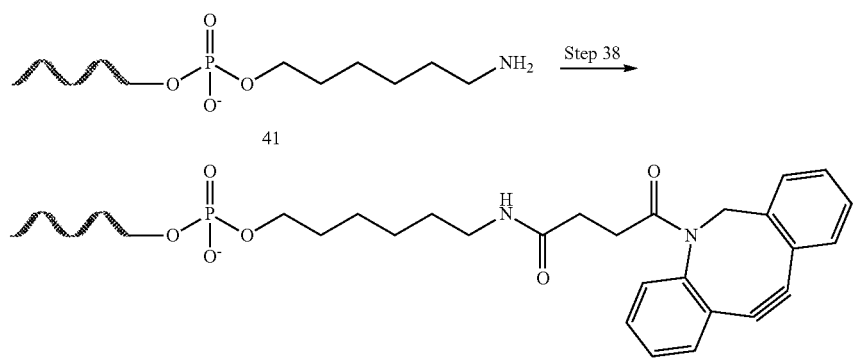

-continued
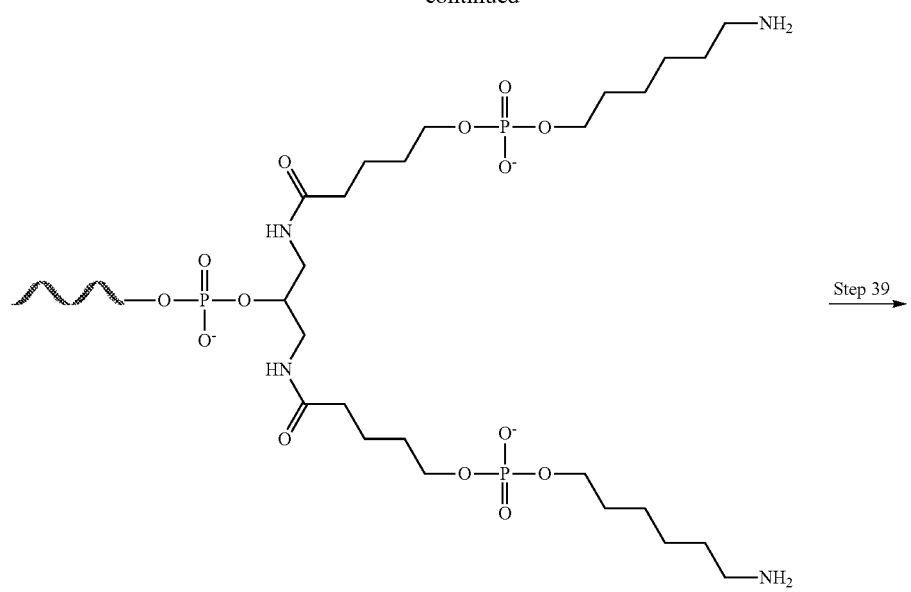
43
Step 39
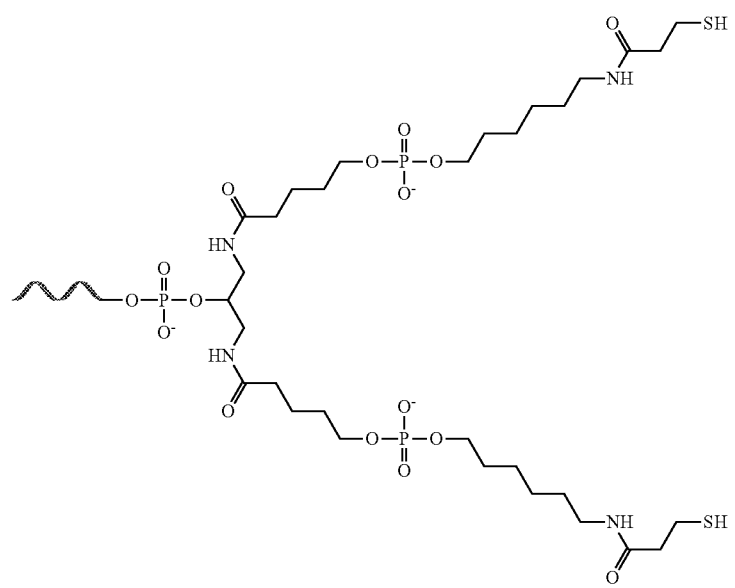
44

-continued
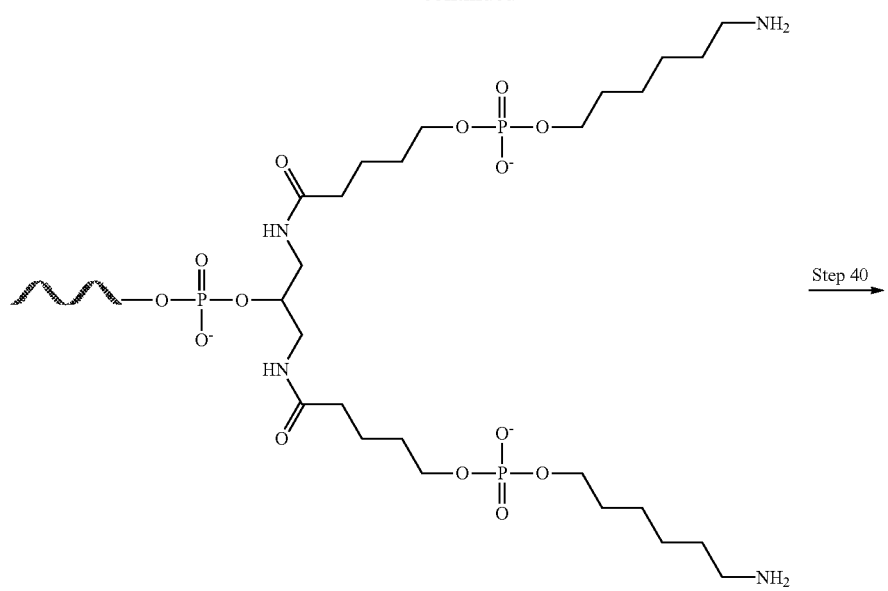
43
Step 40
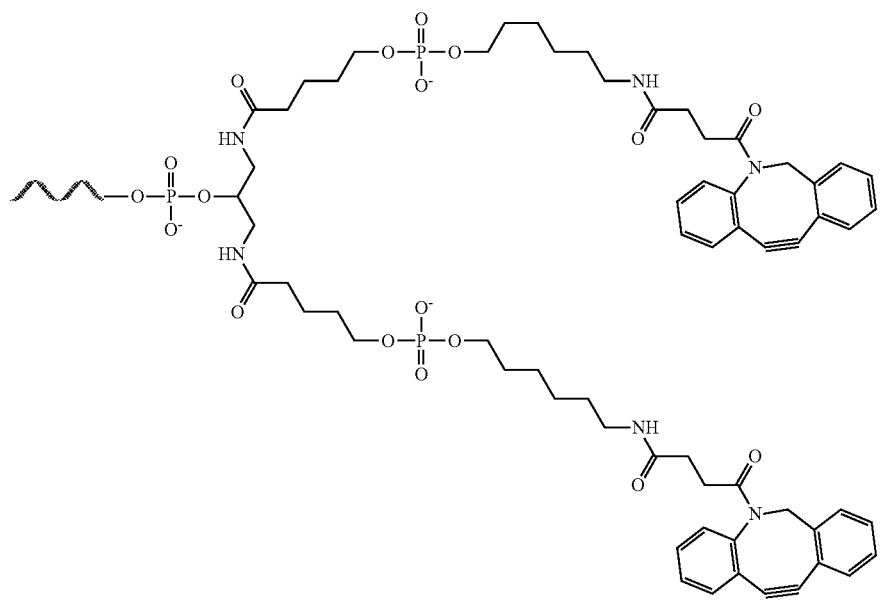
45

Step 38

Compound 42 was obtained by the method described in ACS nano, Vol. 9, p. 9652-9664, 2015 using compound 41 allowed to have a terminal binding functional group synthesized by the method described in Molecules, Vol. 17, p. 13825-13854, 2012.

Step 39

To compound 43 allowed to have a terminal binding functional group synthesized by the method described in Molecules, Vol. 17, p. 13825-13854, 2012 using Symmetric Doubler Phosphoramidite (manufactured by Glen Research Corp., catalog No. 10-1920-90), a solution of N-succinimidyl 3-(2-pyridyldithiol)propionate in dimethyl sulfoxide was added, and the mixture was left standing at room temperature for 4 hours in a phosphate buffer solution. Dithiothreitol was added to the reaction solution, and the mixture was left standing overnight at room temperature. The mixture was subjected to gel filtration treatment (Nap column, manufactured by GE Healthcare Japan Corp., elution solvent: 20 mmol/L acetic acid/sodium acetate buffer solution (pH 5.0) and ultrafiltration to obtain compound 44.

Step 40

Compound 45 was obtained in the same way as in step 39 using dibenzocyclooctyne-N-hydroxysuccinimide ester.

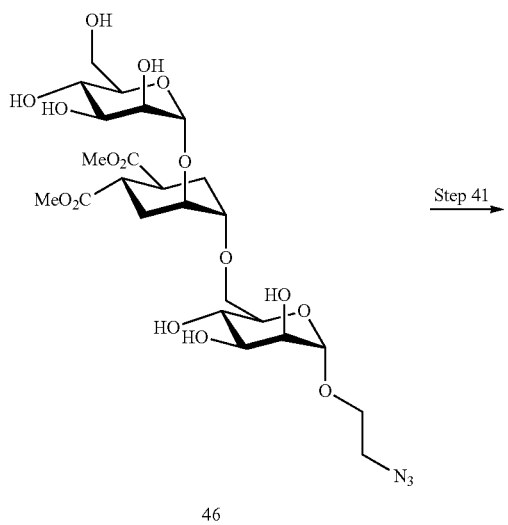

46

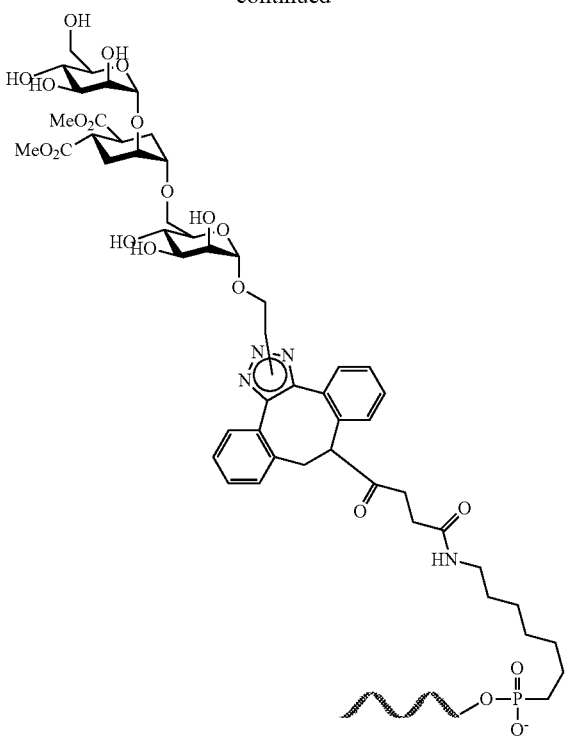

47

Step 41

To compound 46 synthesized by the method described in ACS Chemical Biology, Vol. 5, No. 3, p. 301-312, 2010, compound 42 synthesized in step 38 of Example 8 was added, and the mixture was left standing at room temperature for 1 hour. Single-stranded nucleic acid conjugates 47 were obtained by purification by any method of anion-exchange chromatography (GE Healthcare Japan Corp., Mono Q 5/50 GL, 10 μm, 5.0 mm×50 mm, solution A: 10 mM Tris buffer solution/30% acetonitrile, solution B: gradient with 10 mM Tris buffer solution/30% acetonitrile/1 M NaBr) and reverse-phase liquid chromatography (Waters Corp., X Bridge C18, 5 μm, 4.6 mm×250 mm, 0.1 M triethylammonium acetate buffer solution, solution B: gradient with acetonitrile).

The nucleic acid conjugates of Table 2 were obtained in the same way as above using the compound group of Table 1 or a sugar chain maleimide adduct synthesized by the method described in Bioconjugate Chemistry, Vol. 14, p. 232-238, 2003, and thiol nucleic acid allowed to have a terminal binding functional group synthesized by the method described in Molecules, Vol. 17, p. 13825-13854, 2012, compound 42, 44 or 45.

TABLE 1
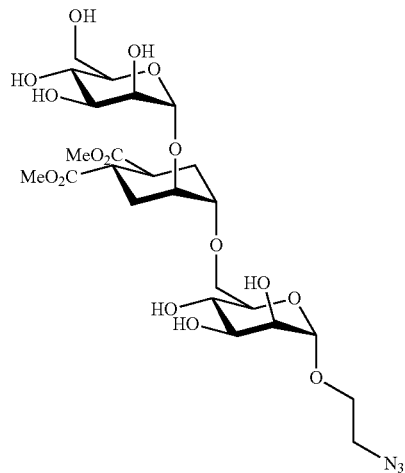
46
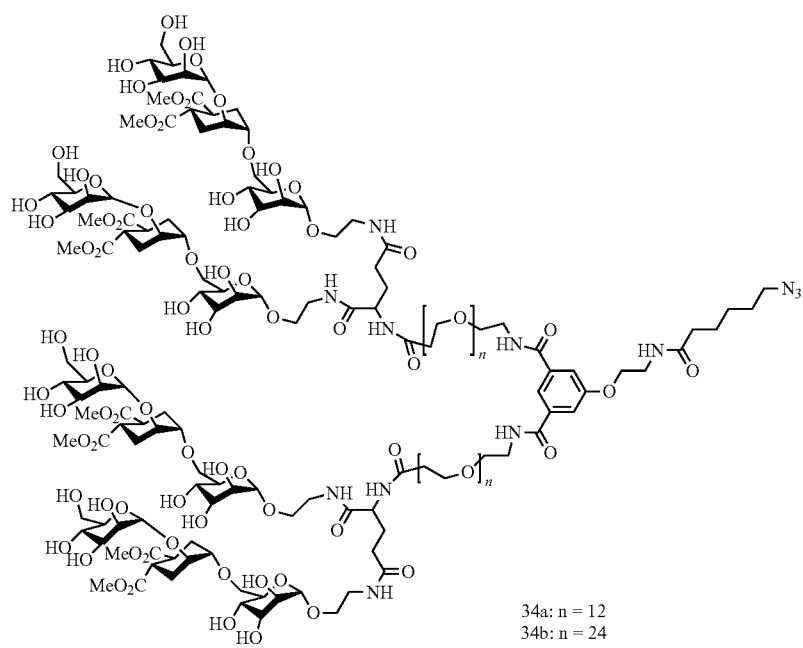
34a: n = 12
34b: n = 24

TABLE 1-continued
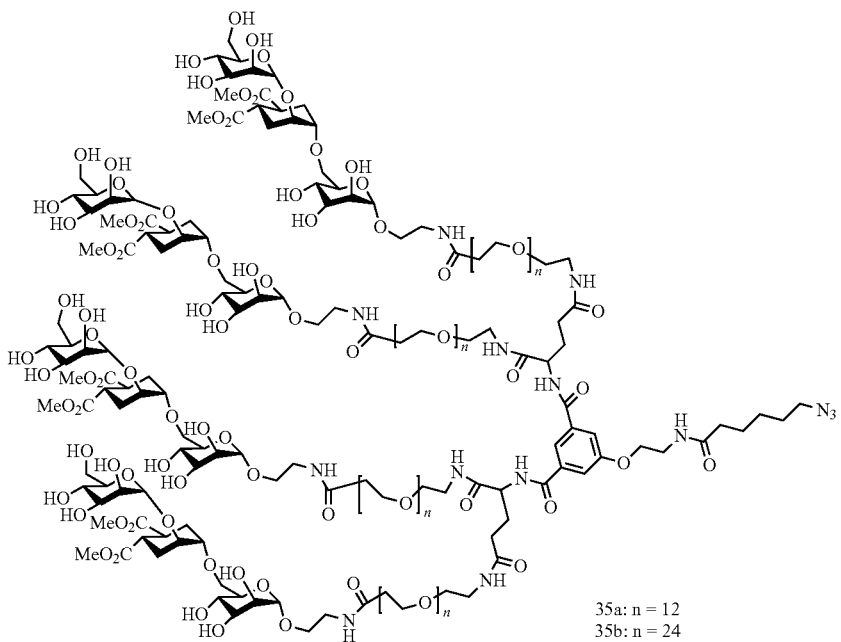
35a: n = 12
35b: n = 24
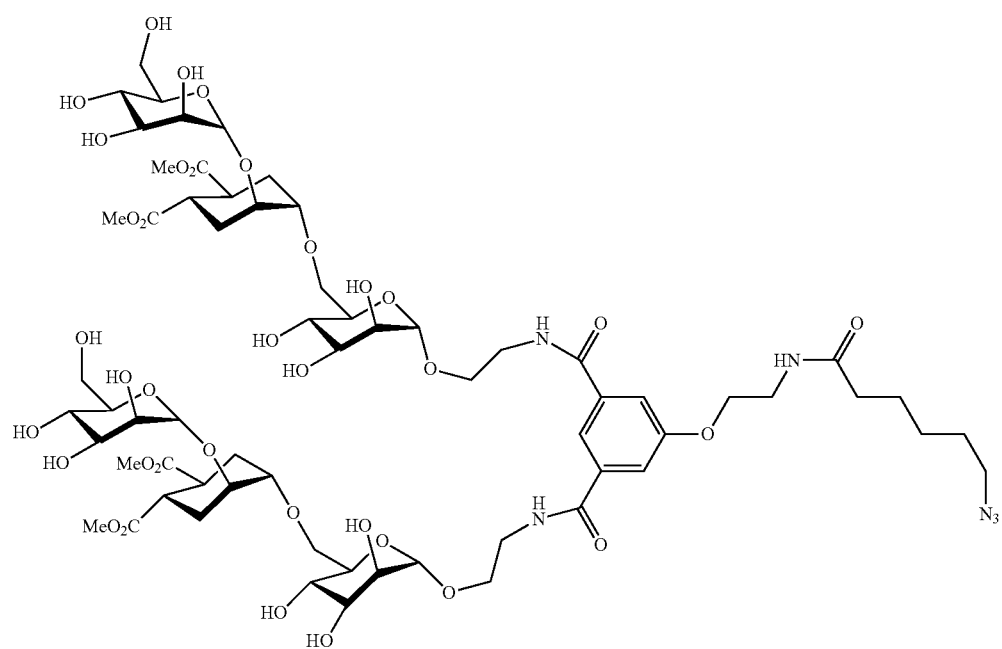
29

TABLE 1-continued
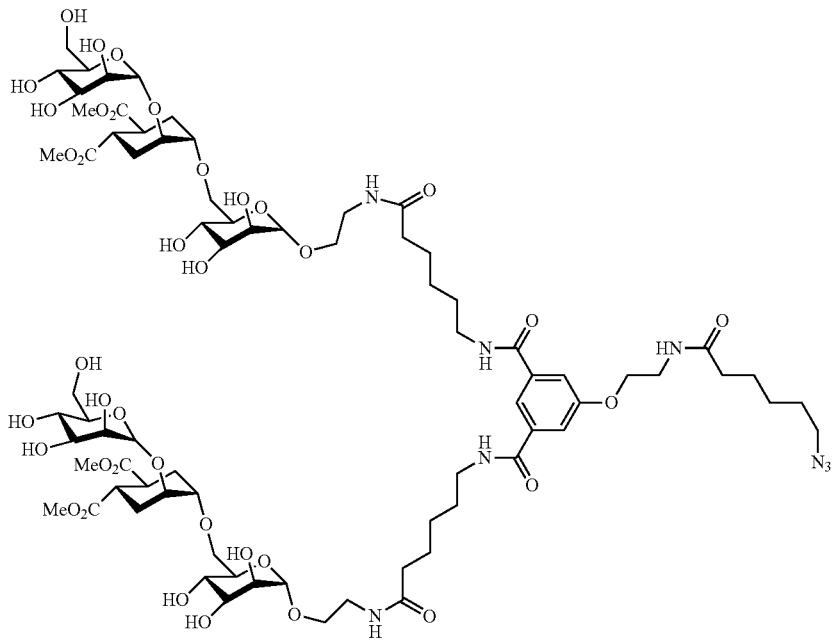
30
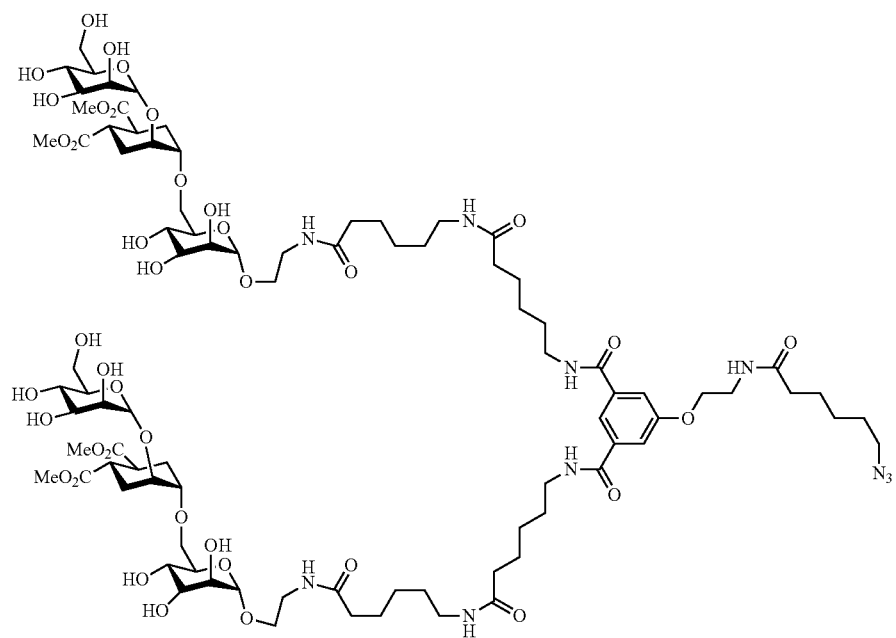
31

TABLE 1-continued
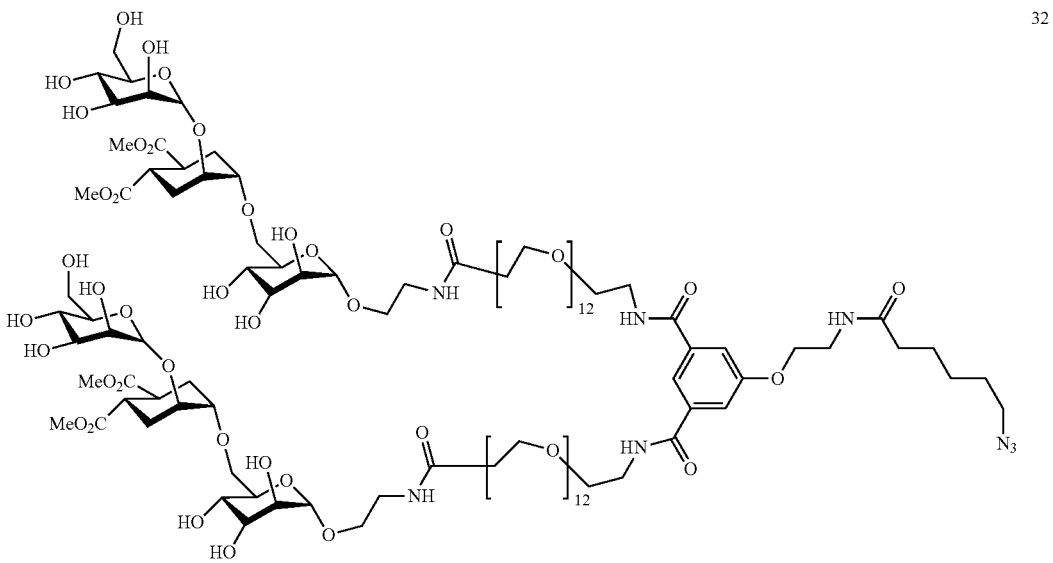
32
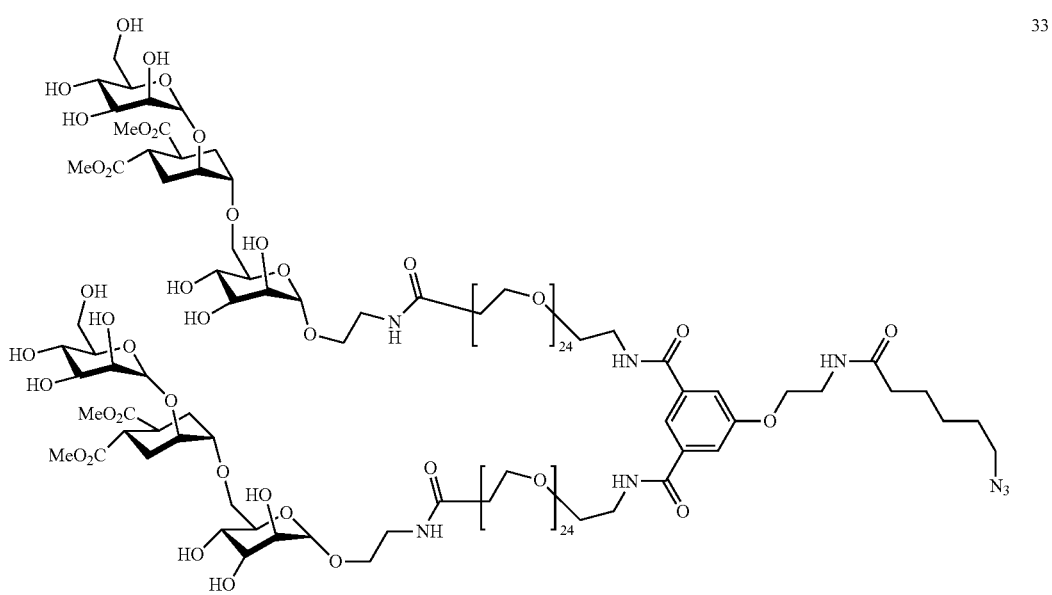
33
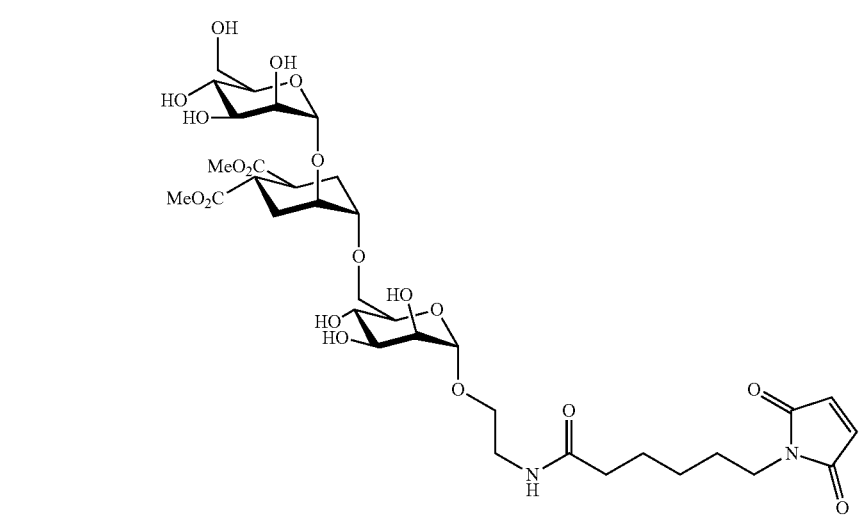
48

TABLE 1-continued
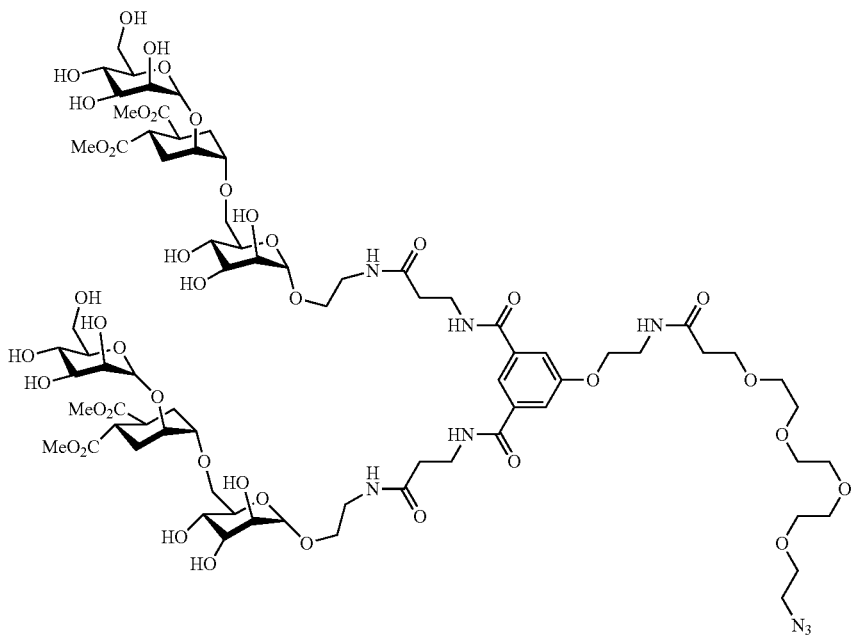
27
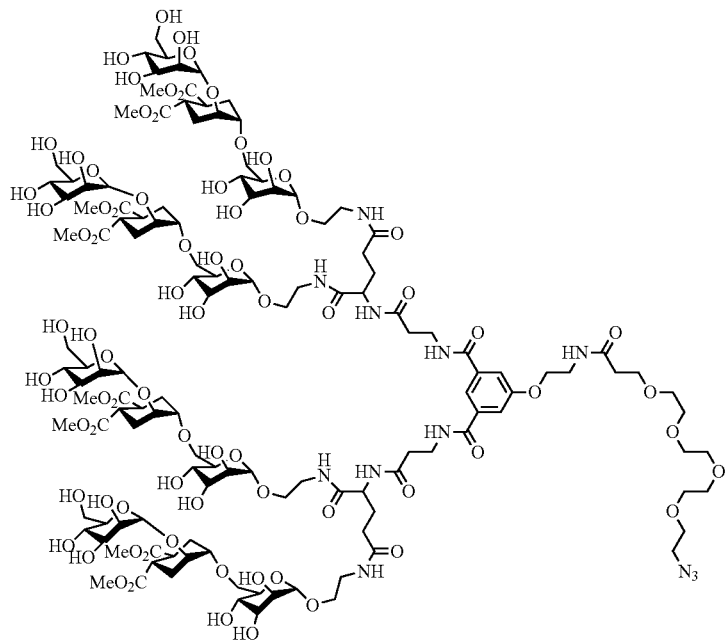
28

TABLE 2
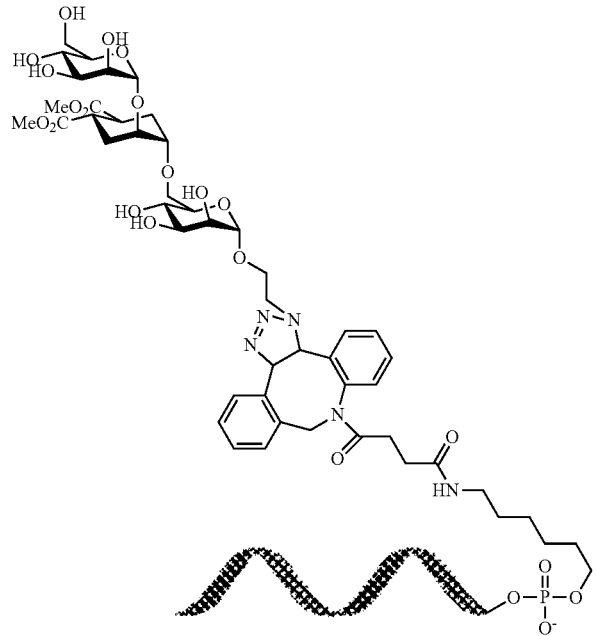
47
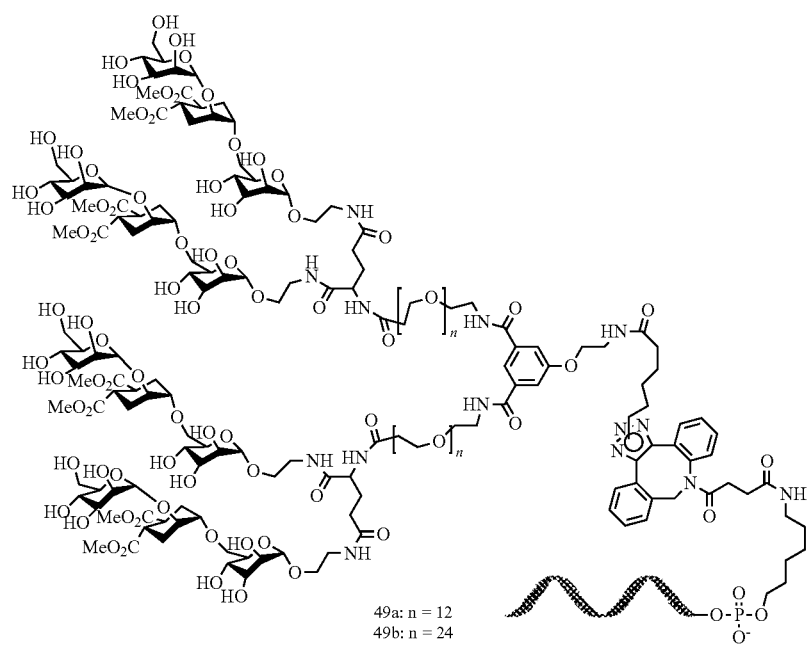

TABLE 2-continued
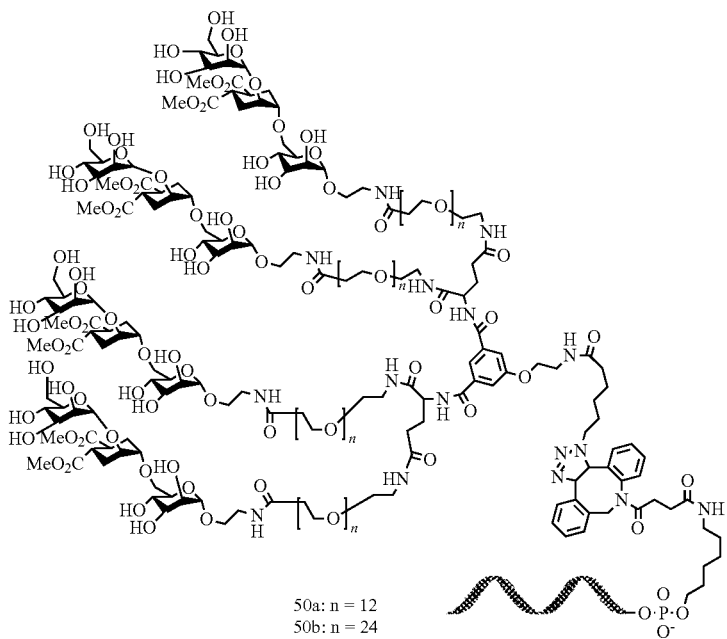
50a: n = 12
50b: n = 24
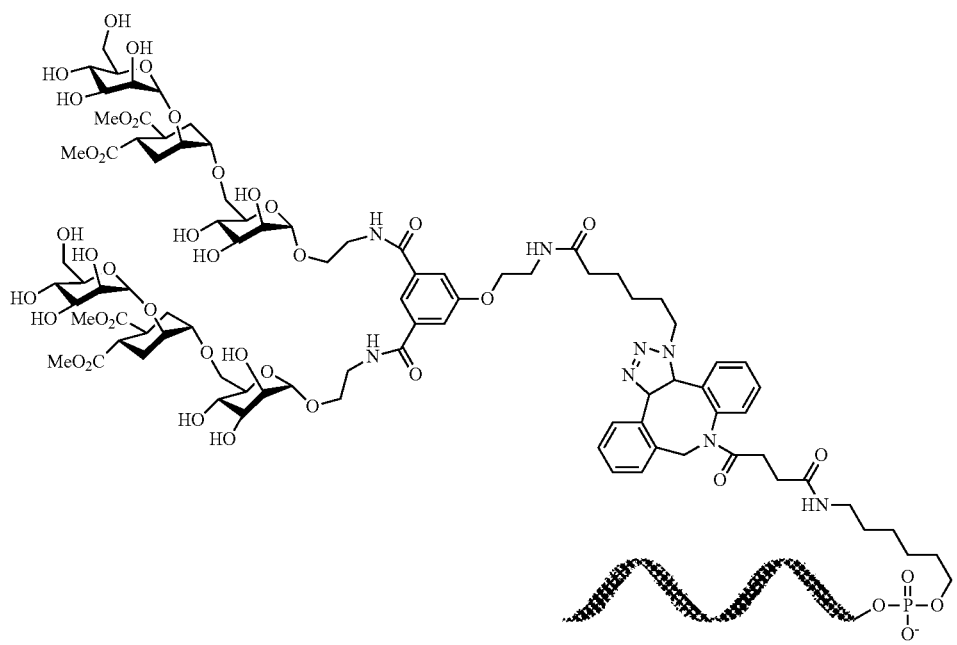
51

TABLE 2-continued
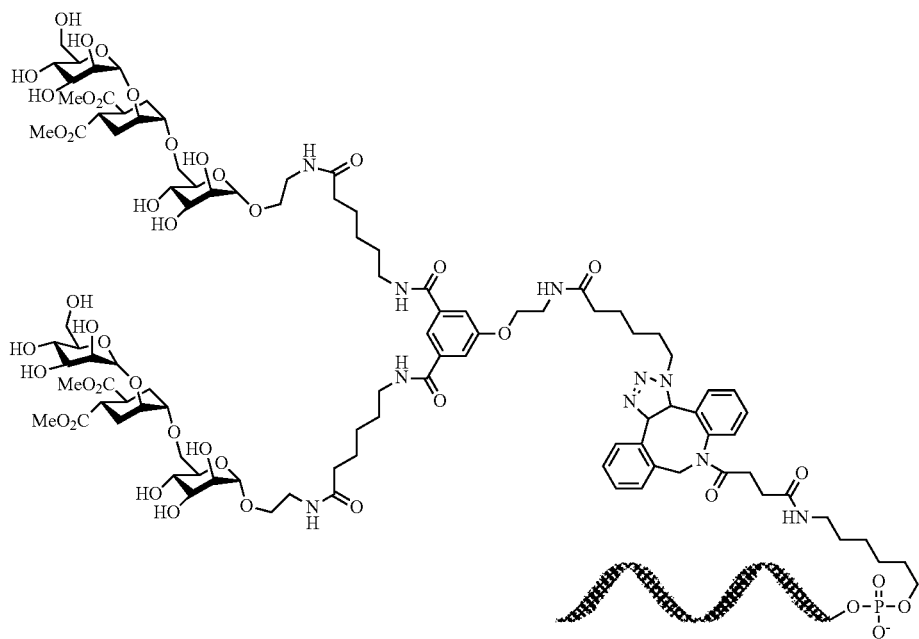
52
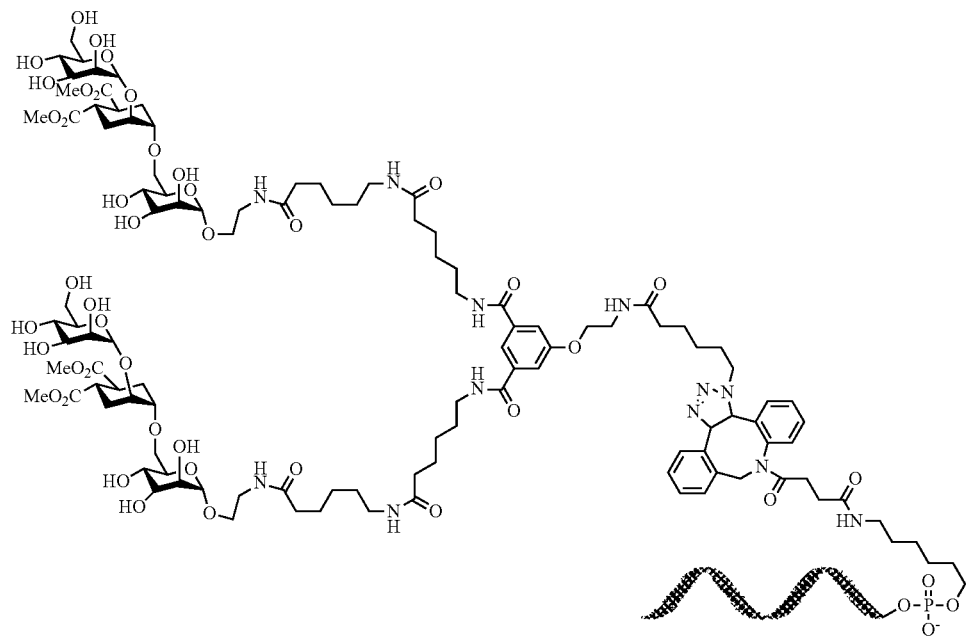
53

TABLE 2-continued
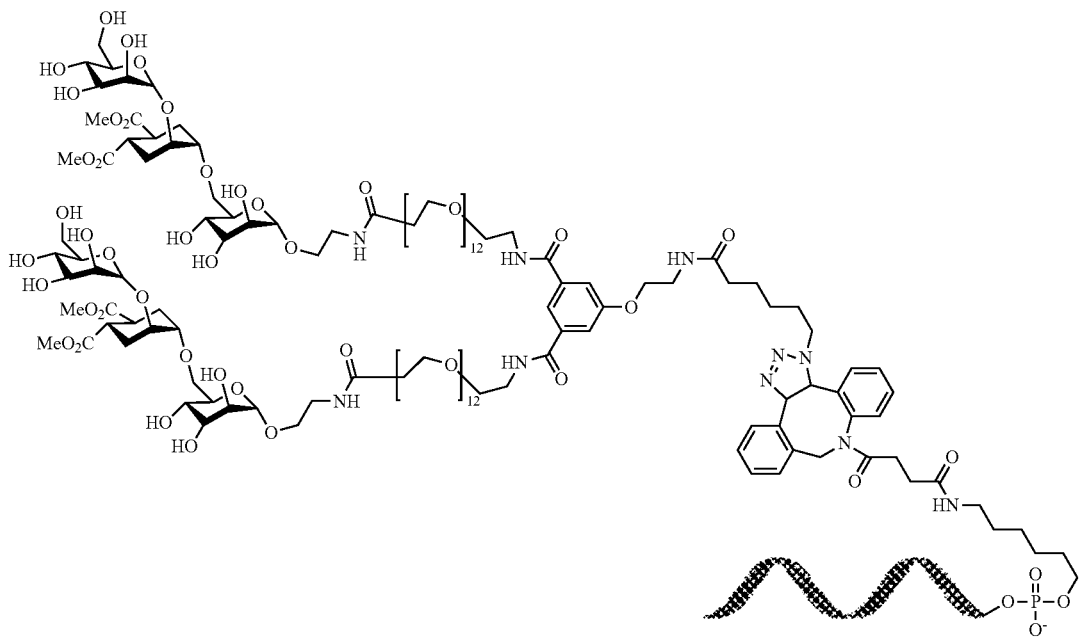
54
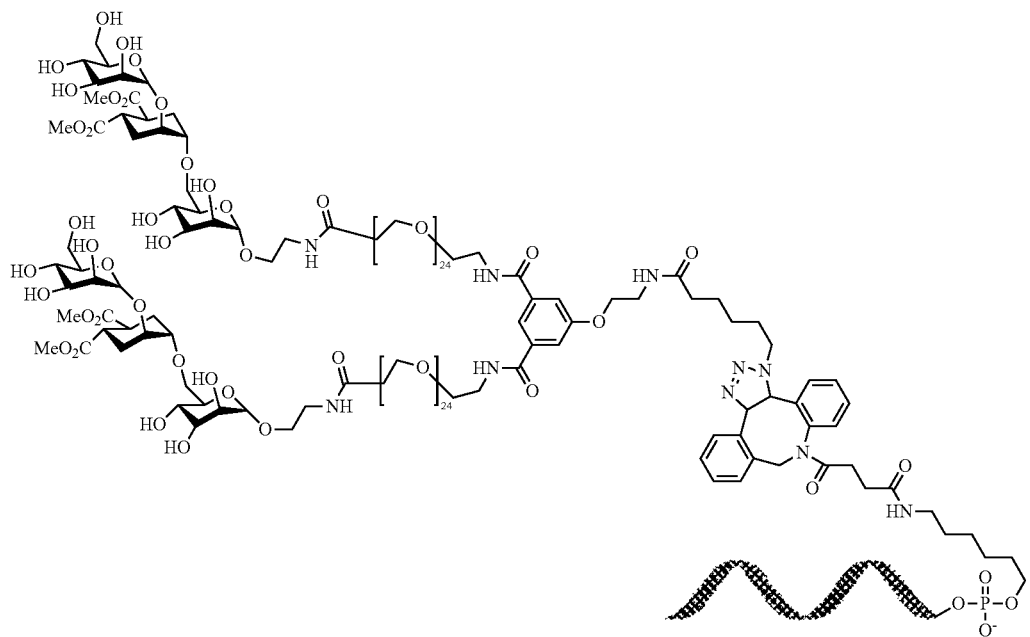
55

TABLE 2-continued
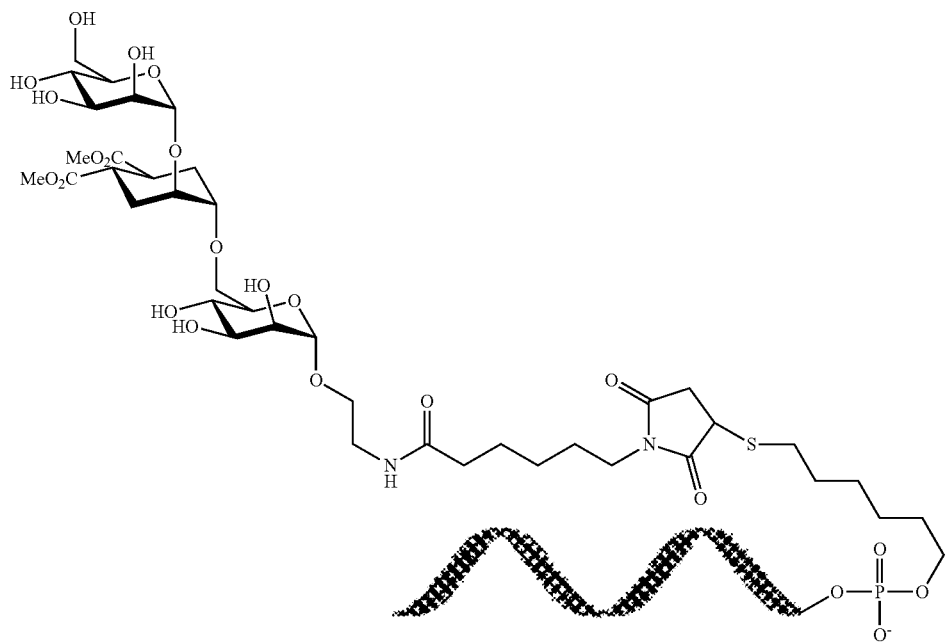
56
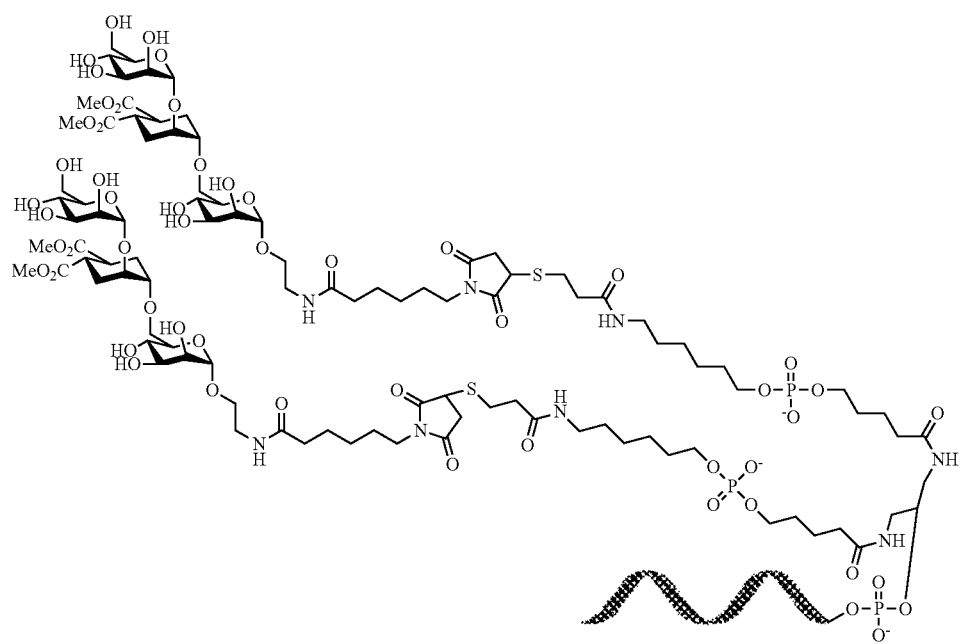
57

TABLE 2-continued
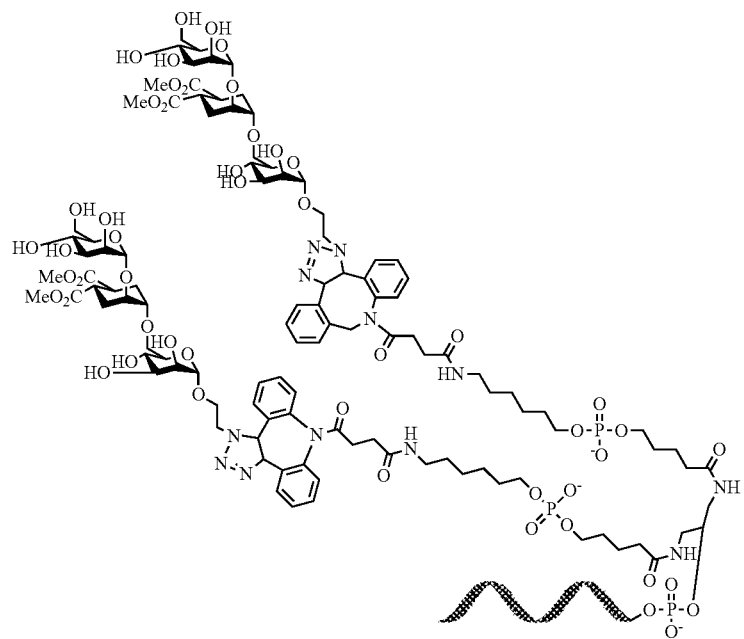
58
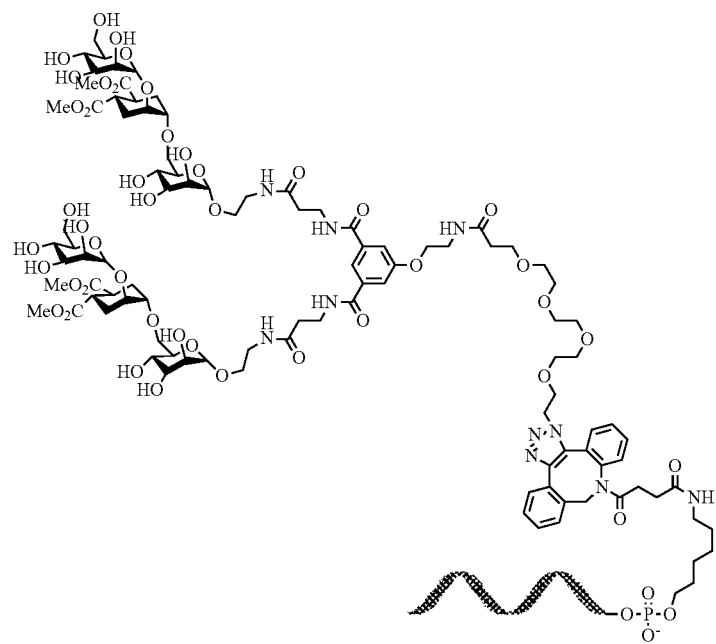
59

TABLE 2-continued

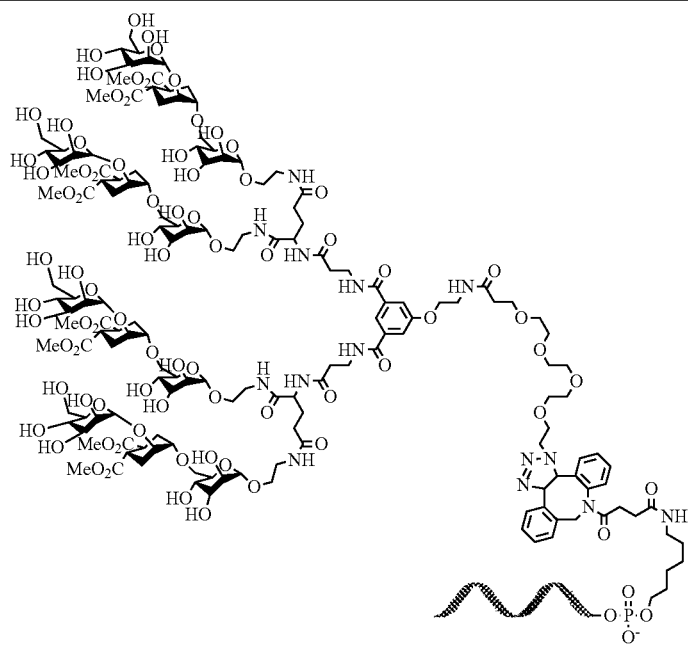

The sequences and mass spectrometry results of nucleic acids in the nucleic acid conjugates synthesized in this Example are shown in Tables 3a and 3b. The description in the box "Compound" in Tables 3a and 3b represents [compound No. in the table]_[position to which a ligand, etc. is bonded in the nucleic acid]_[abbreviation of the nucleic acid sequence in the nucleic acid conjugate]-[type of the nucleic acid (ASO or ssRNA)].

TABLE 3a

| | Compound | L) | Calcd | Found |
|---|---|---|---|---|
| KAC-CTR-001 | CD45-ASO | C(L)^C(L)^A(L)^A(L)^a^t^g^c^c^a^a^g^A(L)^G(L)^T(L)^T(L) | — | — |
| KAC-CTR-002 | ApoB-ASO | G(L)^5(L)^a^t^t^g^g^t^a^t^T(L)^5(L)^A(L) | — | — |
| KAC-CTR-003 | B2M-ASO | T(L)^T(L)^5(L)^T(L)^a^a^g^c^a^g^a^g^T(L)^A(L)^T(L)^G(L) | — | — |
| KAC_001 | 47_5'-CD45-ASO | 47 C(L)^C(L)^A(L)^A(L)^a^t^g^c^c^a^a^g^A(L)^G(L)^T(L)^T(L) | 7441 | 7439 |
| KAC_002 | 51_5'-B2M-ASO | 51 T(L)^T(L)^5(L)^T(L)^a^a^g^c^a^g^a^g^T(L)^A(L)^T(L)^G(L) | 7480 | 7480 |
| KAC_003 | 52_5'-B2M-ASO | 52 T(L)^T(L)^5(L)^T(L)^a^a^g^c^a^g^a^g^T(L)^A(L)^T(L)^G(L) | 7706 | 7700 |
| KAC_004 | 53_5'-B2M-ASO | 53 T(L)^T(L)^5(L)^T(L)^a^a^g^c^a^g^a^g^T(L)^A(L)^T(L)^G(L) | 7933 | 7927 |
| KAC_005 | 54_5'-B2M-ASO | 54 T(L)^T(L)^5(L)^T(L)^a^a^g^c^a^g^a^g^T(L)^A(L)^T(L)^G(L) | 8679 | 8677 |
| KAC_006 | 55_5'-B2M-ASO | 55 T(L)^T(L)^5(L)^T(L)^a^a^g^c^a^g^a^g^T(L)^A(L)^T(L)^G(L) | 9737 | 9737 |
| KAC_007 | 56_5'-CD45-ASO | 56 C(L)^C(L)^A(L)^A(L)^a^t^g^c^c^a^a^g^A(L)^G(L)^T(L)^T(L) | 6514 | 6513 |
| KAC_008 | 57_5'-CD45-ASO | 57 C(L)^C(L)^A(L)^A(L)^a^t^g^c^c^a^a^g^A(L)^G(L)^T(L)^T(L) | 7839 | 7836 |
| KAC_009 | 58_5'-CD45-ASO | 58 C(L)^C(L)^A(L)^A(L)^a^t^g^c^c^a^a^g^A(L)^G(L)^T(L)^T(L) | 7902 | 7904 |

TABLE 3a-continued

| Compound | | L) | Calcd | Found |
|---|---|---|---|---|
| KAC_010 | 59_5'-B2M-ASO | 59 T(L)^T(L)^5(L)^T(L)^a^a^g^c^a^g^a^g^T(L)^A(L)^T(L)^G(L) | 7755 | 7755 |
| KAC_011 | 59_5'-CD45-ASO | 59 C(L)^C(L)^A(L)^A(L)^a^t^g^c^c^a^a^g^A(L)^G(L)^T(L)^T(L) | 8618 | 8620 |
| KAC_012 | 60_5'-B2M-ASO | 60 T(L)^T(L)^5(L)^T(L)^a^a^g^c^a^g^a^g^T(L)^A(L)^T(L)^G(L) | 9176 | 9177 |

TABLE 3b

| Compound | Sequence (5'→3') | Calcd | Found |
|---|---|---|---|
| 49a_3'_3'PS_-B2M-ssRNA | A(F)G(M)G(F)A(M)C(F)U(M)G(F)G(M)U(F)C(M)U(F)U(F)U(M)C(F)U(M)A(F)U(M)C(F)U(M)^C(F)^U(M) 49a | 11395 | 11397 |
| 49b_5-B2M-ssRNA | 49b A(F)G(M)G(F)A(M)C(F)U(M)G(F)G(M)U(F)C(M)U(F)U(F)U(M)C(F)U(M)A(F)U(M)C(F)U(M)^C(F)^U(M) | 12452 | 12452 |
| 50a_3'_3'PS_-B2M-ssRNA | A(F)G(M)G(F)A(M)C(F)U(M)G(F)G(M)U(F)C(M)U(F)U(F)U(M)C(F)U(M)A(F)U(M)C(F)U(M)^C(F)^U(M) 50a | 12594 | 12626 |
| 50b_5-B2M-ssRNA | 50b A(F)G(M)G(F)A(M)C(F)U(M)G(F)G(M)U(F)C(M)U(F)U(F)U(M)C(F)U(M)A(F)U(M)C(F)U(M)^C(F)^U(M) | 14708 | 14724 |
| 51_5'-B2M-ssRNA | 51 A(F)G(M)G(F)A(M)C(F)U(M)G(F)G(M)U(F)C(M)U(F)U(F)U(M)C(F)U(M)A(F)U(M)C(F)U(M)^C(F)^U(M) | 8776 | 8774 |
| 52_5'-B2M-ssRNA | 52 A(F)G(M)G(F)A(M)C(F)U(M)G(F)G(M)U(F)C(M)U(F)U(F)U(M)C(F)U(M)A(F)U(M)C(F)U(M)^C(F)^U(M) | 9002 | 9001 |
| 53_5'-B2M-ssRNA | 53 A(F)G(M)G(F)A(M)C(F)U(M)G(F)G(M)U(F)C(M)U(F)U(F)U(M)C(F)U(M)A(F)U(M)C(F)U(M)^C(F)^U(M) | 9228 | 9229 |
| 54_5'-B2M-ssRNA | 54 A(F)G(M)G(F)A(M)C(F)U(M)G(F)G(M)U(F)C(M)U(F)U(F)U(M)C(F)U(M)A(F)U(M)C(F)U(M)^C(F)^U(M) | 9975 | 9975 |
| 55_3'_5'PS_-B2M-ssRNA | A(F)^G(M)^G(F)A(M)C(F)U(M)G(F)G(M)U(F)C(M)U(F)U(F)U(M)C(F)U(M)A(F)U(M)C(F)U(M)C(F)U(M) 55 | 11033 | 11024 |
| 55_5'-B2M-ssRNA | 55 A(F)G(M)G(F)A(M)C(F)U(M)G(F)G(M)U(F)C(M)U(F)U(F)U(M)C(F)U(M)A(F)U(M)C(F)U(M)^C(F)^U(M) | 11033 | 11033 |
| 55_5'-GAPDH-ssRNA | 55 C(F)C(M)U(F)U(F)U(M)C(F)A(M)U(F)U(M)G(F)A(F)C(F)C(M)U(F)C(M)A(M)A(M)C(F)U(M)A(F)C(M)A(F) | 10949 | 10946 |
| 58_5'-B2M-ssRNA | 58 A(F)G(M)G(F)A(M)C(F)U(M)G(F)G(M)U(F)C(M)U(F)U(F)U(M)C(F)U(M)A()U(M)C(F)U(M)^C(F)^U(M) | 9317 | 9320 |
| 59_5'-B2M-ssRNA | 59 A(F)G(M)G(F)A(M)C(F)U(M)G(F)G(M)U(F)C(M)U(F)U(F)U(M)C(F)U(M)A()U(M)C(F)U(M)^C(F)^U(M) | 9052 | 9051 |
| 60_5'-B2M-ssRNA | 60 A(F)G(M)G(F)A(M)C(F)U(M)G(F)G(M)U(F)C(M)U(F)U(F)U(M)C(F)U(M)A(F)U(M)C(F)U(M)^C(F)^U(M) | 8831 | 8831 |

In the tables, n represents DNA; N(M) represents 2'-O-methyl-modified RNA; N(F) represents 2'-fluorine-modified RNA; N(L) represents LNA; 5(L) represents LNAmC; ^ represents phosphorothioate modification; ss represents a sense strand; as represents an antisense strand; and a boldface number represents a modifying group corresponding to compound No. in Example. The same holds true for each table described below.

Step 38

The single-stranded nucleic acid conjugate synthesized in step 41 was concentration-adjusted (50 μmol/L) with a mixed buffer solution (100 mmol/L potassium acetate, 30 mmol/L 2-[4-(2-hydroxyethyl)piperazin-1-yl]ethanesulfonic acid, HEPES)-KOH (pH 7.4), 2 mmol/L magnesium acetate). The sense strand and an antisense strand (50 μmol/L) were mixed in equal amounts and left standing at 80° C. for 10 minutes. The antisense strand sequence is as described in Table 2. The temperature was gradually decreased, and the resultant was left standing at 37° C. for 1 hour to obtain a double-stranded nucleic acid conjugate.

The nucleic acid conjugates synthesized in this Example are shown in Table 4, and the sequences of nucleic acids in the nucleic acid conjugates are shown in Table 5. The description in the box "Compound" in Table 5 represents [compound No. in the table]_[abbreviation of the nucleic acid sequence in the nucleic acid conjugate]-[type of the nucleic acid (siRNA)]. In the description in the box "Single strand name", the sense strand (ss) is represented by [compound No. in the table]_[position to which a ligand, etc. is bonded in the nucleic acid]_[abbreviation of the nucleic acid sequence in the nucleic acid conjugate]-[type of the nucleic acid (ssRNA)], and the antisense strand (as) is represented by [abbreviation of the nucleic acid sequence in the nucleic acid conjugate]-[type of the nucleic acid (as-RNA)].
TABLE 4
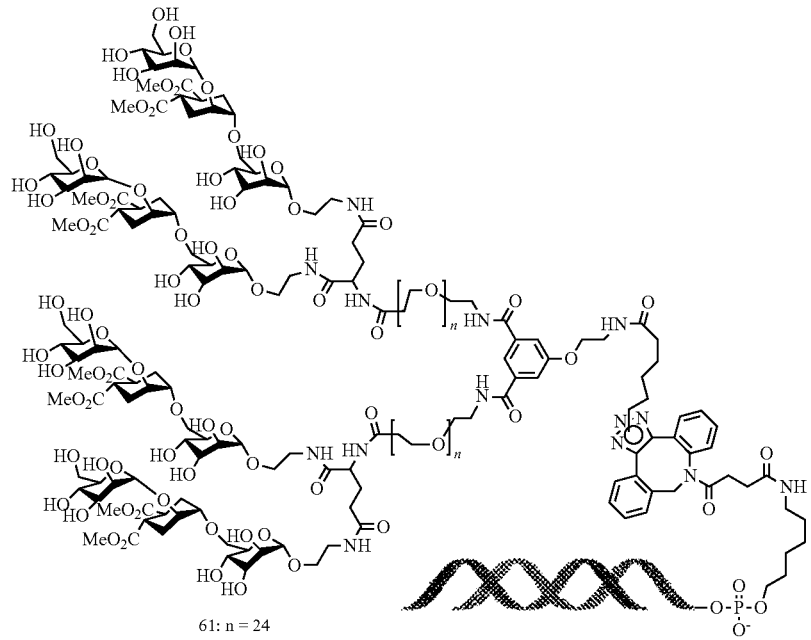
61: n = 24
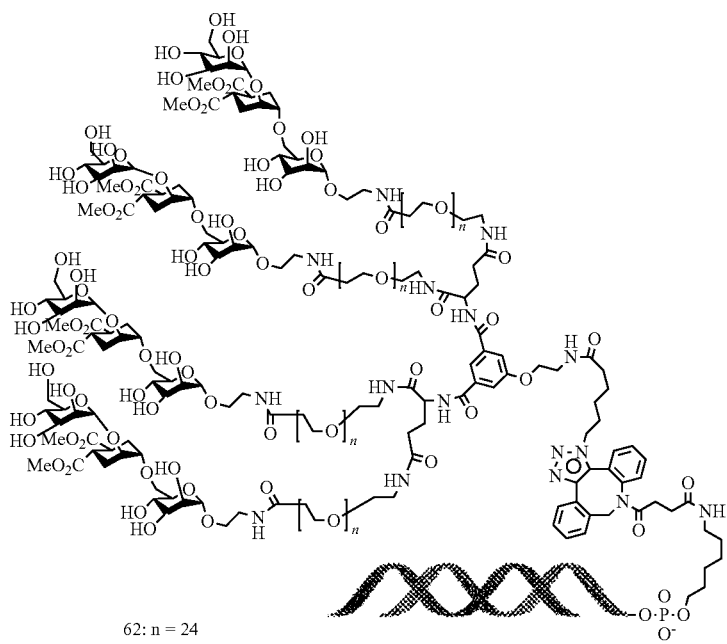
62: n = 24

TABLE 4-continued
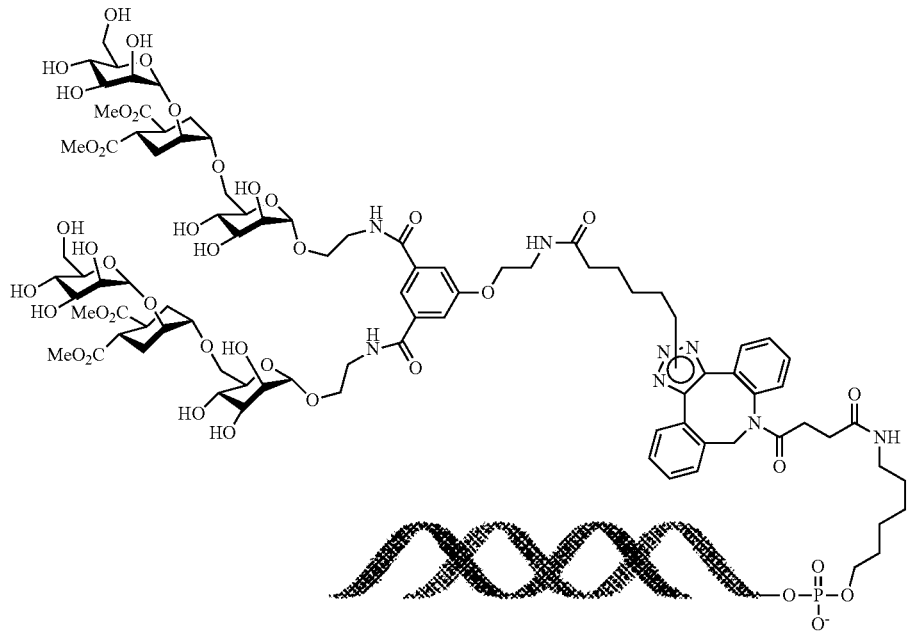
63
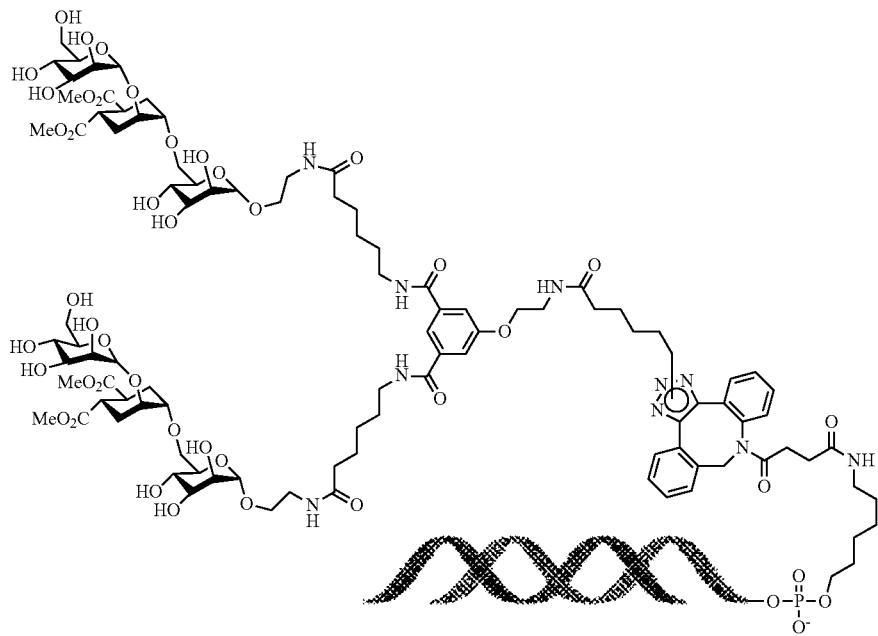
64

TABLE 4-continued
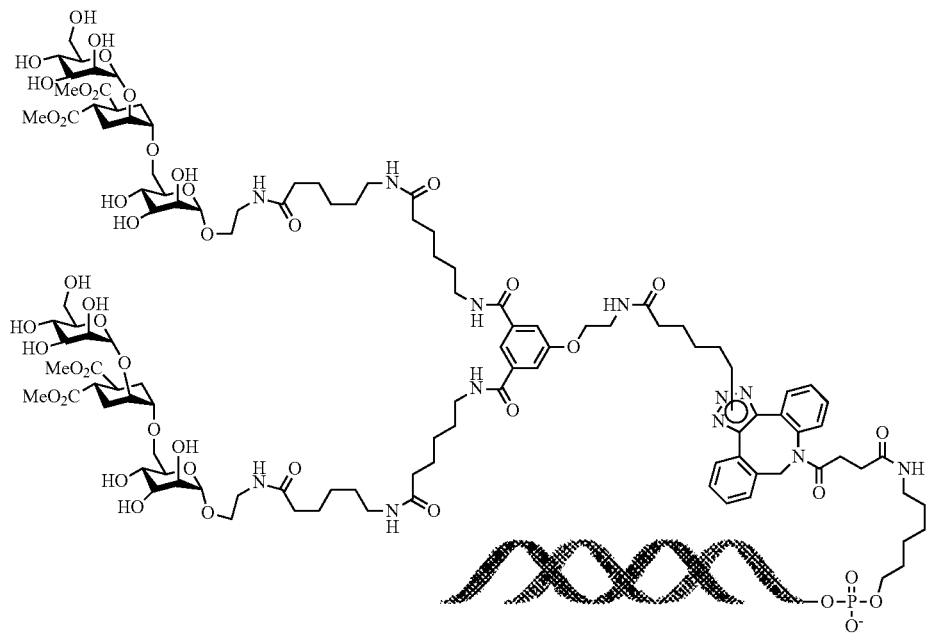
65
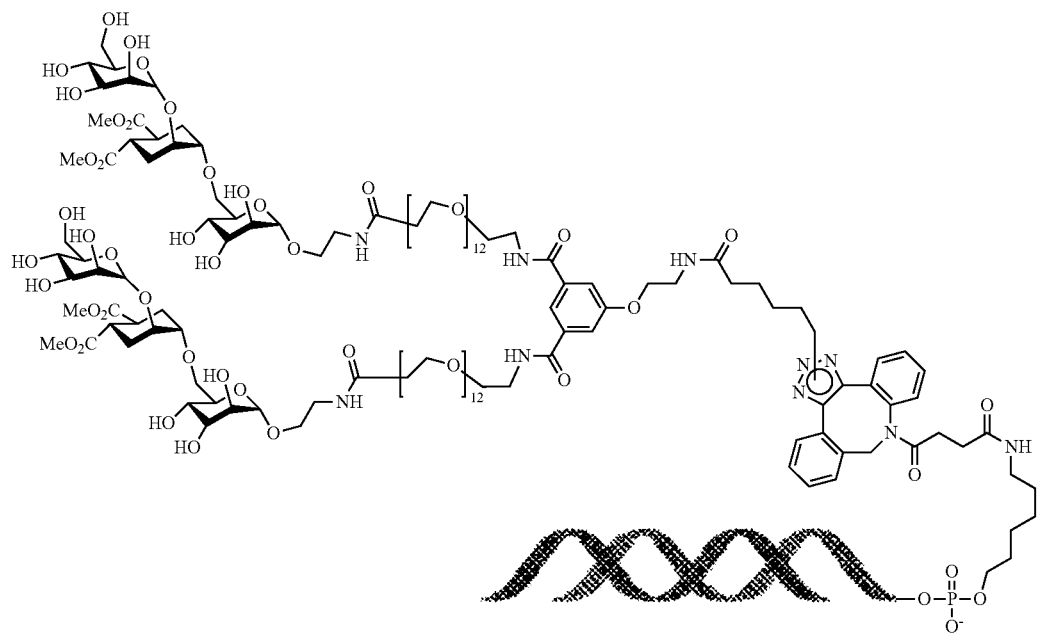
66

TABLE 4-continued
67
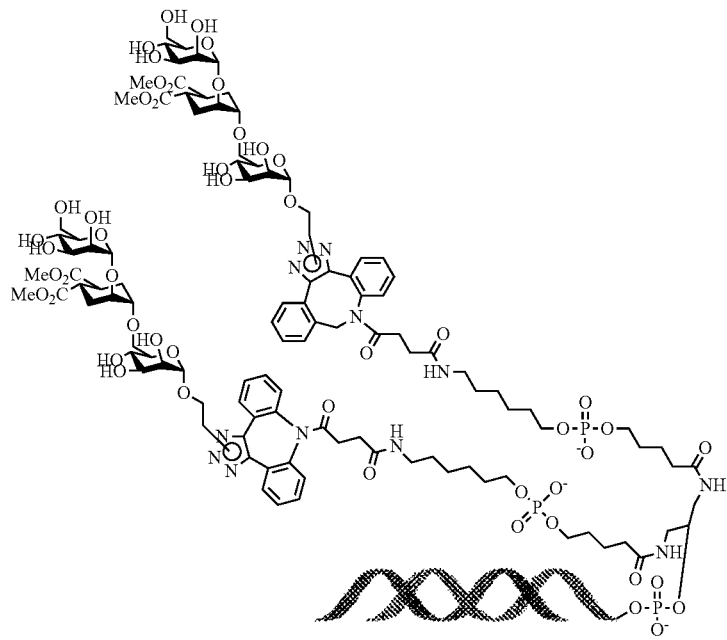
68

TABLE 4-continued
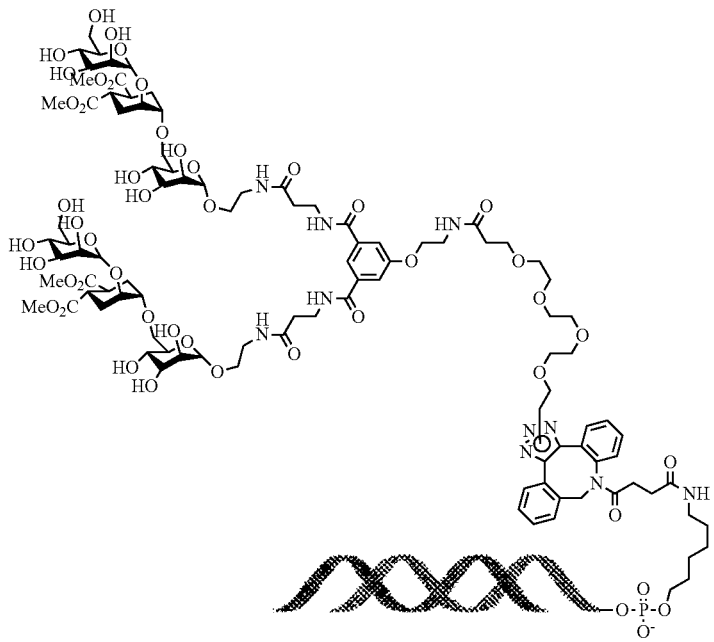
69
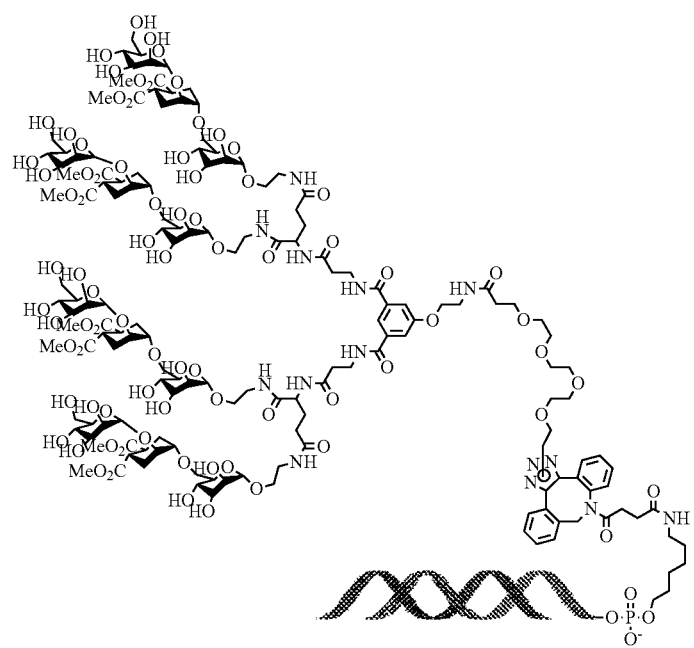
70

TABLE 5

| Compound | Single strand name | Sequence (5'→3') |
|---|---|---|
| KsiRC_CTR_001 | B2M-siRNA | B2M-ssRNA: A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_001 | 61_B2M-siRNA | 49b_5'-B2M-ssRNA: 49 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_002 | 62_B2M-siRNA | 50b_5'-B2M-ssRNA: 50 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_003 | 63_B2M-siRNA | 51_5'-B2M-ssRNA: 51 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_004 | 64_B2M-siRNA | 52_5'-B2M-ssRNA: 52 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_005 | 65_B2M-siRNA | 53_5'-B2M-ssRNA: 53 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_006 | 66_B2M-siRNA | 54_5'-B2M-ssRNA: 54 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_007 | 67_B2M-siRNA | 55_3'_5'PS_-B2M-ssRNA: A(F)^G(M)^G(F)A(M)C(F)U(M)G(F)G(M)U(F)C(M)U(F)U(F)U(M)C(F)U(M)A(F)U(M)C(F)U(M)C(F)U(M) 55<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_008 |  | 55_5'-B2M-ssRNA: 55 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_009 |  | 55_5'-GAPDH-ssRNA: 55 C(F)C(F)U(F)U(M)C(F)A(M)U(F)U(M)G(F)A(F)C(F)C(M)U(F)C(M)A(M)A(M)C(F)U(M)A(F)C(M)A(F)<br>GAPDH-as-RNA: U(M)A(F)G(M)U(F)U(M)G(F)A(F)G(F)G(M)U(F)C(M)A(M)A(M)U(F)G(M)A(F)A(M)G(F)G(M)G(F)^G(M) |
| KsiRC_010 | 68_B2M-siRNA | 58_5'-B2M-ssRNA: 58 A(F)G(M)G(F)A(M)C(F)U(M)G(F)G(M)U(F)C(M)U(F)U(F)U(M)C(F)U(M)A(F)( )U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_011 | 69_B2M-siRNA | 59_5'-B2M-ssRNA: 59 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_012 | 70_B2M-siRNA | 60_5'-B2M-ssRNA: 60 A(F)G(M)G(F)A(M)C(F)U(M)G(F)G(M)U(F)C(M)U(F)U(F)U(M)C(F)U(M)A(F)U(M)C(F)U(M)^C(F)^U(M)<br>B2M-as-RNA: A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |

Comparative Example 3 Synthesis of Nucleic Acid Conjugate—2

Step 43

To compounds 39 and 40 synthesized in steps 36 and 37 of Comparative Example 2, compound 42 synthesized in step 37 of Example 8 was added, and the mixture was left standing at room temperature for 1 hour. Sodium carbonate was added to the reaction mixture, and the mixture was left standing overnight at 4° C. The nucleic acid conjugates of Table 6 were obtained by purification in the same way as in step 41 of Example 8.

TABLE 6

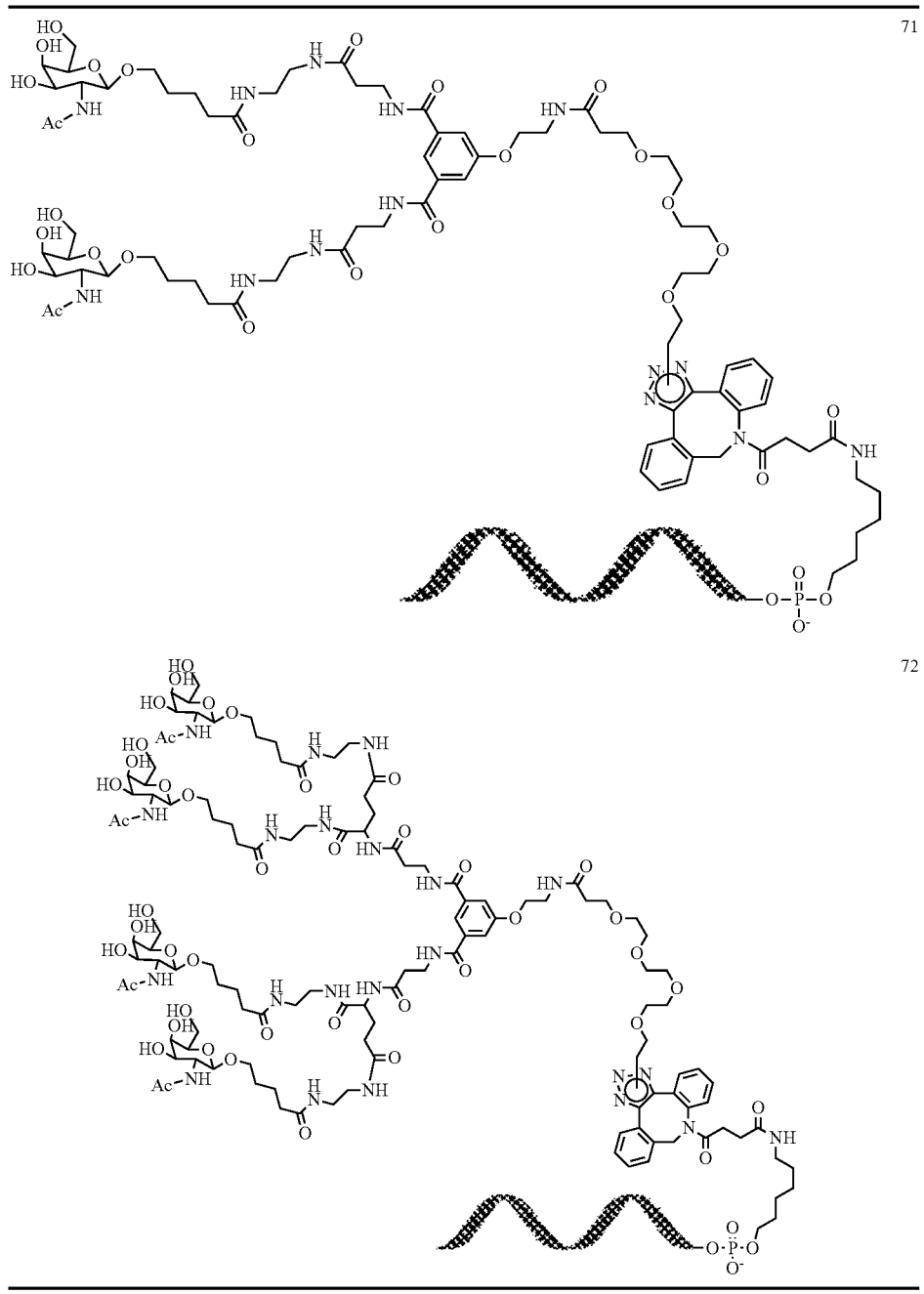

The sequences and mass spectrometry results of nucleic acids in the nucleic acid conjugates synthesized in this Comparative Example are shown in Tables 7a and 7b. The description in the box "Compound" in Tables 7a and 7b represents [compound No. in the table]_[position to which a ligand, etc. is bonded in the nucleic acid]_[abbreviation of the nucleic acid sequence in the nucleic acid conjugate]-[type of the nucleic acid (ASO or ssRNA)].

TABLE 7a

|  | Compound | Sequence (5'→3') | Calcd | Found |
|---|---|---|---|---|
| KAC_13 | 70_5-B2M-ASO | 70T(L)^T(L)^5(L)^T(L)^a^a^g^c^a^g^a^g^T(L)^A(L)^T(L)^G(L) | 7284 | 7282 |
| KAC_14 | 71_5-B2M-ASO | 71T(L)^T(L)^5(L)^T(L)^a^a^g^c^a^g^a^g^T(L)^A(L)^T(L)^G(L) | 8233 | 8231 |

TABLE 7b

| Compound | Sequence (5'→3') | Calcd | Found |
|---|---|---|---|
| 705-B2M-ssRNA | 70 A(F)G(M)G(F)A(M)C(F)U(M)G(F)G(M)U(F)C(M)<br>U(F)U(F)U(M)C(F)U(M)A()U(M)C(F)U(M)^C(F)^U(M) | 8831 | 8831 |
| 715-B2M-ssRNA | 71 A(F)G(M)G(F)A(M)C(F)U(M)G(F)G(M)U(F)C(M)<br>U(F)U(F)U(M)C(F)U(M)A()U(M)C(F)U(M)^C(F)^U(M) | 10033 | 10032 |

Step 40

A double-stranded sugar chain conjugate was obtained in the same way as in step 42 of Example 8 using the single-stranded sugar chain conjugate synthesized in step 43.

The nucleic acid conjugates synthesized in this Comparative Example are shown in Table 8, and the sequences of nucleic acids in the nucleic acid conjugates are shown in Table 9. The description in the box "Compound" in Table 9 represents [compound No. in the table]_[abbreviation of the nucleic acid sequence in the nucleic acid conjugate]_[type of the nucleic acid (siRNA)]. In the description in the box "Single strand name", the sense strand (ss) is represented by [compound No. in the table]_[position to which a ligand, etc. is bonded in the nucleic acid]_[abbreviation of the nucleic acid sequence in the nucleic acid conjugate]-type of the nucleic acid (ssRNA), and the antisense strand (as) is represented by [abbreviation of the nucleic acid sequence in the nucleic acid conjugate]-[type of the nucleic acid (asRNA)].

TABLE 8

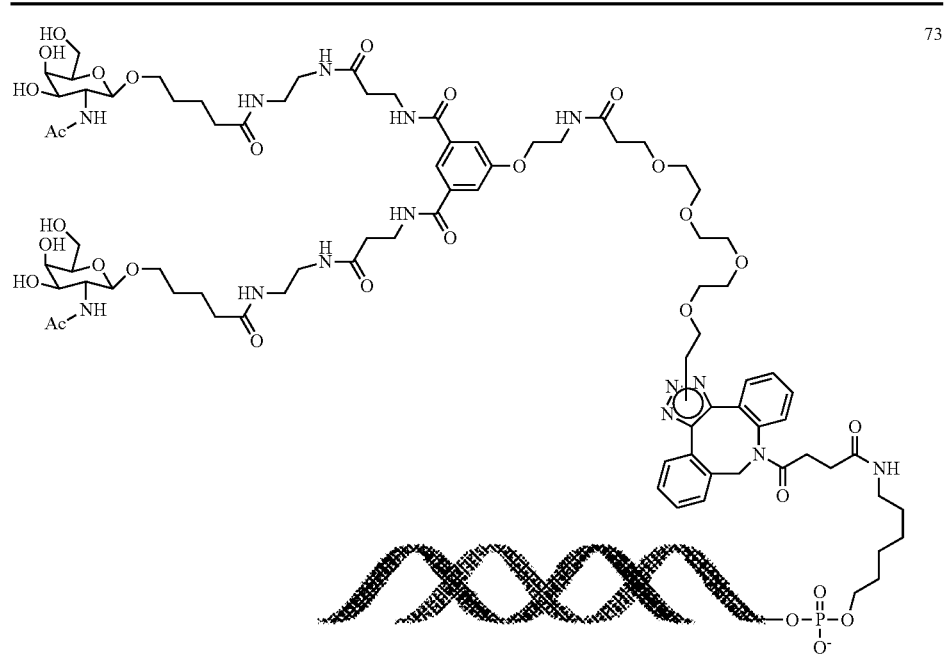

73

TABLE 8-continued

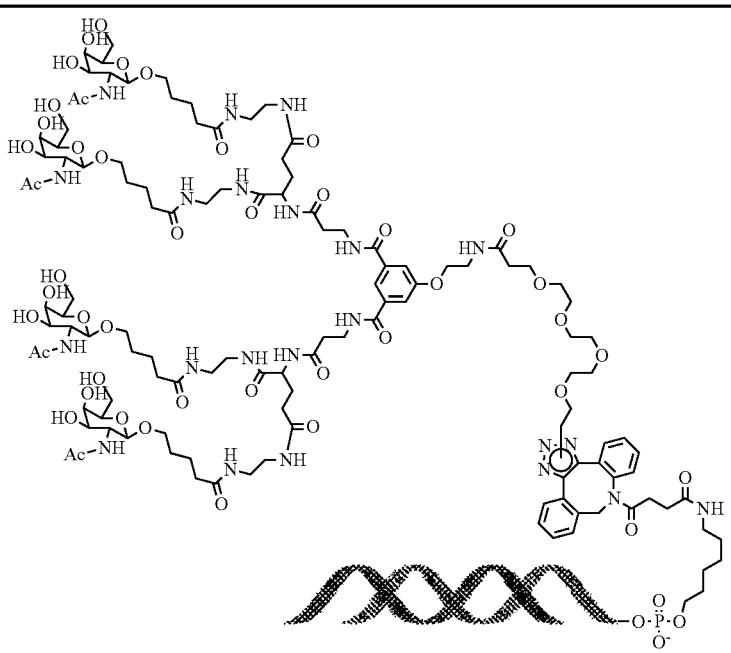

74

TABLE 9

| Compound | | Single strand name | Sequence (5'→3') |
|---|---|---|---|
| KsiRC_13 | 72_B2M-siRNA | 70_5'-B2M-ssRNA | 70 A(F)G(M)G(F)A(M)C(F)U(M)G(F)G(M)U(F)C(M) U(F)U(F)U(M)C(F)U(M)A(F)U(M)C(F)U(M)^C(F)^U(M) |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_14 | 73_B2M-siRNA | 71_5'-B2M-ssRNA | 71 A(F)G(M)G(F)A(M)C(F)U(M)G(F)G(M)U(F)C(M) U(F)U(F)U(M)C(F)U(M)A(F)U(M)C(F)U(M)^C(F)^U(M) |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |

Example 9 Synthesis of Sugar Chain Ligand-Linker Unit—6

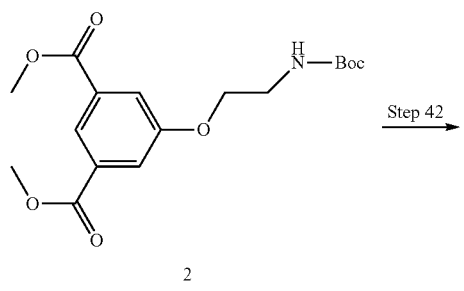

Step 42 →

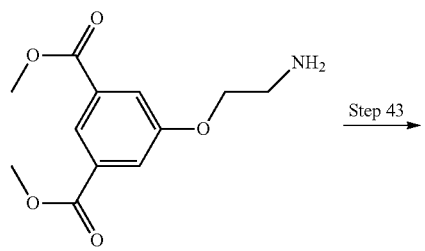

Step 43 →

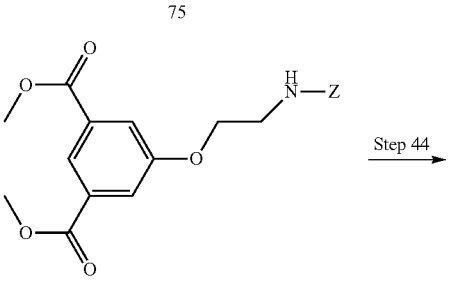

Step 44 →

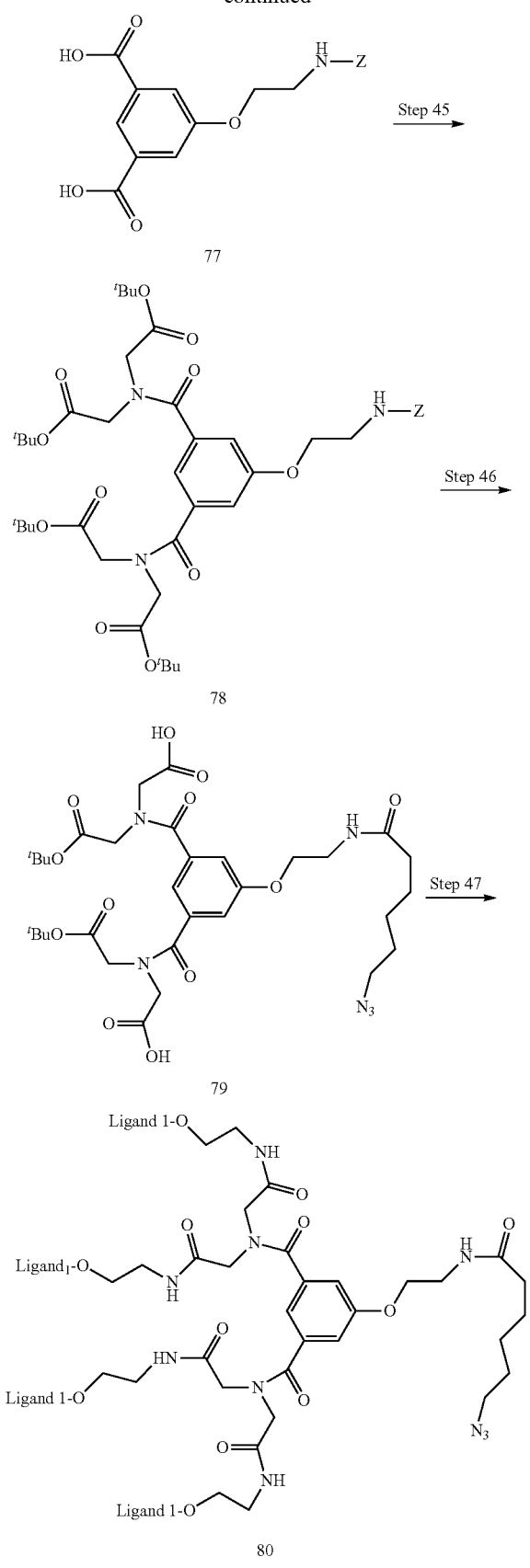

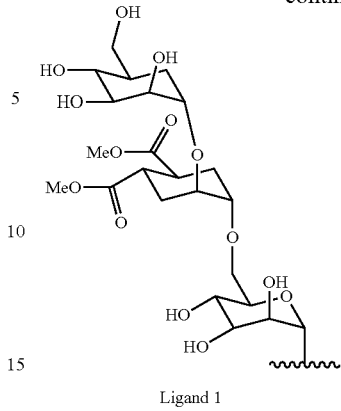

Ligand 1

Step 42

Compound 75 (3.7 g, 14.63 mmol, yield: 63%) was obtained in the same way as in step 4 of Example 1 using compound 2 (8.17 g, 23.12 mmol) synthesized in step 1 of Example 1.

ESI-MS m/z: 254 (M+H)$^+$

Step 43

Compound 75 (3.70 g, 14.63 mmol) synthesized in step 42 of Example 9 was dissolved in tetrahydrofuran (10 mL). To the solution, benzoyl chloride (4.12 mL, 29.3 mmol) was added under ice cooling, and the mixture was stirred at room temperature for 1 hour. The solvent in the reaction solution was distilled off under reduced pressure, and the residue was purified by silica gel column chromatography (chloroform/methanol) to obtain compound 76 (3.82 g, 9.86 mmol, yield: 67%).

ESI-MS m/z: 432 (M+HCOO)$^-$

Step 44

Compound 77 (3.07 g, 8.56 mmol, yield: 87%) was obtained in the same way as in step 2 of Example 1 using compound 76 (3.82 g, 9.86 mmol) synthesized in step 43 of Example 9.

ESI-MS m/z: 360 (M+H)$^+$

Step 45

Compound 78 was quantitatively obtained in the same way as in step 7 of Example 1 using compound 77 (213 mg, 0.592 mmol) synthesized in step 44 of Example 9 and iminodiacetic acid di-tert-butyl ester (375 mg, 1.529 mmol).

ESI-MS m/z: 858 (M+HCOO)$^-$

Step 46

STEP 1: Compound 78 (482 mg, 0.593 mmol) synthesized in step 45 of Example 9 was dissolved in methanol (10 mL), followed by catalytic hydrogen reduction using palladium/carbon. The solvent in the obtained solution fraction was distilled off under reduced pressure.

STEP 2: A coupling compound having an alkyl azide group was obtained in the same way as in step 9 of Example 2 using the obtained crude product.

STEP 3: Compound 79 (238 mg, yield: 92%) was obtained in the same way as in step 8 of Example 1 using the compound obtained in STEP 2.

ESI-MS m/z: 595 (M+H)$^+$

Step 47

Compound 80 (1.3 mg, 0.445 μmol) was obtained in the same way as in step 26 of Example 5 using compound 79 (0.8 mg, 1.346 μmol) synthesized in step 46 of Example 9.

ESI-MS m/z: 2918 (M–H)$^-$

Example 10 Synthesis of Sugar Chain Ligand-Linker Unit—7

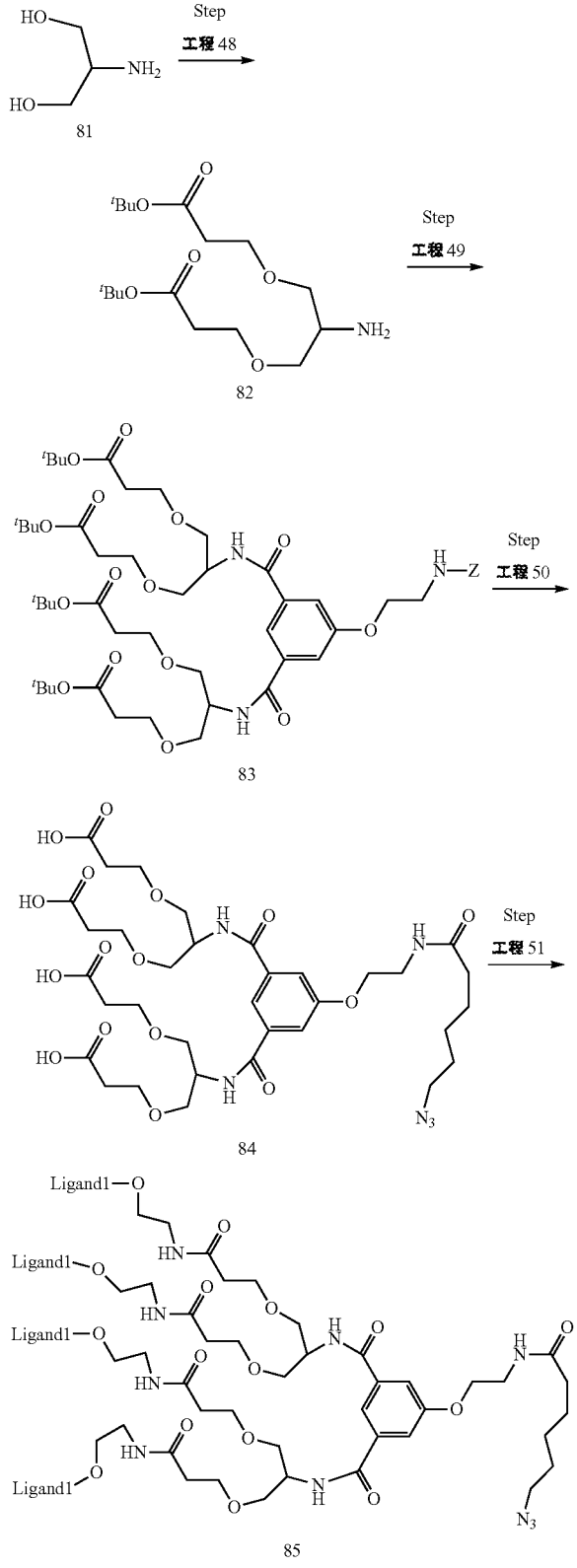

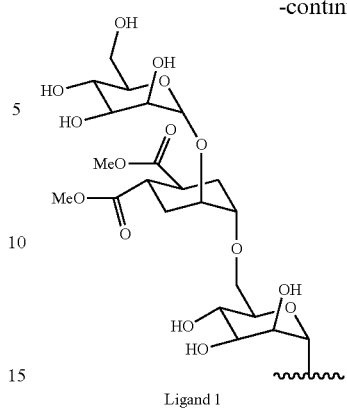

Ligand 1

Step 48

1,3-Dihydroxy 2-aminopropane 81 (manufactured by Tokyo Chemical Industry Co., Ltd., 0.55 g, 6.03 mmol) was dissolved in dimethyl sulfoxide (15 mL). To the solution, an aqueous sodium hydroxide solution (2 mmol/L, 3 mL) was added under ice cooling, then acrylic acid tert-butyl ester (1.93 g, 15.07 mmol) dissolved in dimethyl sulfoxide (2.2 mL) was gradually added, and the mixture was reacted at room temperature for 4 hours. Water was added to the mixture, followed by extraction with ethyl acetate. Then, the organic layer was washed with saturated saline and dried over anhydrous sodium sulfate. The solvent was distilled off under reduced pressure, and the residue was purified by silica gel column chromatography (chloroform/methanol=98/2→90/10) to obtain compound 82 (0.74 g, yield: 35%).

ESI-MS m/z: 348 (M+H)$^+$

Step 49

Compound 83 was quantitatively obtained in the same way as in step 7 of Example 1 using compound 82 (0.150 g, 0.433 mmol) synthesized in step 48 of Example 10.

ESI-MS m/z: 1062 (M+HCOO)$^-$

Step 50 (deprotection of Z, amidation of alkyl azide, and deprotection of TFA)

Compound 84 (91.4 mg, 0.114 mmol, yield: 67%) was obtained in the same way as in step 46 of Example 9 using compound 83 (0.149 g, 0.147 mmol) synthesized in step 49 of Example 10.

ESI-MS m/z: 799 (M+H)$^+$

Step 51

Compound 85 (2.4 mg, 0.768 μmol, yield: 54.9%) was obtained in the same way as in step 26 of Example 5 using compound 84 (1.3 mg, 1.4 μmol) synthesized in step 51 of Example 10.

ESI-MS m/z: 1562 (M+2H)$^{2+}$

Example 11 Synthesis of Sugar Chain Ligand-Linker Unit—8

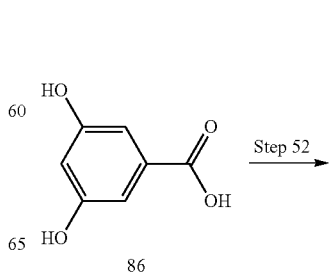

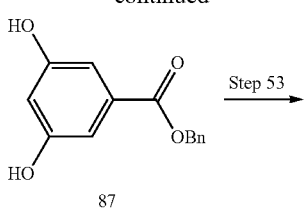

87

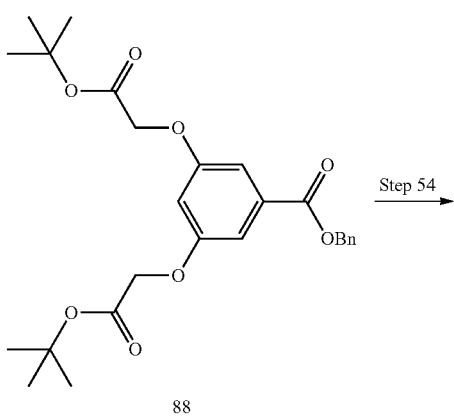

88

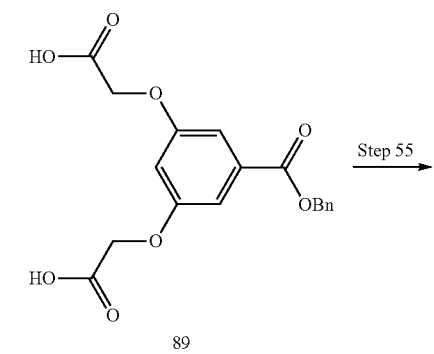

89

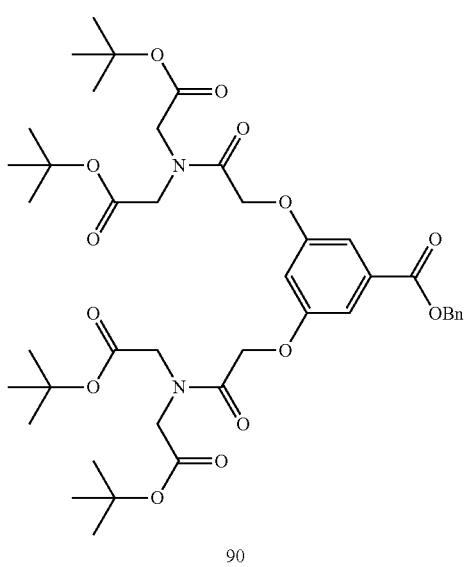

90

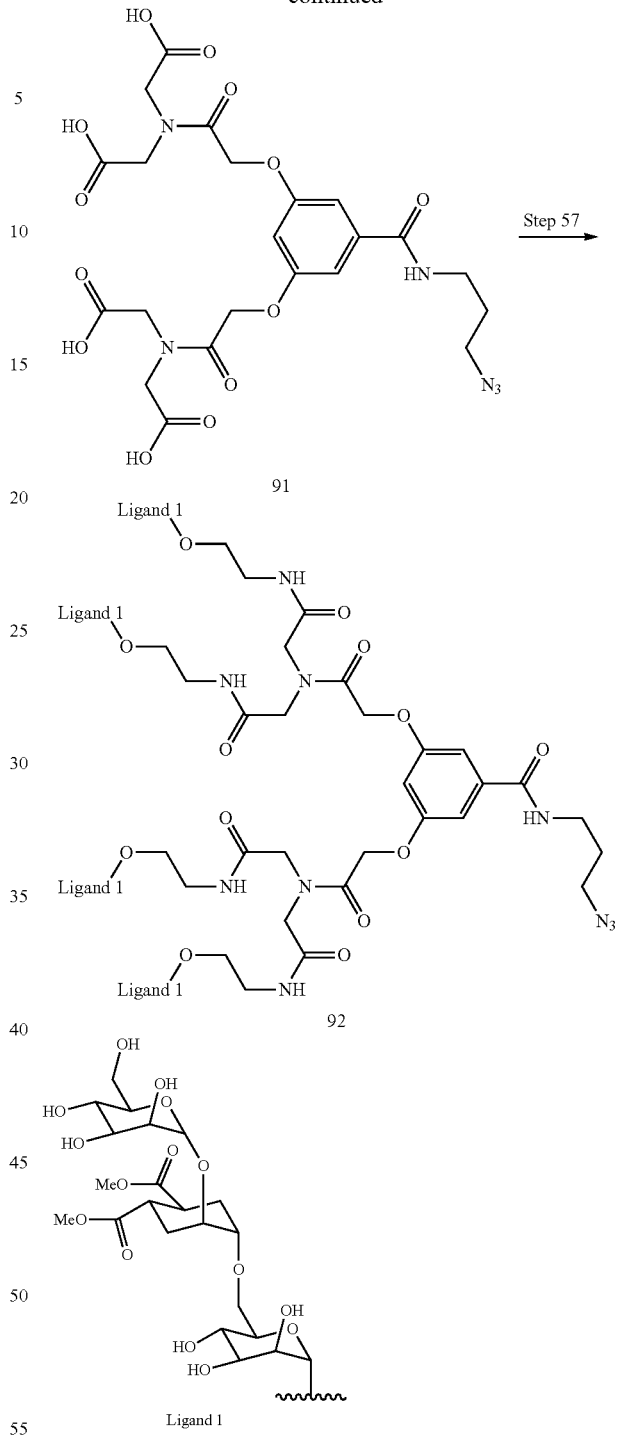

Step 52

3,5-Dihydroxybenzoic acid 86 (manufactured by Tokyo Chemical Industry Co., Ltd., 2.11 g, 13.69 mmol) was dissolved in N,N'-dimethylformamide (35 mL). To the solution, potassium bicarbonate (1.716 g, 17.14 mmol) and benzyl bromide (3.51 g, 2.439 mL, 20.54 mmol) were added, and the mixture was stirred at room temperature for 4 hours. Saturated ammonium chloride was added to the reaction solution, followed by extraction with dichloromethane. Then, the organic layer was washed with water and dried over anhydrous sodium sulfate. The solvent was distilled off under reduced pressure, and the residue was purified by silica gel column chromatography (heptane/ethyl acetate=50/50) to quantitatively obtain compound 87.

ESI-MS m/z: 245 (M+H)$^+$

Step 53

Compound 87 (3.34 g, 13.69 mmol) synthesized in step 52 was dissolved in N,N'-dimethylformamide (40 mL). To the solution, potassium carbonate (7.57 g, 54.8 mmol) and tert-butyl bromoacetic acid (4.42 mL, 30.1 mmol) were added, and the mixture was stirred at 90° C. for 4 hours. Saturated ammonium chloride was added to the reaction solution, followed by extraction with dichloromethane. Then, the organic layer was washed with saturated saline and dried over anhydrous sodium sulfate. The solvent was distilled off under reduced pressure, and the residue was purified by silica gel column chromatography (heptane/ethyl acetate=75/25) to obtain compound 88 (5.67 g, yield: 88%).

ESI-MS m/z: 471 (M−H)$^-$

Step 54

Compound 88 (5.67 g, 12.00 mmol) synthesized in step 53 was dissolved in dichloromethane (40 mL). To the solution, trifluoroacetic acid (10 mL, 130.0 mmol) was added, and the mixture was stirred overnight at room temperature. The solvent was distilled off under reduced pressure to obtain a crude product of compound 89.

ESI-MS m/z: 359 (M−H)$^-$

Step 55

Compound 90 was quantitatively obtained in the same way as in step 7 of Example 1 using iminodiacetic acid di-tert-butyl ester (0.407 g, 1.660 mmol) and compound 89 (0.239 g, 0.664 mmol) synthesized in step 54 of Example 11.

ESI-MS m/z: 813 (M−H)$^-$

Step 56

[STEP 1] Compound 90 (541 mg, 0.664 mmol) synthesized in step 55 of Example 11 was dissolved in methanol (8 mL), followed by catalytic hydrogen reduction using palladium/carbon. The solvent in the obtained solution fraction was distilled off under reduced pressure.

[STEP 2] A coupling compound was obtained in the same way as in step 7 of Example 1 using the obtained crude product and 3-azidopropan-1-amine (0.101 g, 1.009 mmol).

STEP 3: Compound 91 was quantitatively obtained in the same way as in step 8 of Example 1 using the obtained crude product of the compound.

ESI-MS m/z: 583 (M+H)$^+$

Step 57

Compound 92 (2.0 mg, yield: 47%) was obtained in the same way as in step 26 of Example 5 using compound 84 (2.0 mg, 1.476 μmol) synthesized in step 50 of Example 10.

ESI-MS m/z: 1456 (M+2H)$^{2+}$

Example 12 Synthesis of Sugar Chain Ligand-Linker Unit—9

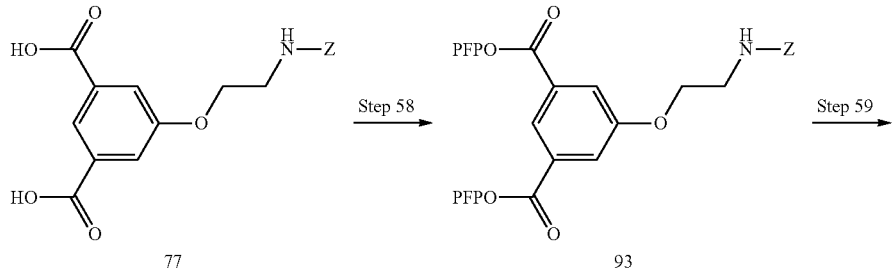

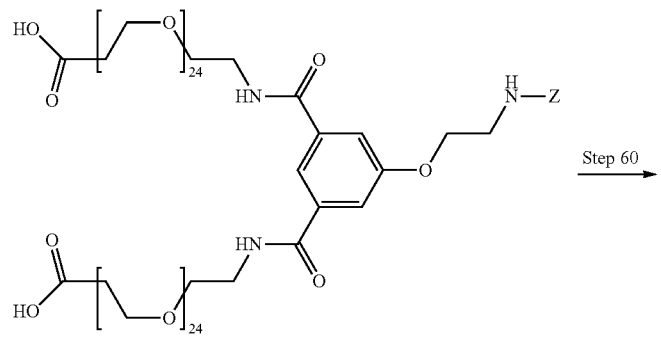

-continued
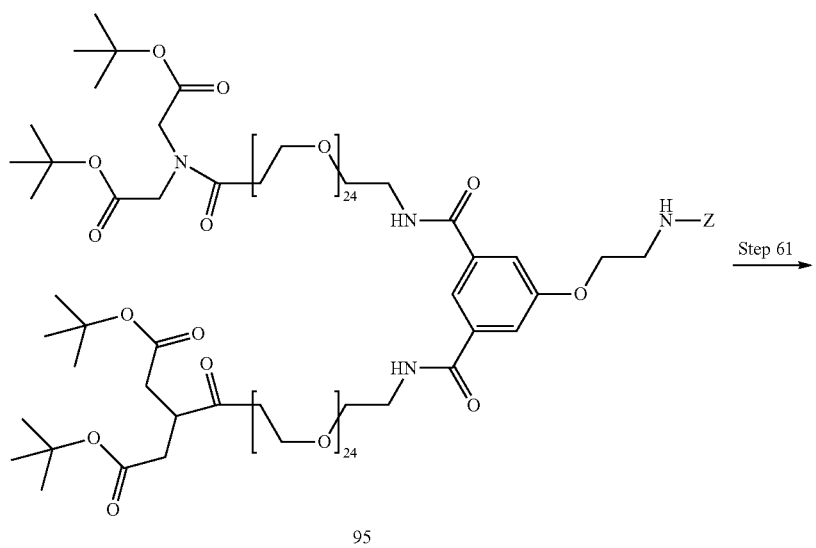
95
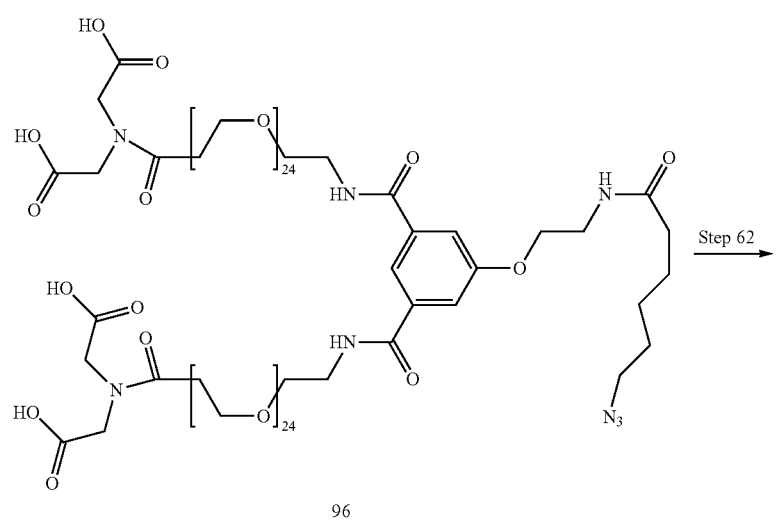
96
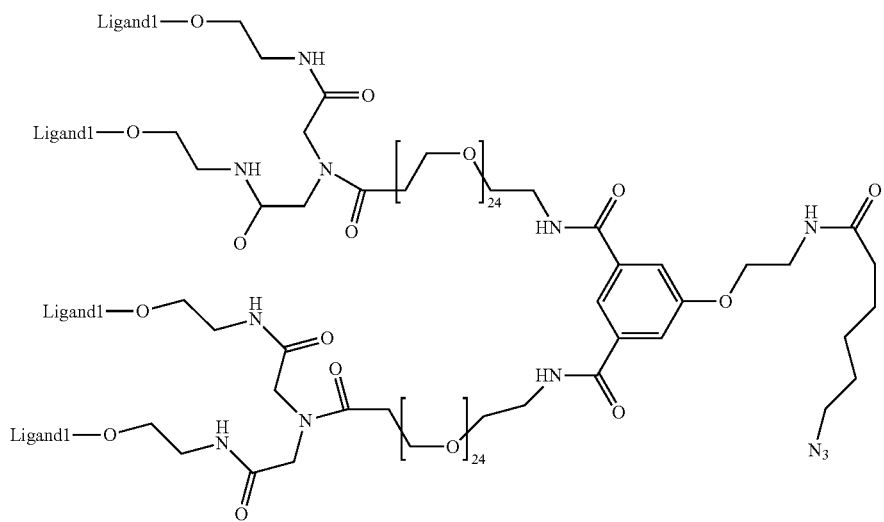
97

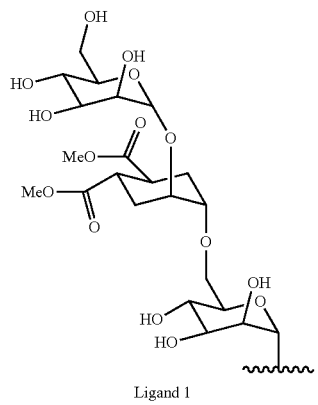 [SMILES: *C1OC(COC2CC(C(=O)OC)C(C(=O)OC)CC2OC2OC(CO)C(O)C(O)C2O)C(O)C(O)C1O]

Ligand 1

Step 58

Compound 77 (63 mg, 0.175 mmol) synthesized in step 44 of Example 9 was dissolved in dichloromethane (5 mL). To the solution, triethylamine (0.24 mL, 1.75 mmol) was added, then pentafluorophenyl-2,2,2-trifluoroacetic acid (0.119 mL, 0.699 mmol) was added, and the mixture was stirred at room temperature for 4 hours. Chloroform was added to the mixture, and the organic layer was washed with a 10% aqueous citric acid solution, saturated saline, and an aqueous sodium bicarbonate solution and dried over anhydrous magnesium sulfate. The solvent was distilled off under reduced pressure to quantitatively obtain compound 93.

ESI-MS m/z: (detected as a monoester form (compound with one PEP added thereto)) 524 (M−H)−

Step 59

Compound 93 (0.121 g, 0.175 mmol) synthesized in step 58 of Example 12 was dissolved in dimethyl sulfoxide (8 mL). To the solution, carboxyl-(12 oligoethylene glycol) ethylamine (0.510 g, 0.444 mmol) was added, and the mixture was stirred at room temperature for 1 hour in an argon atmosphere. The solvent was distilled off under reduced pressure, followed by extraction with chloroform and a 10% aqueous citric acid solution. Then, the organic layer was dried over anhydrous magnesium sulfate. The solvent was distilled off under reduced pressure to obtain a crude product of compound 94.

ESI-MS m/z: 2614 (M−H)−

Step 60

Compound 95 was quantitatively obtained in the same way as in step 7 of Example 1 using compound 94 (0.333 g, 0.092 mmol) synthesized in step 59 of Example 12.

ESI-MS m/z: 1537 (M+2H)$^{2+}$

Step 61

Compound 96 (0.0825 g, yield: 58%) was obtained in the same way as in step 42 of Example 9 using compound 95 (0.138 g, 0.045 mmol) synthesized in step 60 of Example 12.

ESI-MS m/z: 1426 (M+2H)$^{2+}$

Step 62

Compound 97 (2.1 mg, yield: 29%) was obtained in the same way as in step 26 of Example 5 using compound 96 (4.2 mg, 14.04 μmol) synthesized in step 61 of Example 12.

ESI-MS m/z: 2590 (M+2H)$^{2+}$

Example 13 Synthesis of Sugar Chain Ligand-Linker Unit—10

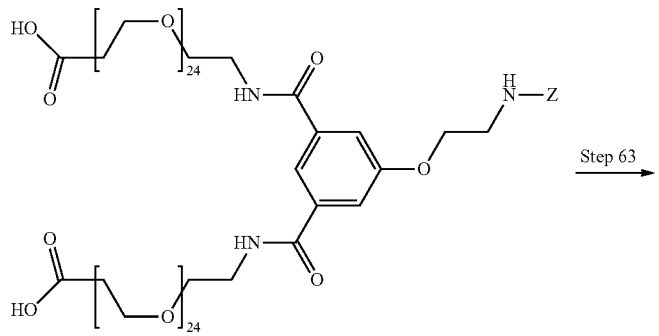

94

-continued
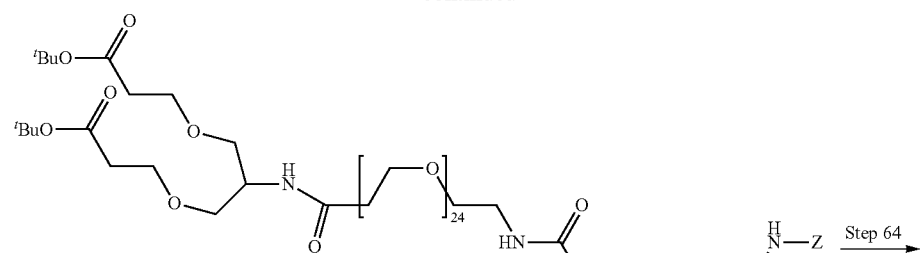
Step 64
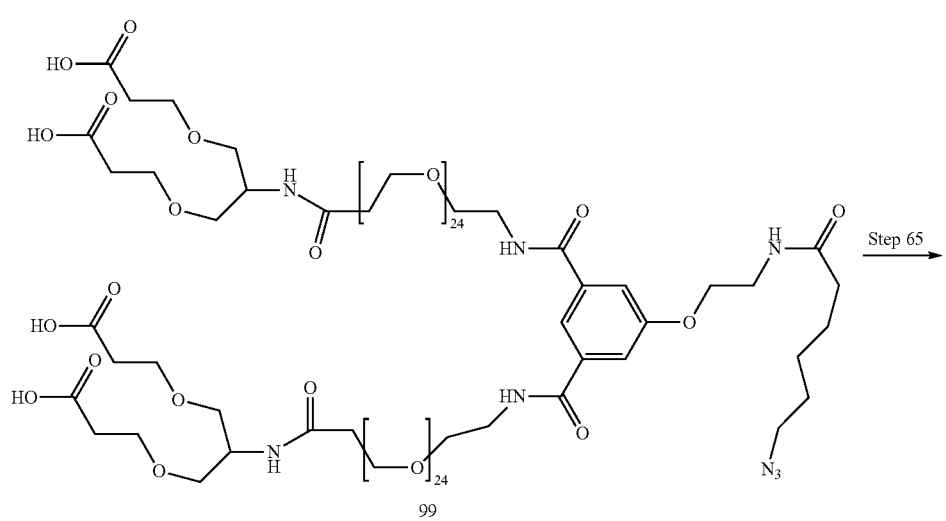
Step 65
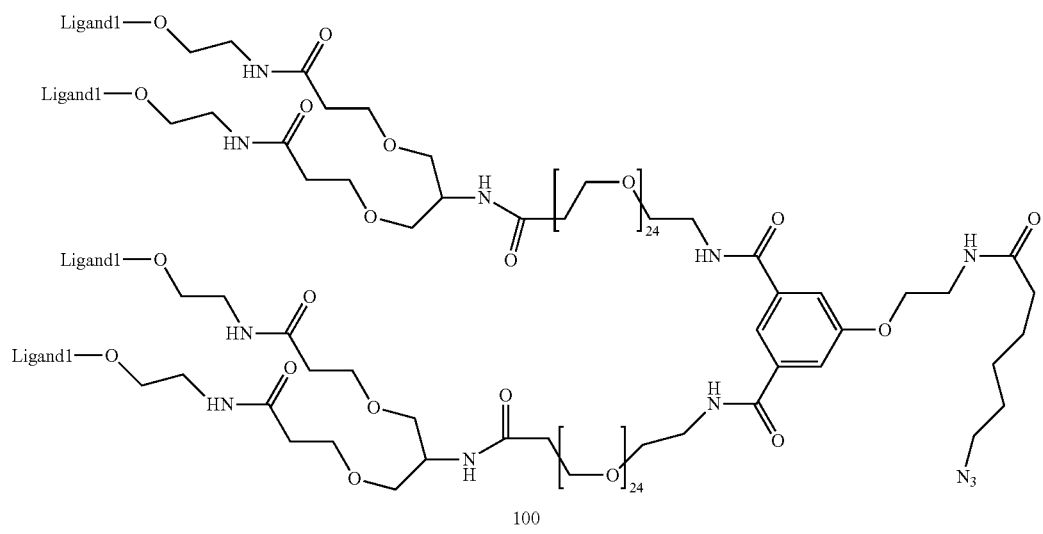

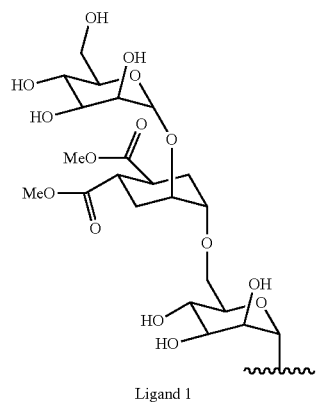 [SMILES: *C1OC(COC2CC(C(=O)OC)C(C(=O)OC)CC2OC2OC(CO)C(O)C(O)C2O)C(O)C(O)C1O]

Ligand 1

Step 63

Compound 98 (0.087 g, yield: 51%) was obtained in the same way as in step 7 of Example 1 using compound 94 (0.189 g, 0.052 mmol) synthesized in step 59 of Example 12 and compound 82 (0.051 g, 0.148 mmol) synthesized in step 48 of Example 10.

ESI-MS m/z: 1639 (M+2H)$^{2+}$

Step 64

Compound 99 (38.5 mg, yield: 43%) was obtained in the same way as in step 42 of Example 9 using compound 98 (0.087 g, 0.027 mmol) synthesized in step 63 of Example 13.

ESI-MS m/z: 1529 (M+2H)$^{2+}$

Step 65

Compound 100 (2.4 mg, yield: 32%) was obtained in the same way as in step 26 of Example 5 using compound 99 (4.7 mg, 1.403 μmol) synthesized in step 64 of Example 13.

ESI-MS m/z: 2689 (M+2H)$^{2+}$

Example 14 Synthesis of Sugar Chain Ligand-Linker Unit—11

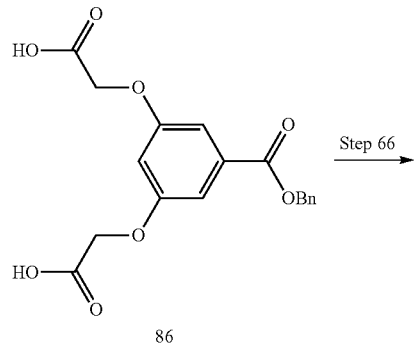

86

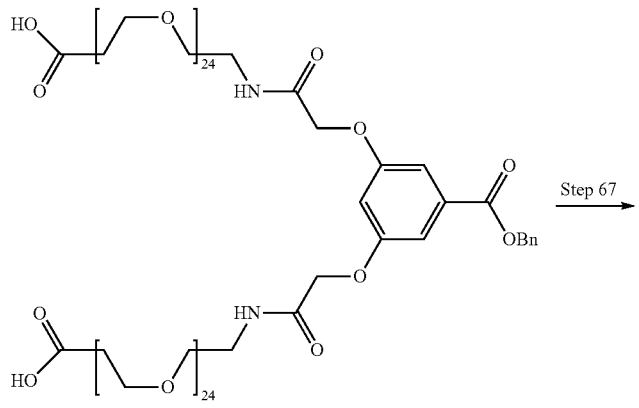

101

-continued
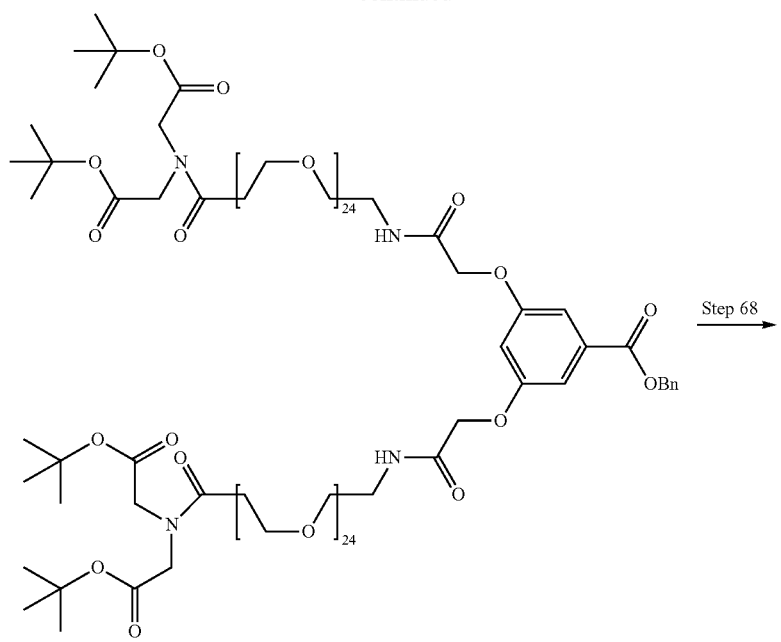
102
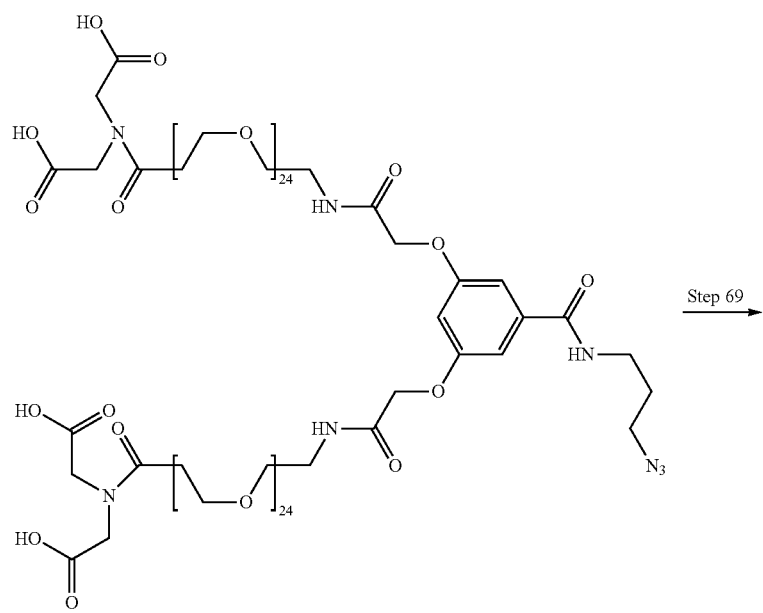
103

-continued

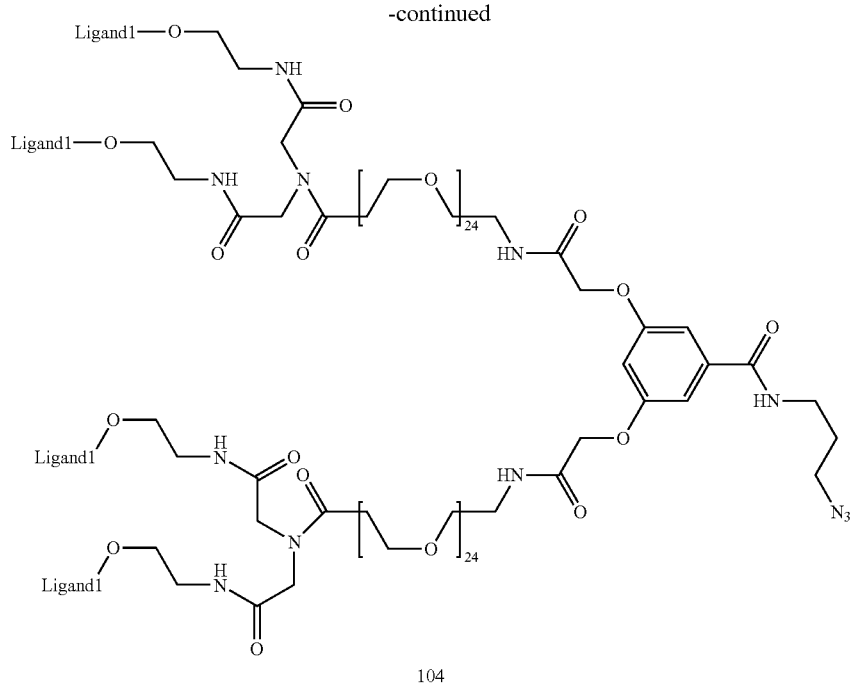

104

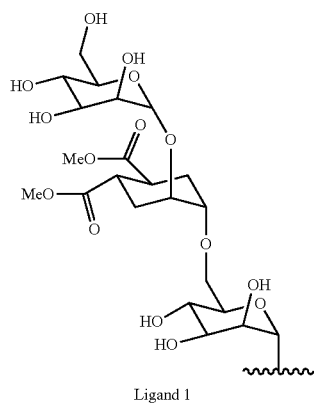 [SMILES: *C1OC(COC2CC(C(=O)OC)C(C(=O)OC)CC2OC2OC(CO)C(O)C(O)C2O)C(O)C(O)C1O]

Ligand 1

Step 66

[STEP 1] An active ester form was obtained in the same way as in step 58 of Example 12 using compound 86 (0.0678 g, 0.1888 mmol) synthesized in step 54 of Example 11.

[STEP 2] Compound 101 (0.2819 g, 0.108 mmol, yield: 58.1%) was obtained in the same way as in step 59 of Example 12 using the active ester (0.1283 g, 0.185 mmol) obtained by STEP 1.

ESI-MS m/z: 2615 (M−H)⁻

Step 64

Compound 102 (0.085 g, 0.028 mmol, yield: 26%) was obtained in the same way as in step 45 of Example 9 using compound 101 (0.282 g, 0.108 mmol) synthesized in step 66 of Example 14.

ESI-MS m/z: (detected in a state from which the tBu group was eliminated) 712 $(M+4H)^{4+}$ Step 64

Compound 103 (57.9 mg, yield: 66%) was obtained in the same way as in step 56 of Example 11 using compound 102 (84.5 mg, 0.028 mmol) synthesized in step 67 of Example 14.

ESI-MS m/z: 2837 (M−H)⁻

Step 69

Compound 104 (2.6 mg, yield: 33%) was obtained in the same way as in step 26 of Example 5 using compound 103 (4.8 mg, 1.528 μmol) synthesized in step 69 of Example 14.

ESI-MS m/z: 2584 $(M+2H)^{2+}$

Example 15 Synthesis of Sugar Chain Ligand-Linker Unit—12

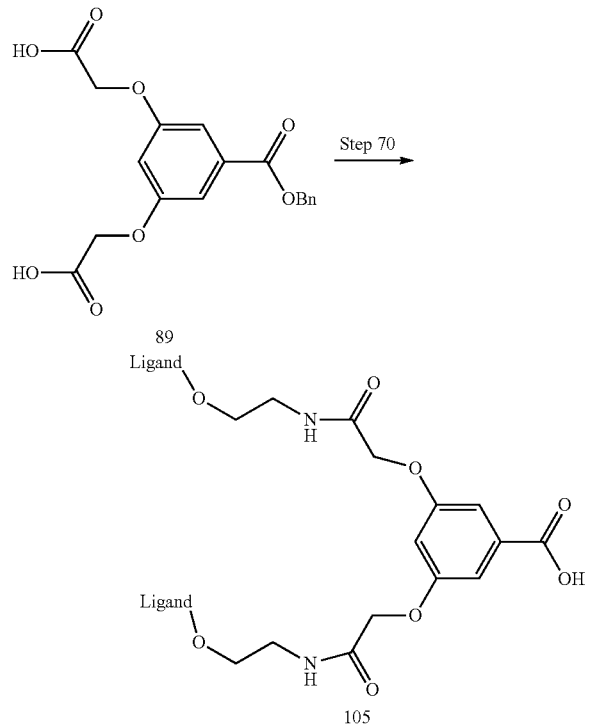

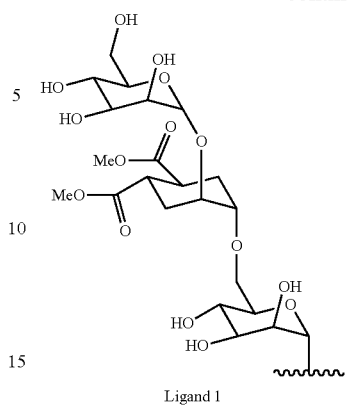

Ligand 1

Step 70

[STEP 1] A ligand-added compound (6.0 mg, yield: 36%) was obtained in the same way as in step 26 of Example 5 using compound 86 (4 mg, 0.011 mmol) synthesized in step 54 of Example 11.

[STEP 2] Compound 105 (5.6 mg, yield: 99%) was obtained in the same way as in STEP 1 of step 42 of Example 9 using the compound (6.0 mg, 3.94 μmol) obtained in STEP 1.

ESI-MS m/z: 1522 (M−H)⁻

Example 16 Synthesis of Sugar Chain Ligand-Linker Unit—13

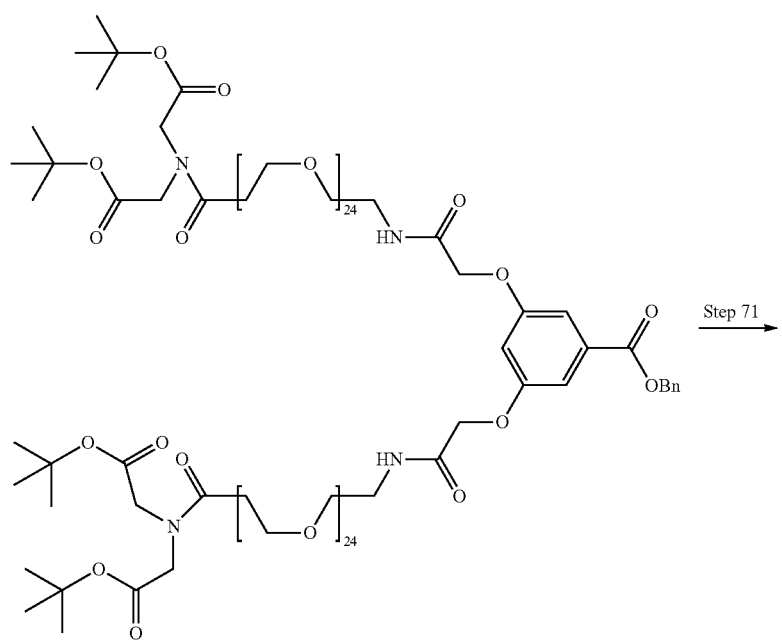

-continued
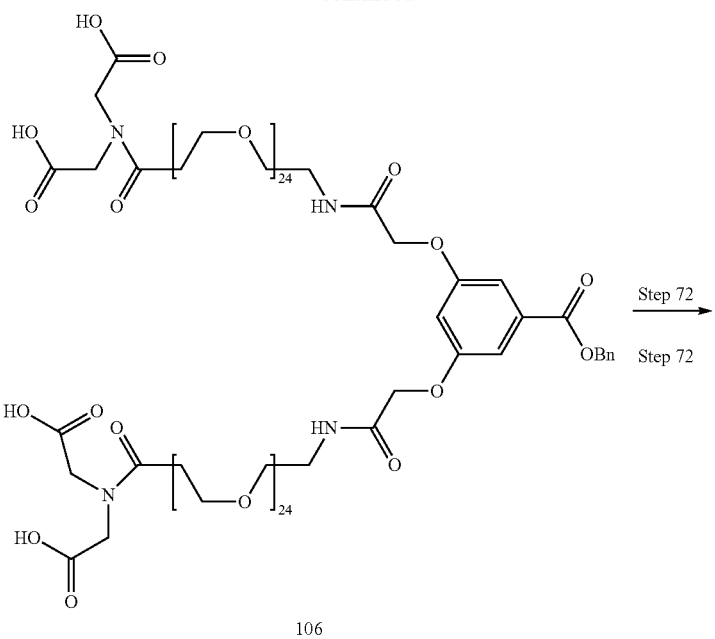
106
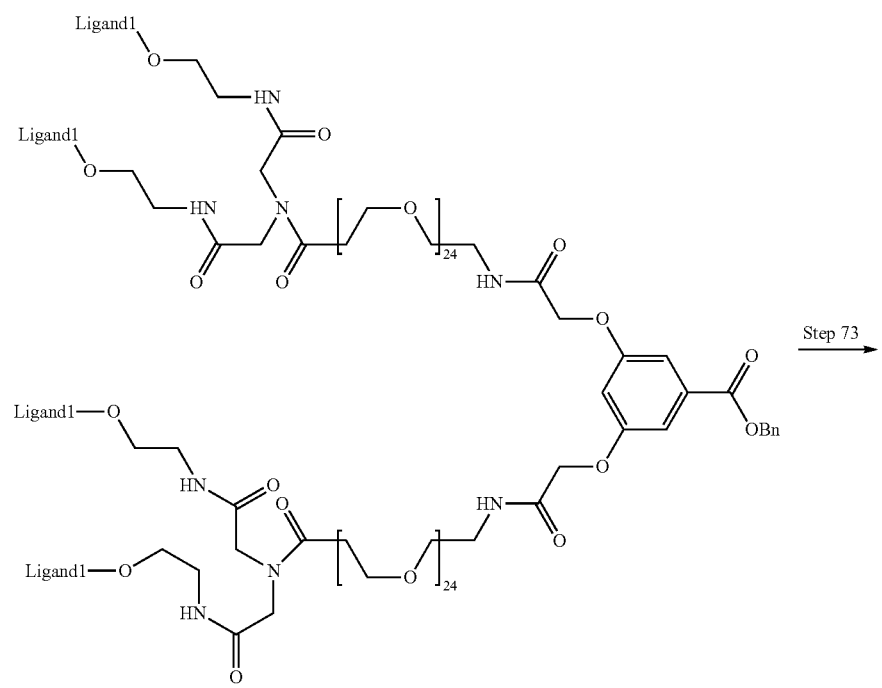
107

-continued
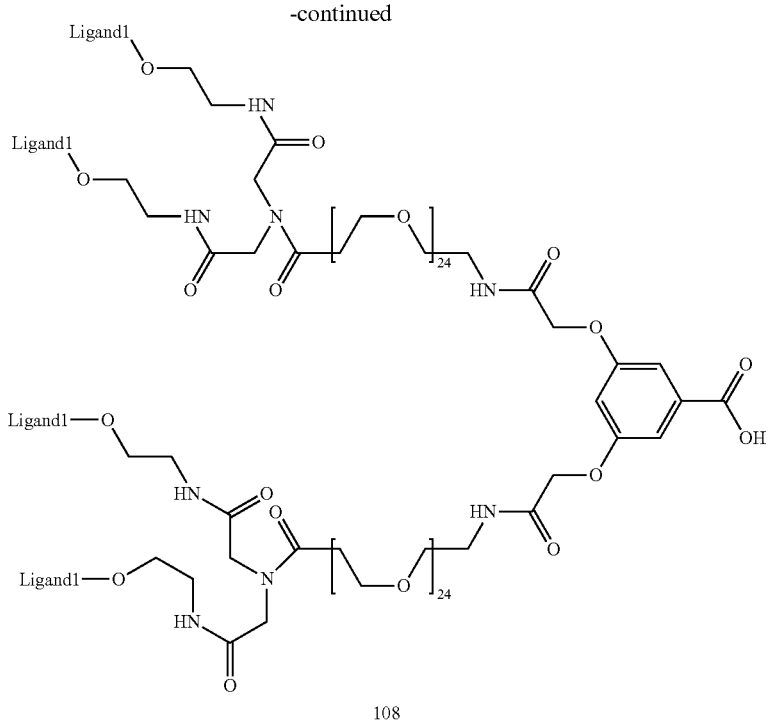
108
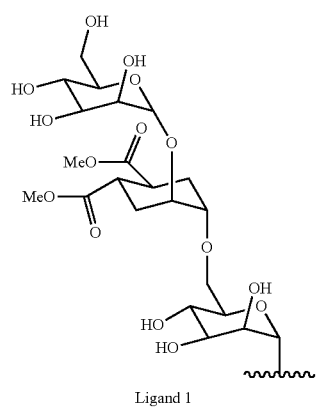
Ligand 1
Step 71
Compound 106 was quantitatively obtained in the same way as in step 45 of Example 9 using compound 99 (0.204 g, 0.067 mmol) synthesized in step 67 of Example 14.
ESI-MS m/z: 2846 (M–H)$^-$
Step 72
Compound 107 (6.3 mg, yield: 23%) was obtained in the same way as in step 26 of Example 5 using compound 106 (16.7 mg, 5.22 μmol) synthesized in step 71 of Example 16.
ESI-MS m/z: 2586 (M–H)$^-$ Step 73

Compound 108 (5.6 mg, yield: 90%) was obtained in the same way as in STEP 1 of step 46 of Example 9 using compound 107 (6.3 mg, 1.218 µmol) synthesized in step 72 of Example 16.

ESI-MS m/z: 2540 (M−2H)$^{2-}$

Example 17 Synthesis of Sugar Chain Ligand-Linker Unit—14

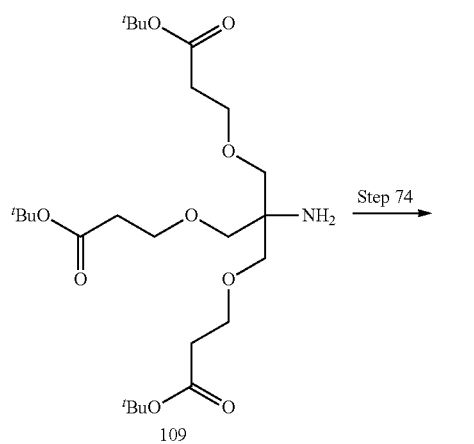
109

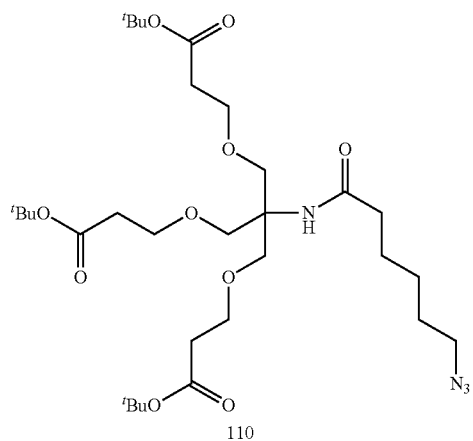
110

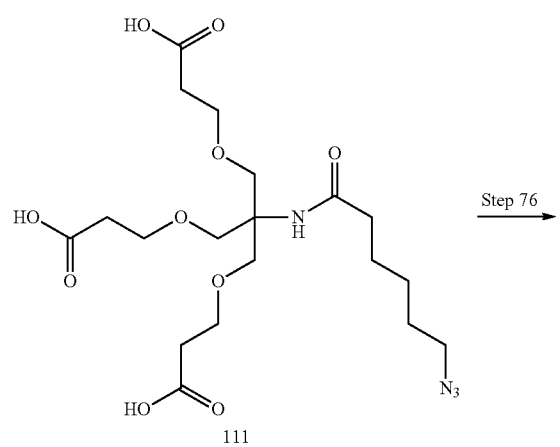
111

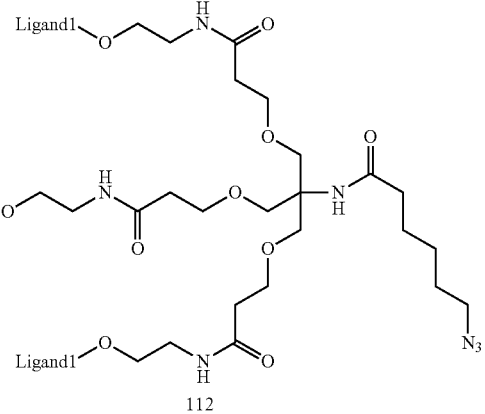
112

Ligand 1

Step 74

Compound 110 (0.116 g, yield: 43%) was obtained in the same way as in step 9 of Example 2 using compound 109 (0.209 g, 0.414 mmol) synthesized by the method described in International Publication No. WO 2009/073809.

ESI-MS m/z: 645 (M+H)$^{+}$

Step 75

Compound 111 was quantitatively obtained in the same way as in step 44 of Example 9 using compound 110 (0.116 g, 0.179 mmol) synthesized in step 74 of Example 17.

ESI-MS m/z: 477 (M+H)$^{+}$

Step 76

Compound 112 (1.6 mg, yield: 40%) was obtained in the same way as in step 26 of Example 5 using compound 111 (1.1 mg, 1.821 µmol) synthesized in step 75 of Example 17.

ESI-MS m/z: 2219 (M−H)$^{-}$

Example 18 Synthesis of Sugar Chain Ligand-Linker Unit—15
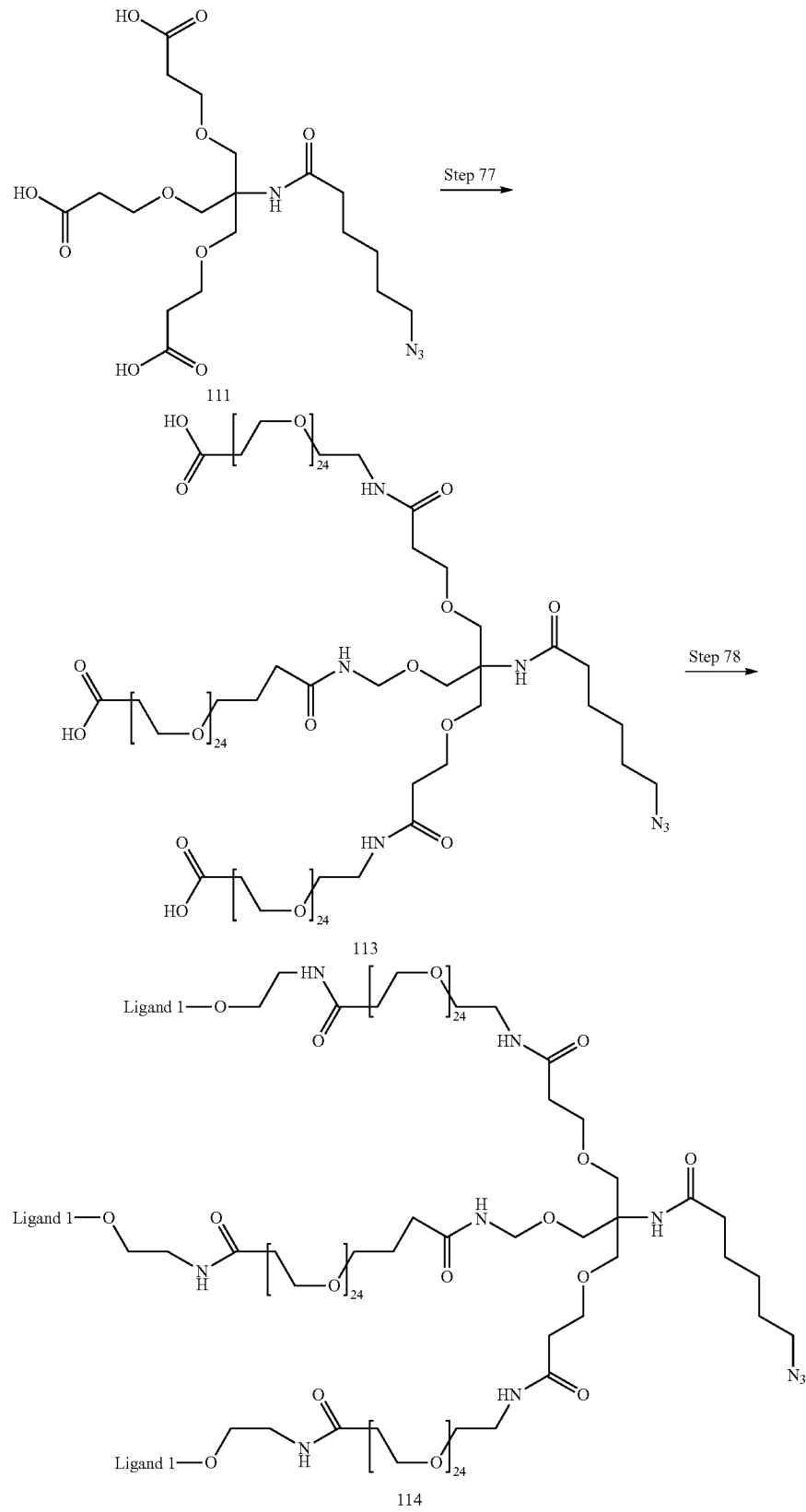

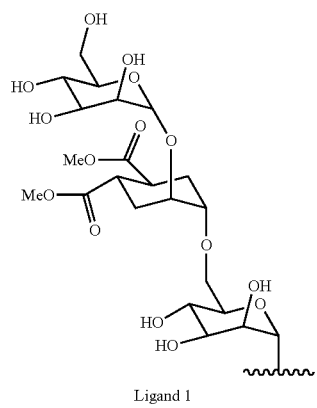

Ligand 1

Step 77

Compound 113 (88.2 mg, yield: 43%) was obtained in the same way as in step 62 of Example 14 using compound 111 (30 mg, 0.05 mmol) synthesized in step 75 of Example 17.

ESI-MS m/z: 1930 (M−2H)$^{2-}$

Step 78

Compound 114 (5.9 mg, yield: 50%) was obtained in the same way as in step 26 of Example 5 using compound 113 (8.1 mg, 2.098 μmol) synthesized in step 77 of Example 18.

ESI-MS m/z: 2801 (M−2H)$^{2-}$

Example 19 Synthesis of Sugar Chain Ligand-Linker Unit—16

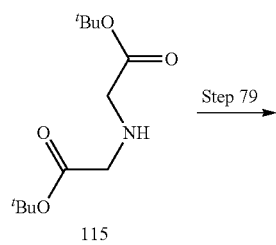

115

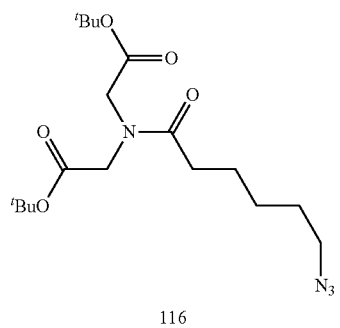

116

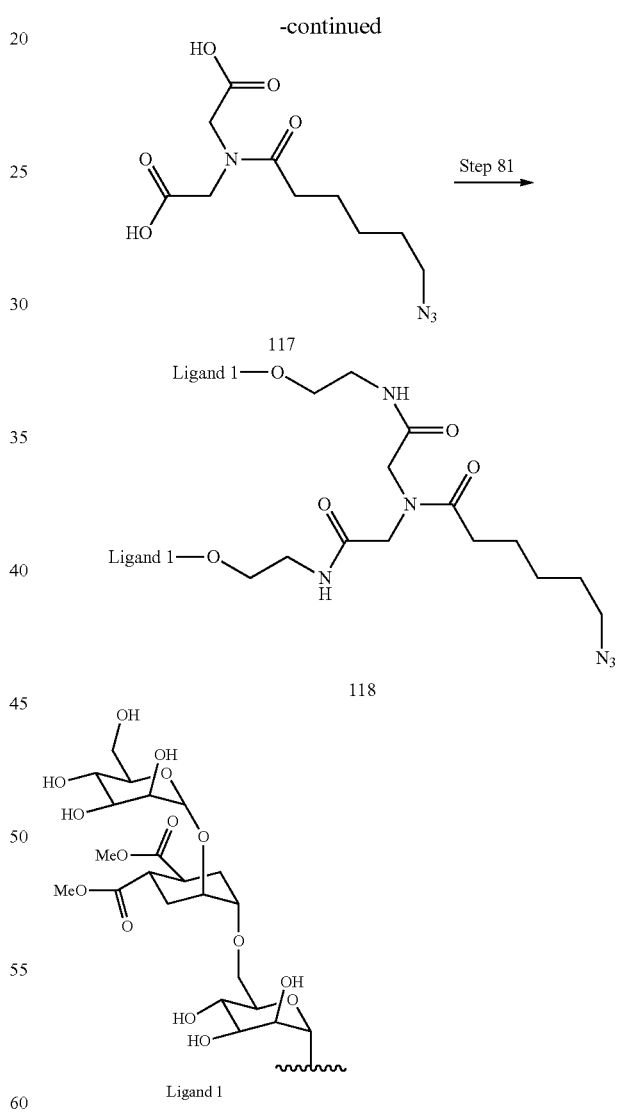

Step 79

Compound 116 was quantitatively obtained in the same way as in step 9 of Example 2 using iminodiacetic acid di-tert-butyl ester 115 (manufactured by Tokyo Chemical Industry Co., Ltd., 0.197 g, 0.803 mmol).

ESI-MS m/z: [detected in a state from which the tBu group was eliminated] 273 (M+H)$^+$ Step 80

Compound 117 was quantitatively obtained in the same way as in step 45 of Example 9 using compound 116 (0.309 g, 0.803 mmol) synthesized in step 79 of Example 19.

ESI-MS m/z: 273 (M+H)$^+$

Step 81

Compound 118 (1.1 mg, 0.766 mmol, yield: 29%) was obtained in the same way as in step 26 of Example 5 using compound 117 (1.2 g, 2.62 mmol) synthesized in step 76 of Example 17.

ESI-MS m/z: 1436 (M+H)$^+$

Example 20 Synthesis of Sugar Chain Ligand-Linker Unit—17

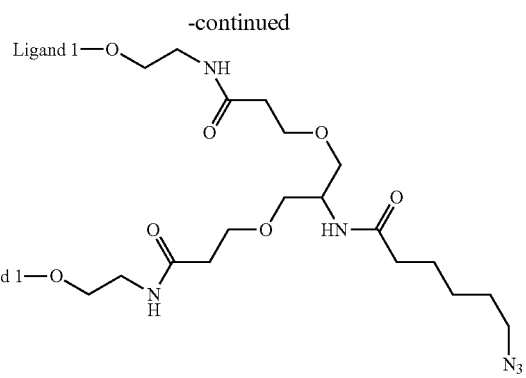

121

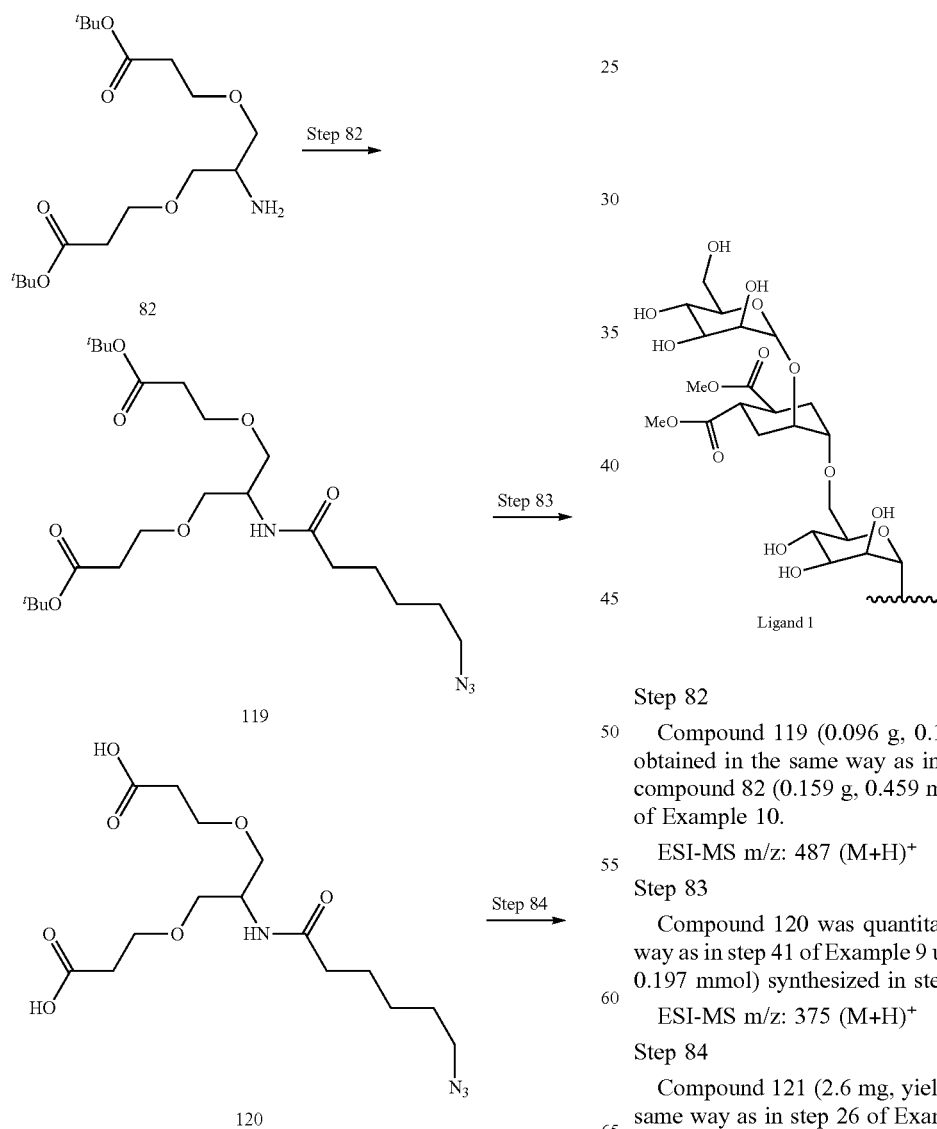

Step 82

Compound 119 (0.096 g, 0.197 mmol, yield: 43%) was obtained in the same way as in step 9 of Example 2 using compound 82 (0.159 g, 0.459 mmol) synthesized in step 47 of Example 10.

ESI-MS m/z: 487 (M+H)$^+$

Step 83

Compound 120 was quantitatively obtained in the same way as in step 41 of Example 9 using compound 119 (96 mg, 0.197 mmol) synthesized in step 82 of Example 20.

ESI-MS m/z: 375 (M+H)$^+$

Step 84

Compound 121 (2.6 mg, yield: 66%) was obtained in the same way as in step 26 of Example 5 using compound 120 (1.0 mg, 2.55 µmol) synthesized in step 83 of Example 20.

ESI-MS m/z: 1539 (M+H)$^+$

Example 21 Synthesis of Sugar Chain Ligand-Linker Unit—18

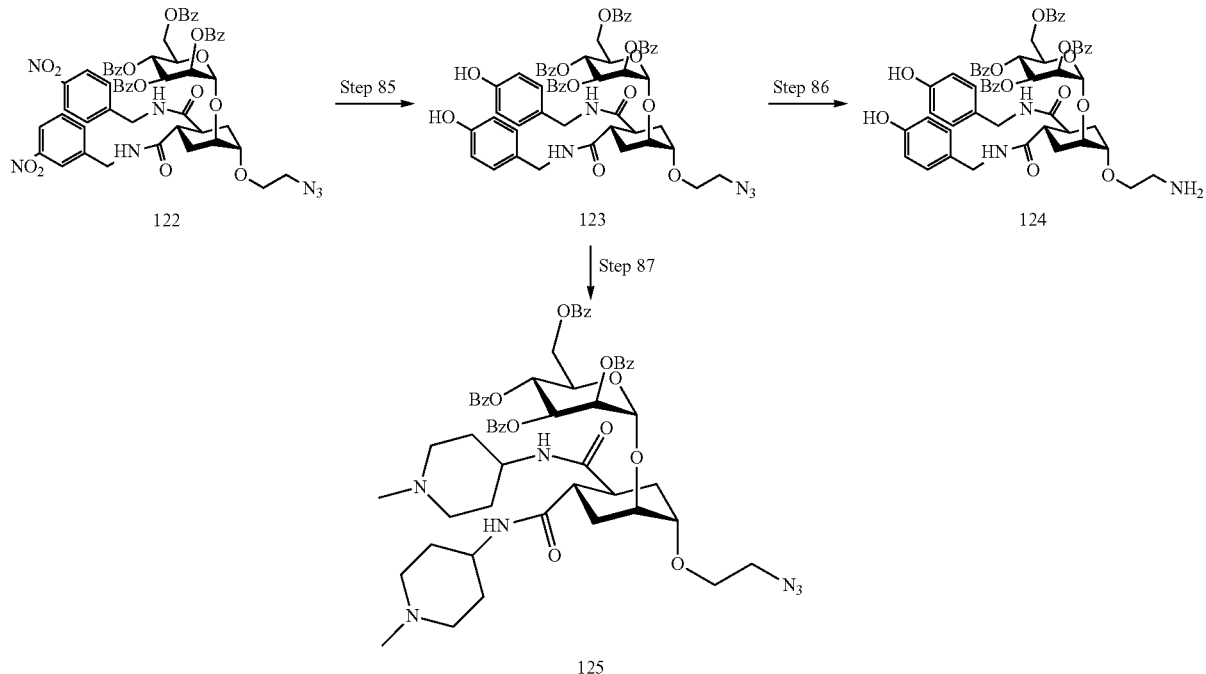

Step 85

Compound 123 (0.22 g, yield: 23%) was obtained by the method described in Chemistry European Journal, Vol. 19, p. 4786-4797, 2013 using compound 122 (1 g, 0.914 mmol) synthesized by the method described in the literature mentioned above and 4-(aminomethyl)phenol hydrochloride (0.362 g, 2.287 mmol).

ESI-MS m/z: 1062 (M+H)$^+$

Step 86

Compound 123 (0.2 g, 0.191 mmol) synthesized in step 85 of Example 21 was dissolved in a 25% aqueous ammonia solution. To the solution, pyridine (2 mL) and trimethylphosphine (0.12 mL) were added, and the mixture was then stirred at room temperature for 16 hours. The mixture was concentrated under reduced pressure, and the residue was purified by column chromatography to obtain compound 124 (0.048 g, yield: 25%).

ESI-MS m/z: 1037 (M+H)$^+$

Step 87

[STEP 1] A coupling compound (0.2 g, yield: 42%) was obtained in the same way as in step 84 using compound 122 (0.5 g, 0.457 mmol) synthesized by the method described in Chemistry European Journal, Vol. 19, p. 4786-4797, 2013.

[STEP 2] The compound (0.2 g, 0.191 mmol) synthesized in STEP 1 was dissolved in normal butanol (2 mL), followed by catalytic reduction for 12 hours using platinum/carbon (200 mg). The reaction solution was concentrated under reduced pressure, and the residue was purified by column chromatography to obtain compound 125 (0.060 g, yield: 30%).

ESI-MS m/z: 1019 (M+H)$^+$

Example 22 Synthesis of Sugar Chain Ligand-Linker Unit—19

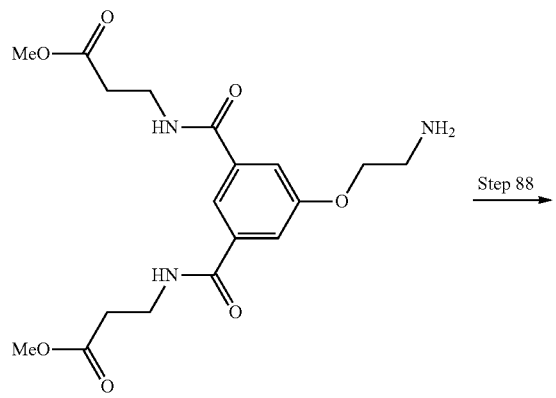

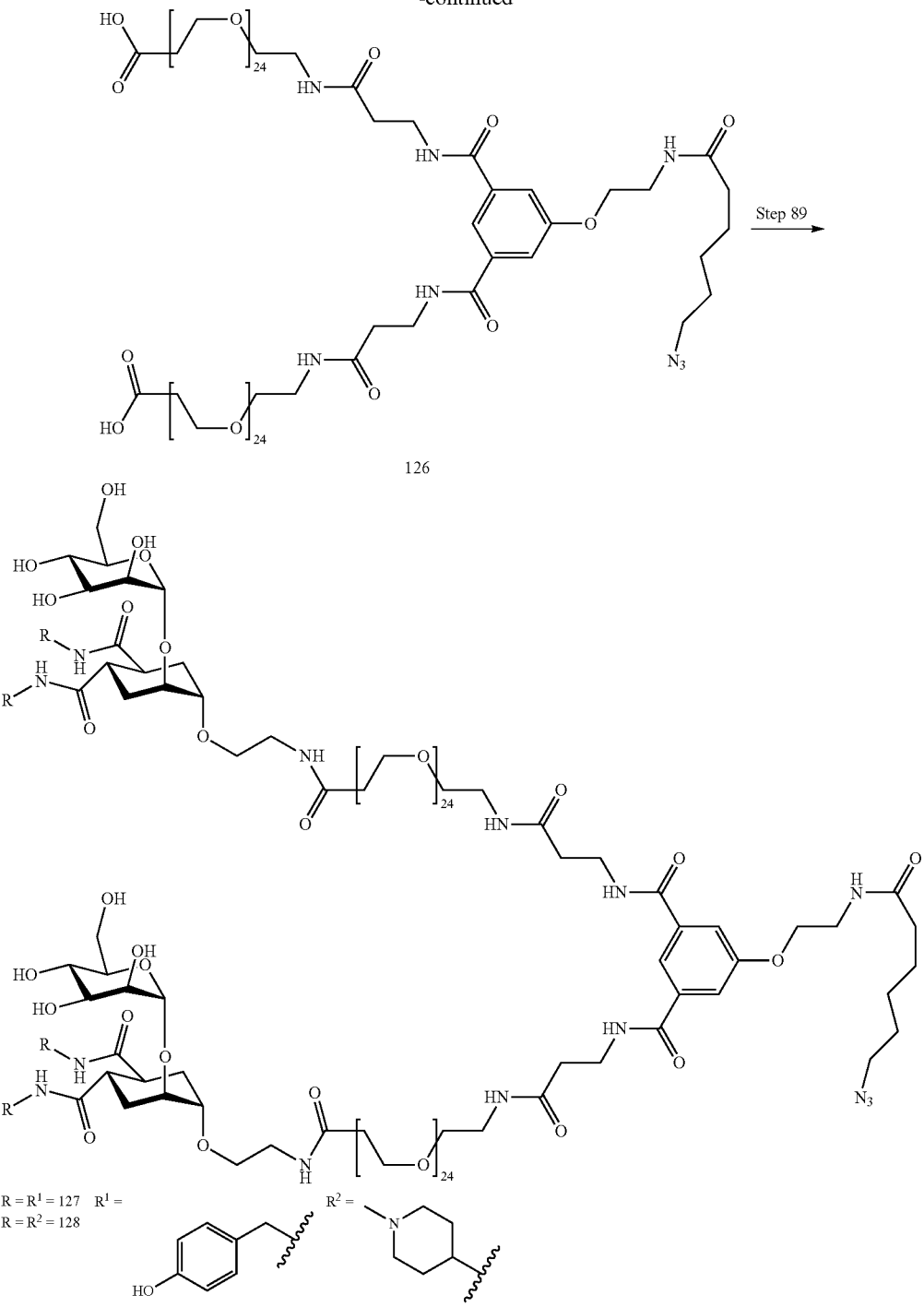

126

R = R¹ = 127  R¹ = 
R = R² = 128  R² =

Step 88

[STEP 1] A coupling compound having an azide group was obtained as a crude product (2.293 g, yield: 50%) in the same way as in step 10 of Example 2 using compound 5 (3.39 g, 8.584 mmol) synthesized in step 4 of Example 1.

[STEP 2] Carboxylic acid ester was obtained as a hydrolysate (2.021 g, yield: 93%) in the same way as in step 2 of Example 1 using the compound (2.293 g, 4.29 mmol) obtained in STEP 1.

[STEP 3] An active ester form was quantitatively obtained in the same way as in step 54 of Example 12 using the compound (0.100 g, 0.197 mmol) obtained in STEP 2.

[STEP 3] Compound 126 (0.216 g, yield: 85%) was obtained in the same way as in step 55 of Example 12 using the active ester (0.214 g, 0.255 mmol) obtained by the method of STEP 3.

ESI-MS m/z: 2763 (M−H)⁻

Step 89

Results obtained from R═R1 will be shown below. Similar results are obtained in the case of R2.

[STEP 1] Compound 124 (9.9 mg, 0.069 mmol) synthesized in step 86 of Example 21 was dissolved in methanol (500 μL). To the solution, a 28% solution of sodium methoxide in methanol (14 uL) was added, and the mixture was then left standing overnight at room temperature. The mixture was purified by reverse-phase chromatography (water/acetonitrile) to quantitatively obtain the compound of interest with the benzoyl group deprotected.

[STEP 2] Compound 127 (0.6 mg, yield: 30%) was obtained in the same way as in step 26 of Example 5 using compound 125 (1.4 mg, 0.502 μmol) obtained in step 87 of Example 21 and the compound (4.2 mg, 5.02 μmol) obtained by STEP 1.

ESI-MS m/z: 1982 (M−2H)$^{2-}$

Example 23 Synthesis of Sugar Chain Ligand-Linker Unit—20

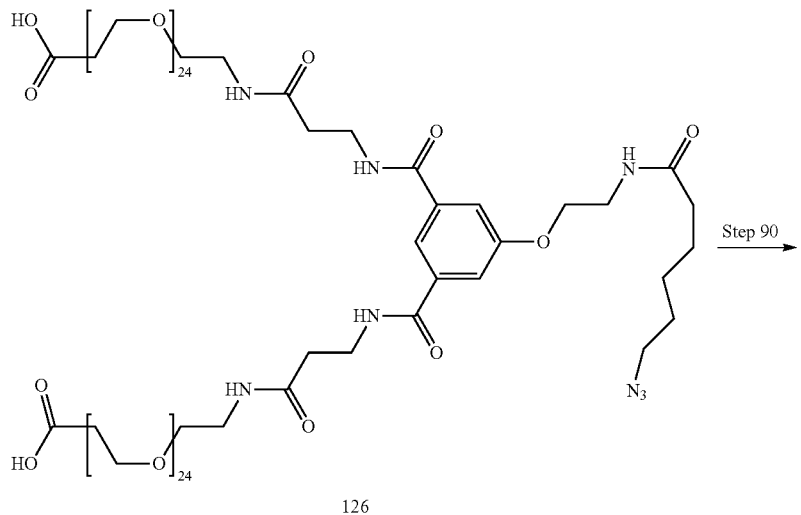

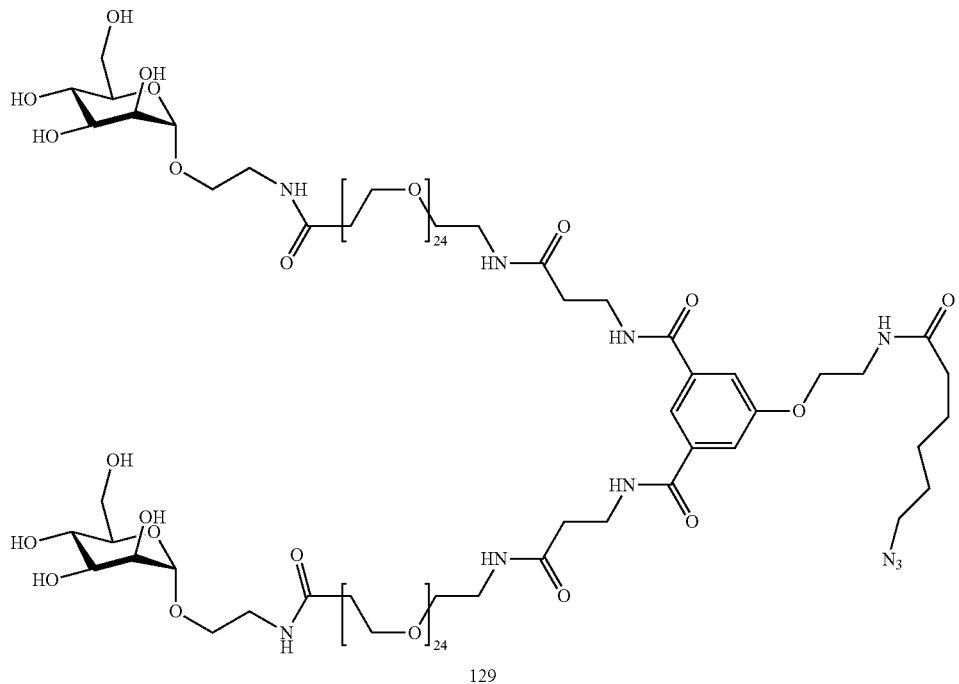

Step 90

Compound 129 (11 mg, 48%) was obtained in the same way as in step 26 of Example 5 using compound 126 (24 mg, 7.30 μmol) synthesized in step 18 of Example 3.

ESI-MS m/z: 1608 (M−2H)$^{2-}$

Example 24 Synthesis of Sugar Chain Ligand-Linker Unit—21
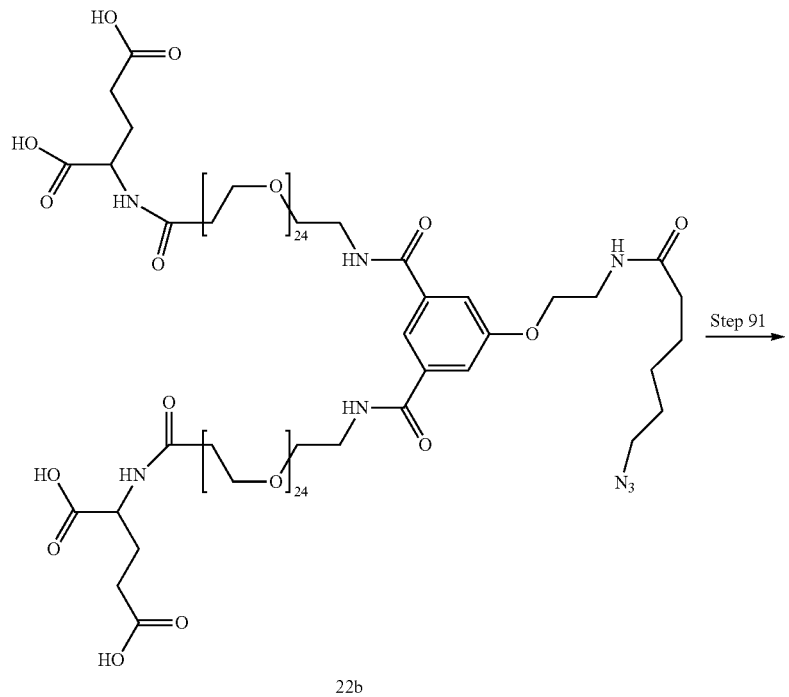
22b
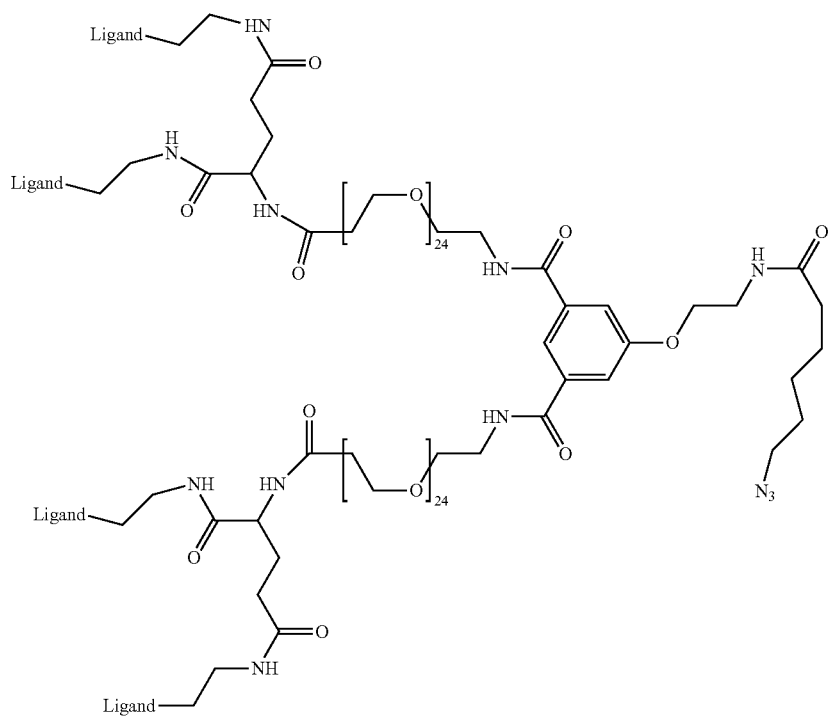
Ligand = Ligand 2: 130
Ligand = Ligand 4: 131

-continued

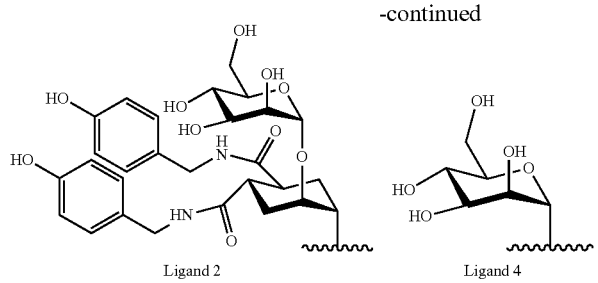

Ligand 2    Ligand 4

Step 91
Synthesis of Compound 130

[STEP 1] A ligand adduct (0.9 mg, 10%) was obtained in the same way as in step 26 of Example 5 using compound 22b (4 mg, 1.342 µmol) synthesized in step 20 of Example 3.

[STEP 2] The compound (0.9 mg, 0.129 µmol) obtained by STEP 1 was dissolved in methanol (0.6 mL). To the solution, sodium methoxide (2 µL, 10 µmol) was added, and the mixture was then reacted at room temperature for 3 hours. The reaction solution was fractionated by reverse-phase chromatography, and the fraction of interest was freeze-dried to obtain compound 130 (0.3 mg, 44%).

ESI-MS m/z: 2642 $(M-2H)^{2-}$

Synthesis of Compound 131

Compound 131 (3.6 mg, 17%) was obtained in the same way as in step 26 of Example 5 using compound 22b (22 mg, 5.88 µmol) synthesized in step 20 of Example 3.

ESI-MS m/z: 1851 $(M+2H)^{2+}$

Example 25 Synthesis of Nucleic Acid Conjugate—3

Step 92

[Method 1] Single-stranded nucleic acid conjugates 132 to 151 described in Tables 11-1 to 11-4 were obtained in the same way as in step 38 of Example 9 using the compounds described in Tables 10-1 to 10-3. In Table 11-3, each of X and Y represents the 3'-terminal nucleotide structure of an oligonucleotide.

[Method 2] Single-stranded nucleic acid conjugates 152 and 153 described in Table 11-3 were obtained by the method of Bioconjugate Chemistry, Vol. 22, p. 1723-1728, 2011 using a terminally amino group-modified oligonucleotide synthesized by the method described in Molecules, Vol. 17, p. 13825-13843, 2012, and compound 105.

The sequences and mass spectrometry results of the nucleic acid conjugates synthesized in this Example are shown in Table 12.

TABLE 10-1

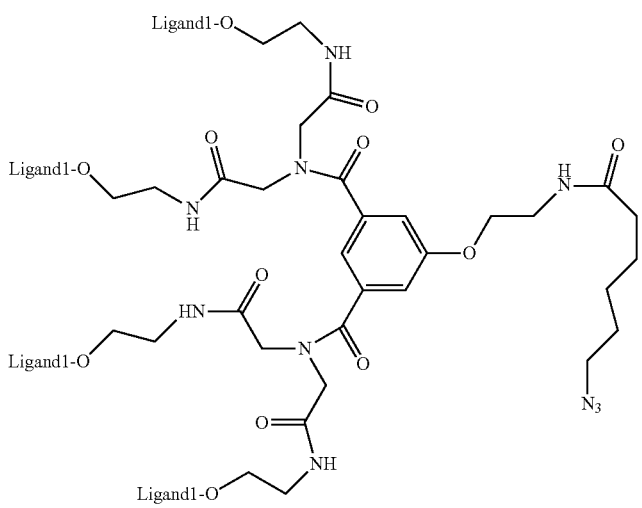

80

TABLE 10-1-continued
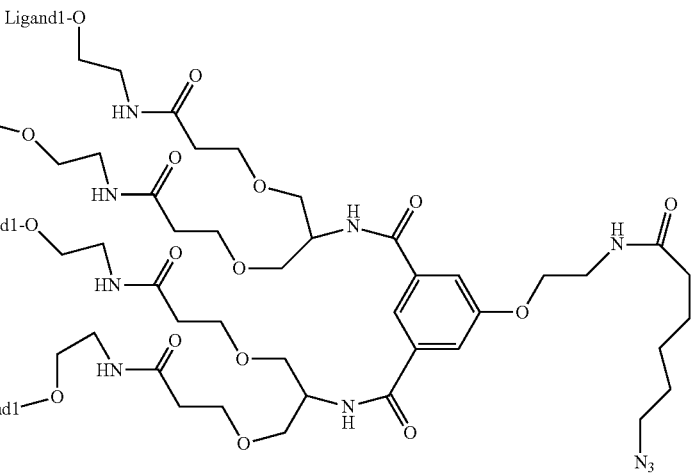
85
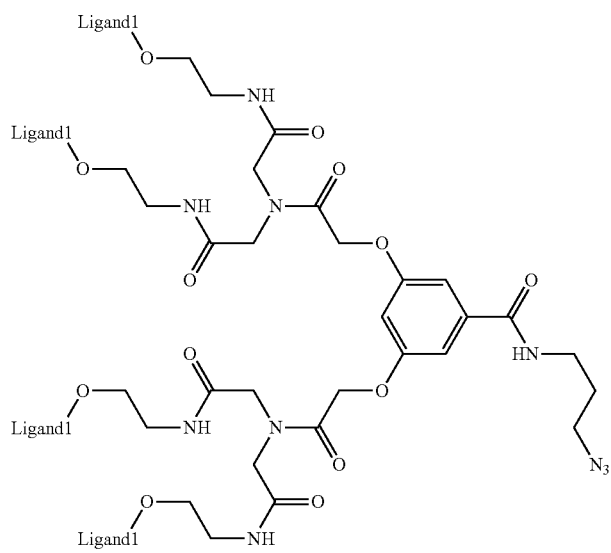
92
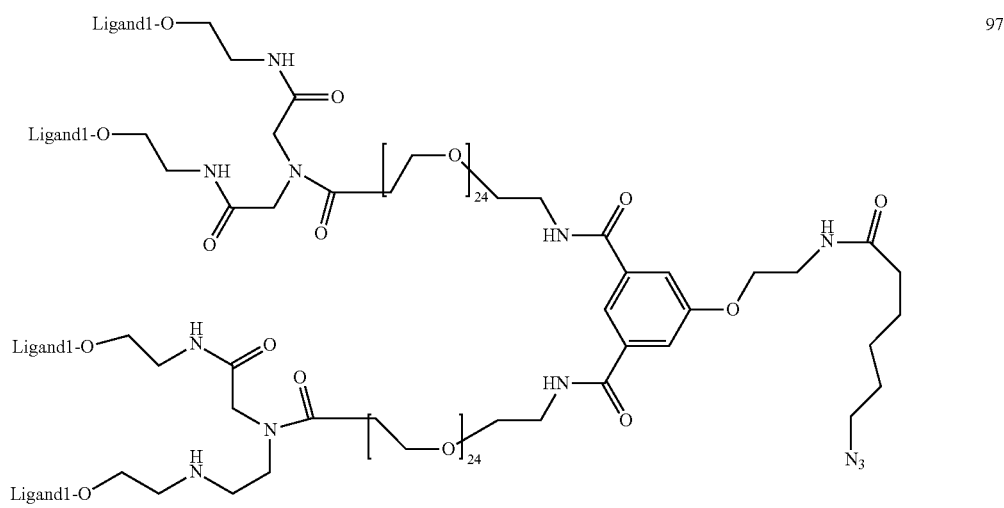
97

TABLE 10-1-continued
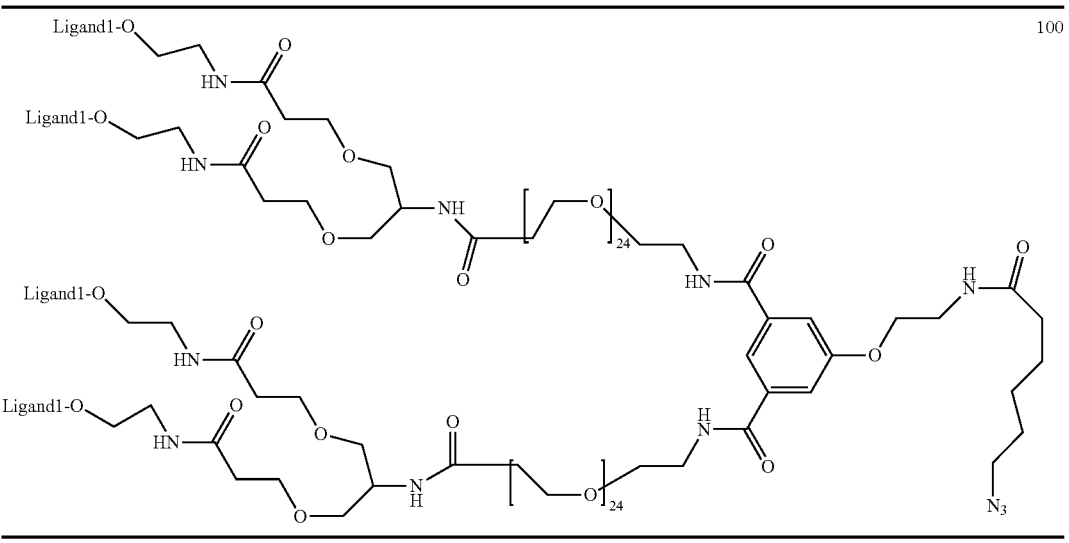
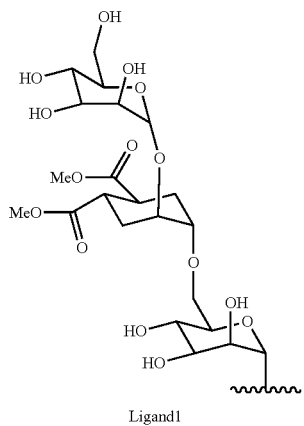 [SMILES: *C1OC(COC2CC(C(=O)OC)C(C(=O)OC)CC2OC2OC(CO)C(O)C(O)C2O)C(O)C(O)C1O]
TABLE 10-2
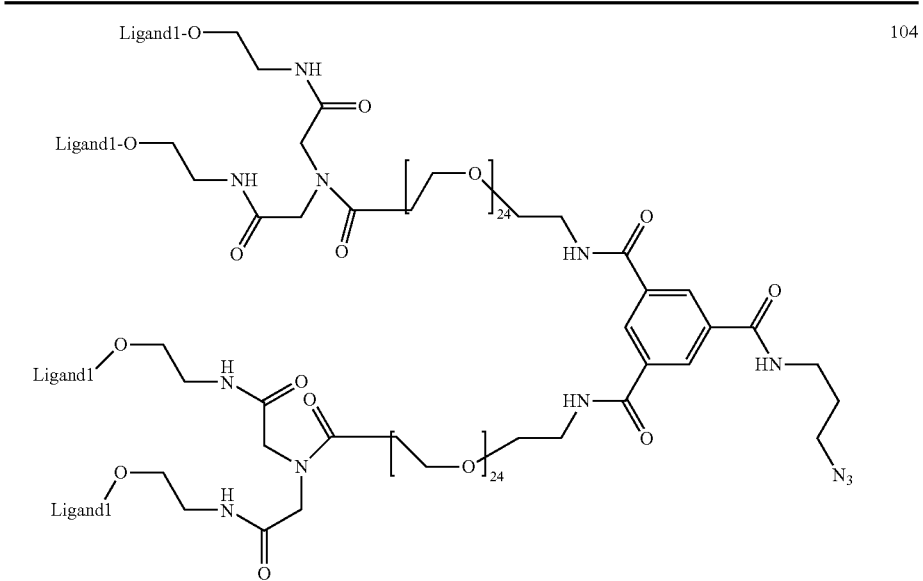

TABLE 10-2-continued
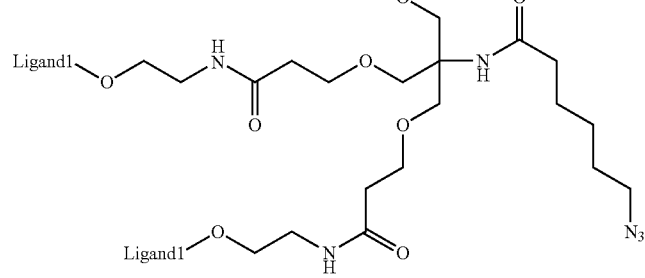
112
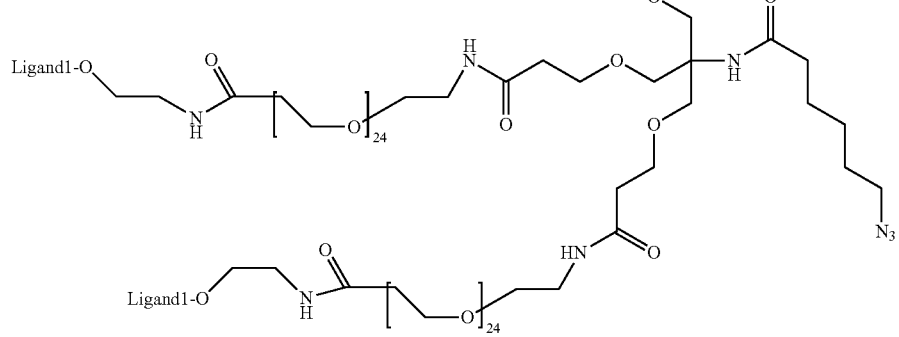
114

TABLE 10-2-continued
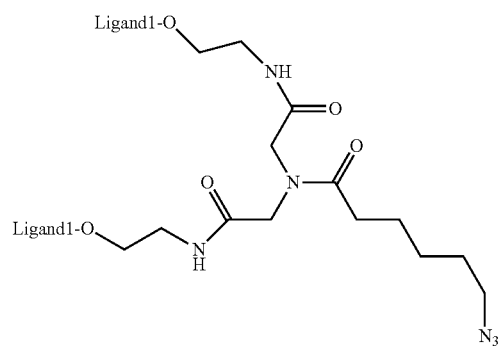
118
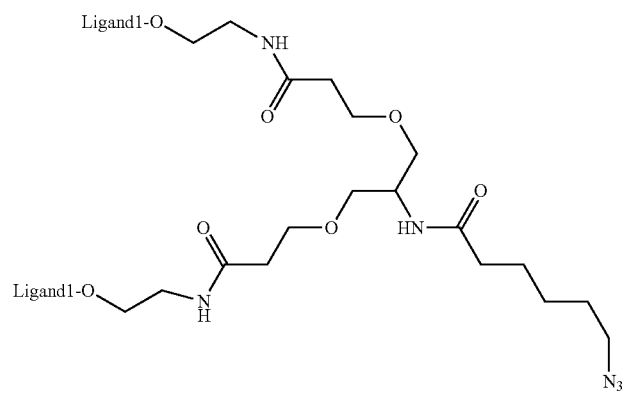
121
TABLE 11-1
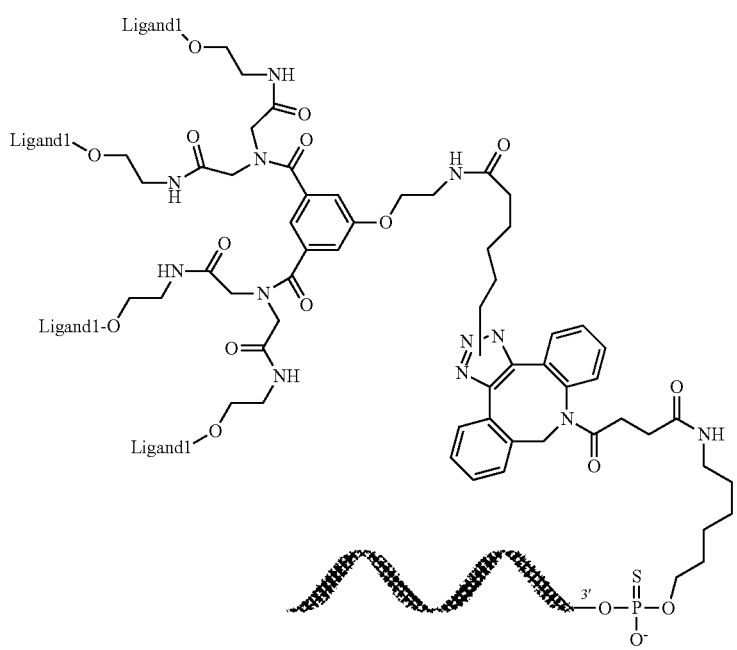
132

TABLE 11-1-continued
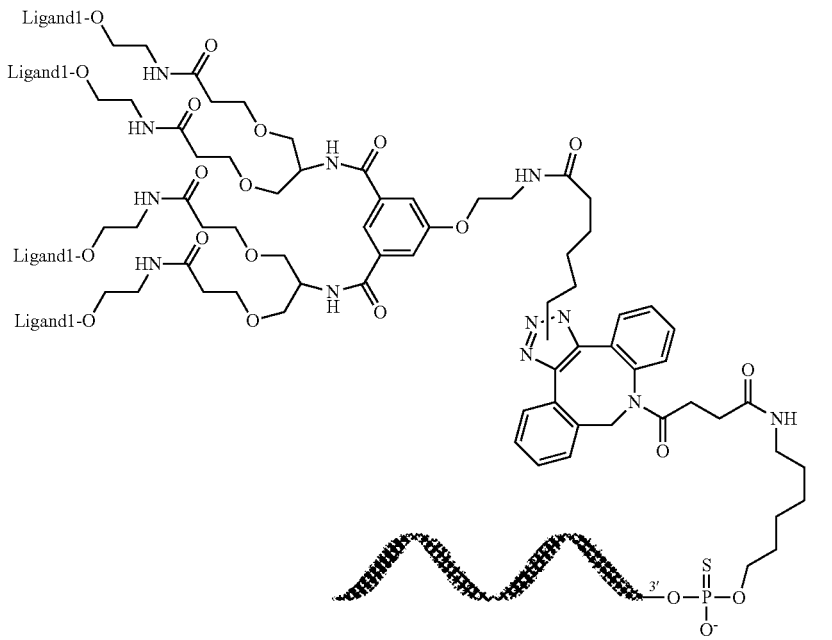
133
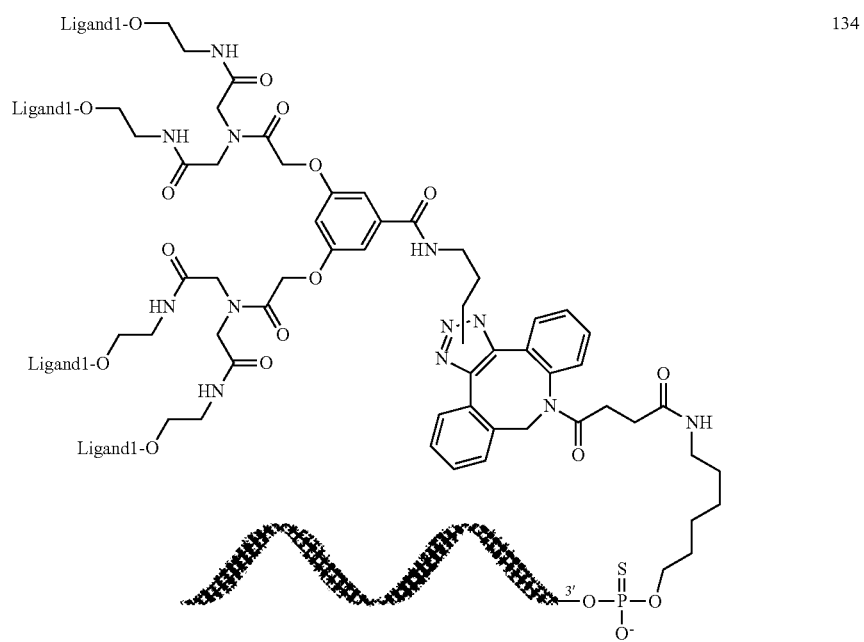
134

TABLE 11-1-continued
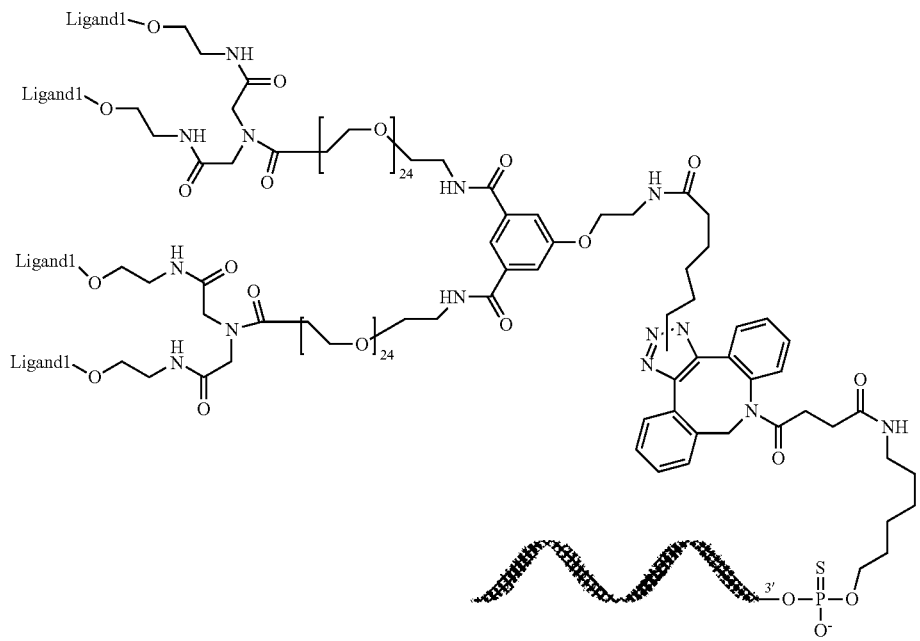
135
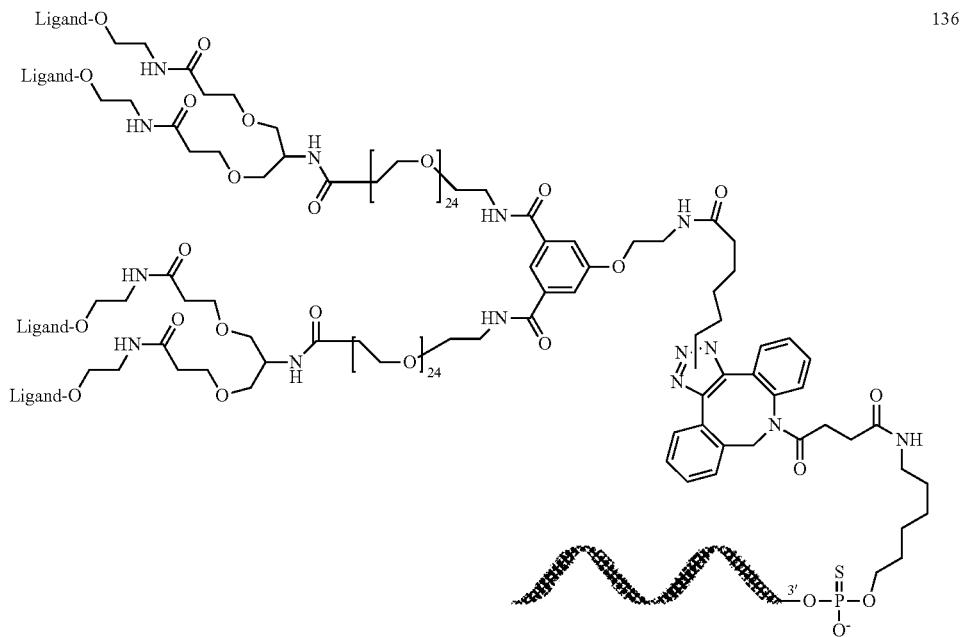
136

TABLE 11-1-continued
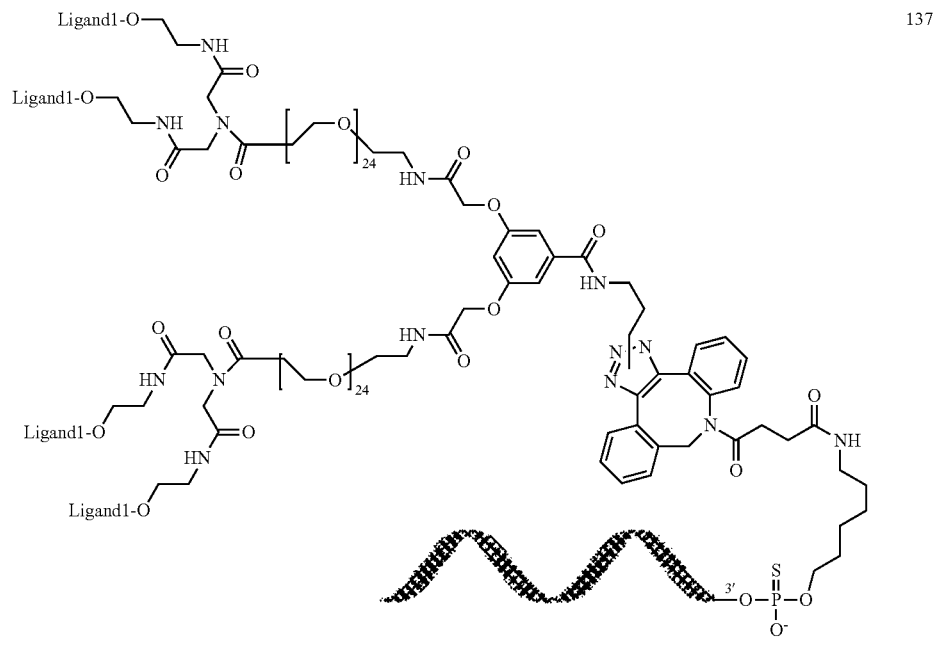
137
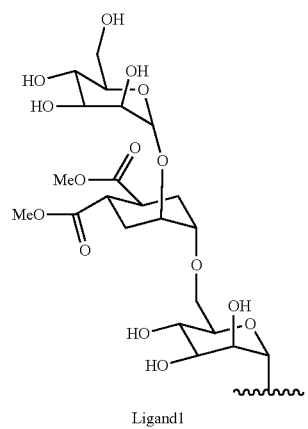 [SMILES: *C1OC(COC2CC(C(=O)OC)C(C(=O)OC)CC2OC2OC(CO)C(O)C(O)C2O)C(O)C(O)C1O]
Ligand1

TABLE 11-2
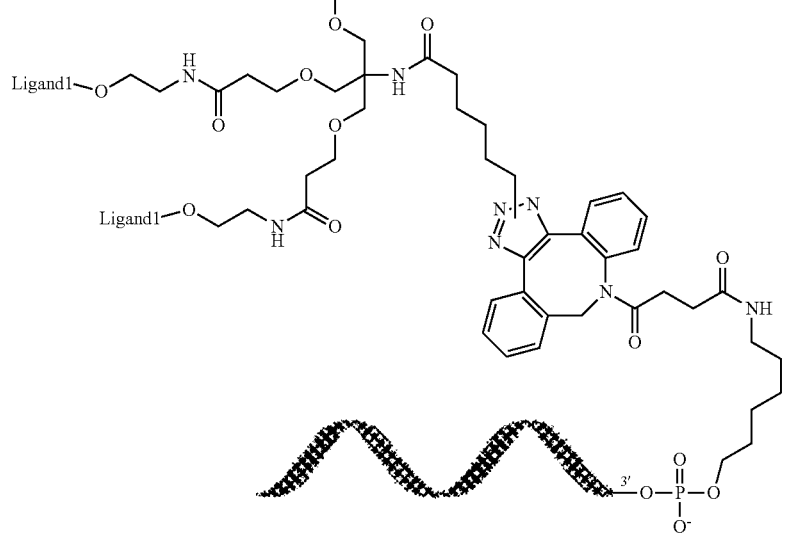
138
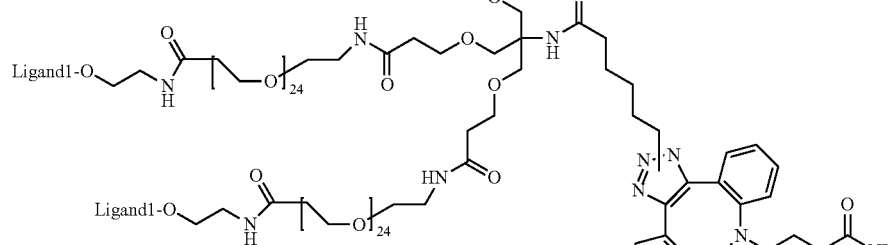
139

TABLE 11-2-continued
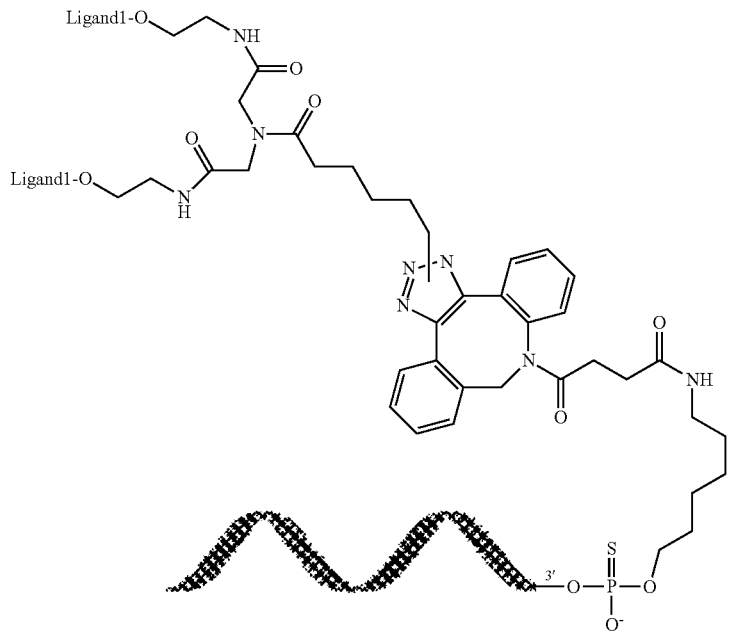
140
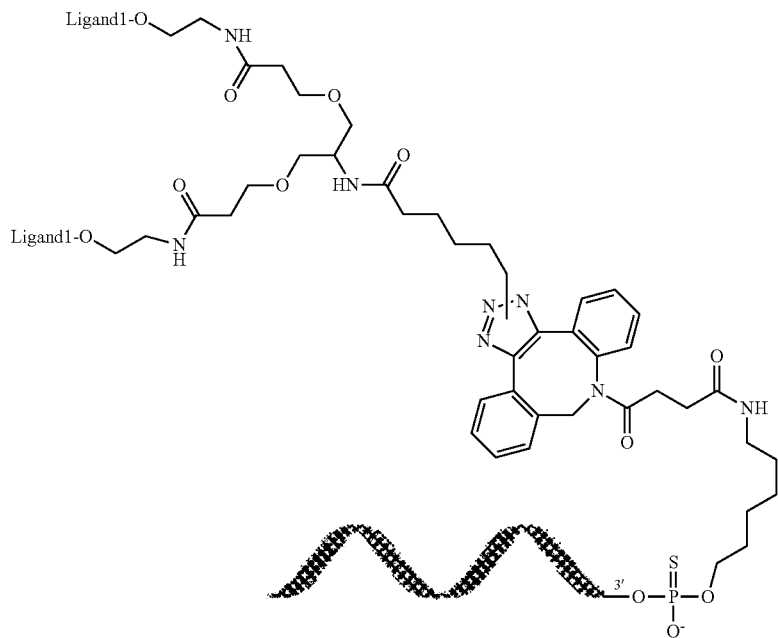
141

TABLE 11-2-continued
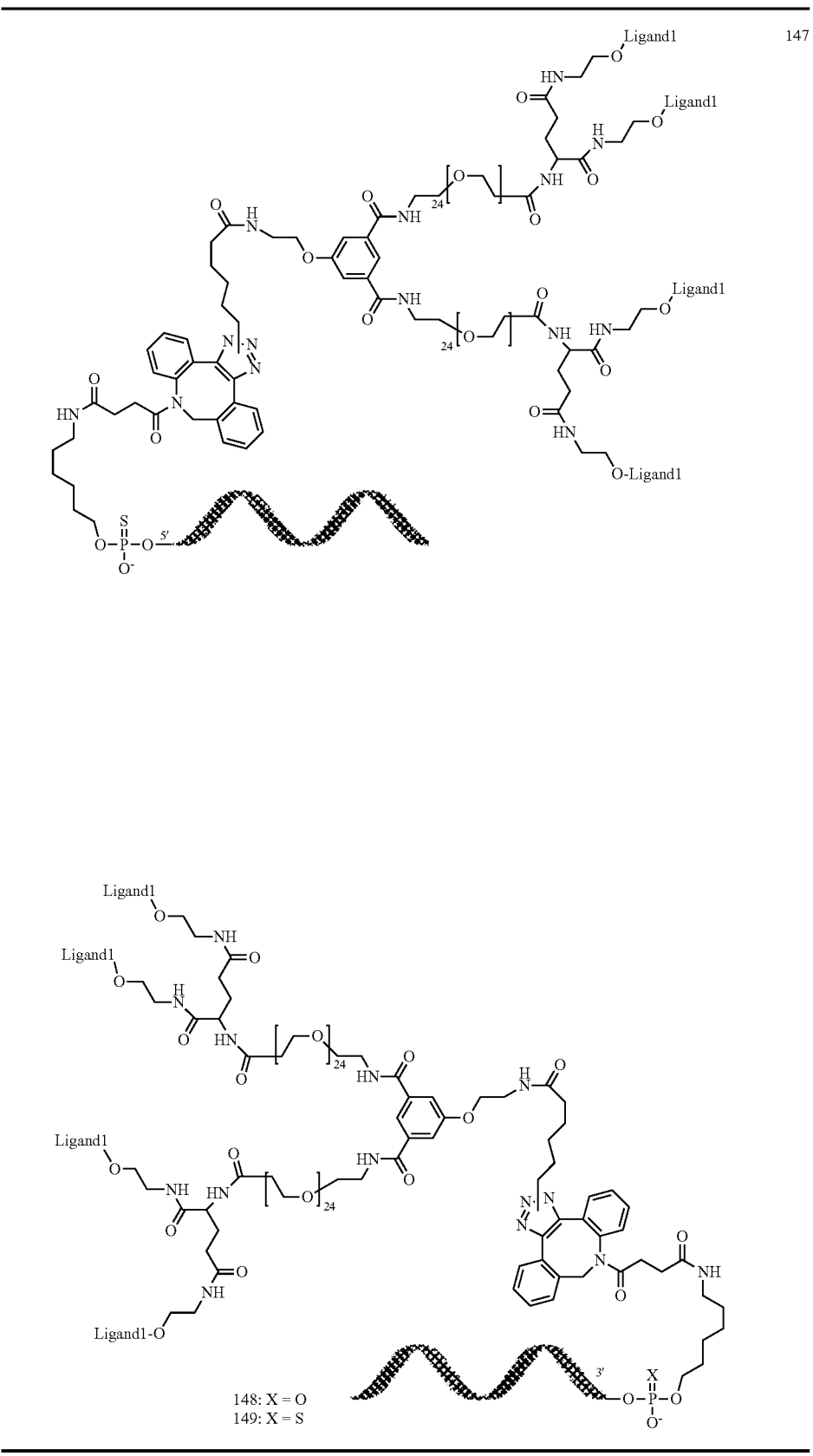
148: X = O
149: X = S

TABLE 11-2-continued
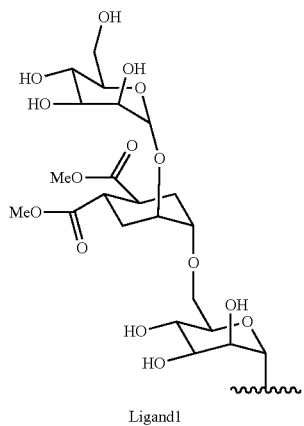 [SMILES: *C1OC(COC2CC(C(=O)OC)C(C(=O)OC)CC2OC2OC(CO)C(O)C(O)C2O)C(O)C(O)C1O]
Ligand1
TABLE 11-3
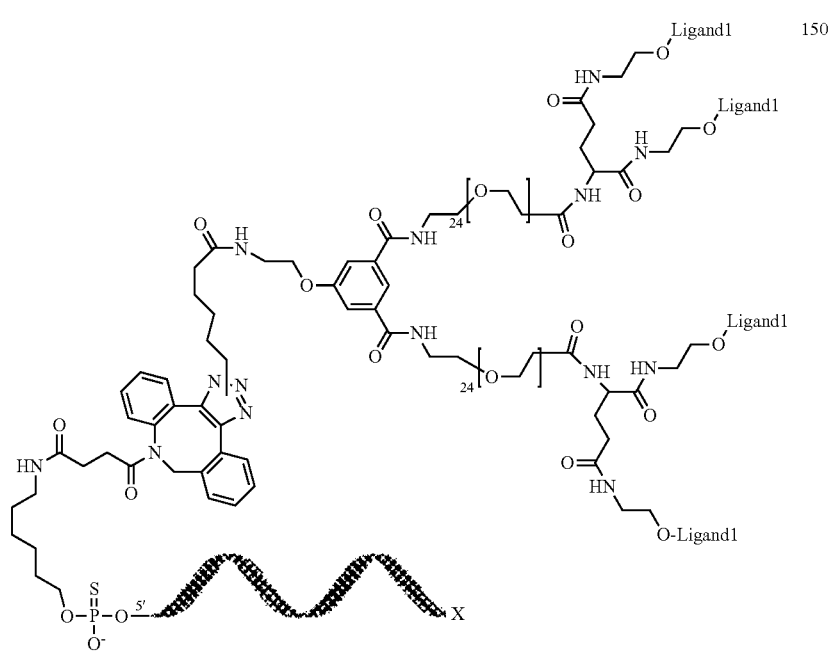

TABLE 11-3-continued
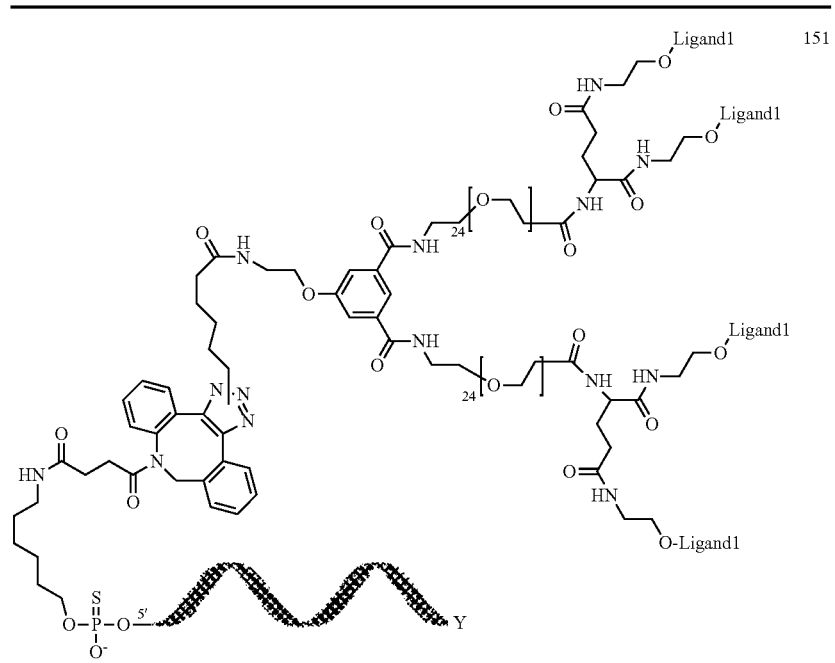
151
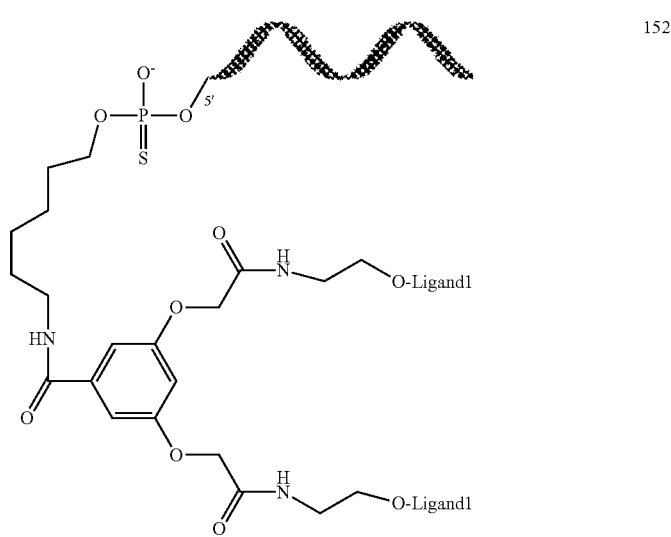
152

TABLE 11-3-continued
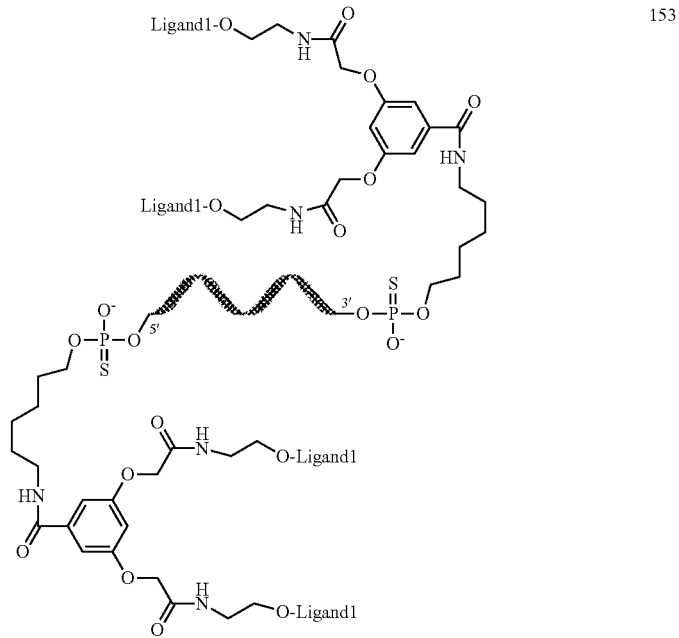
153
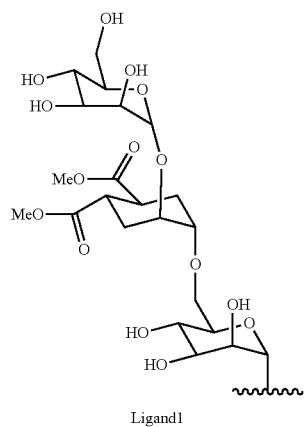 [SMILES: *C1OC(COC2CC(C(=O)OC)C(C(=O)OC)CC2OC2OC(CO)C(O)C(O)C2O)C(O)C(O)C1O]
Ligand1

TABLE 11-3-continued
X =
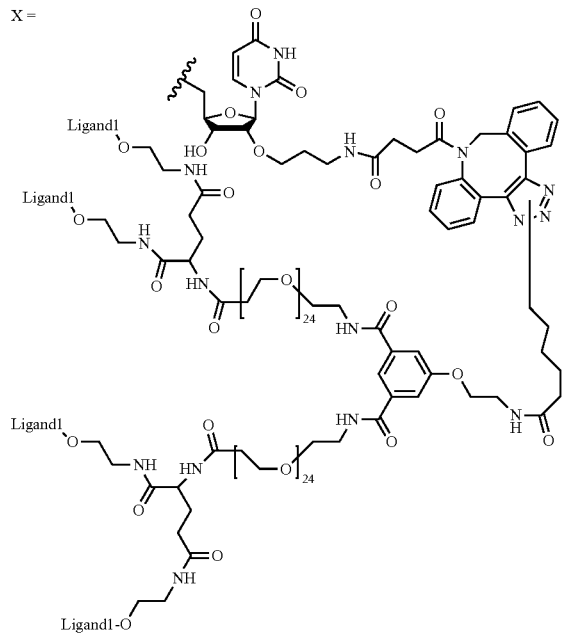
Y =
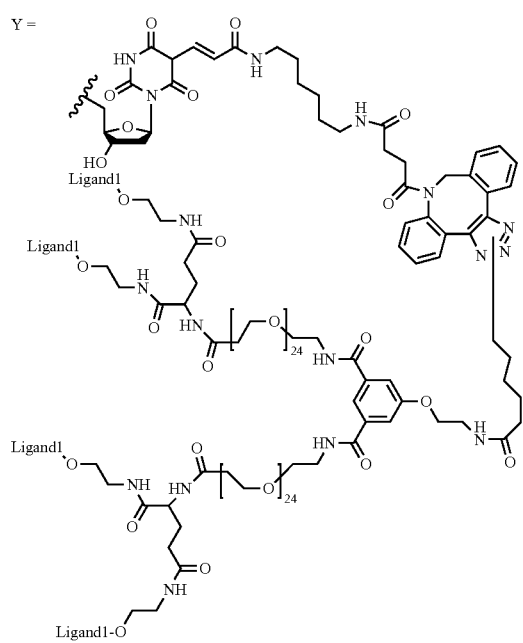

TABLE 11-4
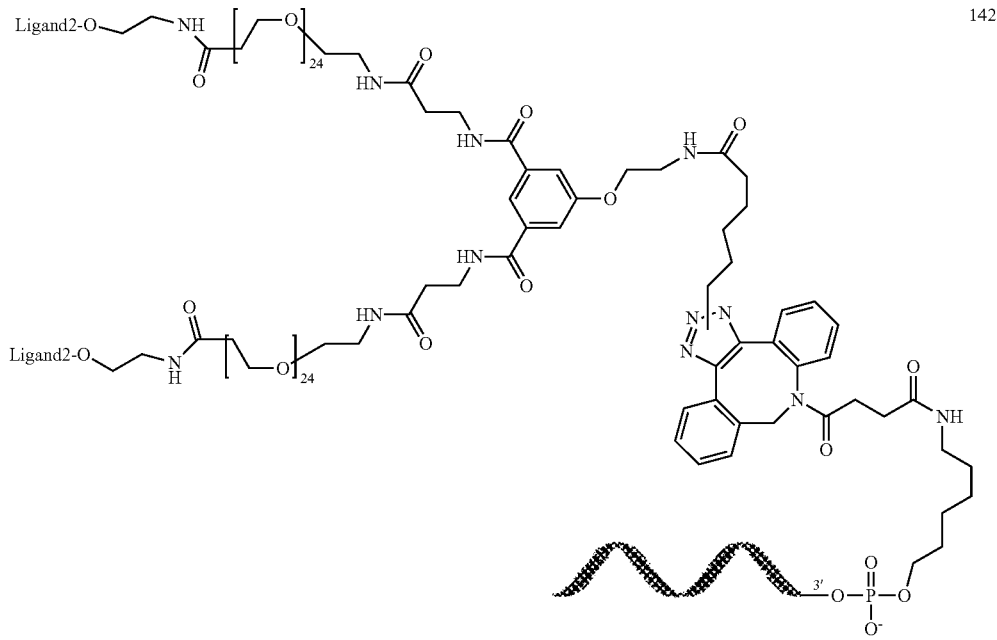
142
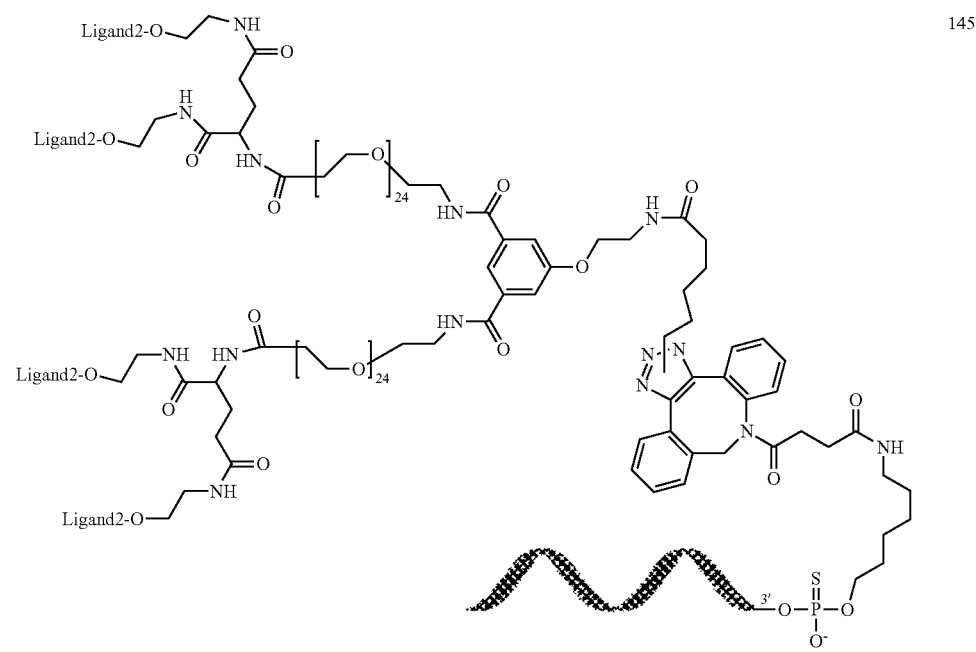
145

TABLE 11-4-continued
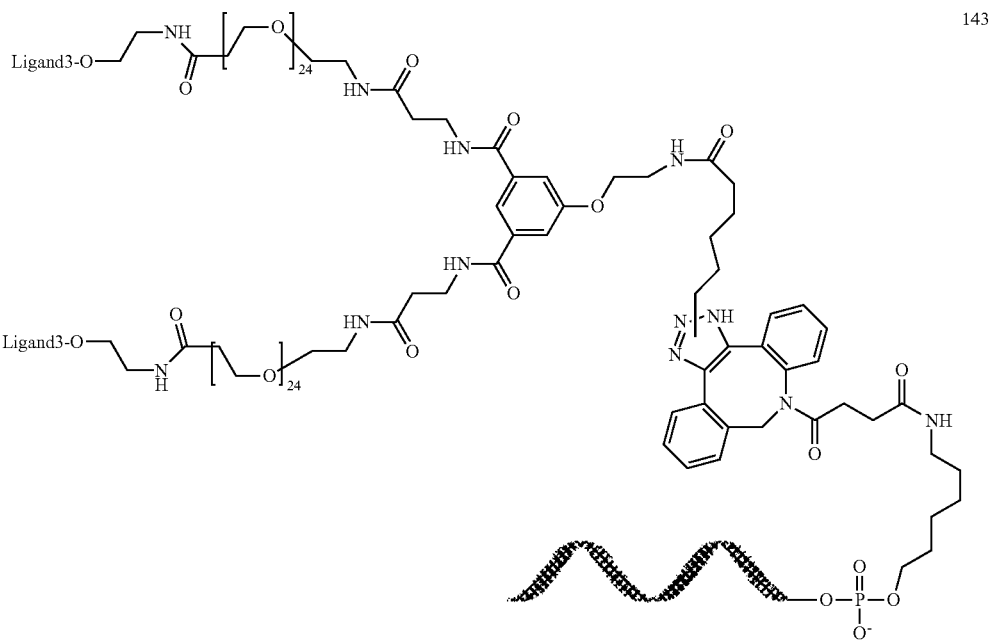
143
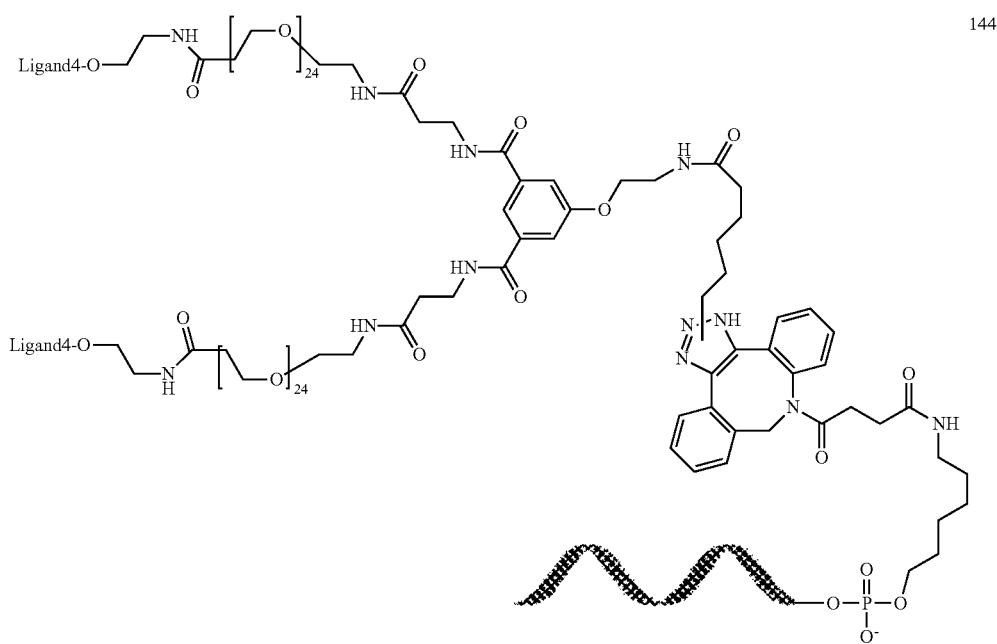
144

TABLE 11-4-continued
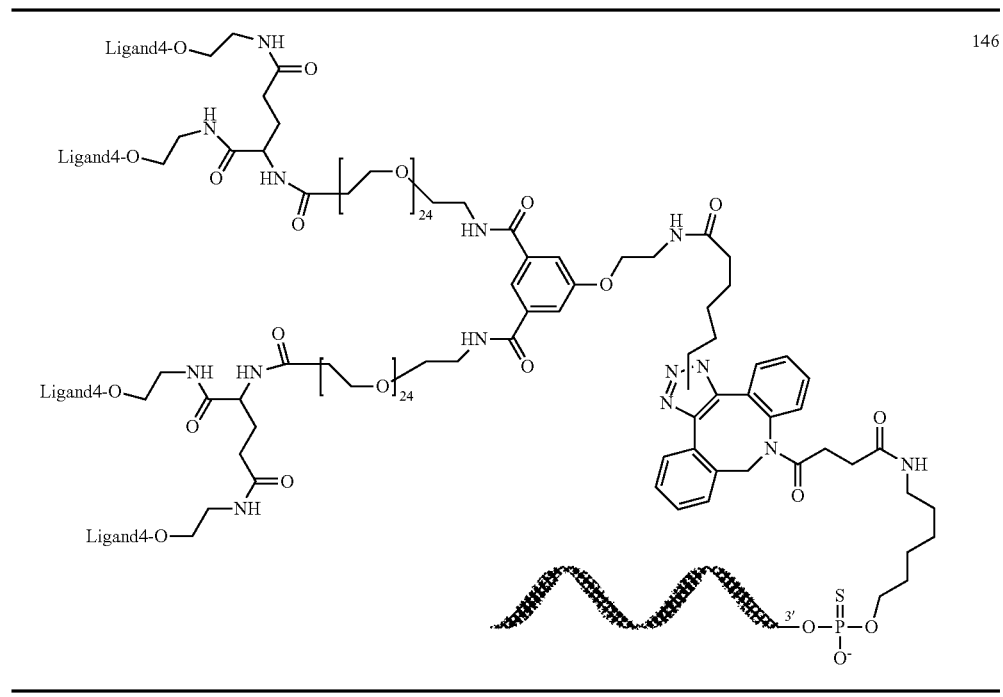
146
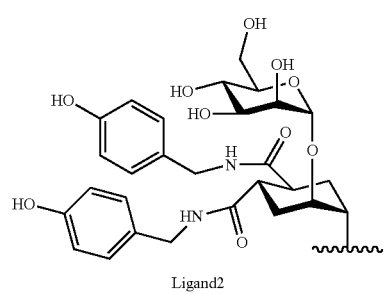
Ligand2
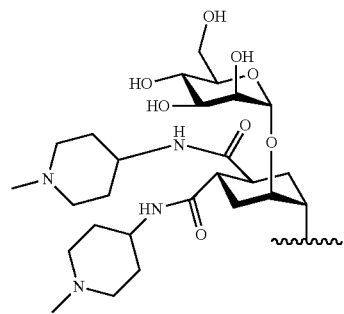
Ligand3
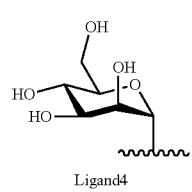
Ligand4

TABLE 12

| Compound | Sequence (5'→3') | Calcd | Found |
|---|---|---|---|
| 132_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 132 | 10216 | 10217 |
| 133_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 133 | 10420 | 10421 |
| 134_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 134 | 10204 | 10205 |
| 135_3V-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 135 | 12472 | 12472 |
| 136_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 136 | 12677 | 12676 |
| 137_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 137 | 12460 | 12461 |
| 138_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 138 | 9516 | 9516 |
| 139_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 139 | 12901 | 12901 |
| 140_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 140 | 8730 | 8732 |
| 141_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 141 | 8832 | 8834 |
| 142_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 142 | 11267 | 11266 |
| 143_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 143 | 11302 | 11301 |
| 144_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 144 | 11422 | 11421 |
| 145_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 145 | 12581 | 12581 |
| 146_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 146 | 11036 | 11037 |
| 147_5'-B2MssRNA | 147A(F)^G(M)^G(F)A(M)C(F)U(M)G(F)G(M)U(F)C(M) U(F)U(F)U(M)C(F)U(M)A(F)U(M)C(F)U(M)^C(F)^U(M) | 12500 | 12501 |
| 148_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 148 | 12454 | 12454 |
| 149_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 149 | 12500 | 12500 |
| 150_5'-B2MssRNA | 150A(F)^G(M)^G(F)A(M)C(F)U(M)G(F)G(M)U(F)C(M) U(F)U(F)U(M)C(F)U(M)A(F)U(M)C(F)U(M)^C(F)^U(M) X | 18374 | 18370 |
| 151_5'-B2MssRNA | 151A(F)^G(M)^G(F)A(M)C(F)U(M)G(F)G(M)U(F)C(M) U(F)U(F)U(M)C(F)U(M)A(F)U(M)C(F)U(M)^C(F)^U(M) Y | 18470 | 18470 |
| 152_5'-B2MssRNA | 152A(F)^G(M)^G(F)A(M)C(F)U(M)G(F)G(M)U(F)C(M) U(F)U(F)U(M)C(F)U(M)A(F)U(M)C(F)U(M)^C(F)^U(M) | 8423 | 8424 |
| 153_5'-B2MssRNA | 153A(F)^G(M)^G(F)A(M)C(F)U(M)G(F)G(M)U(F)C(M) U(F)U(F)U(M)C(F)U(M)A(F)U(M)C(F)U(M)^C(F)^U(M) 152 | 10034 | 10035 |

Example 26 Synthesis of Nucleic Acid Conjugate—4

Step 92

Double-stranded sugar chain conjugates 154 to 175 were obtained in the same way as in step 38 of Example 8 using the single-stranded sugar chain conjugates synthesized in step 91. The nucleic acid conjugates synthesized in this Example are shown in Tables 13-1 to 13-4. In Table 13-3, each of X and Y represents the 3'-terminal nucleotide of a sense strand.

TABLE 13-1
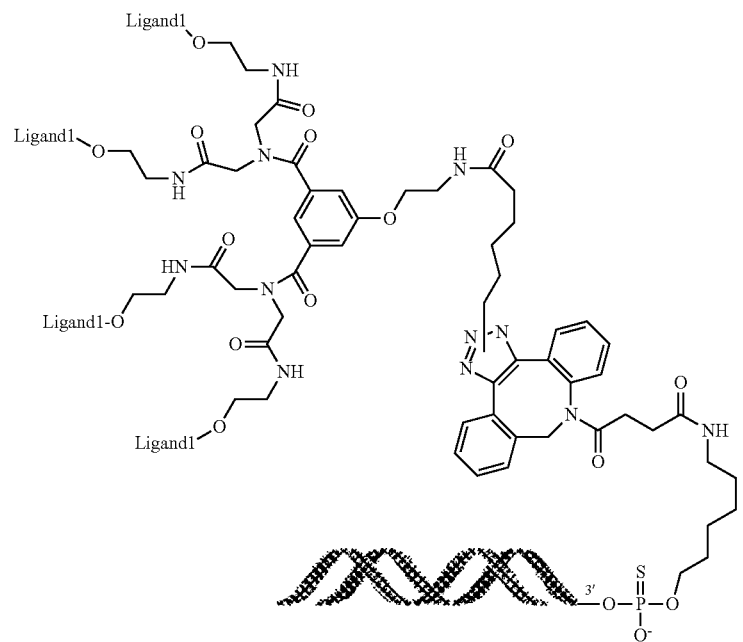
154
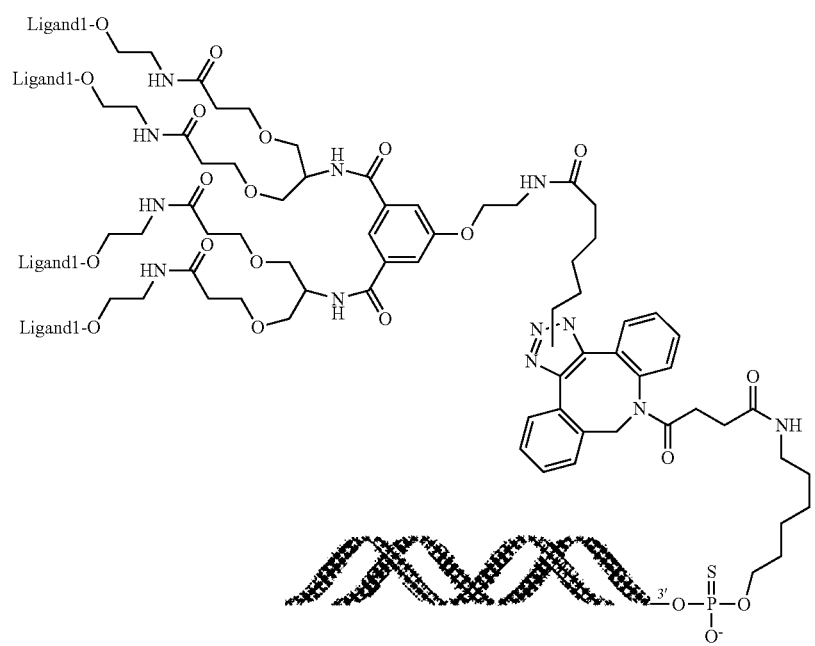
155

TABLE 13-1-continued
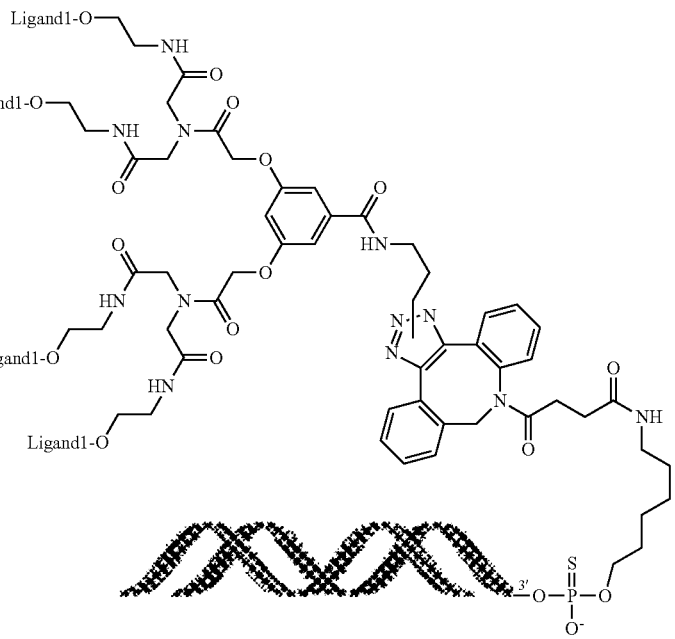
156
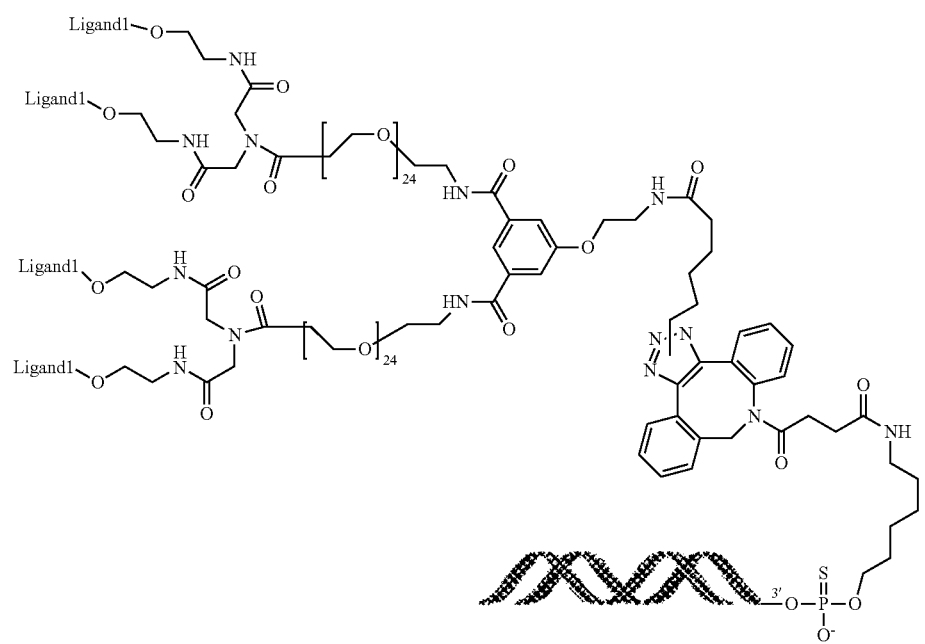
157

TABLE 13-1-continued
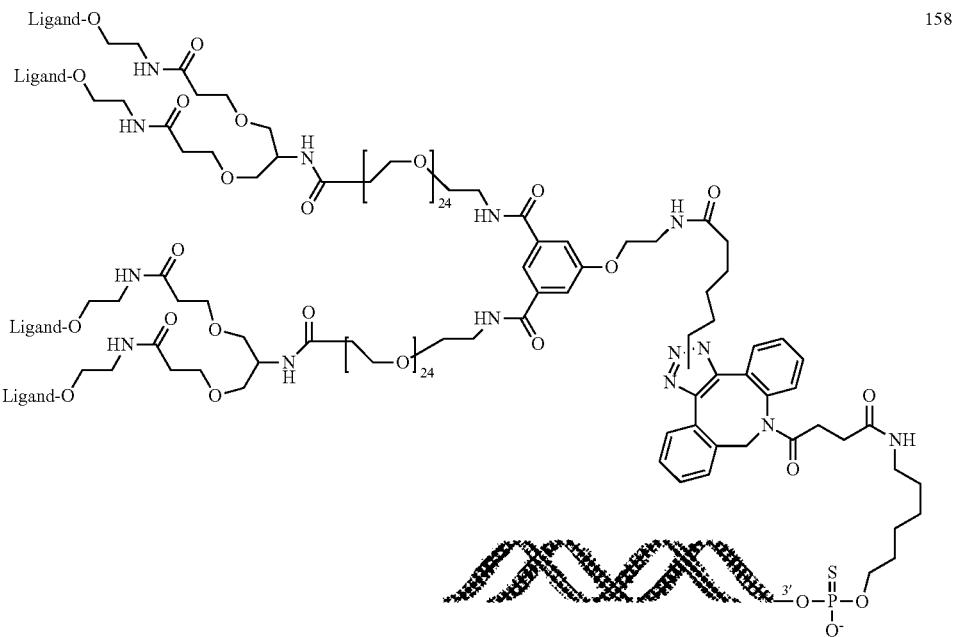
158
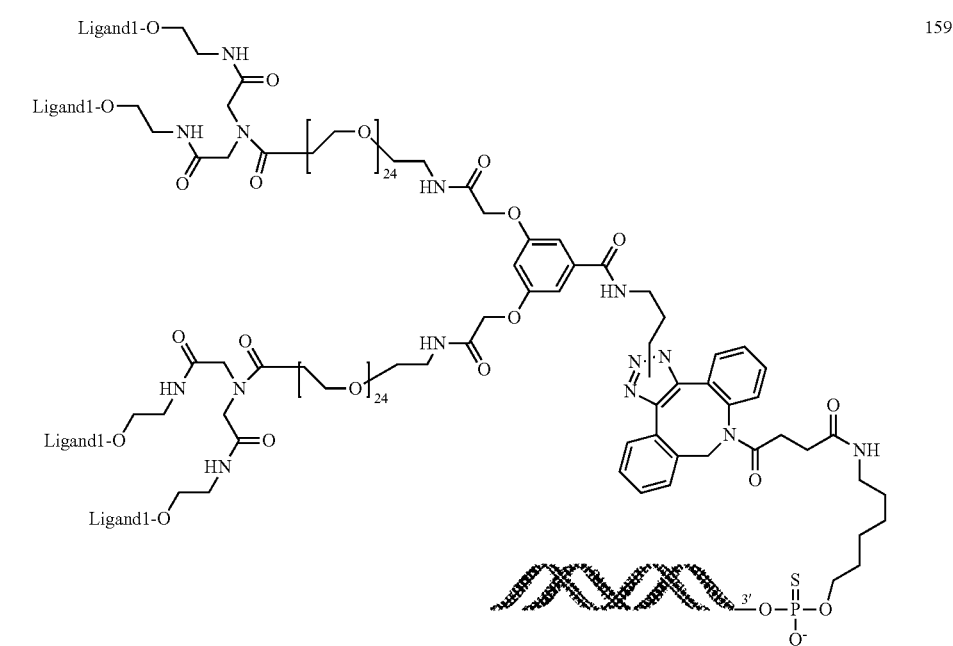
159

TABLE 13-1-continued
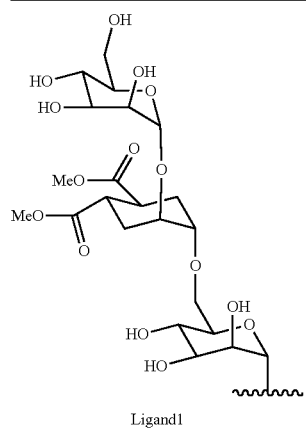
Ligand1
TABLE 13-2
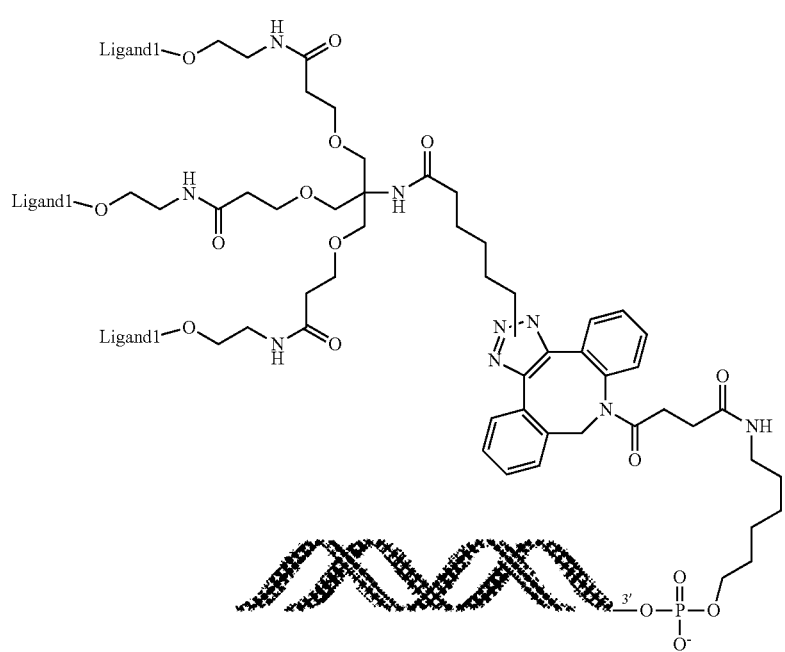
160

TABLE 13-2-continued
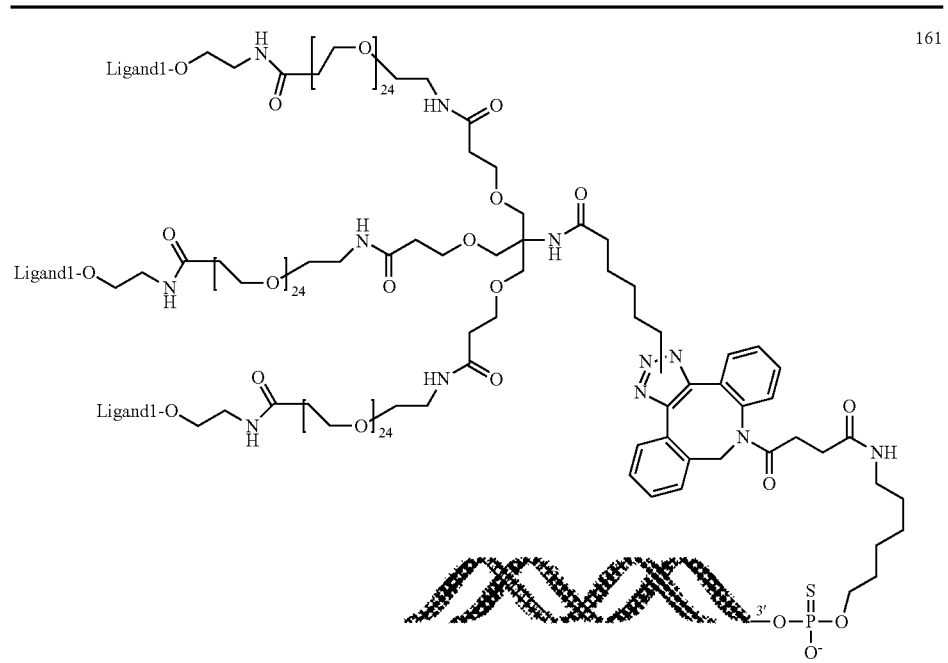
161
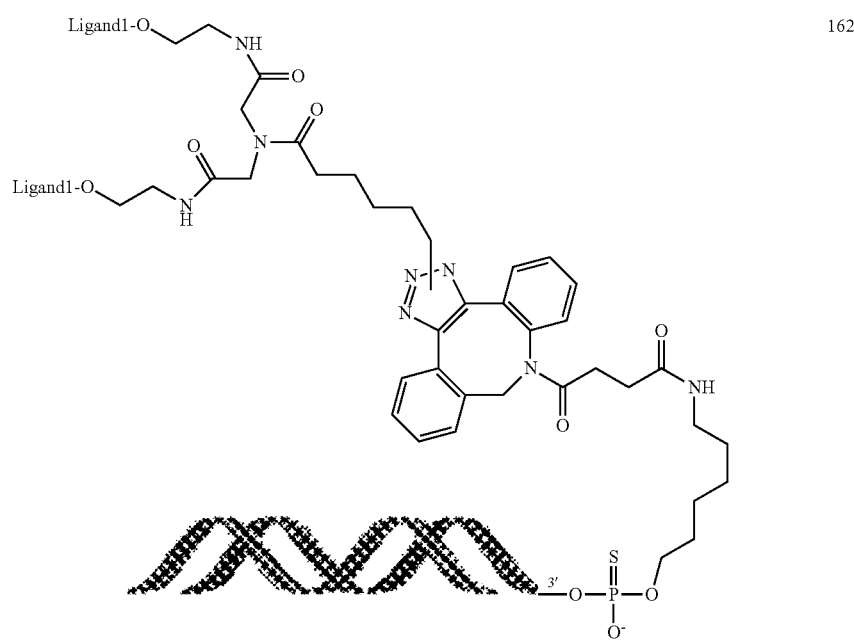
162

TABLE 13-2-continued
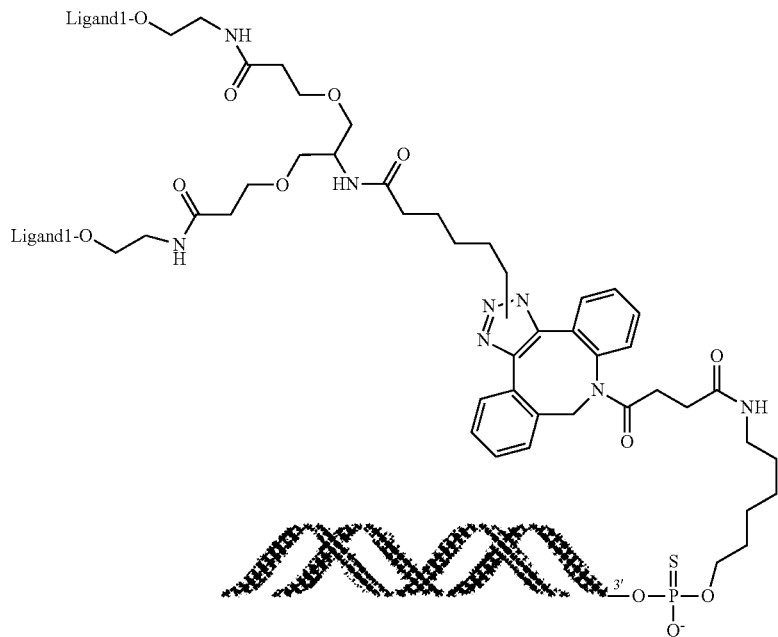
163
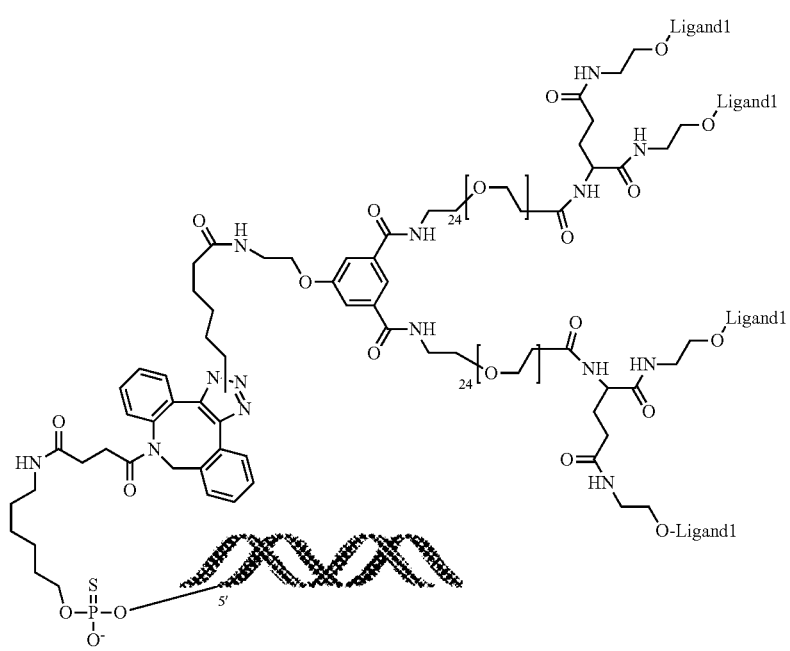
169

TABLE 13-2-continued
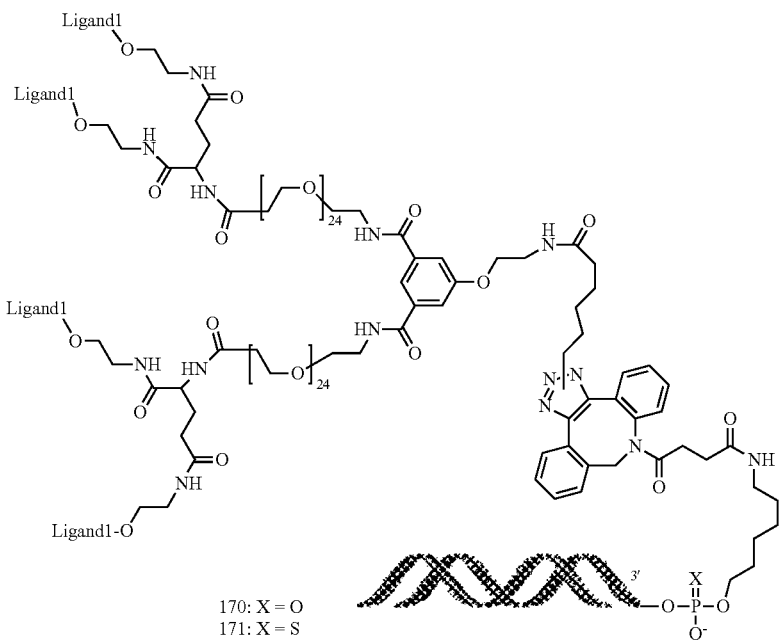
170: X = O
171: X = S
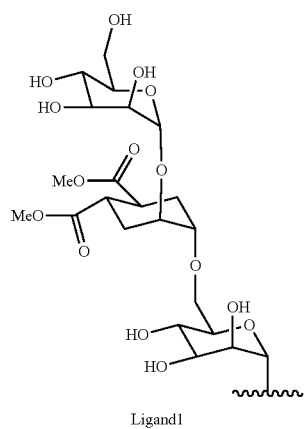 [SMILES: *C1OC(COC2CC(C(=O)OC)C(C(=O)OC)CC2OC2OC(CO)C(O)C(O)C2O)C(O)C(O)C1O]
Ligand1

TABLE 13-3
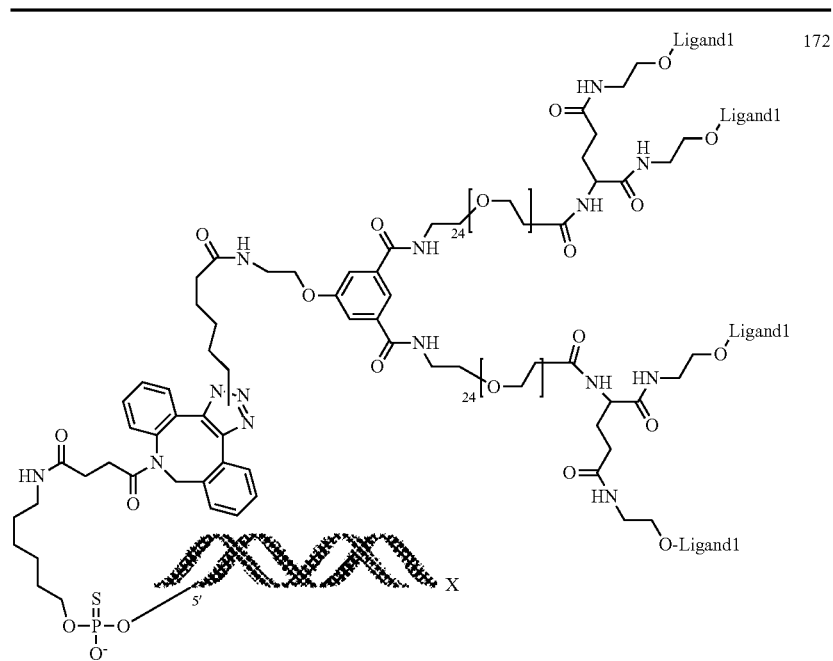
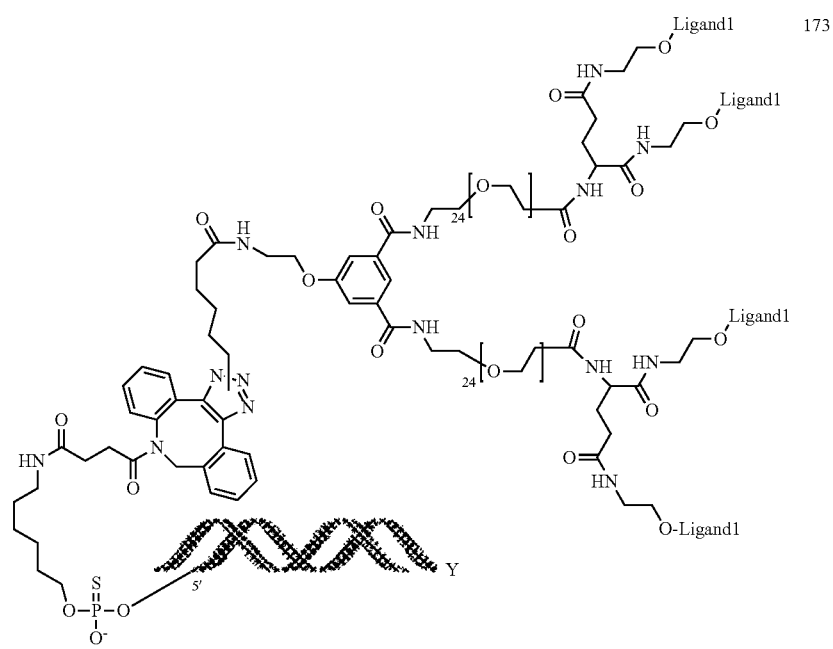

TABLE 13-3-continued
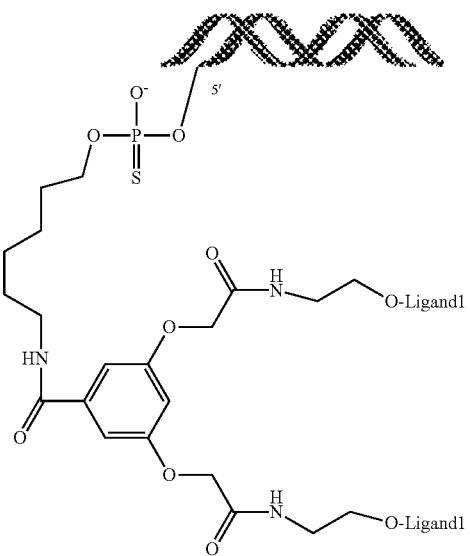
174
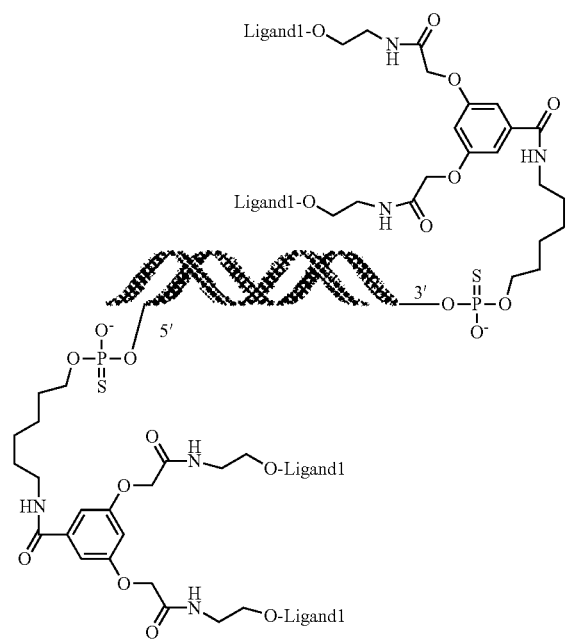
175
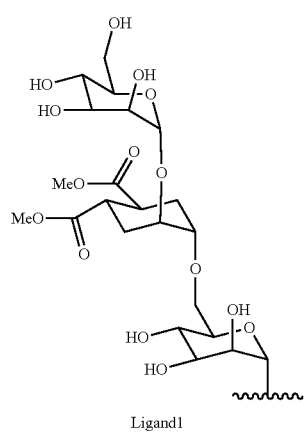 [SMILES: *C1OC(COC2CC(C(=O)OC)C(C(=O)OC)CC2OC2OC(CO)C(O)C(O)C2O)C(O)C(O)C1O]
Ligand1

TABLE 13-3-continued
X =
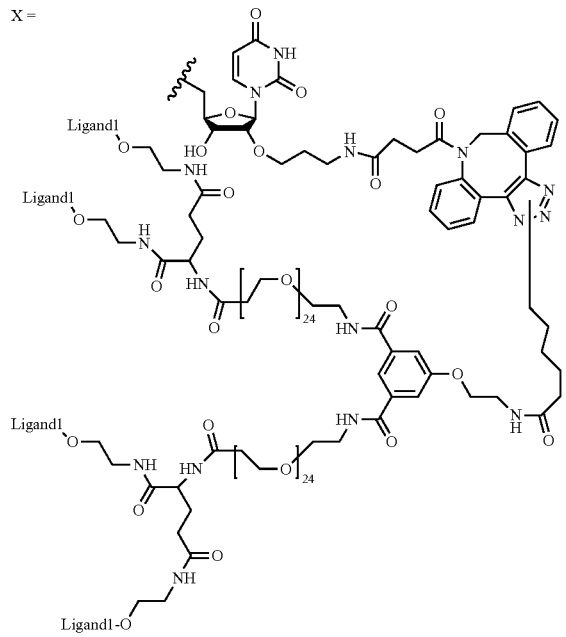
Y =
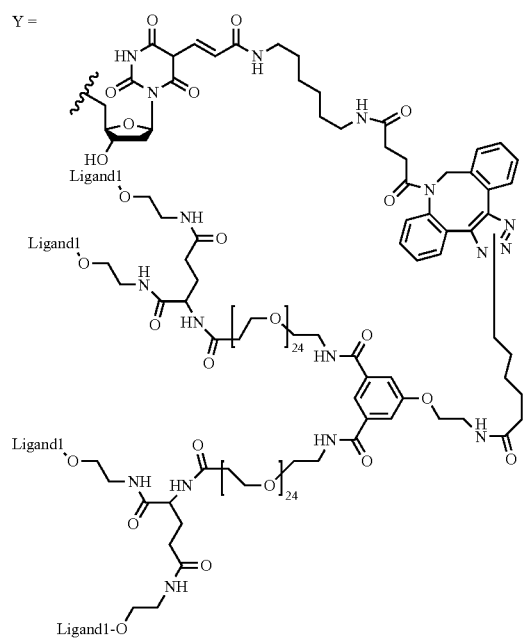

TABLE 13-4
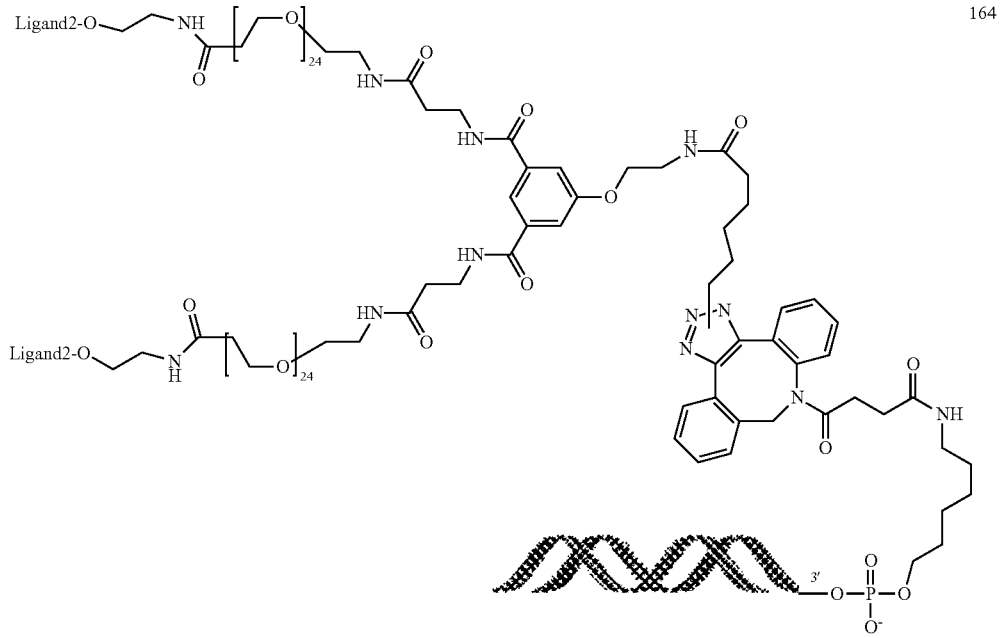
164
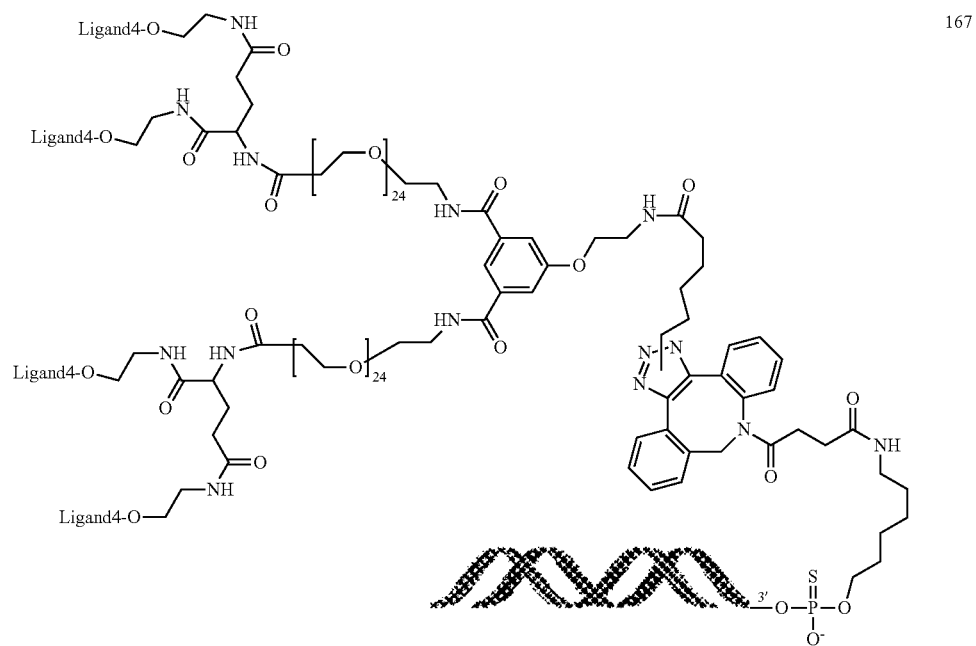
167

TABLE 13-4-continued
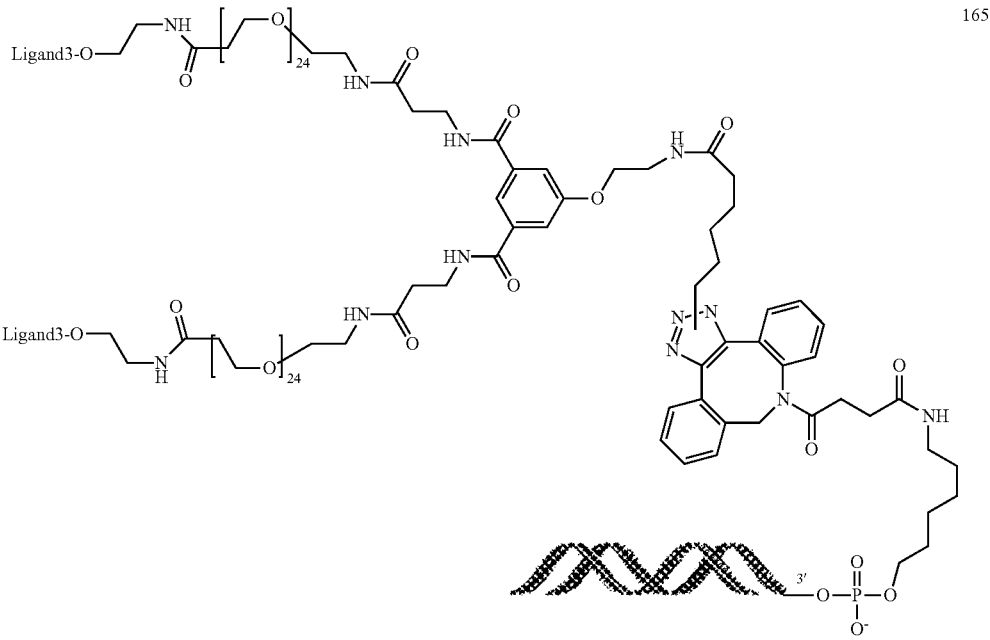
165
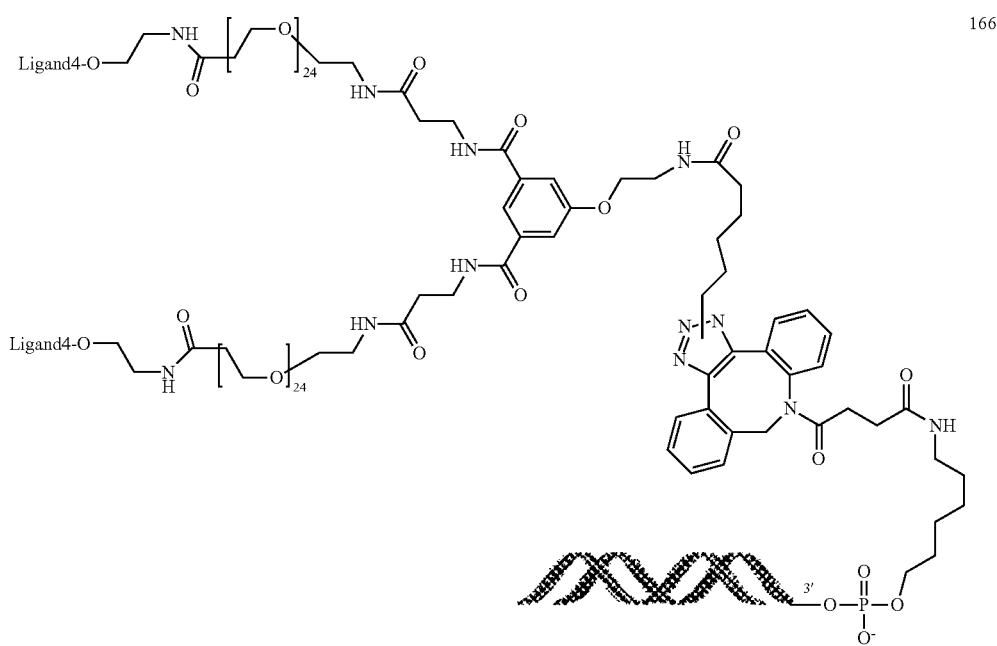
166

TABLE 13-4-continued

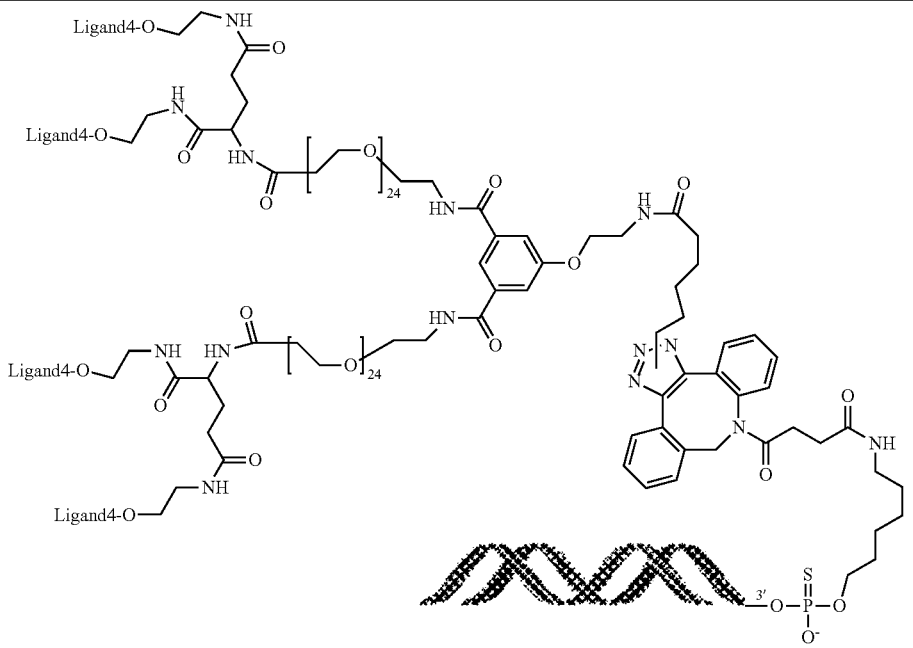

168

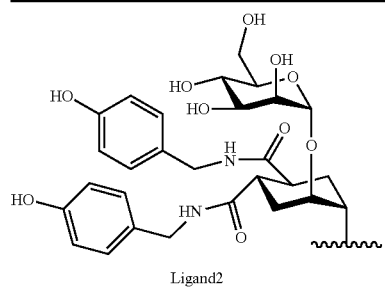

Ligand2

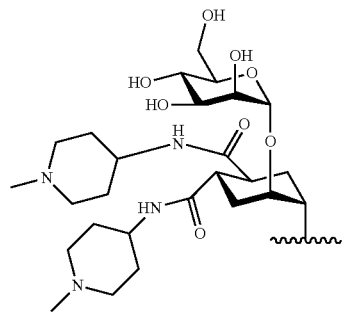

Ligand3

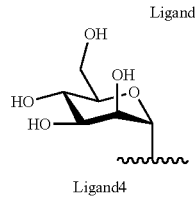

Ligand4

The sequences of the nucleic acid conjugates synthesized in this Example are shown in Table 14. The description in the box "Compound" in Table 14 represents [compound No. in the table]_[abbreviation of the nucleic acid sequence in the nucleic acid conjugate]_[type of the nucleic acid (siRNA)]. In the description in the box "Single strand name", the sense strand (ss) is represented by [compound No. in the table]_[position to which a ligand, etc. is bonded in the nucleic acid]_[abbreviation of the nucleic acid sequence in the nucleic acid conjugate]-type of the nucleic acid (ssRNA), and the antisense strand (as) is represented by [abbreviation of the nucleic acid sequence in the nucleic acid conjugate]-[type of the nucleic acid (as-RNA)].

TABLE 14

| | Compound | Single strand name | Sequence |
|---|---|---|---|
| KsiRC_15 | 154_B2M-siRNA | 132_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 132 |
| | | B2M-as-RN4 | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_16 | 155_B2M-siRNA | 133_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 133 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_17 | 156_B2M-siRNA | 134_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 134 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_18 | 157_B2M-siRNA | 135_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 135 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_19 | 158_B2M-siRNA | 136_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 136 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_20 | 159_B2M-siRNA | 137_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 137 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_21 | 160_B2M-siRNA | 138_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 138 |
| | | B2M-as-RNA | A(F)^G(M)^A(F)G(M)A(F)U(M)A(F)G(M)A(F)A(M)A(M)G(F)A(M)C(F)C(M)A(F)GfM)U(F)C(M)C(F)U(M)^U(F)^G(M) |
| KsiRC_22 | 161_B2M-siRNA | 139_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 139 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_23 | 162_B2M-siRNA | 140_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 140 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_24 | 163_B2M-siRNA | 141_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 141 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_25 | 164_B2M-siRNA | 142_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 142 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_26 | 165_B2M-siRNA | 143_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 143 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_27 | 166_B2M-siRNA | 144_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 144 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_28 | 167_B2M-siRNA | 145_3'-B2MssRNA | A(F)^G(M)^G(F)A(M)C(F)U(M)G(F)G(M)U(F)C(M) U(F)U(F)U(M)C(F)U(M)A(F)U(M)C(F)U(M)^C(F)^U(M) 145 |
| | | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| KsiRC_29 | 168_B2M-siRNA | 146_3'-B2MssRNA | A(F)G(M)G(F)A(M)C(F)U(M)G(F)G(M)U(F)C(M) U(F)U(F)U(M)C(F)U(M)A(F)U(M)C(F)U(M)^C(F)^U(M) 146 |
| | | B2M-as-RN4 | A(F)^G(M)^A(F)G(M)A(F)U(M)A(F)G(M)A(F)A(M)A(M)G(F)A(M)C(F)C(M)A(r)G(M)U(F)C(M)C(F)U(M)^U(F)^G(M) |

TABLE 14-continued

| Compound | | Single strand name | Sequence |
|---|---|---|---|
| KsiRC_30 | 169_B2M-siRNA | 147_5'-B2MssRNA | 147A(F)^G(M)^G(F)A(M)C(F)U(M)G(F)G(M)U(F)C(M) U(F) U(F)U(M)C(F)U(M)A(F)U(M)C(F)U(M)^C(F)^U(M) |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_31 | 170_B2M-siRNA | 143_3-B2MssRNA | A(F)G(M)G(F)A(M)C(F)U(M)G(F)G(M)U(F)C(M) U(F)U(F)U (M)C(F)U(M)A(F)U(M)C(F)U(M)^C(F)^U(M) 148 |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_32 | 171_B2M-siRNA | 149_3'-B2MssRNA | A(F)^G(M)^G(F)A(M)C(F)U(M)G(F)G(M)U(F)C(M) U(F)U(F) U(M)C(F)U(M)A(F)U(M)C(F)U(M)^C(F)^U(M) 149 |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_33 | 172_B2M-siRNA | 150_5'-B2MssRNA | 150A(F)^G(M)^G(F)A(M)C(F)U(M)G(F)G(M)U(F)C(M) U(F) U(F)U(M)C(F)U(M)A(F)U(M)C(F)U(M)^C(F)^U(M) X |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_34 | 173_B2M-siRNA | 151_5'-B2MssRNA | 151A(F)^G(M)^G(F)A(M)C(F)U(M)G(F)G(M)U(F)C(M) U(F) U(F)U(M)C(F)U(M)A(F)U(M)C(F)U(M)^C(F)^U(M) Y |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_35 | 174_B2M-siRNA | 152_5'-B2MssRNA | 152A(F)^G(M)^G(F)A(M)C(F)U(M)G(F)G(M)U(F)C(M) U(F) U(F)U(M)C(F)U(M)A(F)U(M)C(F)U(M)^C(F)^U(M) |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| KsiRC_36 | 175_B2M-siRNA | 153_5'-B2MssRNA | 153A(F)^G(M)AG(F)A(M)C(F)U(M)G(F)G(M)U(F)C(M) U(F) U(F)U(M)C(F)U(M)A(F)U(M)C(F)U(M)^C(F)^U(M) 152 |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |
| | | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |

Example 27 Synthesis of Nucleic Acid Conjugate—5

Step 93

A nucleic acid conjugate having a distinctive sequence was obtained in the same way as in Examples 26 and 27 using compound 148. The sequence and mass spectrometry results of the nucleic acid conjugate are shown in Table 15 below, and the sequences of double-stranded conjugates are shown in Table 16.

TABLE 15

| Compound | Sequence (5'→3') | Calcd | Found |
|---|---|---|---|
| 148_3-HPRT-1ssRNA | U(F)C(M)C(F)U(M)A(F)U(M)G(F)A(M)C(F)U(M) G(F)U(M) A(F)G(M)A(F)U(M)U(F)U(M)U(F)A(M)U(F) 148 | 12431 | 12433 |

TABLE 16

| | | Single strand name | Sequence (5'→3') |
|---|---|---|---|
| Compound | | | |
| KsiRC_CTR_002 | H2NC6_HPRT1-siRNA | H2NC6-3'-HPRT1-ssRNA | U(F)C(M)C(F)U(M)A(F)U(M)G(F)A(M)C(F)U(M)G(F)U (M) A(F)G(M)A(F)U(M)U(F)U(M)U(F)A(M)U(F) C6NH2 |
| | | HPRT-1-as-RNA | pA(M)U(F)A(M)A(F)A(M)A(F)U(M)C(F)U(M)A(F) C(M)A(F)G(M)U(F)C(M)A(F)U(M)A(F)G(M)G(F)A(M)^A (F)^U(M) |

TABLE 16-continued

Single strand

| | Compound | name | Sequence (5'→3') |
|---|---|---|---|
| KsiRC_37 | 170_HPRT-1-siRNA | 148_3'-HPRT-1ssRNA | U(F)C(M)C(F)U(M)A(F)U(M)G(F)A(M)C(F)U(M)G(F)U(M) A(F)G(M)A(F)U(M)U(F)U(M)U(F)A(M)U(F) 148 |
| | | HPRT-1-as-RNA | pA(M)U(F)A(M)A(F)A(M)A(F)U(M)C(F)U(M)A(F)C(M)A(F) G(M)U(F)C(M)A(F)U(M)A(F)G(M)G(F)A(M)^A(F)^U(M) |

Test Example 1: mRNA Knockdown Test on Human Monocyte-Derived Dendritic Cell Using CD45 ASO Human CD14-positive monocyte cells (Untouched Frozen NPB-CD14+ Monocytes, manufactured by AllCells, PB011F) were lysed according to the attached protocol using RPMI1640 medium (manufactured by Nacalai Tesque, Inc., 30264-56) containing 10% fetal bovine serum (hereinafter, referred to as 10% FBS RPMI1640 medium) and DNase I Solution (manufactured by StemCell Technologies Inc., 07900).

Then, recombinant human interleukin-4 (Recombinant Human IL-4 Protein, manufactured by R&D Systems, Inc., 204-IL) (hereinafter, referred to as IL-4) at a final concentration of 100 ng/mL and recombinant human granulocyte macrophage colony-stimulating factor (Recombinant Human GM-CSF Protein CF, manufactured by R&D Systems, Inc., 215-GM-050/CF) (hereinafter, referred to as GM-CSF) at a final concentration of 50 ng/mL were added to the cells, and the cells were inoculated at a density of $10^6$ cells/mL to a multi-plate for floating culture (manufactured by SUMILON/Sumitomo Bakelite Co., Ltd., MS-8006R) and cultured at 37° C. under 5% $CO_2$ conditions.

Three days and 6 days after the start of culture, half the amount of the medium was replaced with 10% FBS RPMI1640 medium containing 100 ng/mL IL-4 and 50 ng/mL GM-CSF to induce dendritic cells.

Eight days after the start of culture, the cells were recovered, and adherent cells were also recovered using an ethylenediamine tetraacetic acid solution (0.2 g/L EDTA Solution, manufactured by Nacalai Tesque, Inc., 14367-74). After centrifugation, the cells were resuspended at 1,250,000 cells/mL in fresh 10% FBS RPMI1640 medium containing 100 ng/mL IL-4 and 50 ng/mL GM-CSF and inoculated at 80 uL/well to an ultralow adsorption 96-well plate (manufactured by Corning Inc., 3474).

The test samples used were KAC_008 and KAC_009, and KAC_CTR_001 having no ligand and KAC_CTR_002 having no complementary site to CD45 gene were established as comparative controls. The final concentration of KAC_008 was set to two concentrations: 1 μmol/L and 0.3 μmol/L. The final concentrations of KAC_009 and KAC_CTR_001 were set to four concentrations: 1 μmol/L, 0.3 μmol/L, 0.1 μmol/L and 0.03 umol/L. The final concentration of KAC_CTR_002 was set to 1 μmol/L. The test was conducted at N=3.

The nucleic acid conjugate solution was diluted by the following procedures: a nucleic acid conjugate solution prepared at 50 μM with a citrate buffer solution (20 mM citrate (pH 7), 150 mM NaCl) was diluted to 5 μM using Opti-MEM® I Reduced Serum Medium (manufactured by Life Technologies Corp., 31985-070). The further dilution of the solution was performed using a solution prepared from a citrate buffer solution and Opti-MEM at a ratio of 1:9. 20 μL of the diluted nucleic acid conjugate solution was added to the cell lysate, while 20 μL of the diluting solution was added to the negative control group, followed by culture at 37° C. for 2 days under 5% $CO_2$ conditions.

A cell lysate containing RNA was prepared using SuperPrep® Cell Lysis & RT Kit for qPCR (manufactured by Toyobo Co., Ltd., SCQ-101), and cDNA was prepared through reverse-transcription reaction using RT Kit for qPCR attached to the kit according to the instruction attached to the kit.

This cDNA was used as a template for PCR reaction, and the Taqman probe method was carried out using QuantStudio 12K Flex Real-Time PCR System (manufactured by Applied Biosystems, Inc.) as follows: CD45 and control glyceraldehyde 3-phosphate dehydrogenase) (hereinafter, referred to as GAPDH) genes were each subjected to PCR reaction. Their respective mRNA amplification levels were measured, and the semi-quantitative value of CD45 mRNA was calculated with the amplification level of GAPDH mRNA as an internal control. The CD45 and GAPDH mRNA amplification levels in the negative control group were also each measured in the same way as above, and the semi-quantitative value of CD45 mRNA was calculated.

The CD45 gene and the GAPDH gene were measured using TaqMan probes Hs00894727_m1 (manufactured by Applied Biosystems, Inc.) and Hs02758991_g1 (manufactured by Applied Biosystems, Inc.), respectively, and using TaqMan Gene Expression Master Mix (manufactured by Applied Biosystems, Inc., 4369542) as a reaction reagent according to the attached protocol. The target mRNA level of the nucleic acid conjugate (ASO-transferred specimen) was calculated as a relative ratio when the CD45 mRNA level in the negative control group (ASO-untransferred group) was defined as 1. Results indicating the relative ratio of the mRNA level by mean±standard deviation are shown in FIG. 1.

These results demonstrated that the test samples (KAC_008 and KAC_009) exhibit a strong knockdown effect, as compared with the comparative controls (KAC_CTR_001 and KAC_CTR_002).

Test Example 2: Protein Knockdown Test on Human Monocyte-Derived Dendritic Cell Using ASO Against Beta-2 Microglobulin (Hereinafter, Referred to as B2M)

Dendritic cells were induced from human CD14-positive monocyte cells by the same procedures as in Test Example 1. The cells were inoculated to an ultralow adsorption 6-well plate (manufactured by Corning Inc., 3471) and cultured at 37° C. under 5% $CO_2$ conditions. Three days later, half the amount of the medium was replaced with 10% FBS RPMI1640 medium containing 100 ng/mL IL-4 and 50 ng/mL GM-CSF to induce dendritic cells.

Six days after the start of culture, the cells were recovered, centrifuged, then resuspended at 125000 cells/mL in fresh 10% FBS RPMI1640 medium containing 100 ng/mL IL-4 and 50 ng/mL GM-CSF, and inoculated at 80 µL/well to an ultralow adsorption 96-well plate (manufactured by Corning Inc., 3474).

The test samples used were KAC_010 and KAC_012, and KAC_CTR_003 having no ligand and KAC_013 and KAC_014 having a GalNAc ligand were established as comparative controls. The final concentration of each ASO was set to two concentrations: 0.3 µmol/L and 0.1 µmol/L. The test was conducted at N=2.

The nucleic acid conjugate solution was diluted by the following procedures: each nucleic acid conjugate solution prepared at 40 µM with a citrate buffer solution was diluted to 1.5 µM using Opti-MEM. The further dilution of the solution was performed using a solution prepared from a citrate buffer solution and Opti-MEM at a ratio of 3:77. 20 µL of the diluted nucleic acid conjugate solution was added to the cell lysate, while 20 µL of the diluting solution was added to the negative control group, followed by culture at 37° C. under 5% $CO_2$ conditions.

One day after the nucleic acid addition, the cells were recovered, centrifuged, then resuspended in 80 µL of fresh 10% FBS RPMI1640 medium containing 100 ng/mL IL-4 and 50 ng/mL GM-CSF, and further cultured at 37° C. for 3 days under 5% $CO_2$ conditions.

A washing solution for cells was prepared by adding 2.5 mL of a 10% sodium azide solution (manufactured by Nacalai Tesque, Inc.) and 685 µL of a 0.5 M EDTA solution (EDTA (0.5 M), pH 8.0, manufactured by Ambion, Inc., AM9260G) to 500 mL of phosphate-buffered saline containing 1% (w/v) BSA. To this washing solution, FcR Blocking Reagent, Human (manufactured by Miltenyi Biotec, 130-059-901) was added at 20% (v/v) to prepare an FcR blocking solution.

Four days after the nucleic acid addition, the cells were recovered, centrifuged, and then washed once with the washing solution. After removal of a supernatant, 90 µL of the FcR blocking solution was added to the resultant, and the mixture was left standing on ice for 30 minutes for blocking reaction.

A fresh plate was provided with a mixed solution of 15 µL of the FcR blocking solution and 5 µL of an antibody against B2M protein (APC anti-human β2-microglobulin Antibody, manufactured by BioLegend, Inc., 316312). 80 uL of the cell lysate after the FcR blocking was added thereto, and the plate was left standing on ice for the antibody reaction.

One hour later, the cells were recovered, washed three times with the washing solution, and then resuspended in 200 µL, followed by measurement using BD FACSCanto™ II flow cytometer (manufactured by Becton, Dickinson and Company).

Analysis was conducted using FlowJo 7.6.5 (manufactured by Tomy Digital Biology Co., Ltd.). Cell fractions were gated with forward scattered light (FSC) vs. side scattered light (SSC), and the expression level of the cell surface antigen was measured from the value of geometric means of the fluorescence intensity as mean fluorescence intensity (hereinafter, referred to as MFI).

Results indicating an average MFI value are shown in FIG. 2. These results demonstrated that the test samples (KAC_010 and KAC_012) strongly knockdown the B2M protein in a low concentration range, as compared with the comparative controls (KAC_013, KAC_014, and KAC_CTR_003).

Test Example 3: Protein Knockdown Test on Human Monocyte-Derived Dendritic Cell Using B2M-siRNA Dendritic cells were induced by the same procedures as in Test 2. Six days after the start of culture, the cells were inoculated to an ultralow adsorption 96-well plate.

The test samples used were KsiRC_010, KsiRC_011 and KsiRC_012, and KsiRC_CTR_001 having no ligand and KsiRC_013 and KsiRC_014 having a GalNAc ligand were established as comparative controls. The final concentration of each siRNA was set to three concentrations: 3 µmol/L, 1 µmol/L, and 0.3 µmol/L. The test was conducted at N=1, and was conducted at N=3 for the nucleic acid-free negative control group.

The nucleic acid conjugate solution was diluted by the following procedures: each nucleic acid prepared at 40 µM with a citrate buffer solution was diluted to 15 µM using Opti-MEM. The further dilution of the solution was performed using a solution prepared from a citrate buffer solution and Opti-MEM at a ratio of 21:35. 20 µL of the diluted nucleic acid conjugate solution was added to the cell lysate, while 20 µL of the diluting solution was added to the negative control group, followed by culture at 37° C. under 5% $CO_2$ conditions.

Four days after the nucleic acid addition, the cells were recovered, centrifuged, and then washed once with the washing solution. The subsequent procedures were the same as in Test Example 2 to carry out the measurement of the expression level of the B2M protein as the cell surface antigen, and analysis.

The results are shown in FIG. 3. The results about the negative control group were indicated by mean±standard deviation. The test samples (KsiRC_010, KsiRC_011, and KsiRC_012) exhibited marked knockdown of the B2M protein, as compared with the comparative controls (KsiRC_013, KsiRC_014, and KsiRC_CTR_001).

Test Example 4: mRNA Knockdown Test on Human Monocyte-Derived Dendritic Cell Using B2M-siRNA Dendritic cells were induced by the same procedures as in Test Example 2. Six days after the start of culture, the cells were inoculated to an ultralow adsorption 96-well plate.

The test sample used was KsiRC_010, and KsiRC_CTR_001 having no ligand was established as a comparative control. The final concentration of each siRNA was set to three concentrations: 3 µmol/L, 1 µmol/L, and 0.3 µmol/L. The test was conducted at N=3.

The dilution and addition of the nucleic acid conjugate solution were performed by the same procedures as in Test Example 3, followed by culture at 37° C. under 5% $CO_2$ conditions.

Four days after the nucleic acid addition, the cells were recovered, centrifuged, and then washed once with the washing solution. The subsequent procedures were the same as in Test Example 1 to measure the expression level of mRNA.

The B2M gene and the GAPDH gene were measured using TaqMan probes Hs00984230_m1 (manufactured by Applied Biosystems, Inc.) and Hs02758991_g1 (manufactured by Applied Biosystems, Inc.), respectively, and using TaqMan Gene Expression Master Mix as a reaction reagent according to the attached protocol. The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 4.

The test sample (KsiRC_010) exhibited marked improvement in knockdown activity, as compared with the comparative control (KsiRC_CTR_001).

Test Example 5: Protein Knockdown Test on Human Monocyte-Derived Dendritic Cell Using B2M-siRNA Dendritic cells were induced by the same procedures as in Test Example 3. Six days after the start of culture, the cells were inoculated to an ultralow adsorption 96-well plate.

The test samples used were KsiRC_010, KsiRC_003, KsiRC_004, KsiRC_005, KsiRC_006, KsiRC_008, KsiRC_001, KsiRC_002, and KsiRC_007, and KsiRC_CTR_001 having no ligand and control KsiRC_009 (GAPDH target sequence) derived from KsiRC_008 by changing the siRNA sequence were established as comparative controls. The final concentration of each siRNA was set to two concentrations: 1 µmol/L and 0.3 µmol/L. The test was conducted at N=1, and was conducted at N=2 for the nucleic acid-free negative control group.

The nucleic acid conjugate solution was diluted by the following procedures: each nucleic acid prepared at 20 µM with a citrate buffer solution was diluted to 5 µM using Opti-MEM. The further dilution of the solution was performed using a solution prepared from a citrate buffer solution and Opti-MEM at a ratio of 1:3. 20 µL of the diluted nucleic acid conjugate solution was added to the cell lysate, while 20 µL of the diluting solution was added to the negative control group, followed by culture at 37° C. under 5% $CO_2$ conditions.

Four days after the nucleic acid addition, the cells were recovered, centrifuged, and then washed once with the washing solution. After removal of a supernatant, 75 µL of the FcR blocking solution was added to the resultant, and the mixture was left standing on ice for 30 minutes for blocking reaction.

A fresh plate was provided with a mixed solution containing 5 µL of an antibody against B2M (APC anti-human β2-microglobulin Antibody, manufactured by BioLegend, Inc., 316312), 1 µL of LIVE/DEAD® Fixable Aqua Dead Cell Stain Kit (Thermo Fisher Scientific Inc., L34957), 5 µL of an antibody against HLA-DR (Brilliant Violet 421™ anti-human HLA-DR Antibody, manufactured by BioLegend, Inc., 307635), and 5 µL of an antibody against CD11c (PE anti-human CD11c Antibody, manufactured by BioLegend, Inc., 301606). 65 uL of the blocked cell lysate was added thereto, and the plate was left standing on ice for 1 hour.

Then, the cells were recovered, washed three times with the washing solution, and then resuspended in 200 µL, followed by measurement using BD FACSVerse™ flow cytometer (manufactured by Becton, Dickinson and Company).

Analysis was conducted using FlowJo 7.6.5. Cells were gated with forward scattered light (FSC) vs. side scattered light (SSC). LIVE/DEAD-negative fractions were regarded as live cells, and HLA-DR- and CD11c-positive fractions were to be analyzed. The expression level of the cell surface antigen was measured from the value of geometric means of the fluorescence intensity as mean fluorescence intensity of the APC channel.

The obtained value is shown in FIG. 5. The negative control group was indicated by mean. The test samples (KsiRC_010, KsiRC_003, KsiRC_004, KsiRC_005, KsiRC_006, KsiRC_008, KsiRC_001, KsiRC_002, and KsiRC_007) exhibited marked knockdown of the B2M protein, as compared with the comparative controls (KsiRC_CTR_001 and KsiRC_009).

Test Example 6: mRNA Knockdown Test on Human Monocyte-Derived Dendritic Cell Using B2M-siRNA Human CD14-positive monocyte cells (Untouched Frozen NPB-CD14+ Monocytes, manufactured by AllCells, PB011F) were lysed according to the attached protocol using X-VIVO 15™ medium (X-VIVO™ 15 Chemically Defined, Serum-free Hematopoietic Cell Medium, manufactured by Lonza Group AG, 04-418Q).

Then, recombinant human interleukin-4 (Recombinant Human IL-4 Protein, manufactured by R&D Systems, Inc., 204-IL) (hereinafter, referred to as IL-4) at a final concentration of 100 ng/mL and recombinant human granulocyte macrophage colony-stimulating factor (Human GM-CSF premium grade, manufactured by Miltenyi Biotec, 130-093-864, 130-093-865) (hereinafter, referred to as GM-CSF) at a final concentration of 100 ng/mL were added to the cells, and the cells were inoculated at a density of $10^6$ cells/mL to a 6-well plate (Falcon® Multiwell Cell Culture Plate 6-well, manufactured by Corning Inc., 353046) and cultured at 37° C. under 5% $CO_2$ conditions. Two days and 3 days after the start of culture, the medium was replaced with fresh one to induce dendritic cells.

Six days after the start of culture, the cells were recovered, and adherent cells were also recovered using an ethylenediamine tetraacetic acid solution (0.2 g/L EDTA Solution, manufactured by Nacalai Tesque, Inc., 14367-74). After centrifugation, the cells were resuspended at 500,000 cells/mL in fresh X-VIVO 15™ medium containing 100 ng/mL IL-4 and 100 ng/mL GM-CSF, inoculated at 200 µL/well to an ultralow adsorption 96-well plate (manufactured by Corning Inc., 3474), and further cultured at 37° C. for 3 days under 5% $CO_2$ conditions.

Nine days after the start of culture, the cells were recovered, centrifuged, then resuspended at 625,000 cells/mL in fresh X-VIVO 15™ medium containing 100 ng/mL IL-4 and 100 ng/mL GM-CSF, and inoculated at 80 µL/well to an ultralow adsorption 96-well plate.

The test samples used were KsiRC_025, KsiRC_027 and KsiRC_029, and KsiRC_CTR_001 having no ligand was established as a comparative control. The final concentration of each siRNA was set to 0.3 µmol/L and 0.1 µmol/L. The test was conducted at N=3.

20 µL of the nucleic acid conjugate solution diluted using Opti-MEM® I Reduced Serum Medium (manufactured by Life Technologies Corp., 31985-070, 31985-088) in the same way as in Test Example 1-5 was added to the cell lysate, while 20 µL of the diluting solution was added to the negative control group, followed by culture at 37° C. for 4 days under 5% $CO_2$ conditions.

Four days after the nucleic acid addition, the cells were recovered. The subsequent procedures were the same as in Test Example 4 to measure the expression level of mRNA.

The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 6.

The test samples (KsiRC_025, KsiRC_027 and KsiRC_029) exhibited marked improvement in knockdown activity, as compared with the comparative control (KsiRC_CTR_001).

Test Example 7: mRNA Knockdown Test on Human Monocyte-Derived Dendritic Cell Using B2M-siRNA Human monocyte-derived dendritic cells were induced by the same procedures as in Test Example 6. Each B2M siRNA was evaluated for its activity.

The test samples used were KsiRC_030, KsiRC_031, KsiRC_032, KsiRC_015, KsiRC_016, KsiRC_018, KsiRC_019 and KsiRC_017, and KsiRC_CTR_001 having no ligand was established as a comparative control. The final concentration of each siRNA was set to 0.03 µmol/L and 0.01 µmol/L. The test was conducted at N=3.

Four days after the nucleic acid addition, the cells were recovered. The subsequent procedures were the same as in Test Example 6 to measure the expression level of mRNA.

The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 7.

The test samples (KsiRC_030, KsiRC_031, KsiRC_032, KsiRC_015, KsiRC_016, KsiRC_018, KsiRC_019 and KsiRC_017) exhibited improvement in knockdown activity, as compared with the comparative control (KsiRC_CTR_001).

Test Example 8: mRNA Knockdown Test on Human Monocyte-Derived Dendritic Cell Using B2M-siRNA Human monocyte-derived dendritic cells were induced by the same procedures as in Test Example 6. Each B2M siRNA was evaluated for its activity.

The test sample used was KsiRC_020, and KsiRC_CTR_001 having no ligand was established as a comparative control. The final concentration of each siRNA was set to 0.03 µmol/L and 0.01 µmol/L. The test was conducted at N=3.

Four days after the nucleic acid addition, the cells were recovered. The subsequent procedures were the same as in Test Example 7 to measure the expression level of mRNA.

The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 8.

The test sample (KsiRC_020) exhibited improvement in knockdown activity, as compared with the comparative control (KsiRC_CTR_001).

Test Example 9: mRNA Knockdown Test on Human Monocyte-Derived Dendritic Cell Using B2M-siRNA Human monocyte-derived dendritic cells were induced by the same procedures as in Test Example 6. Each B2M siRNA was evaluated for its activity.

The test samples used were KsiRC_023, KsiRC_024, KsiRC_021 and KsiRC_028, and KsiRC_CTR_001 having no ligand was established as a comparative control. The final concentration of each siRNA was set to 0.03 µmol/L and 0.01 µmol/L. The test was conducted at N=3.

Four days after the nucleic acid addition, the cells were recovered. The subsequent procedures were the same as in Test Example 8 to measure the expression level of mRNA.

The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 9.

The test samples (KsiRC_023, KsiRC_024, KsiRC_021, and KsiRC_028) exhibited improvement in knockdown activity, as compared with the comparative control (KsiRC_CTR_001).

Test Example 10: mRNA Knockdown Test on Human Monocyte-Derived Dendritic Cell Using B2M-siRNA Human monocyte-derived dendritic cells were induced by the same procedures as in Test Example 6. Each B2M siRNA was evaluated for its activity.

The test samples used were KsiRC_035, KsiRC_036, KsiRC_022, KsiRC_033, and KsiRC_034), and KsiRC_CTR_001 having no ligand was established as a comparative control. The final concentration of each siRNA was set to 0.01 µmol/L and 0.003 µmol/L. The test was conducted at N=3.

Four days after the nucleic acid addition, the cells were recovered. The subsequent procedures were the same as in Test Example 9 to measure the expression level of mRNA.

The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 10.

The test samples (KsiRC_035, KsiRC_036, KsiRC_022, KsiRC_033, and KsiRC_034) exhibited improvement in knockdown activity, as compared with the comparative control (KsiRC_CTR_001).

Test Example 11: mRNA Knockdown Test on Mature Human Monocyte-Derived Dendritic Cell Using B2M-siRNA Human monocyte-derived dendritic cells were induced by the same procedures as in Test Example 6. Six days after the start of culture, the cells were recovered, then resuspended at 500,000 cells/mL in fresh X-VIVO 15™ medium containing 100 ng/mL IL-4 and 100 ng/mL GM-CSF, and inoculated at 200 µL/well to an ultralow adsorption 96-well plate (manufactured by Corning Inc., 3474). In this operation, the CD40 antibody described in the patent literature (International Publication No. WO 02/088186, Clone: KM341-1-19) was added thereto, and the cells were cultured at 37° C. for 3 days under 5% $CO_2$ conditions to prepare mature dendritic cells.

Nine days after the start of culture, the cells were recovered, centrifuged, then resuspended at 625,000 cells/mL in fresh X-VIVO 15™ medium containing 100 ng/mL IL-4, 100 ng/mL GM-CSF, and the CD40 antibody and inoculated at 80 µL/well to an ultralow adsorption 96-well plate (manufactured by Corning Inc., 3474).

The test samples used were KsiRC_003, KsiRC_031, and KsiRC_001, and KsiRC_CTR_001 having no ligand was established as a comparative control. The final concentration of each siRNA was set to 0.3 µmol/L and 0.1 µmol/L. The test was conducted at N=3.

20 µL of the nucleic acid conjugate solution diluted using Opti-MEM in the same way as in Test Example 1-5 was added to the cell lysate, while 20 µL of the diluting solution was added to the negative control group, followed by culture at 37° C. for 4 days under 5% $CO_2$ conditions.

Four days after the nucleic acid addition, the cells were recovered. The subsequent procedures were the same as in Test Example 10 to measure the expression level of mRNA. The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 11.

The test samples (KsiRC_003, KsiRC_031, and KsiRC_001) exhibited improvement in knockdown activity, as compared with the comparative control (KsiRC_CTR_001).

Test Example 12: mRNA Knockdown Test on Human Monocyte-Derived Dendritic Cell Using Hypoxanthine-Guanine Phosphoribosyl Transferase 1 (Hereinafter, Referred to as HPRT1)-siRNA Mature human monocyte-derived dendritic cells were induced by the same procedures as in Test Example 11. Each HPRT1 siRNA was evaluated for its activity.

The test sample used was KsiRC_037, and KsiRC_CTR_002 having no ligand was established as a comparative control. The final concentration of each siRNA was set to 0.3 µmol/L, 0.1 µmol/L, and 0.03 µmol/L. The test was conducted at N=3.

Four days after the nucleic acid addition, the cells were recovered. The subsequent procedures were the same as in Test Example 11 to measure the expression level of mRNA.

The HPRT1 gene and the GAPDH gene were measured using TaqMan probes Hs99999909_m1 (manufactured by Applied Biosystems, Inc.) and Hs02758991_g1 (manufactured by Applied Biosystems, Inc.), respectively, and using TaqMan Gene Expression Master Mix as a reaction reagent according to the attached protocol. The target mRNA level of the siRNA-transferred specimen was calculated as a relative ratio when the HPRT1 mRNA level in the siRNA-untransferred group (negative control group) was defined as 1. Results indicating the relative ratio of the mRNA level by mean±standard deviation are shown in FIG. 12.

The test sample (KsiRC_037) exhibited marked improvement in knockdown activity, as compared with the comparative control (KsiRC_CTR_002).

Test Example 13: mRNA Knockdown Test on Human Monocyte-Derived Macrophage Cell Using B2M-siRNA Human CD14-positive monocyte cells (Untouched Frozen NPB-CD14+ Monocytes, manufactured by AllCells, PB011F) were lysed according to the attached protocol using X-VIVO 15™ medium.

Then, GM-CSF was added to the cells such that the final concentration was 100 ng/mL. The cells were diluted to a density of 375,000 cells/mL, then inoculated at 200 µL/well to a 96-well plate (Nunc™ MicroWell™ 96-Well Microplates, manufactured by Thermo Fisher Scientific Inc., 167008), and cultured at 37° C. under 5% $CO_2$ conditions to prepare monocyte-derived macrophage cells.

Seven days after the start of culture, a supernatant was removed, and 80 µL of fresh X-VIVO 15™ medium containing 125 ng/mL GM-CSF was added to the resultant.

The test samples used were KsiRC_001, KsiRC_030, KsiRC_031 and KsiRC_032, and KsiRC_CTR_001 having no ligand was established as a comparative control. The final concentration of each siRNA was set to 1 µmol/L, 0.3 µmol/L, and 0.1 µmol/L. The test was conducted at N=3.

20 µL of the nucleic acid conjugate solution diluted using Opti-MEM in the same way as in Test Example 1-5 was added to the cell lysate, while 20 µL of the diluting solution was added to the negative control group, followed by culture at 37° C. for 4 days under 5% $CO_2$ conditions.

Four days after the nucleic acid addition, the cells were recovered. The subsequent procedures were the same as in Test Example 12 to measure the expression level of mRNA. The target mRNA level of the siRNA-transferred specimen was calculated as a relative ratio when the B2M mRNA level in the siRNA-untransferred group (negative control group) was defined as 1. Results indicating the relative ratio of the mRNA level by mean±standard deviation are shown in FIG. 13.

The test samples (KsiRC_001, KsiRC_030, KsiRC_031 and KsiRC_032) exhibited improvement in knockdown activity, as compared with the comparative control (KsiRC_CTR_001).

INDUSTRIAL APPLICABILITY

The nucleic acid conjugate of the present invention can be used for treating various related diseases in vivo by administration to mammals.

Free Test of Sequence Listing

SEQ ID NO: 1 represents the nucleotide sequence of CD45-ASO.

SEQ ID NO: 2 represents the nucleotide sequence of ApoB-ASO.

SEQ ID NO: 3 represents the nucleotide sequence of B2M-ASO.

SEQ ID NO: 4 represents the nucleotide sequence of B2M-ssRNA.

SEQ ID NO: 5 represents the nucleotide sequence of B2M-asRNA.

SEQ ID NO: 6 represents the nucleotide sequence of GAPDH-ssRNA.

SEQ ID NO: 7 represents the nucleotide sequence of GAPDH-asRNA.

SEQ ID NO: 8 represents the nucleotide sequence of Hprt-1ssRNA.

SEQ ID NO: 9 represents the nucleotide sequence of Hprt-1asRNA.

The invention claimed is:

1. A nucleic acid conjugate in which a sugar chain ligand is bonded to an siRNA or an antisense oligonucleotide (ASO) via a linker, wherein the sugar chain ligand has the following structure:

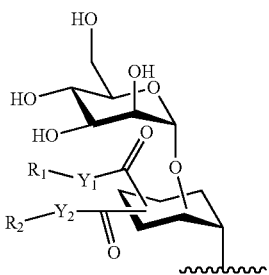

wherein
$R_1$ and $R_2$ are 4-hydroxybenzyl,
$Y_1$ and $Y_2$ are each $NR_3$, and
$R_3$ is a hydrogen atom.

2. The nucleic acid conjugate according to claim 1, wherein the sugar chain ligand has the following structure:

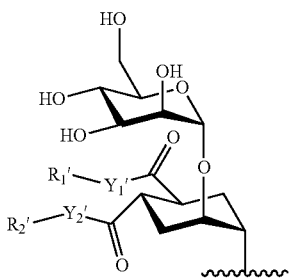

wherein
$R_1'$ and $R_2'$ are 4-hydroxybenzyl,
$Y_1'$ and $Y_2'$ are each $NR_3$, and
$R_3'$ is a hydrogen atom.

3. The nucleic acid conjugate according to claim 1, wherein the linker has any of the following structures:

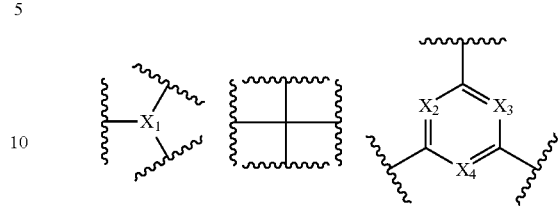

wherein
$X_1$ is CH or a nitrogen atom, and
$X_2$ to $X_4$ are each independently CH or a nitrogen atom.

4. The nucleic acid conjugate according to claim 1, wherein the linker has the following structure:

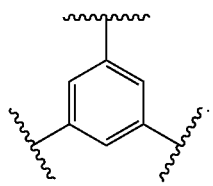 [SMILES: *c1cc(*)cc(*)c1]

5. The nucleic acid conjugate according to claim 1, wherein the linker has the following structure:

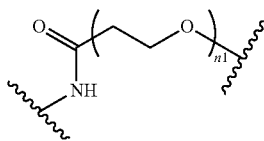

wherein
n1 is an integer of 1 to 100.

6. The nucleic acid conjugate according to claim 1, wherein the linker has any of the following structures:

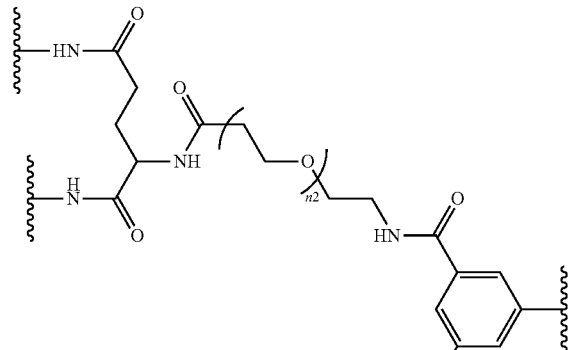

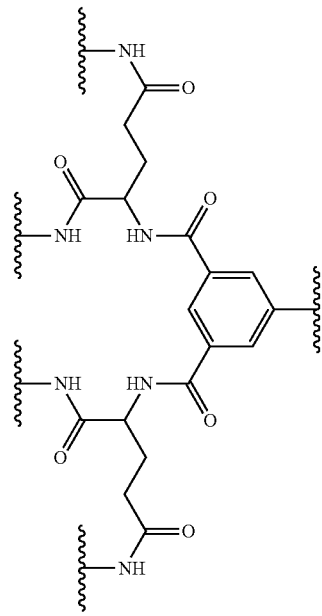

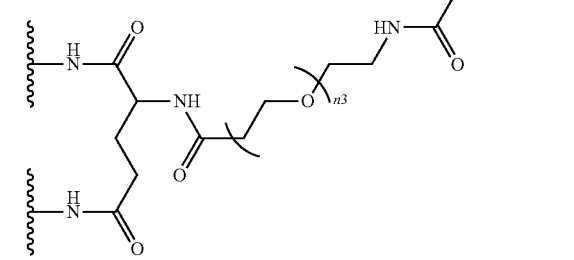

365
366
-continued
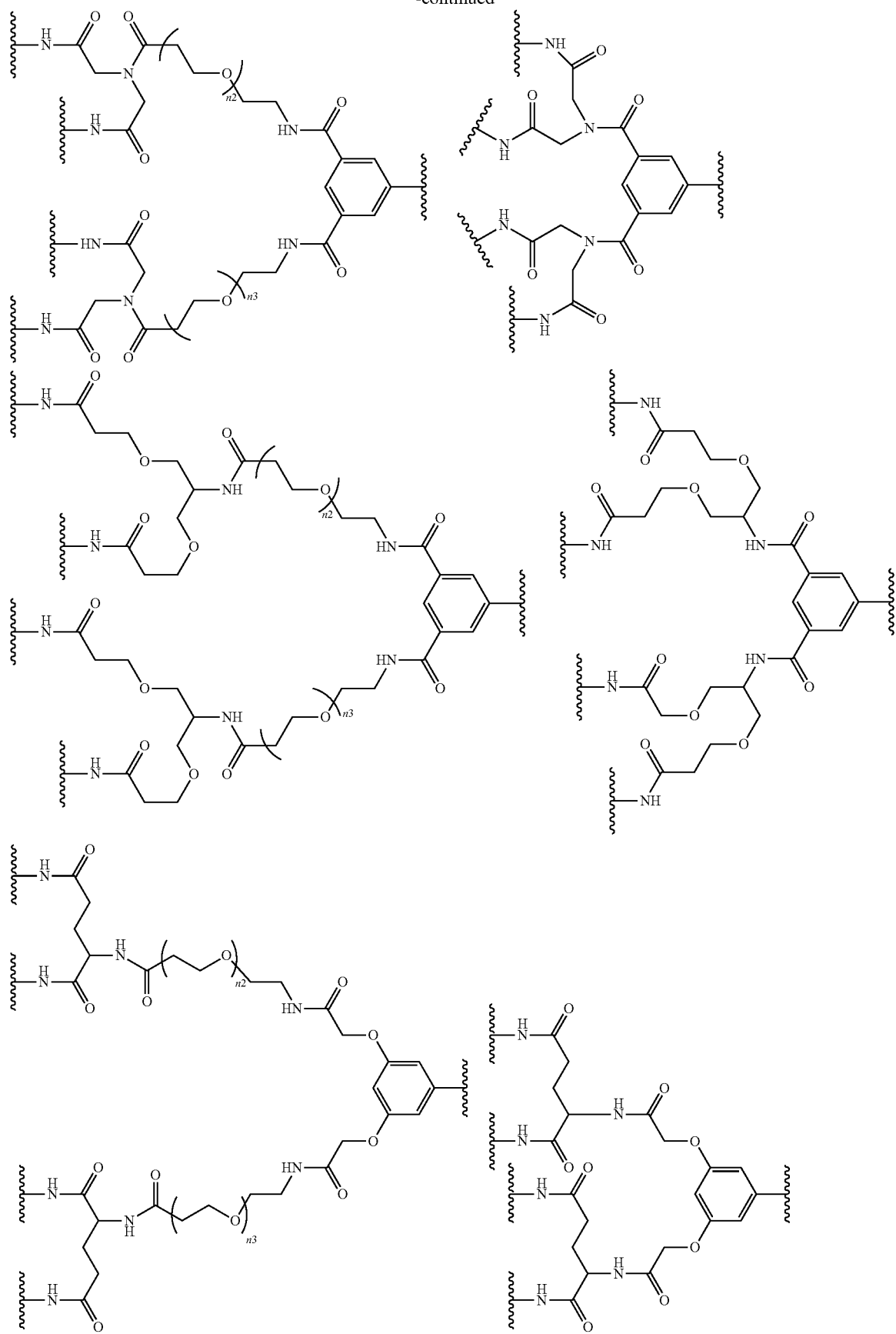

-continued
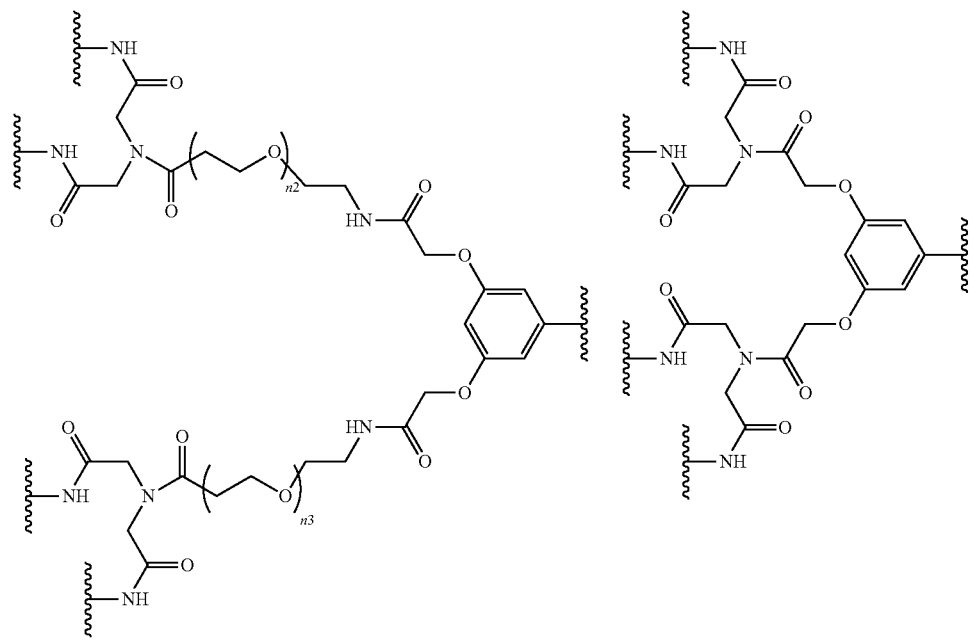
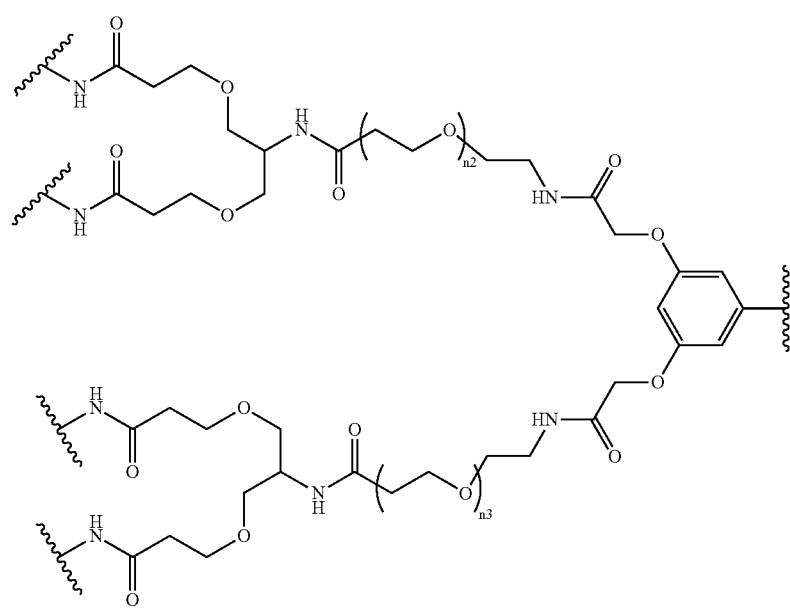

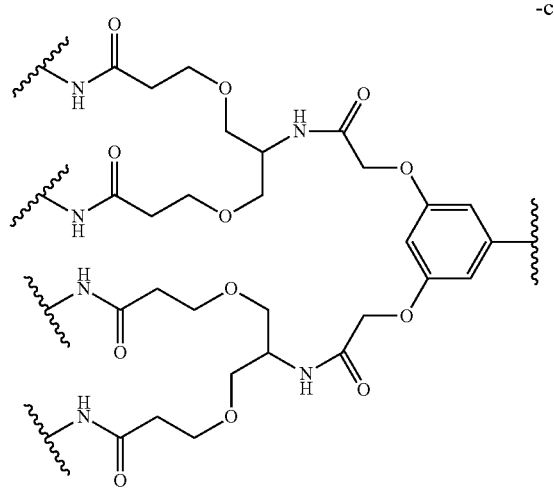

wherein n2 and n3 are each independently an integer of 1 to 100.

7. The nucleic acid conjugate according to claim 1, wherein the siRNA or the antisense oligonucleotide comprises a modified nucleotide.

8. A pharmaceutical composition comprising the nucleic acid conjugate according to claim 1.

9. The pharmaceutical composition according to claim 8, wherein the pharmaceutical composition is for transfer into a cell.

10. The pharmaceutical composition according to claim 9, wherein the cell is a dendritic cell or a macrophage.

11. A method for treating or preventing a disease, comprising administering the nucleic acid conjugate according to claim 1 to a patient in need thereof.

12. The method of claim 11, wherein the nucleic acid conjugate is intravenously administered or subcutaneously administered.

* * * * *

SEQUENCE LISTING

```
<160> NUMBER OF SEQ ID NOS: 9

<210> SEQ ID NO 1
<211> LENGTH: 16
<212> TYPE: DNA
```

```
<213> ORGANISM: Artificial Sequence
<220> FEATURE:
<223> OTHER INFORMATION: CD45-ASO
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (2)..(16)
<223> OTHER INFORMATION: 5'-phosphonothioate
<220> FEATURE:
<221> NAME/KEY: misc_feature
<222> LOCATION: (13)..(16)
<223> OTHER INFORMATION: LNA

<400> SEQUENCE: 1
ccaaatgcca agagtt                                                         16

<210> SEQ ID NO 2
<211> LENGTH: 13
<212> TYPE: DNA
<213> ORGANISM: Artificial Sequence
<220> FEATURE:
<223> OTHER INFORMATION: ApoB-ASO
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNAmC
<220> FEATURE:
<221> NAME/KEY: misc_feature
<222> LOCATION: (2)..(13)
<223> OTHER INFORMATION: 5'-phosphonothioate
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNAmC

<400> SEQUENCE: 2
gnattggtat tna                                                            13

<210> SEQ ID NO 3
<211> LENGTH: 16
<212> TYPE: DNA
<213> ORGANISM: Artificial Sequence
<220> FEATURE:
<223> OTHER INFORMATION: B2M-ASO
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (2)..(16)
<223> OTHER INFORMATION: 5'-phosphonothioate
<220> FEATURE:
<221> NAME/KEY: misc_feature
<222> LOCATION: (3)..(3)
<223> OTHER INFORMATION: LNAmC
<220> FEATURE:
<221> NAME/KEY: misc_feature
<222> LOCATION: (13)..(16)
<223> OTHER INFORMATION: LNA

<400> SEQUENCE: 3
ttntaagcag agtatg                                                         16
```

```
<210> SEQ ID NO 4
<211> LENGTH: 21
<212> TYPE: RNA
<213> ORGANISM: Artificial Sequence
<220> FEATURE:
<223> OTHER INFORMATION: B2M-ssRNA
<220> FEATURE:
<221> NAME/KEY: modified_base
<222> LOCATION: (1)..(1)
<223> OTHER INFORMATION: 2'-deoxy-2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-deoxy-2'-fluoroguanosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-deoxy-2'-fluorocytidine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroguanosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-deoxy-2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(12)
<223> OTHER INFORMATION: 2'-deoxy-2'-fluorouridine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-deoxy-2'-fluorocytidine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-deoxy-2'-fluorocytidine
<220> FEATURE:
<221> NAME/KEY: modified_base
<222> LOCATION: (19)..(19)
```

```
<223> OTHER INFORMATION: um
<220> FEATURE:
<221> NAME/KEY: modified_base
<222> LOCATION: (20)..(20)
<223> OTHER INFORMATION: 2'-deoxy-2'-fluorocytidine
<220> FEATURE:
<221> NAME/KEY: misc_feature
<222> LOCATION: (20)..(21)
<223> OTHER INFORMATION: 5'-phosphonothioate
<220> FEATURE:
<221> NAME/KEY: modified_base
<222> LOCATION: (21)..(21)
<223> OTHER INFORMATION: um

<400> SEQUENCE: 4
aggacugguc uuucuaucuc u                                              21

<210> SEQ ID NO 5
<211> LENGTH: 23
<212> TYPE: RNA
<213> ORGANISM: Artificial Sequence
<220> FEATURE:
<223> OTHER INFORMATION: B2M-as-RNA
<220> FEATURE:
<221> NAME/KEY: modified_base
<222> LOCATION: (1)..(1)
<223> OTHER INFORMATION: 2'-deoxy-2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (2)..(3)
<223> OTHER INFORMATION: 5'-phosphonothioate
<220> FEATURE:
<221> NAME/KEY: modified_base
<222> LOCATION: (3)..(3)
<223> OTHER INFORMATION: 2'-deoxy-2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-deoxy-2'-fluoroadenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroadenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-deoxy-2'-fluoroadenosine
<220> FEATURE:
<221> NAME/KEY: modified_base
<222> LOCATION: (10)..(11)
<223> OTHER INFORMATION: 2'-O-methyladenosine
<220> FEATURE:
<221> NAME/KEY: modified_base
<222> LOCATION: (12)..(12)
<223> OTHER INFORMATION: 2'-deoxy-2'-fluoroguanosine
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
```

```
<222> LOCATION: (14)..(14)
<223> OTHER INFORMATION: 2'-deoxy-2'-fluorocytidine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-deoxy-2'-fluorouridine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-deoxy-2'-fluorocytidine
<220> FEATURE:
<221> NAME/KEY: modified_base
<222> LOCATION: (21)..(21)
<223> OTHER INFORMATION: um
<220> FEATURE:
<221> NAME/KEY: modified_base
<222> LOCATION: (22)..(22)
<223> OTHER INFORMATION: 2'-deoxy-2'-fluorouridine
<220> FEATURE:
<221> NAME/KEY: misc_feature
<222> LOCATION: (22)..(23)
<223> OTHER INFORMATION: 5'-phosphonothioate
<220> FEATURE:
<221> NAME/KEY: modified_base
<222> LOCATION: (23)..(23)
<223> OTHER INFORMATION: gm

<400> SEQUENCE: 5
agagauagaa agaccagucc uug                                              23

<210> SEQ ID NO 6
<211> LENGTH: 21
<212> TYPE: RNA
<213> ORGANISM: Artificial Sequence
<220> FEATURE:
<223> OTHER INFORMATION: GAPDH-ssRNA
<220> FEATURE:
<221> NAME/KEY: modified_base
<222> LOCATION: (1)..(1)
<223> OTHER INFORMATION: 2'-deoxy-2'-fluorocytidine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-deoxy-2'-fluorouridine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-deoxy-2'-fluorocytidine
<220> FEATURE:
<221> NAME/KEY: modified_base
<222> LOCATION: (6)..(6)
<223> OTHER INFORMATION: 2'-O-methyladenosine
<220> FEATURE:
```

```
<221> NAME/KEY: modified_base
<222> LOCATION: (7)..(7)
<223> OTHER INFORMATION: 2'-deoxy-2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: 2'-deoxy-2'-fluoroguanosine
<220> FEATURE:
<221> NAME/KEY: modified_base
<222> LOCATION: (10)..(10)
<223> OTHER INFORMATION: 2'-deoxy-2'-fluoroadenosine
<220> FEATURE:
<221> NAME/KEY: modified_base
<222> LOCATION: (11)..(11)
<223> OTHER INFORMATION: 2'-deoxy-2'-fluorocytidine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: 2'-deoxy-2'-fluorouridine
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-deoxy-2'-fluorocytidine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-deoxy-2'-fluoroadenosine
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: 2'-deoxy-2'-fluoroadenosine

<400> SEQUENCE: 6
ccuucauuga ccucaacuac a                                          21

<210> SEQ ID NO 7
<211> LENGTH: 21
<212> TYPE: RNA
<213> ORGANISM: Artificial Sequence
<220> FEATURE:
<223> OTHER INFORMATION: GAPDH-as-RNA
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-deoxy-2'-fluoroadenosine
<220> FEATURE:
<221> NAME/KEY: modified_base
<222> LOCATION: (3)..(3)
<223> OTHER INFORMATION: gm
```

```
<220> FEATURE:
<221> NAME/KEY: modified_base
<222> LOCATION: (4)..(4)
<223> OTHER INFORMATION: 2'-deoxy-2'-fluorouridine
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: 2'-deoxy-2'-fluoroguanosine
<220> FEATURE:
<221> NAME/KEY: modified_base
<222> LOCATION: (7)..(7)
<223> OTHER INFORMATION: 2'-deoxy-2'-fluoroadenosine
<220> FEATURE:
<221> NAME/KEY: modified_base
<222> LOCATION: (8)..(8)
<223> OTHER INFORMATION: 2'-deoxy-2'-fluoroguanosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-deoxy-2'-fluorouridine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-deoxy-2'-fluorouridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-deoxy-2'-fluoroguanosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-deoxy-2'-fluoroguanosine
<220> FEATURE:
<221> NAME/KEY: modified_base
<222> LOCATION: (21)..(21)
<223> OTHER INFORMATION: gm
<220> FEATURE:
<221> NAME/KEY: misc_feature
<222> LOCATION: (21)..(21)
<223> OTHER INFORMATION: 5'-phosphonothioate

<400> SEQUENCE: 7
uaguugaggu caaugaaggg g                                              21

<210> SEQ ID NO 8
```

```
<211> LENGTH: 21
<212> TYPE: RNA
<213> ORGANISM: Artificial Sequence
<220> FEATURE:
<223> OTHER INFORMATION: HPRT-1ssRNA
<220> FEATURE:
<221> NAME/KEY: modified_base
<222> LOCATION: (1)..(1)
<223> OTHER INFORMATION: 2'-deoxy-2'-fluorouridine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-deoxy-2'-fluorocytidine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-deoxy-2'-fluoroadenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroguanosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-deoxy-2'-fluorocytidine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-deoxy-2'-fluoroguanosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-deoxy-2'-fluoroadenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-deoxy-2'-fluoroadenosine
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (17)..(17)
<223> OTHER INFORMATION: 2'-deoxy-2'-fluorouridine
<220> FEATURE:
<221> NAME/KEY: modified_base
<222> LOCATION: (18)..(18)
<223> OTHER INFORMATION: um
<220> FEATURE:
<221> NAME/KEY: modified_base
```

```
<222> LOCATION: (19)..(19)
<223> OTHER INFORMATION: 2'-deoxy-2'-fluorouridine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: 2'-deoxy-2'-fluorouridine

<400> SEQUENCE: 8
uccuaugacu guagauuuua u                                              21

<210> SEQ ID NO 9
<211> LENGTH: 23
<212> TYPE: RNA
<213> ORGANISM: Artificial Sequence
<220> FEATURE:
<223> OTHER INFORMATION: HPRT-1-as-RNA
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(1)
<223> OTHER INFORMATION: 5'-phosphoryl
<220> FEATURE:
<221> NAME/KEY: modified_base
<222> LOCATION: (2)..(2)
<223> OTHER INFORMATION: 2'-deoxy-2'-fluorouridine
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-deoxy-2'-fluoroadenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-deoxy-2'-fluoroadenosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-deoxy-2'-fluorocytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-deoxy-2'-fluoroadenosine
<220> FEATURE:
<221> NAME/KEY: modified_base
```

```
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-deoxy-2'-fluoroadenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-deoxy-2'-fluorouridine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-deoxy-2'-fluoroadenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-deoxy-2'-fluoroguanosine
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-deoxy-2'-fluoroadenosine
<220> FEATURE:
<221> NAME/KEY: misc_feature
<222> LOCATION: (22)..(23)
<223> OTHER INFORMATION: 5'-phosphonothioate
<220> FEATURE:
<221> NAME/KEY: modified_base
<222> LOCATION: (23)..(23)
<223> OTHER INFORMATION: um

<400> SEQUENCE: 9
auaaaaucua cagucauagg aau                                         23
```